(12) United States Patent
Xiao et al.

(10) Patent No.: US 9,309,211 B2
(45) Date of Patent: Apr. 12, 2016

(54) ARYLALKENE DERIVATIVES AND USE THEREOF AS SELECTIVE ESTROGEN RECEPTOR MODULATORS

(71) Applicant: Centaurus BioPharma Co., Ltd., Beijing (CN)

(72) Inventors: Dengming Xiao, Beijing (CN); Li Zhu, Beijing (CN); Yuandong Hu, Beijing (CN); Rong Yu, Beijing (CN); Wei Hu, Beijing (CN); Na Zhao, Beijing (CN); Yong Peng, Beijing (CN); Hong Luo, Beijing (CN); Yongxin Han, Beijing (CN)

(73) Assignee: Centaurus Biopharma Co., Ltd., Beijing (CN)

( * ) Notice: Subject to any disclaimer, the term of this patent is extended or adjusted under 35 U.S.C. 154(b) by 0 days.

(21) Appl. No.: 14/369,936

(22) PCT Filed: Dec. 28, 2012

(86) PCT No.: PCT/CN2012/087884
§ 371 (c)(1),
(2) Date: Jun. 30, 2014

(87) PCT Pub. No.: WO2013/097773
PCT Pub. Date: Jul. 4, 2013

(65) Prior Publication Data
US 2015/0018341 A1    Jan. 15, 2015

Related U.S. Application Data

(60) Provisional application No. 61/646,668, filed on May 14, 2012, provisional application No. 61/646,628, filed on May 14, 2012.

(30) Foreign Application Priority Data

Dec. 30, 2011   (CN) .......................... 2011 1 0456118
Dec. 30, 2011   (CN) .......................... 2011 1 0457898

(51) Int. Cl.
| | |
|---|---|
| *C07D 307/82* | (2006.01) |
| *C07D 307/79* | (2006.01) |
| *C07D 307/80* | (2006.01) |
| *C07D 307/81* | (2006.01) |
| *C07D 405/06* | (2006.01) |
| *C07D 405/12* | (2006.01) |
| *C07D 405/14* | (2006.01) |
| *C07D 307/76* | (2006.01) |
| *C07C 217/64* | (2006.01) |
| *C07D 213/61* | (2006.01) |
| *C07D 213/64* | (2006.01) |
| *C07D 401/12* | (2006.01) |
| *C07D 333/16* | (2006.01) |
| *C07D 333/28* | (2006.01) |

(52) U.S. Cl.
CPC ............ *C07D 307/76* (2013.01); *C07C 217/64* (2013.01); *C07D 213/61* (2013.01); *C07D 213/64* (2013.01); *C07D 307/80* (2013.01); *C07D 307/81* (2013.01); *C07D 307/82* (2013.01); *C07D 333/16* (2013.01); *C07D 333/28* (2013.01); *C07D 401/12* (2013.01); *C07D 405/06* (2013.01); *C07D 405/12* (2013.01); *C07D 405/14* (2013.01)

(58) Field of Classification Search
CPC .. C07D 307/82; C07D 307/79; C07D 307/80; C07D 307/81; C07D 405/06; C07D 405/12; C07D 405/14
See application file for complete search history.

(56) References Cited

U.S. PATENT DOCUMENTS 3,637,856 A * 1/1972 Landquist et al. ............ 564/323

FOREIGN PATENT DOCUMENTS

EP          589039 A1 *    3/1994

OTHER PUBLICATIONS

Noller et al. J. Am. Chem. Soc. 1936, 58, 24-26.*
Ahmad et al. Breast Cancer Res. Treat. 2010, 122, 579-584.*
National Center for Biotechnology Information. PubChem Compound Database; CID=60199425, https://pubchem.ncbi.nlm.nih.gov/compound/60199425 (accessed Aug. 19, 2015).*

* cited by examiner

*Primary Examiner* — Matthew Coughlin
(74) *Attorney, Agent, or Firm* — Fox Rothschild LLP

(57) ABSTRACT

The invention provides novel ethylene derivatives represented by Formula I, which may be used as selective estrogen receptor modulators (SERMs) and useful in the prophylaxis and/or treatment of estrogen-dependent conditions or conditions.

Formula I

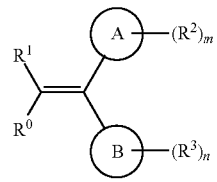

6 Claims, 1 Drawing Sheet

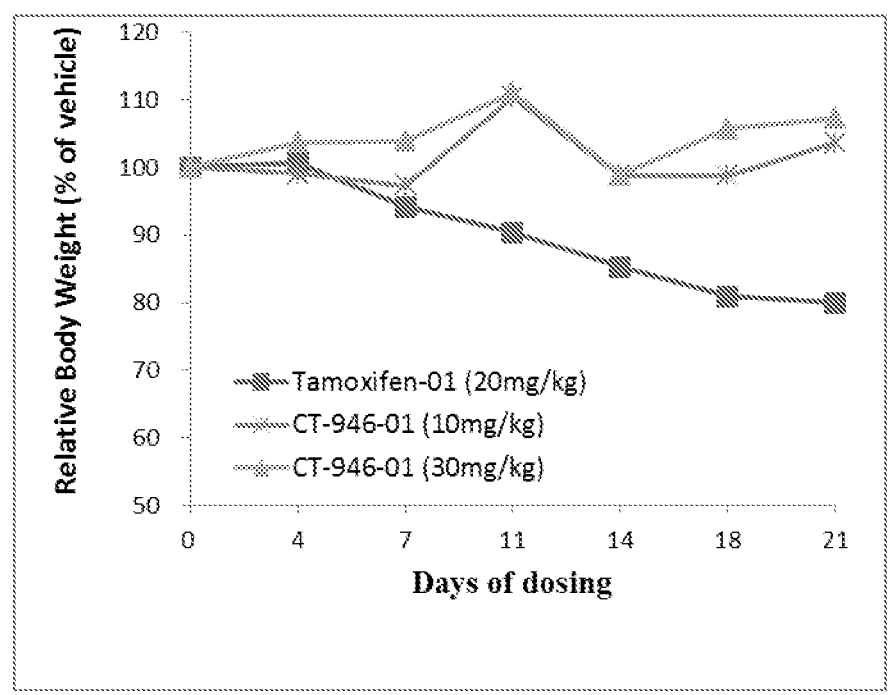

ARYLALKENE DERIVATIVES AND USE THEREOF AS SELECTIVE ESTROGEN RECEPTOR MODULATORS

FIELD OF THE INVENTION

The present invention relates to a series of ethylene derivatives which are selective estrogen receptor modulators (SERMs), a pharmaceutical composition thereof, use thereof in the preparation of a medicament, and a method for preventing and/or treating estrogen-dependent diseases and conditions in mammals, especially humans, by using the same.

BACKGROUND OF THE INVENTION

Estrogen receptor (ER) is an important transcription factor which plays a key role in reproductive, cardiovascular and central nervous systems and bone tissue. In female body, there are more than 400 tissues or organs containing ER, including for example uterus, vagina, breast, pelvic cavity (anadesma and connective tissues), skin, urocyst, urethra, ossature and brain. During the menopause, the secretion of estrogens is dramatically decreased, and the tissues, organs and systems related to estrogen change accordingly. Subsequently, elderly women develop commonly climacteric symptoms including hot flashes, sweating, insomnia, depression, headache, vaginal dryness, cardiovascular symptoms, urinary incontinence, swelling feeling, breast tenderness and fatigue (Payer, L: The menopause in various cultures. In: *A portrait of the menopause. Expert reports on medical and therapeutic strategies for the* 1990s. Ed. Burger H & Boulet M, Parthenon Publishing, Park Ridge, N.J., USA, 1991. pp 3-22; and Rekers H: Mastering the menopause. In: *A portrait of the menopause. Expert reports on medical and therapeutic strategies for the* 1990s. Ed. Burger H & Boulet M, Parthenon Publishing, Park Ridge, N.J., USA, 1991. pp 23-43). Long-term estrogen deficiency would also induce osteoporosis, senile dementia and cardiovascular disorders.

Estrogen replacement therapy is increasingly used for the treatment of climacteric symptoms in women. Estrogen replacement therapy is also shown to be beneficial in decreasing the risk of osteoporotic bone fractures, preventing Alzheimer's disease (Henderson V W: *Estrogen, cognition, and as woman's risk of Alzheimer's disease*. Am J Med 103 (3A): 11S-18S, 1997) and lowering LDL-cholesterol values and thus preventing cardiovascular diseases (Grodstein F, Stampfer, M J: *Estrogen for women at varying risk of coronary disease*. Maturitas 30: 19-26, 1998). However, use of estrogen replacement therapy increases the risk of uterine and breast cancers (Lobo R A: *Benefits and risks of estrogen replacement therapy*. Am J Obstet Gynecol 173:982-990, 1995).

Selective estrogen receptor modulators (SERMs) show different activities to ER in different tissues. They mimic estrogen in some tissues and have anti-estrogen activity in others. It would be most desirable to develop tissue-specific estrogens, which could be ER agonists in bone tissue, cardiovascular system and central nervous system, while being ER antagonists in tissues like breast and uterus, and without estrogenic adverse effects.

As the first SERMs drug approved for the treatment of osteoporosis, Raloxifene exhibits ER antagonism in breast and uterus and ER agonism in bone tissue and cardiovascular system. However, Raloxifene has no advantage over Tamoxifen in terms of therapeutic effect on breast cancer, while it has adverse effects such as hot flashes, leg cramps, headache and weight gain (Davies G C, et al., Obstet Gynecol 193: 558-565(1999)).

Obviously, it would be desirable to develop more potent and safer drugs in preventing and treating estrogen-dependent diseases and conditions.

SUMMARY

In one aspect, the present disclosure provides a compound of formula I,

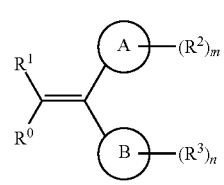

Formula I wherein:
R$^0$ and R$^1$ are independently selected from the group consisting of hydrogen, halogen, alkyl, cycloalkyl, heterocyclyl, aryl and heteroaryl, wherein the alkyl, cycloalkyl, heterocyclyl, aryl and heteroaryl are each optionally substituted with one or more groups selected from the group consisting of halogen, —OH, —NH$_2$, —SH, alkyl, halogenated alkyl, and alkoxy, and the carbon atoms on the ring of the cycloalkyl, the heterocyclyl and the heteroaryl are optionally oxidized;
ring A and ring B are each independently selected from aryl, heteroaryl and heterocyclyl, wherein the carbon atoms on the ring of the heterocyclyl and the heteroaryl are optionally oxidized;
R$^2$ and R$^3$ are independently selected from the group consisting of halogen, —OH, —NH$_2$, —CN, —SH, —COOH, alkyl, alkenyl, alkynyl, cycloalkyl, heterocyclyl, alkoxy, alkylsulfanyl, cycloalkyloxy, heterocyclyloxy, monoalkylamino, dialkylamino, —S(O)-alkyl and —S(O)$_2$-alkyl, wherein the alkyl, alkenyl, alkynyl, cycloalkyl, heterocyclyl, alkoxy, alkylsulfanyl, cycloalkyloxy, heterocyclyloxy, monoalkylamino, dialkylamino, —S(O)-alkyl and —S(O)$_2$-alkyl are each optionally substituted with halogen, —OH, heterocyclyl, or —NR$_4$R$_5$, wherein R$_4$ and R$_5$ are each independently hydrogen, alkyl or cycloalkyl, or R$_4$ and R$_5$, together with the nitrogen atom to which they attach, form a heterocyclyl which is optionally substituted with alkyl;
m and n are the number of group R$^2$ on ring A and the number of group R$^3$ on ring B, respectively, and m and n are each independently 0, 1, 2 or 3,
or a pharmaceutically acceptable salt, stereoisomer, solvate, polymorph, tautomer or prodrug thereof.

In another aspect, the present invention provides a compound of formula I, or a pharmaceutically acceptable salt, stereoisomer, solvate, polymorph, tautomer or prodrug thereof, for modulating estrogen activities.

In another aspect, the present invention provides a compound of formula I, or a pharmaceutically acceptable salt, stereoisomer, solvate, polymorph, tautomer or prodrug thereof, for preventing and/or treating estrogen-dependent diseases and conditions.

In another aspect, the present invention provides a pharmaceutical composition which comprises a compound of formula I, or a pharmaceutically acceptable salt, stereoisomer, solvate, polymorph, tautomer or prodrug thereof, as well as a pharmaceutically acceptable carrier.

In another aspect, the present invention provides use of a compound of formula I, or a pharmaceutically acceptable salt, stereoisomer, solvate, polymorph, tautomer or prodrug thereof, in the manufacture of a medicament for modulating estrogen activities.

In another aspect, the present invention provides use of a compound of formula I, or a pharmaceutically acceptable salt, stereoisomer, solvate, polymorph, tautomer or prodrug thereof, in the manufacture of a medicament for preventing and/or treating estrogen-dependent diseases and conditions.

In another aspect, the present invention provides a method for modulating estrogen activities in mammals, especially in humans, which method comprises administering to a mammal, especially a human, in need thereof a therapeutically effective amount of a compound of formula I, or a pharmaceutically acceptable salt, stereoisomer, solvate, polymorph, tautomer or prodrug thereof.

In another aspect, the present invention provides a method for preventing and/or treating estrogen-dependent diseases and conditions in mammals, especially in humans, which method comprises administering to a mammal, especially a human, in need thereof a therapeutically effective amount of a compound of formula I, or a pharmaceutically acceptable salt, stereoisomer, solvate, polymorph, tautomer or prodrug thereof.

BRIEF DESCRIPTION OF THE DRAWINGS

FIG. 1 shows weight change of nude mice during anti-tumor (MCF-7) test.

MODES FOR CARRYING OUT THE INVENTION

Unless defined otherwise, all technical and scientific terms used herein have the same meanings as are commonly understood by one of skilled in the art to which the claimed subject matter belongs. All patents, patent applications, published materials referred to throughout the entire disclosure herein, unless noted otherwise, are incorporated by reference in their entirety.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

Where substituent groups are specified by their conventional chemical formulas, written from left to right, they equally encompass the chemically identical substituents that would result from writing the structure from right to left. As a non-limiting example, —$CH_2O$— is equivalent to —$OCH_2$—.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Certain chemical groups named herein may be preceded by a shorthand notation indicating the total number of carbon atoms that are to be found in the indicated chemical group. For example; $C_1$-$C_6$ alkyl describes an alkyl group, as defined below, having a total of 1 to 6 carbon atoms. The total number of carbons in the shorthand notation does not include carbons that may exist in substituents of the group described.

In addition to the foregoing, as used in the specification and appended claims, unless specified to the contrary, the following terms have the meaning indicated.

"Halo" or "halogen" refers to bromo, chloro, fluoro or iodo.

The term "aromatic" as used herein, refers to a planar, cyclic or polycyclic, ring moiety having a delocalized at-electron system containing 4n+2 n electrons, where n is an integer. Aromatic rings can be formed by five, six, seven, eight, nine, or more than nine atoms. Aromatics can be optionally substituted and can be monocyclic or fused-ring polycyclic. The term aromatic encompasses both all carbon containing rings (e.g., phenyl) and those rings containing one or more heteroatoms (e.g., pyridine).

The terms "heteroatom" or "hetero" as used herein, alone or in combination, refer to an atom other than carbon and hydrogen. Heteroatoms are independently selected from among oxygen, nitrogen, sulfur, phosphor, silicon, selenium and tin but are not limited to these atoms. In embodiments in which two or more heteroatoms are present, the two or more heteroatoms can be the same as each another, or some or all of the two or more heteroatoms can each be different from the others.

The term "fused" as used herein, alone or in combination, refers to cyclic structures in which two or more rings share one or more bonds.

As used alone or as a part of another moiety, such as in halogen-substituted alkyl, the term "alkyl" refers to a straight or branched mono-valent hydrocarbon chain radical consisting solely of carbon and hydrogen atoms, containing no unsaturation, having from one to twelve carbon atoms, preferably one to eight carbon atoms and more preferably one to six carbon atoms, and which is attached to the rest of the molecule by a single bond, e.g., methyl, ethyl, n-propyl, iso-propyl, n-butyl, iso-butyl, sec-butyl, tert-butyl, n-pentyl, hexyl, heptyl, 2-methylhexyl, 3-methylhexyl, octyl, nonyl, decyl, and the like.

As used herein, the term "alkoxy" refers to a radical of the formula —$OR_a$ where $R_a$ is an alkyl radical as defined above. Examples of the alkoxy radical include, but not limited to, methoxy, ethoxy, iso-propoxy, n-butoxy, iso-butoxy, sec-butoxy, tert-butoxy, and the like.

As used herein, the term "alkylsulfanyl" refers to a radical of the formula —$SR_a$ where $R_a$ is an alkyl radical as defined above. Examples of the alkylsulfanyl radical include, but not limited to, methylsulfanyl, ethylsulfanyl, iso-propylsulfanyl, and the like.

As used herein, the term "monoalkylamino" refers to a radical of the formula —$NHR_a$ where $R_a$ is an alkyl radical as defined above. Examples of the monoalkylamino radical include, but not limited to, methylamino, ethylamino, iso-propylamino, and the like.

As used herein, the term "dialkylamino" refers to a radical of the formula —$NR_aR_b$ where $R_a$ and $R_b$ are each independently an alkyl radical as defined above. Examples of the dialkylamino radical include, but not limited to, dimethylamino, diethylamino, dipropylamino, methylethylamino, and the like.

As used alone or as a part of another moiety, the term "alkenyl" refers to a straight or branched mono-valent hydrocarbon chain radical group consisting solely of carbon and hydrogen atoms, containing at least one double bond, having from two to fourteen carbon atoms, preferably from two to ten carbon atoms, more preferably form two to six carbon atoms, and which is attached to the rest of the molecule by a single bond, e.g., ethenyl, prop-1-enyl, allyl, but-1-enyl, but-2-enyl, pent-1-enyl, penta-1,4-dienyl, and the like.

As used alone or as a part of another moiety, the term "alkynyl" refers to a straight or branched mono-valent hydrocarbon chain radical group comprising solely of carbon and hydrogen atoms, containing at least one triple bond, optionally containing more or more double bonds, having from two to fourteen carbon atoms, preferably from two to ten carbon atoms, more preferably from two to six carbon atoms, and which is attached to the rest of the molecule by a single bond, for example, ethynyl, prop-1-ynyl, but-1-ynyl, pent-1-en-4-ynyl, and the like.

As used alone or as a part of another moiety, the term "cycloalkyl" refers to a stable mono-valent non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, more preferably having from three to eight carbon atoms, and which is saturated or unsaturated and attached to the rest of the molecule by a single bond. Examples of cycloalkyl include, but not limited to, cyclopropyl, cyclobutyl, cyclopentyl, cyclohexyl, cyclohexanonyl, cycloheptyl, cyclooctyl, 1H-indenyl, 2,3-dihydro-indenyl, 1,2,3,4-tetrahydro-naphthyl, 5,6,7,8-tetrahydro-naphthyl, 8,9-dihydro-7H-benzocyclohepten-6-yl, 6,7,8,9-tetrahydro-5H-benzocycloheptenyl, 5,6,7,8,9,10-hexahydro-benzocyclooctenyl, fluorenyl, dicyclo[2.2.1]heptyl, 7,7-dimethyl-dicyclo[2.2.1]heptyl, dicyclo[2.2.1]heptenyl, dicyclo[2.2.2]octyl, dicyclo[3.1.1]heptyl, dicyclo[3.2.1]octyl, dicyclo[2.2.2]octenyl, dicyclo[3.2.1]octenyl, adamantyl, octahydro-4,7-methylene-1H-indenyl, octahydro-2,5-methylene-pentalinyl, norbornyl, decalinyl, and the like. In the present application, the heterocyclyl comprises preferably three to eight carbon atoms, and is more preferably cyclopentyl, cyclohexyl, cyclohexanonyl, or cycloheptyl.

As used herein, the term "cycloalkyloxy" refers to a radical of the formula —$OR_b$ where $R_b$ is a cycloalkyl radical as defined above.

As used alone or as a part of another moiety, the term "heterocyclyl" refers to a stable 3- to 18-membered mono-valent non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. A heterocyclyl may be connected to the rest of the molecule by a single bond via a carbon atom or a heteroatom on the ring. In a heterocyclyl comprising a fused ring, one or more of the rings may be an aryl or heteroaryl, provided that the site for connecting to the rest of the molecule is a non-aromatic ring atom. For the purpose of the present application, the heterocyclyl is preferably a stable 4- to 11-membered mono-valent non-aromatic mono- or di-cyclic ring radical which comprises one to three heteroatoms selected from the group consisting of nitrogen, oxygen and sulfur, and more preferably a stable 4- to 8-membered mono-valent non-aromatic monocyclic ring radical which comprises one to three heteroatoms selected from the group consisting of nitrogen, oxygen and sulfur. Examples of heterocyclyl radicals include, but are not limited to, azepanyl, azetidinyl, decahydroisoquinolyl, dihydrofuranyl, dihydroindolyl, dioxolanyl, 1,1-dioxo-thiomorpholinyl, imidazolidinyl, imidazolinyl, isothiazolidinyl, isoxazolidinyl, morpholinyl, octahydroindolyl, octahydroisoindolyl, oxazinyl, oxazolidinyl, 1-oxo-thiomorpholinyl, 2-oxopiperazinyl, 2-oxopiperidinyl, 2-oxopyrrolidinyl, phthalimido, piperazinyl, piperidinyl, 4-piperidonyl, pyranyl, pyrazolidinyl, pyrrolidinyl, quinolizinyl, quinuclidinyl, tetrahydrofuryl, tetrahydroisoquinolyl, tetrahydropyranyl, thiazolidinyl, thienyl[1,3]dithianyl, thiomorpholinyl, trithianyl, and the like.

As used herein, the term "heterocyclyloxy" refers to a radical of the formula —$OR_c$ where $R_c$ is a heterocyclyl radical as defined above.

As used alone or as a part of another moiety, the term "aryl" or the prefix "ar-" (such as in "aralkyl") refers to a hydrocarbon ring system radical comprising hydrogen, 6 to 18 carbon atoms, preferably 6 to 10 carbon atoms, and at least one aromatic ring. For purposes of this invention, the aryl radical may be a monocyclic, bicyclic, tricyclic or tetracyclic ring system, which may included fused or bridged ring systems. An aryl may be connected to the rest of the molecule by a single bond via an aromatic ring atom. Aryl radicals include, but are not limited to, phenyl, naphthyl, anthracenyl, phenanthrenyl, fluorenyl, 2-benzooxazolinonyl, 2H-1,4-benzooxazon-3(4H)-on-7-yl, and the like. In the present application, the aryl is preferably a $C_6$-$C_{10}$ aryl, and more preferably phenyl.

As used alone or as a part of another moiety, the term "heteroaryl" refers to a 5- to 16-membered ring system radical comprising one to fifteen carbon atoms, preferably one to ten carbon atoms, one to four heteroatoms selected from the group consisting of nitrogen, oxygen and sulfur, and at least one aromatic ring. Unless specified otherwise in the Specification, the heteroaryl radical may be a monocyclic, bicyclic, tricyclic or tetracyclic ring system, which may include fused or bridged ring systems, provided that the site for connection to the rest of the molecule is an aromatic ring atom. The nitrogen, carbon or sulfur atoms in the heteroaryl radical may be optionally oxidized; the nitrogen atom may be optionally quaternized. For purposes of this invention, the heteroaryl is preferably a stable 4- to 11-membered aromatic mono-cyclic ring radical which comprises one to three heteroatoms selected from the group consisting of nitrogen, oxygen and sulfur, and more preferably a stable 5- to 8-membered aromatic mono-cyclic ring radical which comprises one to three heteroatoms selected from the group consisting of nitrogen, oxygen and sulfur. Examples of heteroaryl radicals include, but are not limited to, acridinyl, azepinyl, benzimidazolyl, benzindolyl, 1,4-benzodioxanyl, benzo[6][1,4]dioxepinyl, benzodioxinyl, benzodioxolyl, benzofuranonyl, benzofuranyl, benzo[4,6]imidazo[1,2-a]pyridinyl, benzonaphthofuranyl, benzopyranonyl, benzopyranyl, benzopyrazolyl, benzothiadiazolyl, benzothiazolyl, benzothienyl (benzothiophenyl), benzotriazolyl, benzoxazolyl, carbazolyl, carbolinyl, cinnolinyl, dibenzofuranyl, dibenzothiophenyl, furanonyl, furanyl, imidazolyl, indazolyl, indolinyl, indolizinyl, indolyl, isoindazolyl, isoindolinyl, isoindolyl, isoquinolinyl, isoquinolyl, isothiazolyl, isoxazolyl, naphthyridinyl, oxadiazolyl, oxatriazolyl, oxazolyl, 1-oxidopyrazinyl, 1-oxidopyridazinyl, 1-oxidopyridinyl, 1-oxidopyrimidinyl, oxiranyl, 2-oxoazepinyl, oxopyridinyl, phenanthridinyl, phenanthrolinyl, phenazinyl, phenothiazinyl, phenoxazinyl, 1-phenyl-1H-pyrrolyl, phthalazinyl, pteridinyl, purinyl, pyrazinyl, pyrazolyl, pyridazinyl, 1H-pyridin-2-onyl, 1H-pyridin-4-onyl, 1H-pyridin-2-on-4-yl, pyridinyl, pyrimidinyl, pyrrolyl, quinazolinyl, quinolinyl, quinolyl, quinoxalinyl, quinuclidinyl, tetrahydroquinolinyl, 4,5,6,7-tetrahydrobenzo[b]thiophenyl, tetrazolyl, thiadiazolyl, thiazolyl, thiophenyl (i.e. thienyl), triazinyl, triazolyl, and the like. In the present application, the heteroaryl is preferably a 5- to 8-membered heteroaryl comprises one to three heteroatoms selected from the group consisting of nitrogen, oxygen and sulfur, and more preferably pyridinyl, pyrimidinyl, thiazolyl, oxo-pyridinyl, 1H-pyridin-2-on-4-yl or thienyl.

"Optional" or "optionally" as used herein means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

The terms "moiety", "chemical moiety", "group" and "chemical group", as used herein, refer to a specific segment or functional group of a molecule. Chemical moieties are often recognized chemical entities embedded in or appended to a molecule.

A "stereoisomer" refers to a compound made up of the same atoms bonded by the same bonds but having different three-dimensional structures. The present invention contemplates various stereoisomers and mixtures thereof.

As the compounds described herein contain olefinic double bonds, unless specified otherwise, it is intended that the compounds include both E and Z geometric isomers.

A "tautomer" refers to an isomer resulted from a proton shift from one atom of a molecule to another atom of the same molecule. The present invention includes tautomers of any said compounds.

The term "polymorph" or "polymorphism" as used herein refers to a compound of this invention present in different crystal lattice forms. Some of the compounds of the present invention may have more than one crystal forms, and the present invention tends to encompass all the polymorphs or mixtures thereof.

Also within the scope of the invention are intermediate compounds of formula (I) and all polymorphs of the aforementioned species and crystal habits thereof. Likewise, all tautomeric forms are also intended to be included.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (+) and (−), or (R)—and (S)— isomers may be prepared using chiral synthons or chiral reagents, or resolved using conventional techniques, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). See, for example, Gerald Gübitz and Martin G. Schmid (Eds.), Chiral Separations, Methods and Protocols, *Methods in Molecular Biology*, Vol. 243, 2004; A. M. Stalcup, Chiral Separations, *Annu. Rev Anal. Chem.* 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem. Res. 1990, 23, 128.

As used herein, the term "pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations often produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent. The compounds of the present invention may react in a solvent or deposit or crystallize from a solvent. The solvates of the compounds of the present invention are also encompassed in the scope of the present invention.

The present invention also contemplates prodrugs of the compounds of the present invention. "Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism. Prodrugs include amino protective groups and carboxy protective groups which are known to persons skilled in the art. Methods for preparing specific prodrugs are provided in e.g. Saulnier, M. G., et al., Bioorg. Med. Chem. Lett. 1994, 4, 1985-1990; Greenwald, R. B., et al., J. Med. Chem. 2000, 43, 475.

As used herein, "pharmaceutical composition" refers to a formulation of a compound of the invention and a medium generally accepted in the art for the delivery of the biologically active compound to mammals, e.g., humans. Such a medium includes all pharmaceutically acceptable carriers therefor.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by relevant government administration as being acceptable for use in humans or domestic animals.

The term "SERMs" as used herein, refers to selective estrogen receptor modulators, which are compounds that exhibit estrogen receptor agonism in one or more target tissues, and estrogen receptor antagonism in one or more other target tissues.

The term "subject", "patient" or "individual" as used herein in reference to individuals suffering from a disease, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "prevention of", "prophylaxis" and "prevent" includes reducing the likelihood of a patient incurring or developing breast cancer.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer", "administering", "administration", and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, *Pharmaceutical Sciences* (current edition), Mack Publishing Co., Easton, Pa. In preferred embodiments, the compounds and compositions described herein are administered orally.

The term "agonist", as used herein, refers to a molecule such as a compound, a drug, an enzyme activator or a hormone modulator which enhances the activity of another molecule or the activity of a receptor site.

The term "antagonist", as used herein, refers to a molecule such as a compound, a drug, an enzyme inhibitor, or a hormone modulator, which diminishes, or prevents the action of another molecule or the activity of a receptor site.

The term "modulate", as used herein, means to interact with a target either directly or indirectly so as to alter the activity of the target, including, by way of example only, to enhance the activity of the target (up-regulate), to inhibit the activity of the target (down-regulate), to limit the activity of the target, or to extend the activity of the target.

The term "modulator", as used herein, refers to a molecule that interacts with a target either directly or indirectly. The interactions include, but are not limited to, the interactions of an agonist and an antagonist.

The terms "enhance" or "enhancing," as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

An "enhancing-effective amount," as used herein, refers to an amount adequate to enhance the effect of another therapeutic agent in a desired system.

The terms "pharmaceutical combination", "administering an additional therapy", "administering an additional therapeutic agent" and the like, as used herein, refer to a pharmaceutical therapy resulting from mixing or combining more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

The terms "co-administration", "administered in combination with" and their grammatical equivalents or the like, as used herein, are meant to encompass administration of the selected therapeutic agents to a single patient, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent (s) are administered in a single composition.

The term "metabolite," as used herein, refers to a derivative of a compound which is formed when the compound is metabolized.

The term "active metabolite," as used herein, refers to a biologically active derivative of a compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free mercapto groups. Further information on metabolism may be obtained from *The Pharmacological Basis of Therapeutics*, 9th Edition, McGraw-Hill (1996).

In one aspect, the present invention provides a compound of formula I,

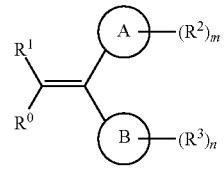

Formula I wherein:
$R^0$ and $R^1$ are independently selected from the group consisting of hydrogen, halogen, alkyl, cycloalkyl, heterocyclyl, aryl and heteroaryl, wherein the alkyl, cycloalkyl, heterocyclyl, aryl and heteroaryl are each optionally substituted with one or more groups selected from the group consisting of halogen, —OH, —NH₂, —SH, alkyl, halogenated alkyl and alkoxy, and the carbon atoms on the ring of the cycloalkyl, the heterocyclyl and the heteroaryl are optionally oxidized;

ring A and ring B are each independently selected from aryl, heteroaryl and heterocyclyl, wherein the carbon atoms on the ring of the heterocyclyl and the heteroaryl are optionally oxidized;

$R^2$ and $R^3$ are independently selected from the group consisting of halogen, —OH, —NH₂, —CN, —SH, —COOH, alkyl, alkenyl, alkynyl, cycloalkyl, heterocyclyl, alkoxy, alkylsulfanyl, cycloalkyloxy, heterocyclyloxy, monoalkylamino, dialkylamino, —S(O)-alkyl and —S(O)₂-alkyl, wherein the alkyl, alkenyl, alkynyl, cycloalkyl, heterocyclyl, alkoxy, alkylsulfanyl, cycloalkyloxy, heterocyclyloxy, monoalkylamino, dialkylamino, —S(O)-alkyl and —S(O)$_2$-alkyl are each optionally substituted with halogen, —OH, heterocyclyl, or —NR$_4$R$_5$, wherein R$_4$ and R$_5$ are each independently hydrogen, alkyl or cycloalkyl, or R$_4$ and R$_5$, together with the nitrogen atom to which they attach, form a heterocyclyl which is optionally substituted with alkyl;

m and n are the number of group R$^2$ on ring A and the number of group R$^3$ on ring B, respectively, and m and n are each independently 0, 1, 2 or 3, or a pharmaceutically acceptable salt, stereoisomer, solvate, polymorph, tautomer or prodrug thereof.

In one embodiment, the present invention provides a compound of formula I, or a pharmaceutically acceptable salt, stereoisomer, solvate, polymorph, tautomer or prodrug thereof, wherein:

R$^0$ and R$^1$ are independently selected from the group consisting of alkyl, cycloalkyl, heterocyclyl, aryl and heteroaryl, wherein the alkyl, cycloalkyl, heterocyclyl, aryl and heteroaryl are each optionally substituted with one or more groups selected from the group consisting of halogen, —OH, alkyl, halogenated alkyl and alkoxy, and the carbon atoms on the ring of the cycloalkyl, the heterocyclyl, and the carbon atoms on the ring of the cycloalkyl or the heteroaryl are optionally oxidized.

In another embodiment, the present invention provides a compound of formula I, or a pharmaceutically acceptable salt, stereoisomer, solvate, polymorph, tautomer or prodrug thereof, wherein:

R$^0$ and R$^1$ are independently selected from the group consisting of alkyl, cycloalkyl, aryl and heteroaryl, wherein the alkyl, cycloalkyl, aryl and heteroaryl are each optionally substituted with one or more groups selected from the group consisting of halogen, —OH, alkyl and alkoxy, and the carbon atoms on the ring of the cycloalkyl or the heteroaryl are optionally oxidized.

In another embodiment, the present invention provides a compound of formula I, or a pharmaceutically acceptable salt, stereoisomer, solvate, polymorph, tautomer or prodrug thereof, wherein:

one of R$^0$ and R$^1$ is alkyl, and the other of R$^0$ and R$^1$ is selected from the group consisting of cycloalkyl, aryl and heteroaryl, each optionally substituted with one or more groups independently selected from the group consisting of halogen, —OH, —NH$_2$, —SH, alkyl, alkoxy, and halogen-substituted alkyl, wherein the carbon atoms on the ring of the cycloalkyl or the heteroaryl are optionally oxidized.

In one embodiment, the present invention provides a compound of formula I, or a pharmaceutically acceptable salt, stereoisomer, solvate, polymorph, tautomer or prodrug thereof, wherein:

one of R$^0$ and R$^1$ is alkyl or halogen-substituted alkyl, and the other of R$^0$ and R$^1$ is selected from the group consisting of:

a) 5-membered heteroaryl comprising at least one heteroatom selected from the group consisting of nitrogen, sulfur and oxygen, optionally substituted with one or more groups independently selected from the group consisting of halogen, —OH, alkyl, alkoxy, and halogen-substituted alkyl; preferably thiophenyl optionally substituted with one or more halogen;

b) 6-membered heteroaryl comprising one or two heteroatoms selected from the group consisting of nitrogen, sulfur and oxygen, optionally substituted with one or more groups independently selected from the group consisting of halogen, —OH, alkyl, alkoxy, and halogen-substituted alkyl, wherein the carbon atoms on the ring of the heteroaryl are optionally oxidized; preferably pyridinyl optionally substituted with one or more —OH;

c) 5- or 6-membered cycloalkyl optionally substituted with one or more groups independently selected from the group consisting of halogen, —OH, alkyl, alkoxy, and halogen-substituted alkyl, wherein the carbon atoms on the ring of the cycloalkyl are optionally oxidized; preferably cyclohexanonyl or cyclohexyl optionally substituted with one or more —OH; and d) phenyl optionally substituted with one or more groups independently selected from the group consisting of halogen, —OH, alkyl and alkoxy.

In one embodiment, the present invention provides a compound of formula I, or a pharmaceutically acceptable salt, stereoisomer, solvate, polymorph, tautomer or prodrug thereof, wherein:

one of R$^0$ and R$^1$ is selected from the group consisting of hydrogen, halogen and alkyl, wherein the alkyl is optionally substituted with one or more groups independently selected from the group consisting of halogen, —OH, —NH$_2$, alkoxy; or is alkyl optionally substituted with one or more halogen; and the other of R$^0$ and R$^1$ is represented by the following Formula II:

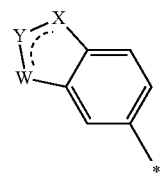

Formula II wherein the dashed line in Formula II indicates that the 5-membered ring formed by X, Y and W together with the carbon atoms to which they attach is saturated or unsaturated, wherein:

X, Y and W are each independently selected from the group consisting of C, N, O and S; and said 5-membered ring is optionally substituted with one or more groups independently selected from the group consisting of halogen, —OH, —SH, alkyl, cycloalkyl, alkoxy and alkylsulfanyl, wherein the alkyl, cycloalkyl, alkoxy and alkylsulfanyl are each optionally substituted with one or more groups independently selected from the group consisting of halogen, —OH, —NH$_2$, monoalkylamino, dialkylamino and heterocyclyl.

In another embodiment, the present invention provides a compound of formula I, or a pharmaceutically acceptable salt, stereoisomer, solvate, polymorph, tautomer or prodrug thereof, wherein:

at least one of X, Y and W is a heteroatom selected from the group consisting of N, O and S; and said 5-membered ring is optionally substituted with one or more groups independently selected from the group consisting of halogen and alkyl;

In another embodiment, the present invention provides a compound of formula I, or a pharmaceutically acceptable salt, stereoisomer, solvate, polymorph, tautomer or prodrug thereof, wherein:

Formula II is selected from:

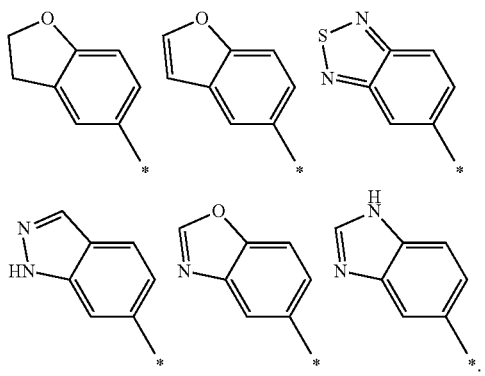

In one embodiment, the present invention provides a compound of formula I, or a pharmaceutically acceptable salt, stereoisomer, solvate, polymorph, tautomer or prodrug thereof, wherein:
ring A and ring B are each independently selected from aryl and heteroaryl, wherein the carbon atoms on the ring of the heteroaryl are optionally oxidized.

In another embodiment, the present invention provides a compound of formula I, or a pharmaceutically acceptable salt, stereoisomer, solvate, polymorph, tautomer or prodrug thereof, wherein:
ring A and ring B are each independently selected from aryl and a 6-membered heteroaryl comprising 1 or 2 nitrogen atoms, wherein the carbon atoms on the ring of the heteroaryl are optionally oxidized.

In another embodiment, the present invention provides a compound of formula I, or a pharmaceutically acceptable salt, stereoisomer, solvate, polymorph, tautomer or prodrug thereof, wherein:
ring A and ring B are each independently selected from phenyl and pyridinyl.

In one embodiment, the present invention provides a compound of formula I, or a pharmaceutically acceptable salt, stereoisomer, solvate, polymorph, tautomer or prodrug thereof, wherein:
$R^2$ and $R^3$ are independently selected from the group consisting of halogen, —OH, —$NH_2$, —CN, alkyl, alkenyl, alkynyl, alkoxy, alkylsulfanyl, heterocyclyloxy, monoalkylamino and dialkylamino, wherein the alkyl, alkenyl, alkynyl, alkoxy, alkylsulfanyl, heterocyclyloxy, monoalkylamino and dialkylamino are each optionally substituted with halogen, —OH, heterocyclyl or —$NR_4R_5$, wherein $R_4$ and $R_5$ are each independently hydrogen, alkyl or cycloalkyl, or $R_4$ and $R_5$, together with the nitrogen atom to which they attach, form a heterocyclyl which is optionally substituted with alkyl.

In another embodiment, the present invention provides a compound of formula I, or a pharmaceutically acceptable salt, stereoisomer, solvate, polymorph, tautomer or prodrug thereof, wherein:
$R^2$ and $R^3$ are independently selected from the group consisting of halogen, —OH, —$NH_2$, —CN, alkyl, alkenyl, alkynyl, alkoxy, alkylsulfanyl, heterocyclyloxy, monoalkylamino and dialkylamino, wherein the alkyl, alkenyl, alkynyl, alkoxy, alkylsulfanyl, heterocyclyloxy, monoalkylamino and dialkylamino are each optionally substituted with heterocyclyl or —$NR_4R_5$, wherein $R_4$ and $R_5$ are each independently hydrogen or alkyl, or $R_4$ and $R_5$, together with the nitrogen atom to which they attach, form a heterocyclyl which is optionally substituted with alkyl.

In one embodiment, the present invention provides a compound of formula I, or a pharmaceutically acceptable salt, stereoisomer, solvate, polymorph, tautomer or prodrug thereof, wherein:
ring A is selected from phenyl and a 6-membered heteroaryl, and $R^2$ is at least at para-position of the phenyl or the 6-membered heteroaryl;
or
ring B is selected from phenyl and a 6-membered heteroaryl, and $R^3$ is at least at para-position of the phenyl or the 6-membered heteroaryl.

In one embodiment, the present invention provides a compound of formula I, or a pharmaceutically acceptable salt, stereoisomer, solvate, polymorph, tautomer or prodrug thereof, wherein:
m and n are each independently 1 or 2.

In one embodiment, the present invention provides a compound of formula I, or a pharmaceutically acceptable salt, stereoisomer, solvate, polymorph, tautomer or prodrug thereof, wherein the compound is selected from the group consisting of:

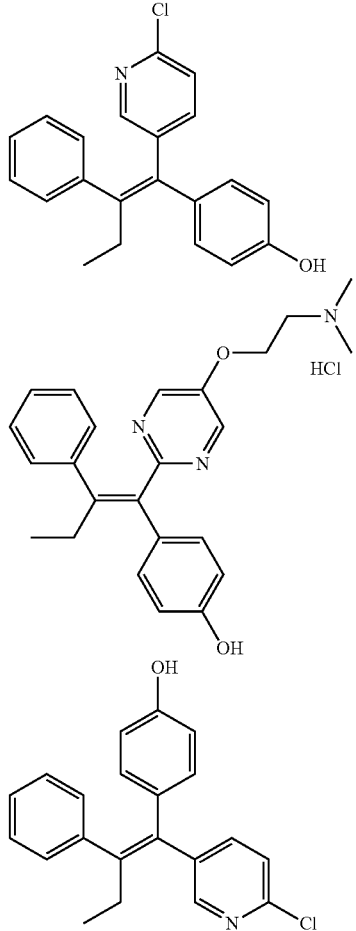

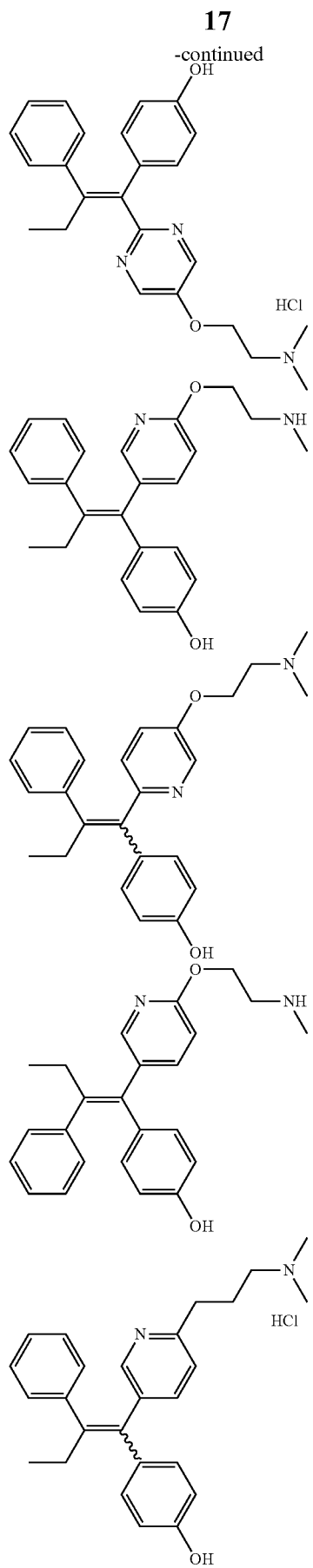
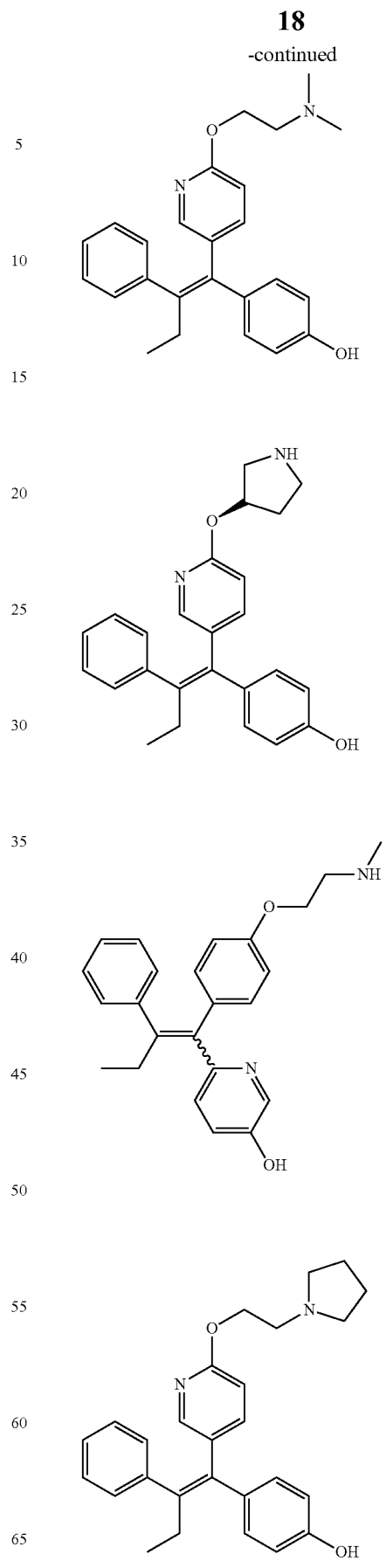

19
-continued
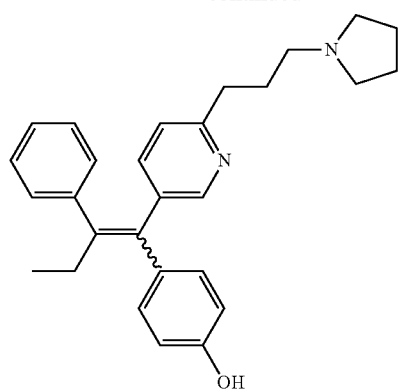
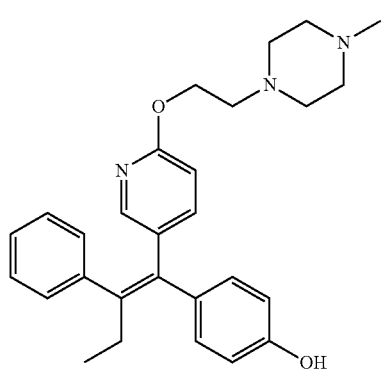
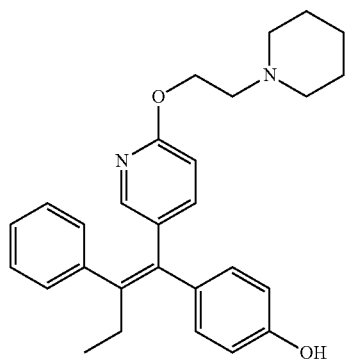
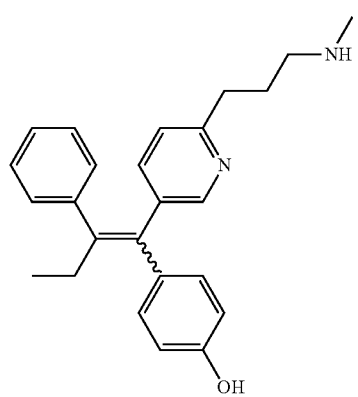
20
-continued
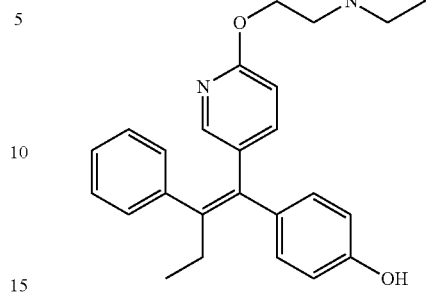
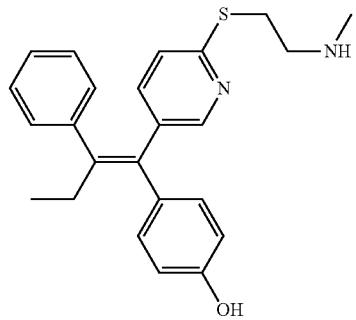
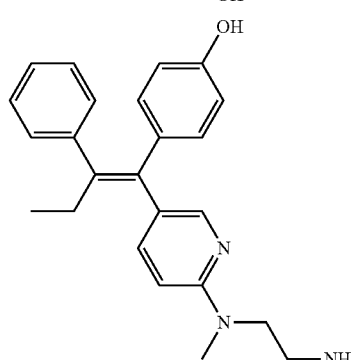
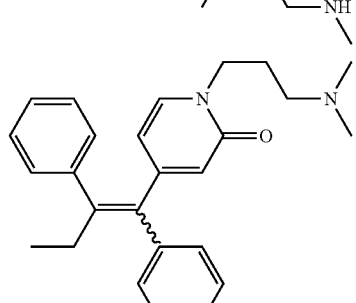
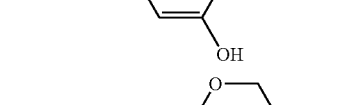
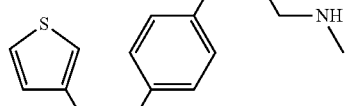
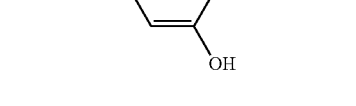

21
-continued
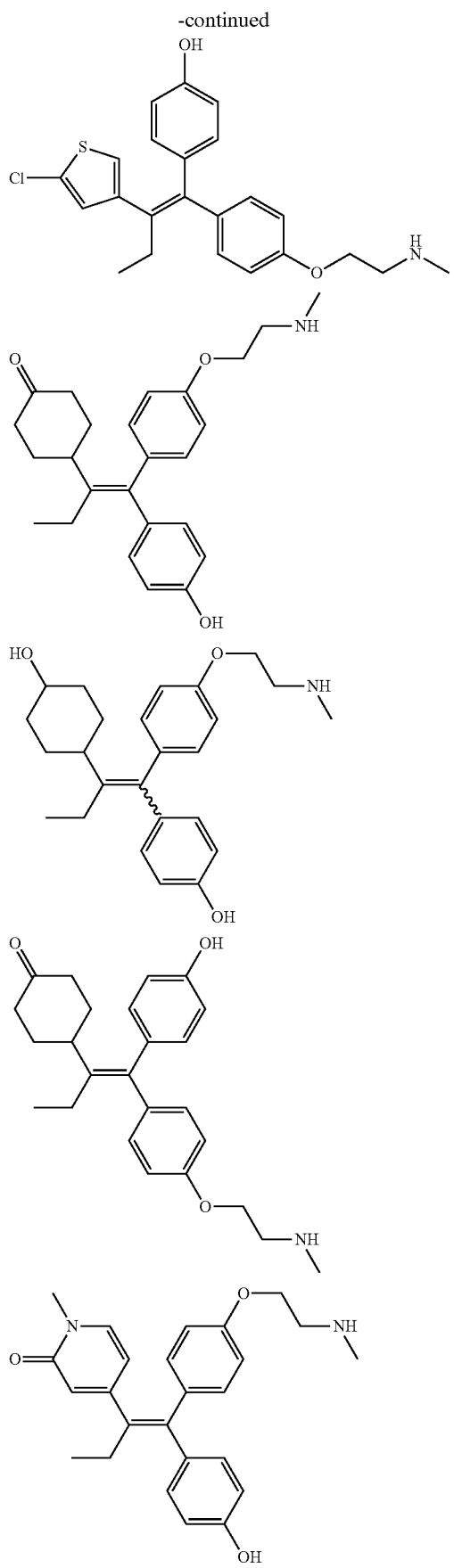
22
-continued
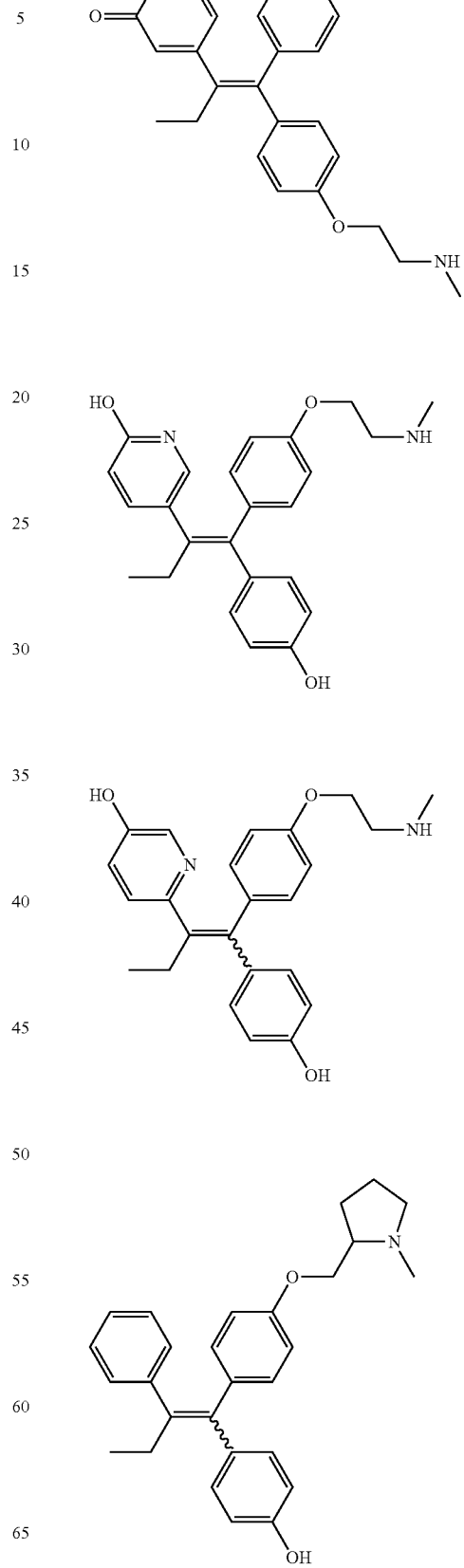

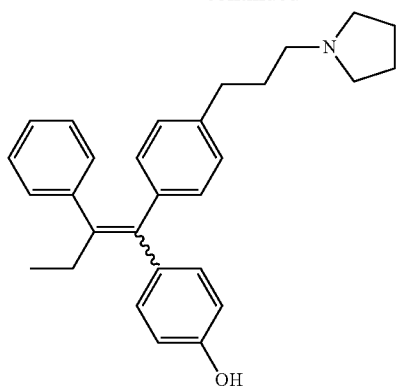
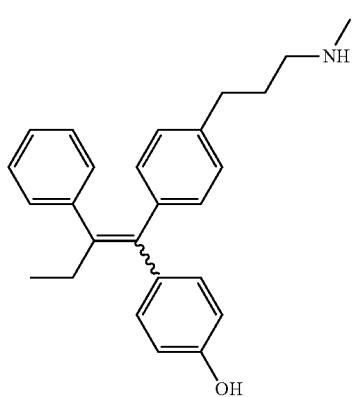
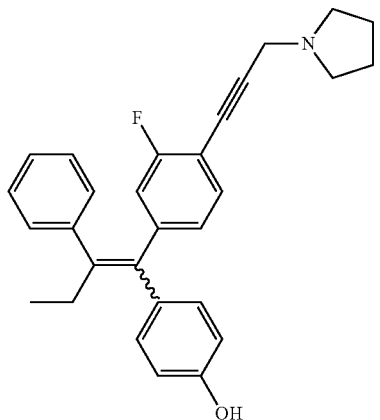
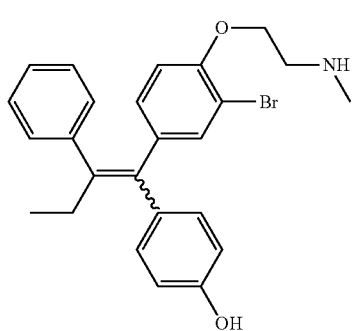
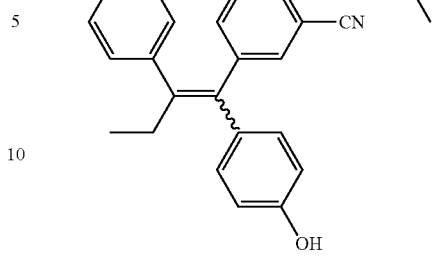
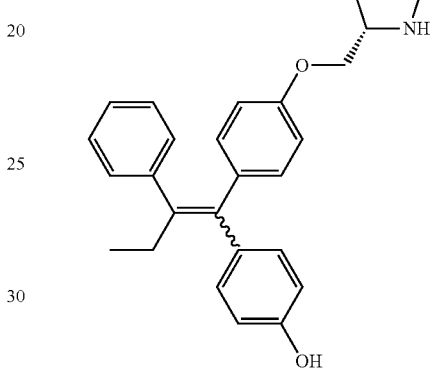
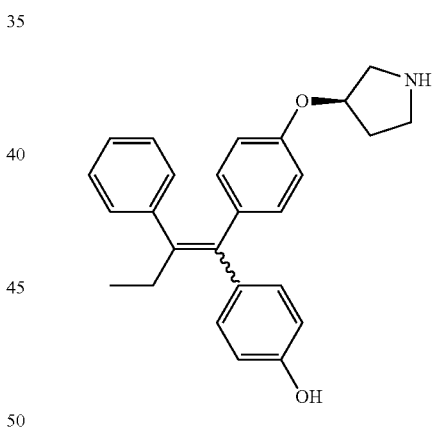
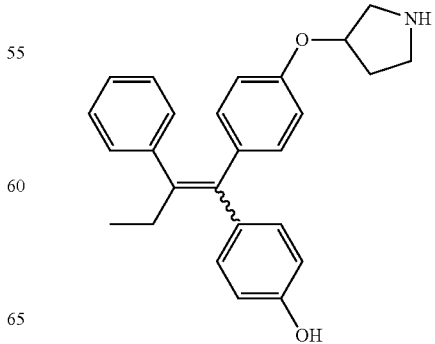

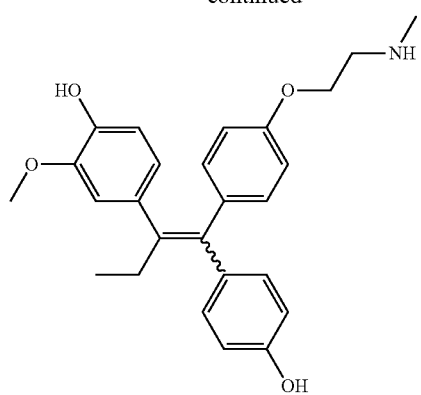
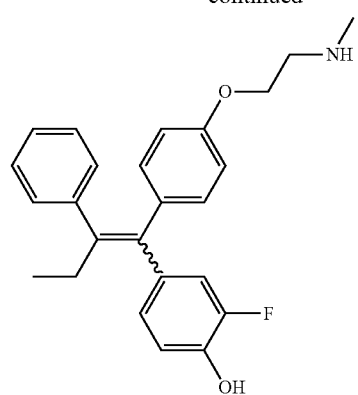
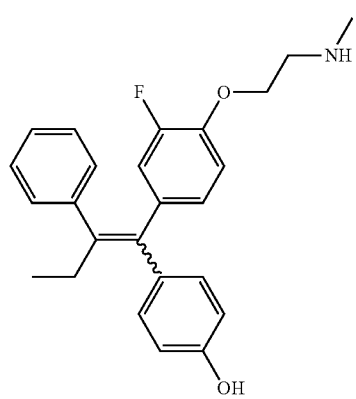
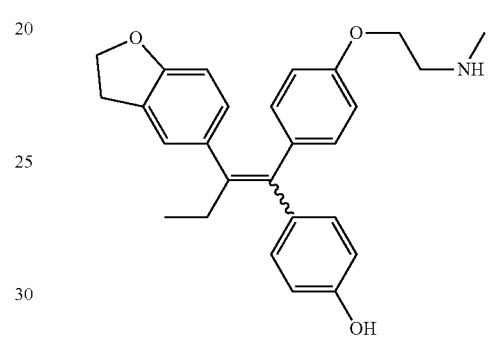
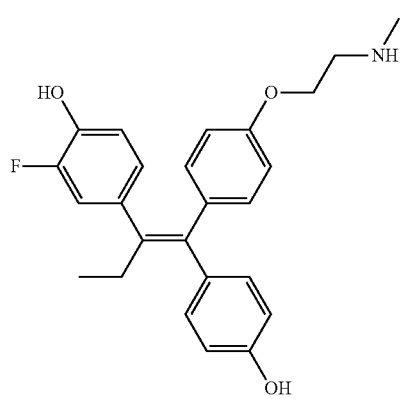
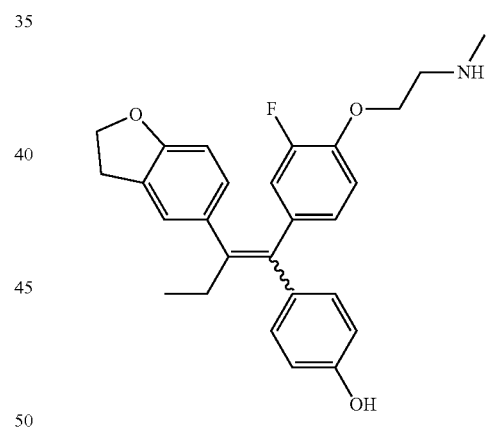
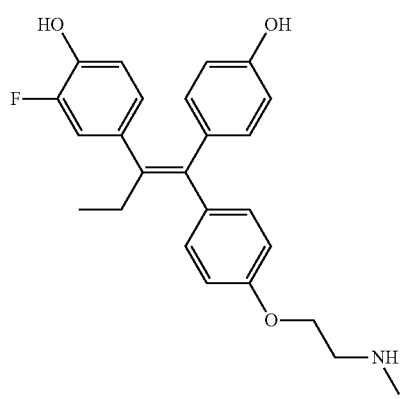
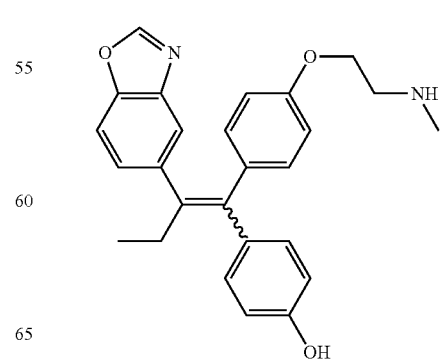

27
-continued
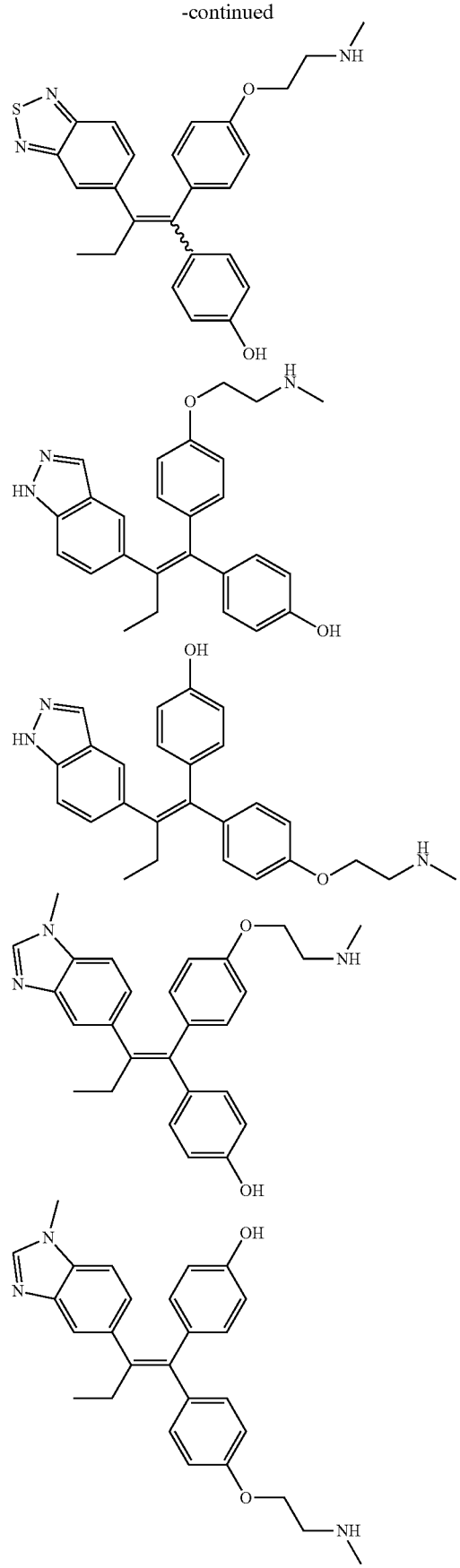
28
-continued
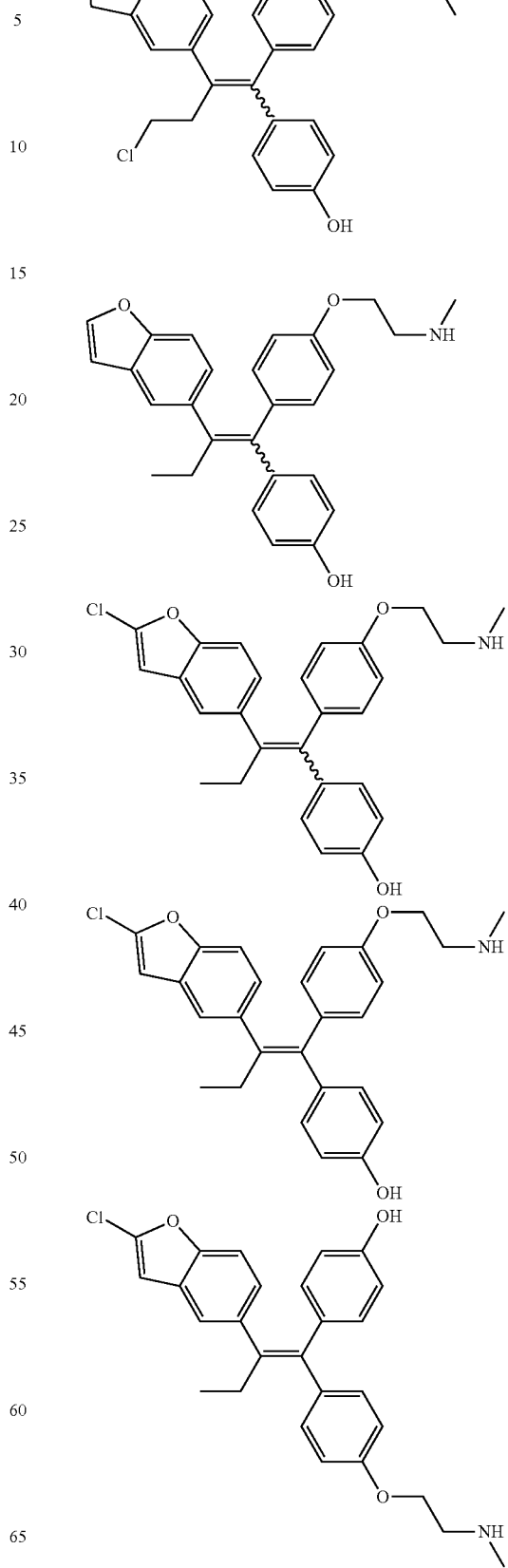

-continued
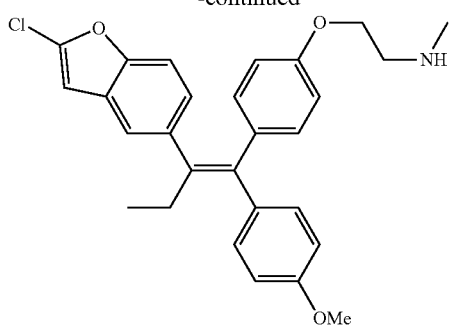
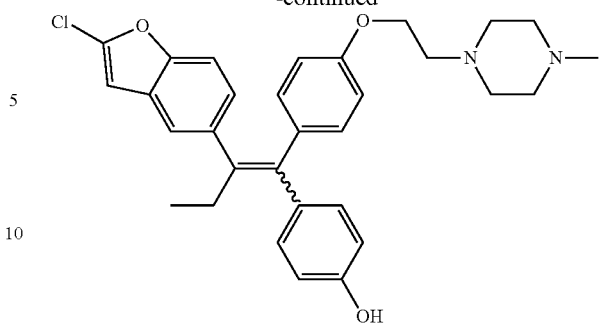
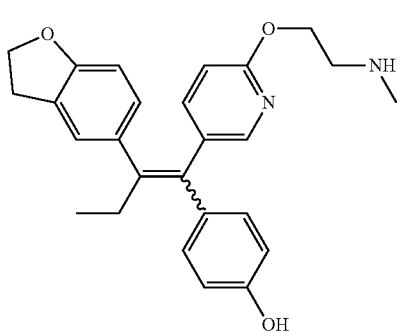
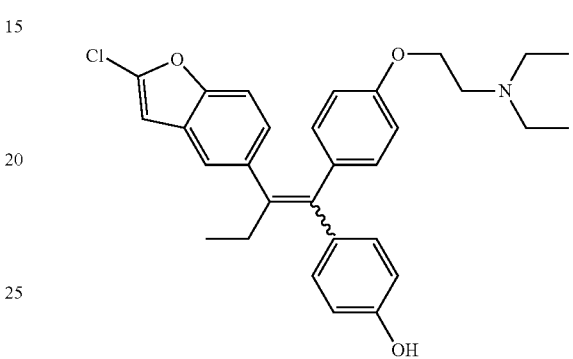
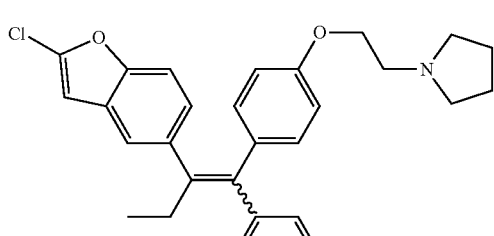
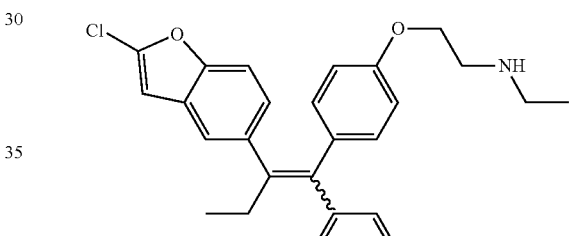
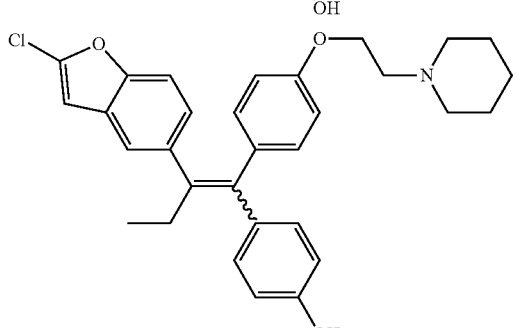
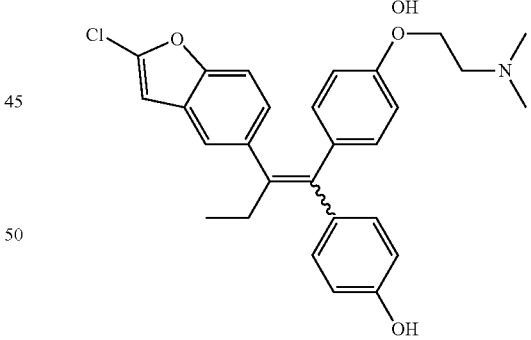
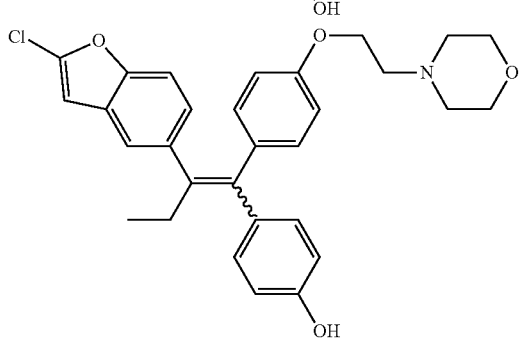
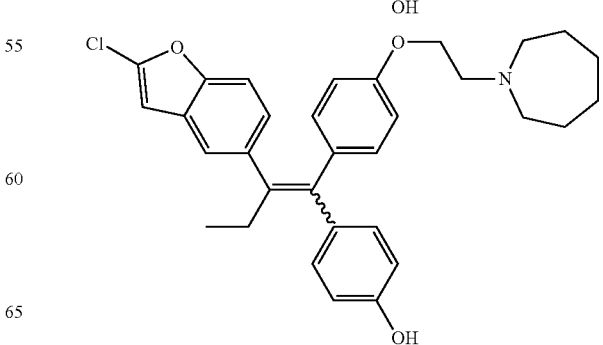

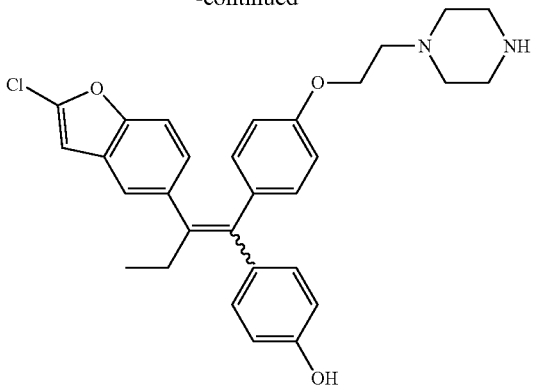
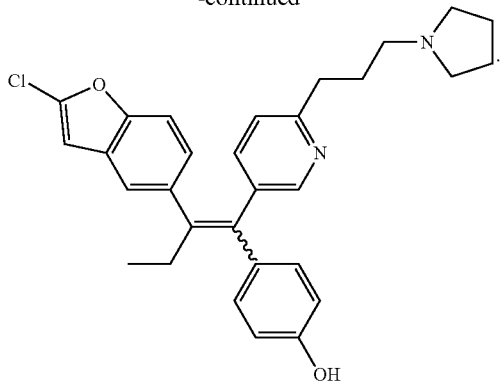
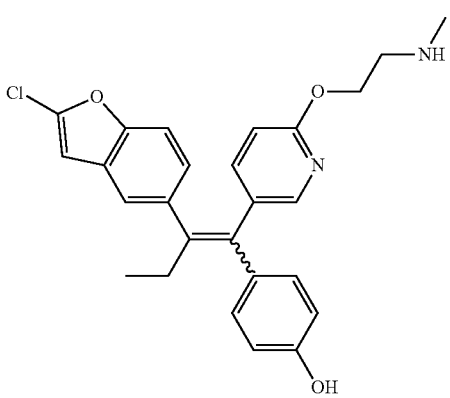
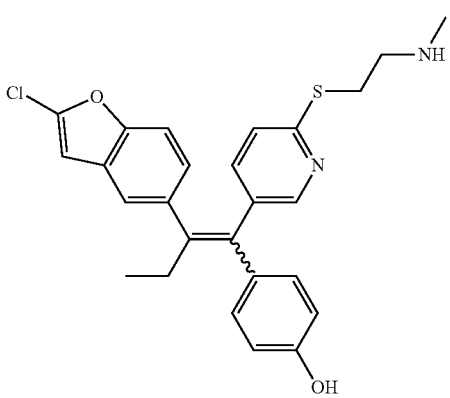
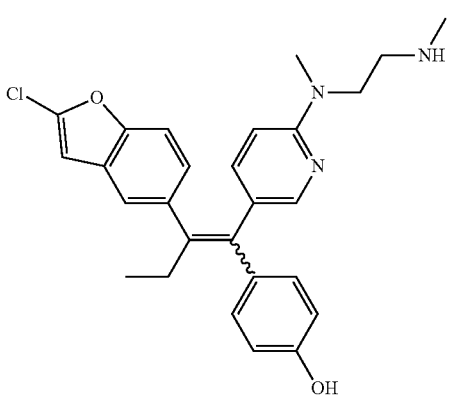

In another aspect, the present invention provides a compound of formula I, or a pharmaceutically acceptable salt, stereoisomer, solvate, polymorph, tautomer or prodrug thereof, for modulating estrogen activities.

In another aspect, the present invention provides use of a compound of formula I, or a pharmaceutically acceptable salt, stereoisomer, solvate, polymorph, tautomer or prodrug thereof, in the manufacture of a medicament for modulating estrogen activities.

In another aspect, the present invention provides a compound of formula I, or a pharmaceutically acceptable salt, stereoisomer, solvate, polymorph, tautomer or prodrug thereof, for preventing and/or treating estrogen-dependent diseases and conditions.

In another aspect, the present invention provides use of a compound of formula I, or a pharmaceutically acceptable salt, stereoisomer, solvate, polymorph, tautomer or prodrug thereof, in the manufacture of a medicament for preventing and/or treating estrogen-dependent diseases and conditions.

In another aspect, the present invention provides a pharmaceutical composition which comprises a compound of formula I, or a pharmaceutically acceptable salt, stereoisomer, solvate, polymorph, tautomer or prodrug thereof, as well as a pharmaceutically acceptable carrier.

Normally, a compound of the invention, or a pharmaceutically acceptable salt thereof, may be administered by formulating it into an appropriate pharmaceutical composition with one or more pharmaceutically acceptable carrier can. The pharmaceutical composition of the invention may be formulated into preparations in solid, semi-solid, liquid or gaseous forms, such as tablets, capsules, powders, granules, ointments, solutions, suppositories, injections, inhalants, gels, microspheres, and aerosols.

The pharmaceutical composition of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Actual methods of preparing such dosage forms are known, or will be apparent, to those skilled in this art; for example, see *The Science and Practice of Pharmacy*, 20th Edition (Philadelphia College of Pharmacy and Science, 2000).

Typical routes of administering such pharmaceutical compositions include, without limitation, oral, topical, transdermal, inhalation, parenteral, sublingual, rectal, vaginal, and intranasal. For example, dosage forms suitable for oral administration include capsules, tablets, granules, and syrups. The compound of the present invention included in these dosage forms may be solid powders or granules; solutions or suspensions in aqueous or non-aqueous liquids; emulsions of oil-in-water type of water-in-oil type; and the like. The above mentioned dosage forms may be prepared from active compounds and one or more carriers or auxiliaries through common pharmacological methods. The carriers shall be compatible with the active compounds or the other auxiliaries. For solid formulation, commonly used non-toxic carriers include, but are not limited to, mannitol, lactose, starch, magnesium stearate, cellulose, glucose, sucrose, and the like. Carriers for liquid formulations include, but are not limited to, water, physiological saline, aqueous solution of glucose, ethylene glycol, polyethylene glycol, and the like. The active compound may form a solution or a suspension with the above carriers. The specific route of administration and dosage form depend on the physical/chemical properties of the compound per se and the severity of the disease to be treated, and can be routinely determined by a person skilled in the art.

In another aspect, the present invention provides a method for modulating estrogen activities in mammals, especially in humans, which method comprises administering to a mammal, especially a human, in need thereof a therapeutically effective amount of a compound of formula I, or a pharmaceutically acceptable salt, stereoisomer, solvate, polymorph, tautomer or prodrug thereof.

In one embodiment of the present invention, estrogen receptor is up-regulated by a compound of formula I, or a pharmaceutically acceptable salt, stereoisomer, solvate, polymorph, tautomer or prodrug thereof in bone tissue, cardiovascular system and central nervous system, and down-regulated by a compound of formula I, or a pharmaceutically acceptable salt, stereoisomer, solvate, polymorph, tautomer or prodrug thereof in tissues like breast and uterus.

In another aspect, the present invention provides a method for preventing and/or treating estrogen-dependent diseases and conditions in mammals, especially in humans, which method comprises administering to a mammal, especially a human, in need thereof a therapeutically effective amount of a compound of formula I, or a pharmaceutically acceptable salt, stereoisomer, solvate, polymorph, tautomer or prodrug thereof.

As used herein, estrogen-dependent diseases and conditions refer to diseases and conditions in which the regulation of estrogen receptor is involved. In one embodiment of the present invention, estrogen-dependent diseases and conditions are selected from the group consisting of menopausal or postmenopausal disorders, vasomotor symptoms, urogenital or vulvar vaginal atrophy, atrophic vaginitis, endometriosis, female sexual dysfunction, cancers (e.g. uterine cancer, breast cancer, etc.), depressive symptoms, diabetes, bone demineralization, and osteoporosis.

The compound of the invention, or a pharmaceutically acceptable salt, stereoisomer, solvate, polymorph, tautomer or prodrug thereof, is administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Generally, a therapeutically effective daily dose is from about 0.001 mg/Kg body weight to about 100 mg/Kg body weight; preferably a therapeutically effective dose is from about 0.01 mg/Kg body weight to about 50 mg/Kg body weight; more preferably a therapeutically effective dose is from about 1 mg/Kg body weight to about 25 mg/Kg body weight. In particular, the parenteral dose of the compound of the present invention may be from about 1 mg/Kg body weight to about 100 mg/Kg body weight; the oral dose may be from about 1 mg/Kg body weight to about 500 mg/Kg body weight.

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., The Merck Manual, 16$^{th}$ edition, Merck and Co., Rahway, N.J., 1992).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any mammals. The preferred recipients are mammals of the Orders Primate (including humans, apes and monkeys), Arteriodactyla (including horses, goats, cows, sheep, pigs), Rodenta (including mice, rats, rabbits, and hamsters), and Camivora (including cats, and dogs). The most preferred recipients are humans.

Preparation of the Compound of the Invention

The following Reaction Schemes illustrate methods to make compounds of this invention.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxyl, amino, mercapto and carboxylic acid. Suitable protecting groups for hydroxyl include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R' (where R' is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (2006), 4th Ed., Wiley. The protecting group may also be a polymer resin.

The compound of formula I of the present invention may be prepared following the procedures illustrated in Scheme 1.

Scheme 1

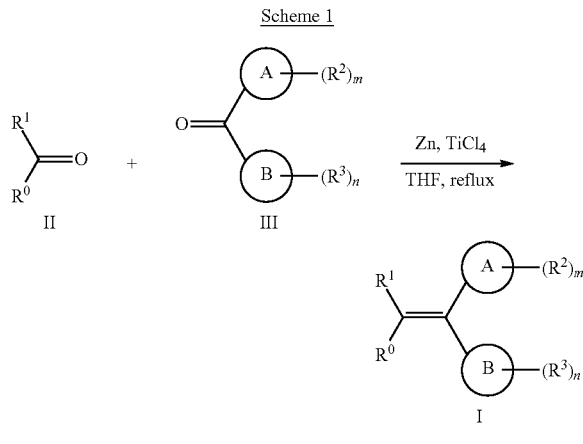

In Scheme 1, McMurry coupling is carried out between compounds II and III to provides the ethylene derivative I. Compounds II and III are either commercially available or may be prepared by synthetic methods appreciated by those skilled in the art.

EXAMPLES

The following experiments, preparation methods and the intermediates involved are provided as an illustration of the present invention, and are not intended as a limitation on the scope of the invention.

Example 1

(Z)-4-(1-(6-chloropyridin-3-yl)-2-phenylbut-1-enyl)phenol

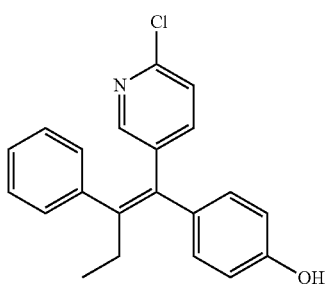 [SMILES: CC/C(=C(\c1ccc(O)cc1)c1ccc(Cl)nc1)c1ccccc1]

Step A: (6-chloropyridin-3-yl)(4-(tetrahydro-2H-pyran-2-yloxy)phenyl)methanone

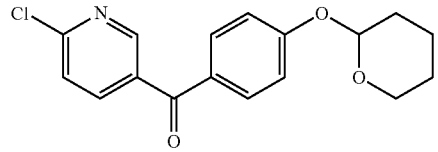 [SMILES: O=C(c1ccc(OC2CCCCO2)cc1)c1ccc(Cl)nc1]

Mg (1.67 g, 1.2 eq) was added to dry THF (50 mL). The mixture was heated to 55° C., then $I_2$ was added in one lot followed by EtBr. 2-(4-Bromophenoxy)tetrahydro-2H-pyran (16 g, 1.1 eq) was dissolved in THF. Part of this solution was added at once to the Mg-THF mixture. After the initiation after about 30 min and reflux started, the remaining above solution was added, and the resulting mixture was refluxed for 2 h to give a MgBr-THF solution, which will be used in the next step.

To a solution of 6-chloronicotinoyl chloride (10.0 g, 1.0 eq) in dry THF at 0° C. under $N_2$, was added dropwise the above MgBr-THF solution over 20 min. The resulting mixture was warmed to rt, and stirred overnight.

Water was added and the resulting mixture was extracted with EtOAc. The extract was dried, concentrated, and purified by column chromatography with petroleum ether:EtOAc=5:1 to give the desired product (13.6 g, 76% yield). $^1$H NMR (400 MHz, CDCl$_3$) δ 8.78 (s, 1H), 8.05 (d, J=8.4 Hz, 1H), 7.78 (d, J=8.0 Hz, 2H), 7.46 (d, J=8.4 Hz, 1H), 7.15 (d, J=8.0 Hz, 2H), 5.56 (t, J=3.2 Hz, 1H), 3.83-3.90 (m, 1H), 3.63-3.67 (m, 1H), 2.02-2.05 (m, 1H), 1.89-1.92 (m, 2H), 1.69-1.75 (m, 2H), 1.59-1.65 (m, 1H).

Step B: (Z)-4-(1-(6-chloropyridin-3-yl)-2-phenylbut-1-enyl)phenol

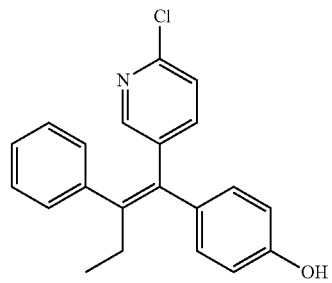 [SMILES: CC/C(=C(\c1ccc(O)cc1)c1ccc(Cl)nc1)c1ccccc1]

To a stirred mixture of Zn powder (8.06 g, 6 eq) in dry THF at rt under $N_2$ was slowly added TiCl$_4$ (6.8 mL, 3 eq). The resulting mixture was heated to 80° C. and refluxed for 1 h. After cooling to rt, a mixture of propiophenone (8.2 g, 3.0 eq) and (6-chloropyridin-3-yl)(4-(tetrahydro-2H-pyran-2-yloxy)phenyl)methanone (6.5 g, 1.0 eq) in dry THF was added. The resulting mixture was refluxed for additional 2 h, then quenched with saturated aq. Na$_2$CO$_3$ solution, extracted with EtOAc. The extract was dried, concentrated, and purified by column chromatography to give a Z/E mixture of the product (6.3 g, 92%, Z/E=1/1). The Z/E mixture was recrystallized in petroleum ether/CH$_2$Cl$_2$ to give the pure Z-isomer (2.8 g, 41% yield). $^1$H NMR (400 MHz, CDCl$_3$) δ 7.85 (s, 1H), 7.06-7.25 (m, 8H), 6.97 (d, J=8.4 Hz, 1H), 6.83 (d, J=8.0 Hz, 2H), 2.51 (q, J=7.6 Hz, 2H), 0.94 (t, J=7.6 Hz, 3H); m/z=336 [M+1]$^+$.

Example 2

(E)-4-(1-(6-chloropyridin-3-yl)-2-phenylbut-1-enyl)phenol

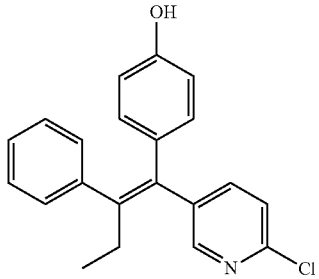 [SMILES: CC/C(=C(/c1ccc(O)cc1)c1ccc(Cl)nc1)c1ccccc1]

The title compound was obtained (3.0 g, E-isomer) via recrystallization from the Z/E mixture (example 1, step B) in MeOH. $^1$H NMR (400 MHz, CDCl$_3$) δ 8.34 (s, 1H), 7.07-7.48 (m, 7H), 6.70 (d, J=8.4 Hz, 2H), 6.50 (d, J=8.0 Hz, 2H), 2.45 (q, J=7.2 Hz, 2H), 0.94 (t, J=7.6 Hz, 3H); m/z=336 [M+1]$^+$.

Example 3

(Z)-4-(1-(6-(2-(methylamino)ethoxy)pyridin-3-yl)-2-phenylbut-1-enyl)phenol

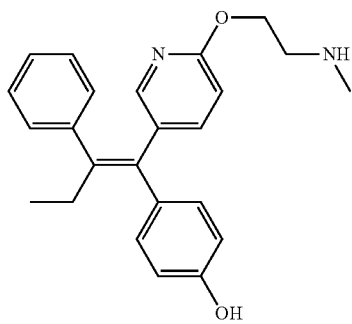 [SMILES: CC/C(=C(\c1ccc(O)cc1)c1ccc(OCCNC)nc1)c1ccccc1]

To a stirred solution of 2-(methylamino)ethanol (672 mg, 10 eq) in 20 mL anhydrous THF was added NaH (373 mg, 8.0 eq) at 0° C. The mixture was stirred at rt for 1 h, then to the mixture was added (Z)-4-(1-(6-chloropyridin-3-yl)-2-phenylbut-1-enyl)phenol (300 mg, 1 eq, made from example 1). The reaction was heated at reflux for 16 h, cooled, quenched with sat. NH$_4$Cl, and extracted with CH$_2$Cl$_2$. The extract was dried, concentrated, and purified by column chromatography to give the desired product (200 mg, 60% yield). $^1$H NMR (400 MHz, CDCl$_3$) δ 7.59 (s, 1H), 7.18-7.20 (m, 2H), 7.08-7.16 (m, 3H), 7.01-7.06 (m, 3H), 6.77 (d, J=8.4 Hz, 1H), 6.28 (d, J=8.4 Hz, 1H), 4.28 (t, J=5.2 Hz, 2H), 2.93 (t, J=5.2 Hz, 2H), 2.46-2.55 (m, 5H), 0.92 (t, J=7.6 Hz, 3H); m/z=375 [M+1]$^+$.

Example 4

(E)-4-(1-(6-(2-(methylamino)ethoxy)pyridin-3-yl)-2-phenylbut-1-enyl)phenol

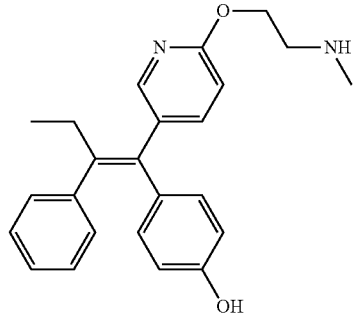 [SMILES: CC/C(=C(/c1ccc(O)cc1)c1ccc(OCCNC)nc1)c1ccccc1]

Following the same procedure as described in example 3, (E)-4-(1-(6-chloropyridin-3-yl)-2-phenylbut-1-enyl)phenol (100 mg, prepared from example 2) were used as starting material to get the desired product (53 mg, 48%). $^1$H NMR (400 MHz, CDCl$_3$) δ 8.09 (s, 1H), 7.31-7.7.34 (m, 1H), 7.09-7.10 (m, 5H), 6.68 (d, J=8.8 Hz, 2H), 6.62 (d, J=8.4 Hz, 1H), 6.47 (d, J=8.4 Hz, 2H), 4.44 (t, J=5.2 Hz, 2H), 3.01 (t, J=5.2 Hz, 2H), 2.46-2.52 (m, 5H), 0.9 (t, J=7.2 Hz, 3H); m/z=375 [M+1]$^+$.

Example 5

(Z)-4-(1-(6-(2-(dimethylamino)ethoxy)pyridin-3-yl)-2-phenylbut-1-enyl)phenol

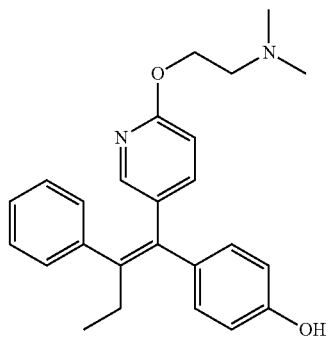 [SMILES: CC/C(=C(\c1ccc(O)cc1)c1ccc(OCCN(C)C)nc1)c1ccccc1]

Following the same procedure as described in example 3, 2-(dimethylamino)ethanol (798 mg, 10 eq) and (Z)-4-(1-(6-chloropyridin-3-yl)-2-phenylbut-1-enyl)phenol (300 mg, 1 eq, prepared from example 1) were reacted to get the desired product (260 mg, 75% yield). $^1$H NMR (400 MHz, CDCl$_3$) δ 7.54 (s, 1H), 7.14-7.20 (m, 2H), 7.01-7.09 (m, 5H), 6.93 (d, J=8.0 Hz, 1H), 6.78 (d, J=8.0 Hz, 2H), 5.84 (d, J=8.8 Hz, 1H), 4.22 (t, J=5.2 Hz, 2H), 2.70 (t, J=5.2 Hz, 2H), 2.50 (q, J=7.2 Hz, 2H), 2.35 (s, 6H), 0.91 (t, J=7.6 Hz, 3H); m/z=389 [M+1]+.

Example 6

(S,Z)-4-(2-phenyl-1-(6-(pyrrolidin-3-yloxy)pyridin-3-yl)but-1-enyl)phenol

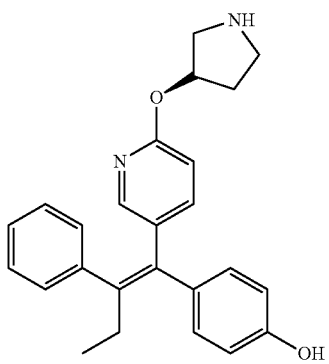

Following the same procedure as described in example 3, (S)-pyrrolidin-3-ol (558 mg, 10 eq) was reacted with (Z)-4-(1-(6-chloropyridin-3-yl)-2-phenylbut-1-enyl)phenol (100 mg, 1 eq, prepared from example 1) to give the desired product (87 mg, 76% yield). $^1$H NMR (400 MHz, DMSO-d$^6$) δ 9.50 (s, 1H), δ 7.54 (s, 1H), 7.20-7.23 (m, 2H), 7.10-7.16 (m, 4H), 7.00(d, J=8.4 Hz, 2H), 6.77 (d, J=8.4 Hz, 2H), 6.49 (d, J=8.4 Hz, 1H), 5.28 (bs, 1H), 3.15-3.32 (m, 2H), 2.94-3.05 (m, 2H), 2.43 (q, J=7.6 Hz, 1H) 1.90-2.10 (m, 1H), 1.79-1.89 (m, 1H), 0.86 (t, J=7.6 Hz, 3H); m/z=387 [M+1]+.

Example 7

(Z)-4-(2-phenyl-1-(6-(2-(pyrrolidin-1-yl)ethoxy)pyridin-3-yl)but-1-enyl)phenol

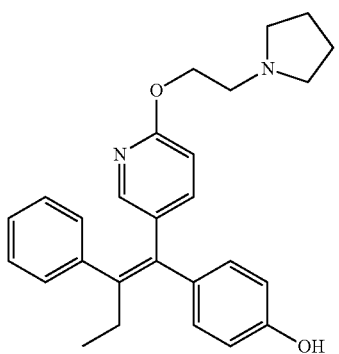 [SMILES: CC/C(=C(\c1ccc(O)cc1)c1ccc(OCCN2CCCC2)nc1)c1ccccc1]

Following the same procedure as described in example 3, 2-(pyrrolidin-1-yl)ethanol (343 mg, 10 eq) and (Z)-4-(1-(6-chloropyridin-3-yl)-2-phenylbut-1-enyl)phenol (100 mg, 1 eq, prepared from example 1) were used as starting material to get the desired product (140 mg, 95%). $^1$H NMR (400 MHz, CDCl$_3$) δ 7.53 (s, 1H), 7.15-7.20 (m, 2H), 7.01-7.13 (m, 6H), 6.92 (d, J=8.0 Hz, 1H), 6.76 (d, J=8.4 Hz, 2H), 5.68 (brs, 1H), 4.26 (bs, 2H), 2.91 (brs, 2H), 2.72 (brs, 4H), 2.50 (q, J=7.2 Hz, 2H), 1.89 (brs, 4H), 0.91 (t, J=7.6 Hz, 3H); m/z=415 [M+1]+.

Example 8

(Z)-4-(1-(6-(2-(4-methylpiperazin-1-yl)ethoxy)pyridin-3-yl)-2-phenyl but-1-enyl)phenol

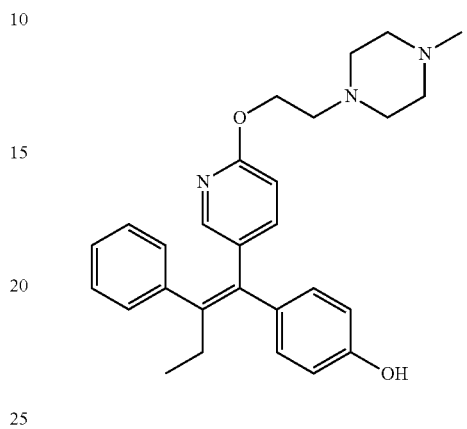

Following the same procedure as described in example 3, 2-(4-methylpiperazin-1-yl)ethanol (430 mg, 10 eq) was reacted with (Z)-4-(1-(6-chloropyridin-3-yl)-2-phenylbut-1-enyl)phenol (100 mg, 1 eq, prepared from example 1) to give the desired product (160 mg, 95% yield). $^1$H NMR (400 MHz, CDCl$_3$) δ 7.57 (s, 1H), 7.17-7.22 (m, 2H), 7.00-7.15 (m, 5H), 6.97 (d, J=8.0 Hz, 1H), 6.76 (d, J=8.8 Hz, 2H), 6.03 (d, J=8.8 Hz, 1H), 4.27 (t, J=5.6 Hz, 2H), 2.75 (t, J=5.6 Hz, 2H), 2.48-2.57 (m, 12H), 2.32 (s, 3H), 0.92 (t, J=7.6 Hz, 3H); m/z=444 [M+1]+.

Example 9

(Z)-4-(2-phenyl-1-(6-(2-(piperidin-1-yl)ethoxy)pyridin-3-yl)but-1-enyl)phenol

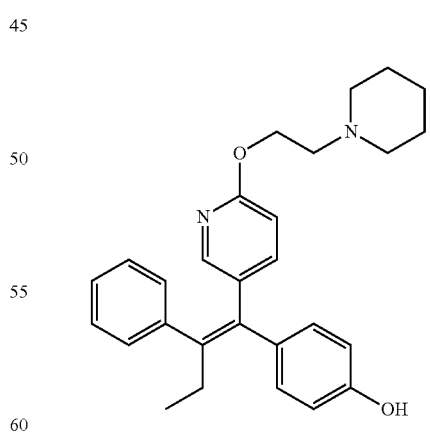

Following the same procedure as described in example 3, 2-(piperidin-1-yl)ethanol (385 mg, 10 eq) was reacted with (Z)-4-(1-(6-chloropyridin-3-yl)-2-phenyl but-1-enyl)phenol (100 mg, 1 eq, prepared from example 1) to give the desired product (106 mg, 83% yield). $^1$H NMR (400 MHz, CDCl$_3$) δ

7.53 (s, 1H), 7.16-7.21 (m, 2H), 7.01-7.15 (m, 6H), 6.88 (d, J=8.8 Hz, 1H), 6.77 (d, J=8.8 Hz, 2H), 5.63 (d, J=8.0 Hz, 1H), 4.25 (t, J=5.6 Hz, 2H), 2.73 (t, J=5.6 Hz, 2H), 2.40-2.62 (m, 6H), 1.63-1.75 (m, 4H), 1.44-1.56 (m, 2H), 0.92 (t, J=7.2 Hz, 3H); m/z=429 [M+1]⁺.

Example 10

(Z)-4-(1-(6-(2-morpholinoethoxy)pyridin-3-yl)-2-phenylbut-1-enyl)phenol

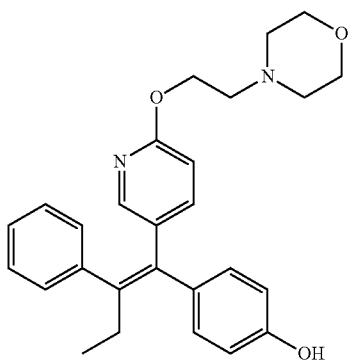 [SMILES: CC/C(=C(\c1ccc(O)cc1)c1ccc(OCCN2CCOCC2)nc1)c1ccccc1]

Following the same procedure as described in example 3, 2-morpholinoethanol (391 mg, 10 eq) was reacted with (Z)-4-(1-(6-chloropyridin-3-yl)-2-phenylbut-1-enyl)phenol (100 mg, 1 eq, prepared from example 1) to give the desired product (110 mg, 86% yield). ¹H NMR (400 MHz, CDCl₃) δ 7.59 (s, 1H), 7.01-7.18 (m, 8H), 6.79 (d, J=8.8 Hz, 2H), 6.27 (d, J=8.4 Hz, 1H), 4.29 (t, J=5.6 Hz, 2H), 2.70 (t, J=5.6 Hz, 2H), 2.46-2.52 (m, 6H), 1.29-1.40 (m, 4H), 0.92 (t, J=7.6 Hz, 3H); m/z=431[M+1]⁺.

Example 11

4-(1-(4-(2-(Methylamino)ethoxy)phenyl)-2-(thiophen-3-yl)but-1-enyl)phenol

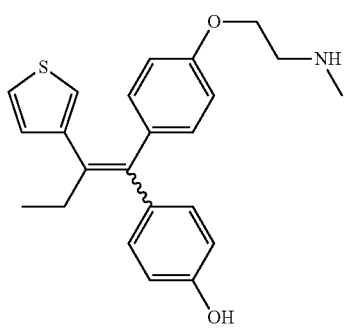 [SMILES: CCC(=C(c1ccc(O)cc1)c1ccc(OCCNC)cc1)c1ccsc1]

Step A:
N-methoxy-N-methylthiophene-3-carboxamide

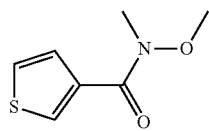

To a stirred solution of thiophene-3-carboxylic acid (20 g, 1.0 eq) in CH₂Cl₂ at 0° C. was added SOCl₂ (59 mL, 5.2 eq). After gas evolution became less vigorous, the reaction mixture was refluxed for 3 h at 50° C. The mixture was then concentrated and the residue was used directly in the next step without further purification.

N,O-dimethylhydroxylamine hydrochloride (16.8 g, 1.1 eq) was added to a solution of the above residue in CH₂Cl₂ at 0° C., then to the resulting solution was added dropwise Et₃N (44 mL, 2.0 eq). The mixture was stirred at rt for 3 h, washed with water, and extracted by CH₂Cl₂. The extract was dried, concentrated, and purified by column chromatography with petroleum ether:EtOAc=5:1 to give the desired product as a yellow solid (17.2 g, 64% yield). ¹H NMR (400 MHz, CDCl₃) δ 8.07 (s, 1H), 7.57 (d, J=8.8 Hz, 1H), 7.28 (d, J=8.4 Hz, 1H), 3.65 (s, 3H), 3.36 (s, 3H).

Step B: 1-(thiophen-3-yl)propan-1-one

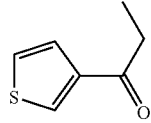

EtMgBr (3 M, 1.2 eq, 18.6 mL) was added to a solution of N-methoxy-N-methylthiophene-3-carboxamide (8 g, 1.0 eq) in dry THF. Once the addition was complete, the mixture was stirred at rt overnight. The reaction mixture was washed with saturated NH₄Cl (aq), dried, concentrated, and purified by column chromatography with petroleum ether:EtOAc=5:1 to give the desired product as a yellow oil (3.4 g, 52% yield). ¹H NMR (400 MHz, CDCl₃) δ 8.05 (s, 1H), 7.56 (d, J=8.0 Hz, 1H), 7.31 (d, J=8.4 Hz, 1H), 2.92 (q, J=7.6 Hz, 2H), 1.21 (t, J=7.6 Hz, 3H).

Step C: 4-(1-(4-(2-chloroethoxy)phenyl)-2-(thiophen-3-yl)but-1-enyl)phenol

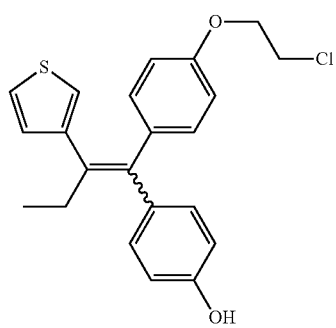 [SMILES: CCC(=C(c1ccc(O)cc1)c1ccc(OCCCl)cc1)c1ccsc1]

Following general procedure of McMurry reaction as described in example 1, step B, 1-(thiophen-3-yl)propan-1-one (0.5 g, 1.0 eq) was reacted with (4-(2-chloroethoxy)phenyl)(4-hydroxyphenyl)methanone (1.5 g, 1.5 eq) to give 1.3 g desired product (95% yield, Z/E=1/1). ¹H NMR (400 MHz, CDCl₃) δ 7.10-7.14 (m, 1H), 7.02-7.09 (m, 2H), 6.76-6.92 (m, 5H), 6.68-6.71 (m, 1H), 6.60-6.66 (m, 1H), 6.55-6.59 (m, 1H), 4.62 (s, 1H), 4.49 (s, 1H), 4.24 (t, J=6.0 Hz, 1H), 4.14 (t, J=6.0 Hz, 1H), 3.82 (t, J=6.0 Hz, 1H), 3.76 (t, J=6.0 Hz, 1H), 2.43-2.49 (m, 2H), 0.98 (t, J=7.6 Hz, 3H).

Step D: 4-(1-(4-(2-(methylamino)ethoxy)phenyl)-2-(thiophen-3-yl)but-1-enyl)phenol

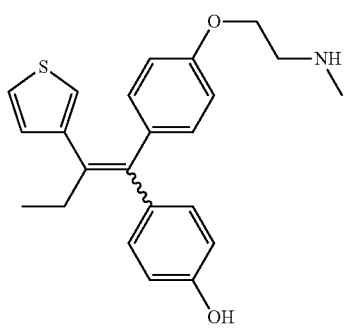 [SMILES: CCC(=C(c1ccc(O)cc1)c1ccc(OCCNC)cc1)c1ccsc1]

To a stirred solution of 4-(1-(4-(2-chloroethoxy)phenyl)-2-(thiophen-3-yl)but-1-enyl)phenol (0.3 g, 1.0 eq) in 10 mL MeOH was added 10 mL MeNH₂ (30% in water). The mixture was refluxed at 80° C. overnight, and purified by column chromatography with CH₂Cl₂:MeOH(NH₃)=10:1 to give the desired product (185 mg, 63% yield, Z/E=1/1). ¹H NMR (400 MHz, CDCl₃) δ 7.00-7.12 (m, 3H), 6.90-6.95 (m, 1H), 6.80-6.89 (m, 2H), 6.72-6.79 (m, 2H), 6.68-6.72 (m, 1H), 6.58 (d, J=8.8 Hz, 1H), 6.53 (d, J=8.8 Hz, 1H), 4.09 (t, J=5.2 Hz, 1H), 3.99 (t, J=5.2 Hz, 1H), 3.00 (t, J=5.2 Hz, 1H), 2.94 (t, J=5.2 Hz, 1H), 2.40-2.54 (m, 5H), 0.98 (t, J=5.2 Hz, 3H); m/z=380 [M+1]⁺.

Example 12

(E)-4-(2-(5-chlorothiophen-3-yl)-1-(4-(2-(methylamino)ethoxy)phenyl)but-1-enyl)phenol

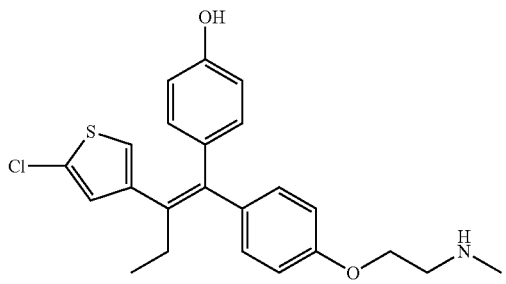 [SMILES: CC/C(=C(/c1ccc(O)cc1)c1ccc(OCCNC)cc1)c1csc(Cl)c1]

Step A:
5-chloro-N-methoxy-N-methylthiophene-3-carboxamide

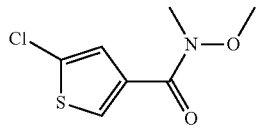

To a stirred solution of N-methoxy-N-methylthiophene-3-carboxamide (5.0 g, 1.0 eq, prepared from Example 12 step A) in 50 mL CH₃COOH was added N-chlorosuccinimide (3.88 g, 1.0 eq). The mixture was then reflux at 120° C. for 4 h. After quenching with water, the mixture was extracted with ethyl acetate. The extract was washed with brine, dried, concentrated, and purified by column chromatography to get 3.0 g desired product (40% yield).

Step B: 1-(5-chlorothiophen-3-yl)propan-1-one

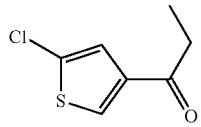

Following the same procedure as described in example 11, step B, the title compound was obtained.

Step C: (E)-4-(1-(4-(2-chloroethoxy)phenyl)-2-(5-chlorothiophen-3-yl)-but-1-enyl)phenol

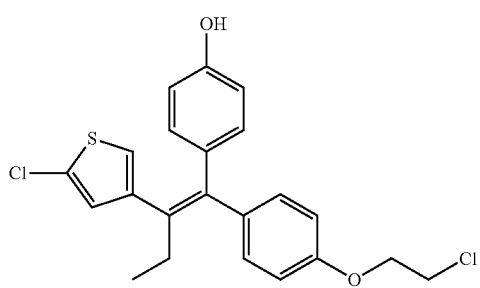 [SMILES: CC/C(=C(/c1ccc(O)cc1)c1ccc(OCCCl)cc1)c1csc(Cl)c1]

Following general procedure of McMurry reaction as described in example 1, step B, 1-(5-chlorothiophen-3-yl)propan-1-one (1.5 g, 1.0 eq) was reacted with (4-(2-chloroethoxy)phenyl)(4-hydroxyphenyl)methanone (2.0 g, 1.2 eq) to give 0.8 g desired product (45% yield, E).

Step D: (E)-4-(2-(5-chlorothiophen-3-yl)-1-(4-(2-(methylamino)ethoxy)-phenyl)but-1-enyl)phenol

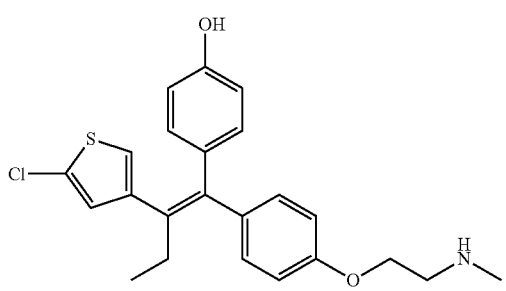 [SMILES: CC/C(=C(/c1ccc(O)cc1)c1ccc(OCCNC)cc1)c1csc(Cl)c1]

Following the same procedure as described in example 11, step D, (E)-4-(1-(4-(2-chloroethoxy)phenyl)-2-(5-chlorothiophen-3-yl)but-1-enyl)phenol (0.8 g, 1.0 eq) was reacted with MeNH$_2$ (30% wt in water, 10 mL) in MeOH (20 mL) at reflux to give 120 mg desired product (35% yield, E). $^1$H NMR (400 MHz, DMSO-d$^6$) δ 9.30 (bs, 1H), 6.99-7.02 (m, 3H), 6.84-6.89 (m, 2H), 6.62-6.70 (m, 2H), 6.50-6.56 (m, 3H), 3.97 (t, J=5.6 Hz, 2H), 2.78 (t, J=5.6 Hz, 2H), 2.26-2.38 (m, 5H), 0.89 (t, J=7.2 Hz, 3H); m/z=414[M+1]$^+$.

Example 13

4-(2-(4-Hydroxycyclohexyl)-1-(4-(2-(methylamino)ethoxy)phenyl)but-1-enyl)phenol

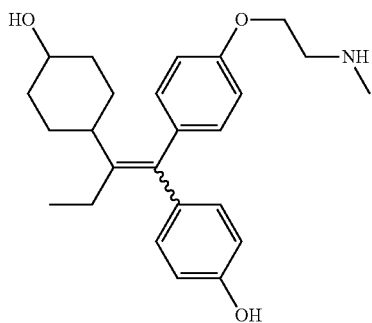 [SMILES: CCC(=C(c1ccc(O)cc1)c1ccc(OCCNC)cc1)C1CCC(O)CC1]

Step A: 1-(4-hydroxycyclohexyl)propan-1-one

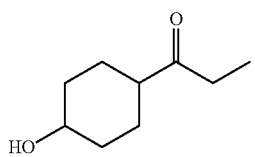

EtMgBr (1 M, 3.0 eq, 20 mL) was added to a solution of 4-hydroxy-N-methoxy-N-methylcyclohexanecarboxamide (1.0 g, 1.0 eq) in dry THF at 0° C. Once addition was complete, the mixture was stirred overnight. The reaction mixture was washed with saturated NH$_4$Cl (aq), and extracted by EtOAc. The extract was dried, concentrated, and purified by column chromatography with petroleum ether:EtOAc=1:1 to give the desired product (0.6 g, 72% yield). $^1$H NMR (400 MHz, CDCl$_3$) δ 3.50-3.64 (m, 1H), 2.47 (q, J=7.2 Hz, 2H), 2.28-2.37 (m, 1H), 2.00-2.10 (m, 2H), 1.88-1.94 (m, 2H), 1.70-1.80 (m, 1H), 1.21-1.49 (m, 4H), 1.05 (t, J=7.2 Hz, 3H).

Step B: 4-(1-(4-(2-chloroethoxy)phenyl)-2-(4-hydroxycyclohexyl)but-1-enyl)phenol

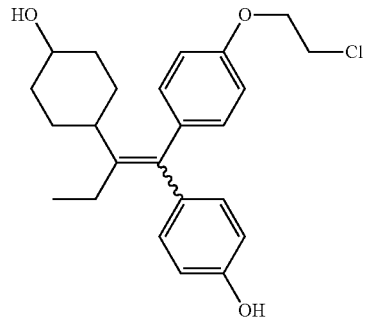 [SMILES: CCC(=C(c1ccc(O)cc1)c1ccc(OCCCl)cc1)C1CCC(O)CC1]

Following general procedure of McMurry reaction as described in example 1, step B, 1-(4-hydroxycyclohexyl)propan-1-one (0.6 g, 1.0 eq) was reacted with (4-(2-chloroethoxy)phenyl)(4-hydroxyphenyl)methanone (1.6 g, 1.5 eq) to give 0.8 g desired product (52% yield, Z/E=1/1). $^1$H NMR (400 MHz, CDCl$_3$) δ 7.11-7.20 (m, 1H), 7.00-7.10 (m, 2H), 6.90-6.70 (m, 1H), 6.60-6.89 (m, 3H), 6.58 (d, J=7.6 Hz, 1H), 4.08-4.20 (m, 2H), 3.70-3.80 (m, 2H), 3.60 (brs, 1H), 2.47 (q, J=7.6 Hz, 2H), 2.28-2.38 (m, 1H), 2.00-2.08 (m, 2H), 1.86-1.94 (m, 2H), 1.72-1.80 (m, 1H), 1.20-1.49 (m, 4H), 1.04 (t, J=7.6 Hz, 3H)

Step C: 4-(2-(4-hydroxycyclohexyl)-1-(4-(2-(methylamino)ethoxy)-phenyl)but-1-enyl)phenol

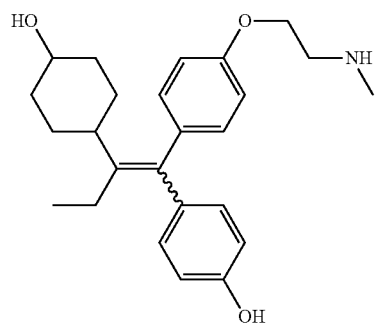 [SMILES: CCC(=C(c1ccc(O)cc1)c1ccc(OCCNC)cc1)C1CCC(O)CC1]

Following the same procedure as described in example 11, step D, 4-(1-(4-(2-chloroethoxy)phenyl)-2-(4-hydroxycyclohexyl)but-1-enyl)phenol (0.8 g, 1.0 eq) was reacted with MeNH$_2$ (30% wt in water, 10 mL) in MeOH (20 mL) at reflux to give 20 mg desired product (3% yield, Z/E=1/1). $^1$H NMR (400 MHz, CDCl$_3$) δ 7.03 (d, J=8.4 Hz, 2H), 6.94 (d, J=8.4 Hz, 2H), 6.78 (d, J=8.4 Hz, 2H), 6.71 (d, J=8.4 Hz, 2H), 4.04 (t, J=4.8 Hz, 2H), 2.96 (t, J=4.8 Hz, 2H), 2.50 (s, 3H), 2.36-

2.47 (m, 1H), 2.04 (q, J=7.6 Hz, 2H), 1.90-2.01 (m, 2H), 1.40-1.80 (m, 6H), 0.87 (t, J=7.6 Hz, 3H); m/z=396[M+1]$^+$.

Example 14

4-(1-(3-Bromo-4-(2-(methylamino)ethoxy)phenyl)-2-phenylbut-1-en yl)phenol

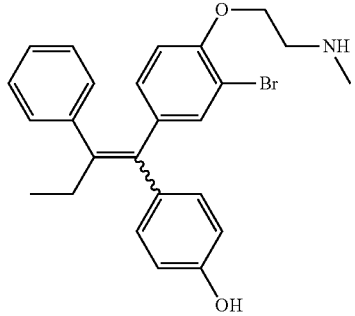

Step A: methyl 3-bromo-4-(2-bromoethoxy)benzoate

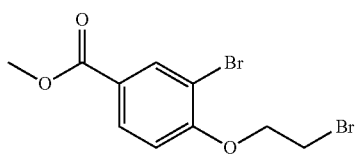

To a stirred solution of methyl 3-bromo-4-hydroxybenzoate (5.0 g, 1.0 eq) in 20 mL DMF were added BrCH$_2$CH$_2$Br (11 mL, 6.0 eq) and K$_2$CO$_3$ (6.0 g, 2.0 eq). The mixture was heated to 60° C. for 6 h and purified by column chromatography with petroleum ether:EtOAc=3:1 to give the desired product (6.0 g, 80% yield). $^1$H NMR (400 MHz, CDCl$_3$) δ 8.24 (s, 1H), 7.96 (d, J=8.8 Hz, 1H), 6.90 (d, J=8.8 Hz, 1H), 4.40 (t, J=6.8 Hz, 2H), 3.90 (s, 3H), 3.71 (t, J=6.4 Hz, 2H)

Step B: 3-bromo-4-(2-bromoethoxy)benzoic acid

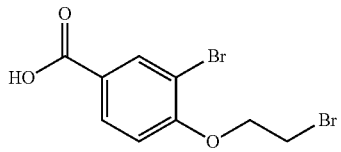 [SMILES: O=C(O)c1ccc(OCCBr)c(Br)c1]

To a stirred solution of methyl 3-bromo-4-(2-bromoethoxy)benzoate (4.0 g, 1.0 eq) in MeOH/H$_2$O (v/v 2:1, 60 mL) was added NaOH (0.715 g, 1.5 eq). The mixture was then refluxed for 25 min, and concentrated under reduced pressure. The residue was poured into water and washed with EtOAc. To the aqueous layer was added 3 N HCl to give the desired product as a white solid (3.4 g, 87% yield). $^1$H NMR (400 MHz, DMSO-d$^6$) δ 8.07 (s, 1H), 7.92 (d, J=8.4 Hz, 1H), 7.23 (d, J=8.4 Hz, 1H), 4.50 (t, J=5.6 Hz, 2H), 3.85 (t, J=5.6 Hz, 2H)

Step C: (3-bromo-4-(2-bromoethoxy)phenyl)(4-methoxyphenyl)methanone

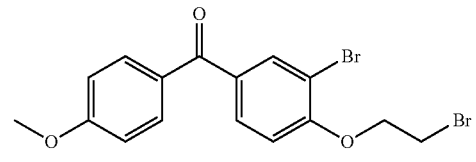 [SMILES: COc1ccc(C(=O)c2ccc(OCCBr)c(Br)c2)cc1]

To a stirred solution of 3-bromo-4-(2-bromoethoxy)benzoic acid (2.0 g, 1.0 eq) in 20 mL CH$_2$Cl$_2$, was added SOCl$_2$ (5.0 eq, 2.2 mL). The mixture was refluxed for 3 h, then evaporated to give the benzoyl chloride without further purification.

To a stirred solution of benzoyl chloride, AlCl$_3$ (1.65 g, 2.0 eq) in 50 mL CH$_2$Cl$_2$ was added anisole (1.34 g, 2.0 eq). The mixture was then stirred at rt overnight and purified by column chromatography with petroleum ether:EtOAc=3:1 to give the desired product (1.47 g, 57%). $^1$H NMR (400 MHz, DMSO-d$^6$) δ 8.03 (s, 1H), 7.71-7.84 (m, 3H), 6.91-7.04 (m, 3H), 4.43 (t, J=6.4 Hz, 2H), 3.90 (s, 3H), 3.74 (t, J=6.4 Hz, 2H)

Step D: (3-bromo-4-(2-bromoethoxy)phenyl)(4-hydroxyphenyl)-methanone

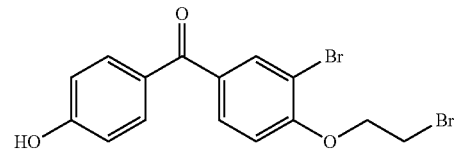 [SMILES: O=C(c1ccc(O)cc1)c1ccc(OCCBr)c(Br)c1]

To a stirred solution of (3-bromo-4-(2-bromoethoxy)phenyl)(4-methoxyphenyl)methanone (0.6 g, 1.0 e q) in 50 mL CH$_2$Cl$_2$ was added BBr$_3$ (3.0 eq, 0.4 mL) dropwise. After addition, the mixture was stirred at rt overnight, concentrated, and purified by column chromatography with petroleum ether:EtOAc=2:1 to give the desired product (0.36 g, 62% yield). $^1$H NMR (400 MHz, CDCl$_3$) δ 8.03 (s, 1H), 7.70-7.79 (m, 3H), 6.90-7.00 (m, 3H), 4.43 (t, J=6.4 Hz, 2H), 3.72 (t, J=6.0 Hz, 2H).

Step E: 4-(1-(3-bromo-4-(2-bromoethoxy)phenyl)-2-phenylbut-1-enyl)phenol

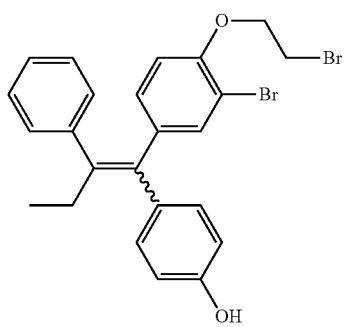 [SMILES: CCC(=C(c1ccc(O)cc1)c1ccc(OCCBr)c(Br)c1)c1ccccc1]

Following general procedure of McMurry reaction as described in example 1, step B, propiophenone (0.2 g, 3.0 eq) was reacted with (3-bromo-4-(2-bromoethoxy) phenyl)(4-hydroxyphenyl)methanone (0.2 g, 1.0 eq) to give 0.09 g desired product (36% yield, Z/E=1/1). $^1$H NMR (400 MHz, CDCl$_3$) δ 7.42 (s, 1H), 7.01-7.0 (m, 7H), 6.87 (d, J=8.4 Hz, 1H), 6.82 (d, J=8.4 Hz, 1H), 6.71 (d, J=8.4 Hz, 1H), 6.48 (d, J=8.4 Hz, 1H), 4.36 (t, J=6.8 Hz, 1H), 4.19 (t, J=6.4 Hz, 1H), 3.70 (t, J=6.4 Hz, 1H), 3.59 (t, J=6.8 Hz, 1H), 2.46 (q, J=6.4 Hz, 2H), 0.92 (t, J=6.0 Hz, 3H)

Step F: 4-(1-(3-bromo-4-(2-(methylamino)ethoxy) phenyl)-2-phenylbut-1-enyl)phenol

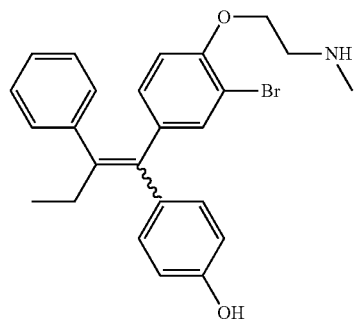 [SMILES: CCC(=C(c1ccc(O)cc1)c1ccc(OCCNC)c(Br)c1)c1ccccc1]

Following the same procedure as described in example 11, step D, 4-(1-(3-bromo-4-(2-bromoethoxy)phenyl)-2-phenylbut-1-enyl)phenol (0.09 g, 1.0 eq) was reacted with MeNH$_2$ (30% wt in water, 10 mL) in MeOH (20 mL) under reflux to give 73 mg desired product (90% yield, Z/E=1/1). $^1$H NMR (400 MHz, CDCl$_3$) δ 7.40 (s, 1H), 6.98-7.20 (m, 7H), 6.87 (d, J=8.4 Hz, 1H), 6.78 (d, J=8.4 Hz, 1H), 6.68 (d, J=8.8 Hz, 1H), 6.45 (d, J=8.4 Hz, 1H), 4.17 (t, J=5.2 Hz, 1H), 4.01 (t, J=4.8 Hz, 1H), 3.06 (t, J=4.8 Hz, 1H), 2.96 (t, J=5.2 Hz, 1H), 2.40-2.60 (m, 5H), 0.88 (t, J=5.2 Hz, 3H); m/z=452 [M+1]$^+$.

Example 15

5-(1-(4-Hydroxyphenyl)-2-phenylbut-1-enyl)-2-(2-(methylamino)ethoxy)benzonitrile

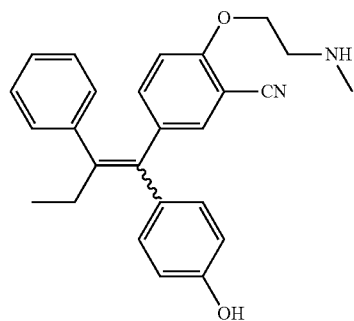 [SMILES: CCC(=C(c1ccc(O)cc1)c1ccc(OCCNC)c(C#N)c1)c1ccccc1]

To a stirred solution of 4-(1-(3-bromo-4-(2-(methylamino) ethoxy)phenyl)-2-phenylbut-1-enyl)phenol (150 mg, 1.0 eq) in 5 mL DMF was added CuCN (36 mg, 1.2 eq) at rt. The mixture was then heated at 120° C. overnight, poured into water, and the resulting mixture was extracted with EtOAc. The extract was washed with water and brine, dried, concentrated, and purified by column chromatography with CH$_2$Cl$_2$: MeOH(NH$_3$)=1:1 to give the desired product (10 mg, 6% yield, Z/E=1/1). $^1$H NMR (400 MHz, CDCl$_3$) δ 7.36 (s, 1H), 6.99-7.21 (m, 7H), 6.90 (d, J=8.8 Hz, 1H), 6.81 (d, J=8.8 Hz, 1H), 6.68 (d, J=8.8 Hz, 1H), 6.49 (d, J=8.8 Hz, 1H), 4.32 (t, J=5.6 Hz, 1H), 4.20 (t, J=5.2 Hz, 1H), 3.46 (t, J=5.6 Hz, 1H), 3.30 (t, J=5.2 Hz, 1H), 3.29 (s, 3H), 2.40-2.50 (m, 2H), 0.90 (t, J=5.6 Hz, 3H); m/z=399 [M+1]$^+$.

Example 16

(S)-4-(2-phenyl-1-(4-(pyrrolidin-2-ylmethoxy)phenyl)but-1-enyl)phenol

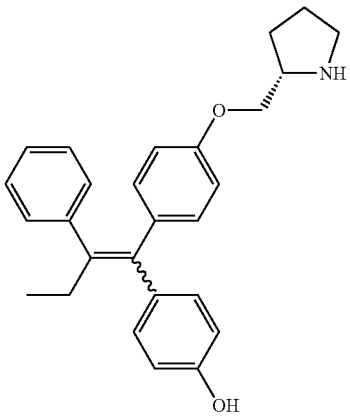 [SMILES: CCC(=C(c1ccc(O)cc1)c1ccc(OC[C@@H]2CCCN2)cc1)c1ccccc1]

Step A: (S)-pyrrolidin-2-ylmethanol

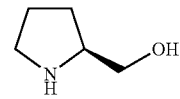

To a stirred solution of (S)-pyrrolidine-2-carboxylic acid (11.5 g, 1.0 eq) in 250 mL anhydrous THF was added LiAlH$_4$ (6 g, 1.6 eq) very slowly at 0° C. The reaction was stirred at 0° C. for 1 h., and then quenched with 6 mL water slowly at 0° C., After 6 mL 10% NaOH (aq) was added, the suspension was filtered and washed with EtOAc. The filtrate was dried and concentrated to give a residue, which was purified by distillation under reduced pressure to give the product (5.75 g, 57% yield). $^1$H NMR (400 MHz, DMSO-d$^6$) δ 3.22 (d, J=1.2 Hz, 2H), 2.95-3.01 (m, 1H), 2.73-2.79 (m, 1H), 2.64-2.70 (m, 1H), 1.53-1.68 (m, 3H), 1.27-1.34 (m, 1H).

Step B: (S)-tert-butyl 2-(hydroxymethyl)pyrrolidine-1-carboxylate

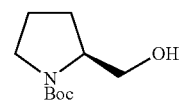

To a stirred solution of (S)-pyrrolidin-2-ylmethanol (3 g, 1 eq) in 100 mL THF, was added (Boc)$_2$O (7.1 g, 1.1 eq) at 0°

C. After a solution of NaHCO$_3$ (5 g, 2.0 eq) in 100 mL water was added, the reaction was stirred overnight at rt. Then added water to the mixture and extracted with EtOAc. The extract was dried, concentrated, and purified by column chromatography to give the desired product (5.7 g, 95% yield). $^1$H NMR (400 MHz, CDCl$_3$) δ 4.68 (brs, 1H), 3.96 (brs, 1H), 3.55-3.66 (m, 2H), 3.43-3.49 (m, 1H), 3.28-3.34 (m, 1H), 1.97-2.05 (m, 1H), 1.76-1.85 (m, 2H), 1.47 (s, 9H).

Step C: 4-(1-(4-hydroxylphenyl)-2-phenylbut-1-enyl)phenol

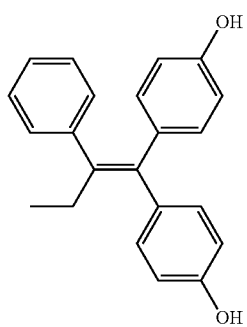 [SMILES: CCC(=C(c1ccc(O)cc1)c1ccc(O)cc1)c1ccccc1]

Following general procedure of McMurry reaction as described in example 1, step B, propiophenone (1.9 g, 3.0 eq) was reacted with bis(4-hydroxyphenyl)-methanone (1.0 g, 1.0 eq) to give 1.3 g desired product (88% yield).

Step D: (S)-tert-butyl 2-((4-(1-(4-hydroxyphenyl)-2-phenylbut-1-enyl)-phenoxy)methyl)pyrrolidine-1-carboxylate

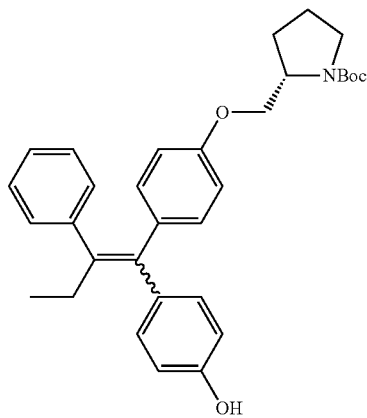 [SMILES: CCC(=C(c1ccc(O)cc1)c1ccc(OC[C@@H]2CCCN2C(=O)OC(C)(C)C)cc1)c1ccccc1]

To a stirred mixture of 4-(1-(4-hydroxylphenyl)-2-phenylbut-1-enyl)phenol (500 mg, 1.0 eq), (S)-tert-butyl 2-(hydroxymethyl)pyrrolidine-1-carboxylate (480 mg, 1.5 eq) and PPh$_3$ (625 mg, 1.5 eq) in 25 mL anhydrous THF under nitrogen was added DIAD (480 mg, 1.5 eq) dropwise at 0° C. The reaction was stirred for 48 h at rt. Then the reaction was quenched with water and extracted with EtOAc. The extract was dried, concentrated and purified by column chromatography to give the desired product (400 mg, 51% yield, Z/E=1/1).

Step E: (S)-4-(2-phenyl-1-(4-(pyrrolidin-2-ylmethoxy)phenyl)but-1-enyl)phenol

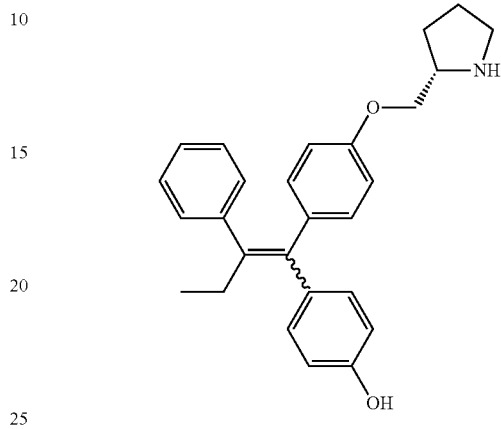

To a stirred solution of tert-butyl 2-((4-(1-(4-hydroxyphenyl)-2-phenylbut-1-enyl)phenoxy)methyl)pyrrolidine-1-carboxylate (400 mg, 1.0 eq) in 20 mL CH$_2$Cl$_2$ was added 1 mL TFA dropwise at 0° C. The reaction was stirred at rt for 3 h, then quenched with sat. NaHCO$_3$, and extracted with CH$_2$Cl$_2$. The extract was dried, concentrated and purified by column chromatography to give the desired product (210 mg, 68% yield, Z/E=1/1). $^1$H NMR (400 MHz, CDCl$_3$) δ 7.07-7.17 (m, 6H), 7.05 (d, J=8.4 Hz, 1H), 6.84 (d, J=8.8 Hz, 1H), 6.77 (d, J=8.8 Hz, 1H), 6.74 (d, J=8.8 Hz, 1H), 6.68 (d, J=8.4 Hz, 1H), 6.49 (d, J=8.8 Hz, 1H), 6.44 (d, J=8.4 Hz, 1H), 3.96-4.00 (m, 0.5H), 3.89-3.93 (m, 0.5H), 3.82-3.85 (m, 0.5H), 3.73-3.77 (m, 0.5H), 3.53-3.59 (m, 0.5H), 3.43-3.49 (m, 0.5H), 2.90-3.11 (m, 2H), 2.44-2.51 (m, 2H), 1.77-1.99 (m, 3H), 1.52-1.66 (m, 1H), 0.92 (t, J=7.2 Hz, 3H); m/z=400 [M+1]$^+$.

Example 17

(R)-4-(2-phenyl-1-(4-(pyrrolidin-3-yloxy)phenyl)but-1-enyl)phenol

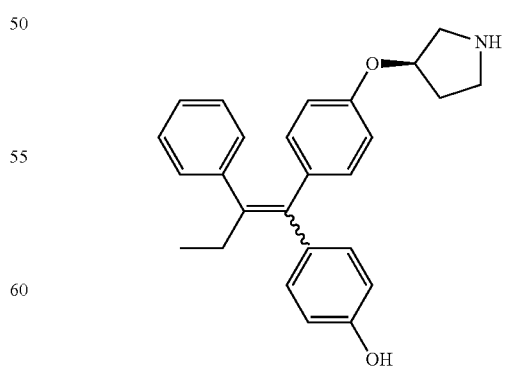

Following the same procedure as described in example 16, step D & E, 4-(1-(4-hydroxylphenyl)-2-phenylbut-1-enyl)phenol (150 mg, 0.474 mmol) was reacted with (S)-tert-butyl 3-hydroxypyrrolidine-1-carboxylate (107 mg, 0.571 mmol), followed by de-Boc in condition of TFA/CH$_2$Cl$_2$, to give the desired product (36 mg, 20% yield, Z/E=1/1). m/z=386[M+1]$^+$.

Example 18

4-(2-Phenyl-1-(4-(pyrrolidin-3-yloxy)phenyl)but-1-enyl)phenol

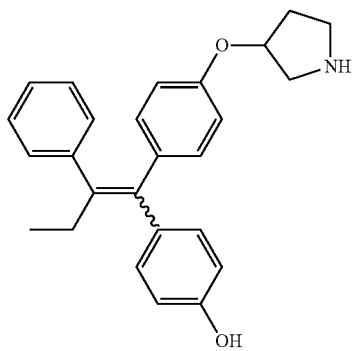 [SMILES: CCC(=C(c1ccc(O)cc1)c1ccc(OC2CCNC2)cc1)c1ccccc1]

Step A: tert-butyl 3-(methylsulfonyloxy)pyrrolidine-1-carboxylate

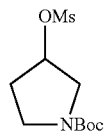

To a stirred solution of tert-butyl 3-hydroxypyrrolidine-1-carboxylate (16 g, 85.4 mmol) and triethylamine (19 mL, 129 mmol) in 130 mL CH$_2$Cl$_2$ was added methanesulfonyl chloride (10 mL, 129 mmol) in 20 mL CH$_2$Cl$_2$ dropwise at 0° C. After addition, the reaction was stirred for 2.5 h at rt, then quenched with sat. NaHCO$_3$ (aq.), and extracted with CH$_2$Cl$_2$. The extract was dried and concentrated to give the desired product (22.7 g, 100% yield) as a yellow solid.

Step B: tert-butyl 3-(4-(4-hydroxybenzoyl)phenoxy)pyrrolidine-1-carboxylate

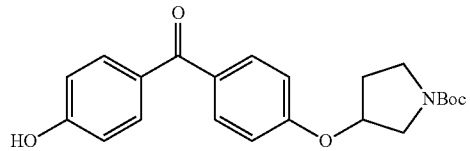 [SMILES: CC(C)(C)OC(=O)N1CCC(Oc2ccc(C(=O)c3ccc(O)cc3)cc2)C1]

A mixture of tert-butyl 3-(methylsulfonyloxy)pyrrolidine-1-carboxylate (0.6 g, 2.26 mmol), bis(4-hydroxyphenyl) methanone (2.15 g, 10.0 mmol) and K$_2$CO$_3$ (313 mg, 2.26 mmol) in 12 mL DMF was heated at 100° C. for 3.5 h, then quenched with water, and extracted with EtOAc. The extract was washed with water, dried, and concentrated to give a residue, to which was added CH$_2$Cl$_2$ and the white suspension thus formed removed and filtration. The filtrate was concentrated in vacuo and the residue was purified by column chromatography (petroleum ether/CH$_2$Cl$_2$/acetone=4/2/1) to give the desired product (400 mg, 46% yield).

Step C: 4-(2-phenyl-1-(4-(pyrrolidin-3-yloxy)phenyl)but-1-enyl)phenol

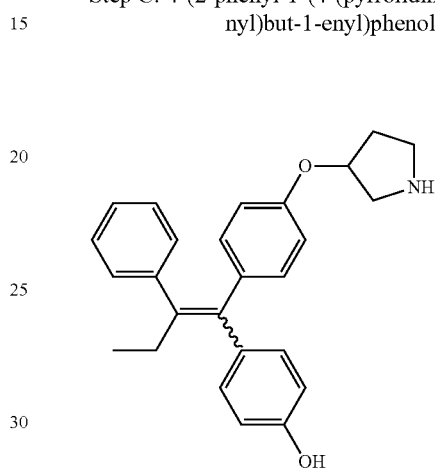

Following general procedure of McMurry reaction as described in example 1, step B, tert-butyl 3-(4-(4-hydroxybenzoyl)phenoxy)pyrrolidine-1-carboxylate (395 mg, 1.03 mmol) was reacted with propiophenone (276 mg, 2.06 mmol) to give 340 mg desired product (86% yield, Z/E=1/1) as a light yellow solid. m/z=386[M+1]$^+$.

Example 19

4-(1-(4-Hydroxyphenyl)-1-(4-(2-(methylamino)ethoxy)phenyl)but-1-en-2-yl)-2-methoxyphenol

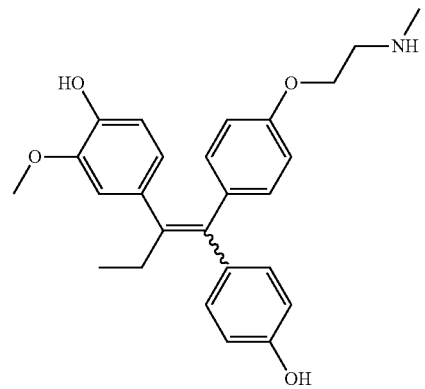

Step A: 2-methoxyphenyl propionate

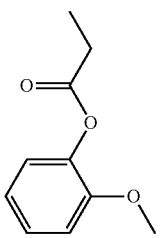

To a stirred solution of 2-methoxyphenol (4.4 g, 35.4 mmol) and triethylamine (6.2 mL, 42.3 mmol) in 20 mL CH$_2$Cl$_2$, was added propionyl chloride (3.3 g, 35.7 mmol) dropwise at 0° C. After addition, the reaction was stirred for 5 h at rt, then quenched with sat. NaHCO$_3$ (aq.), and extracted with CH$_2$Cl$_2$. The extract was dried and evaporated in vacuo to give the desired product (6.0 g, 94% yield) as a yellow solid.

Step B:
1-(4-hydroxy-3-methoxyphenyl)propan-1-one

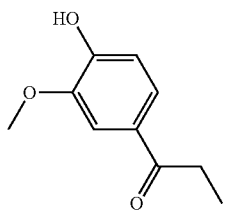

Powdered anhydrous aluminum chloride (3.0 g, 22.5 mmol) was dissolved in anhydrous nitrobenzene (10 mL) at 100° C. The solution was cooled and 2-methoxyphenyl propionate (2.0 g, 11.1 mmol) was added rapidly. The reaction mixture was heated at 60° C. for 1.5 h and cooled, 3 N NaOH was added, and the mixture was stirred for 15 min. The suspension was filtered off, washed with water. The filtrate was then washed with CH$_2$Cl$_2$ twice, acidified with 3 N HCl, extracted with CH$_2$Cl$_2$. The extract was dried, concentrated, and purified by column chromatography (petroleum ether/EtOAc=10/1 to 5/1) to give the desired product (874 mg, 44% yield) as a yellow oil.

Step C: 4-(1-(4-(2-chloroethoxy)phenyl)-1-(4-hydroxyphenyl)but-1-en-2-yl)-2-methoxyphenol

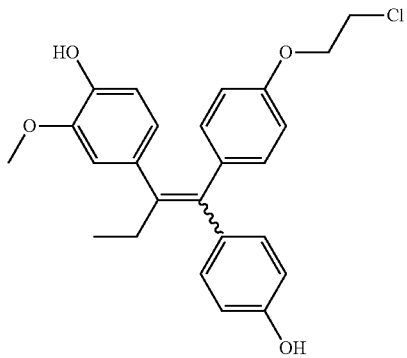 [SMILES: CCC(=C(c1ccc(O)cc1)c1ccc(OCCCl)cc1)c1ccc(O)c(OC)c1]

Following general procedure of McMurry reaction as example 1, step B described, 1-(4-hydroxy-3-methoxyphenyl)propan-1-one (207 mg, 1.15 mmol) was reacted with (4-(2-chloroethoxy)phenyl)(4-hydroxyphenyl)methanone (318 mg, 1.15 mmol) to give 188 mg desired product (38.5% yield).

Step D: 4-(1-(4-hydroxyphenyl)-1-(4-(2-(methylamino)ethoxy)phenyl)-but-1-en-2-yl)-2-methoxyphenol

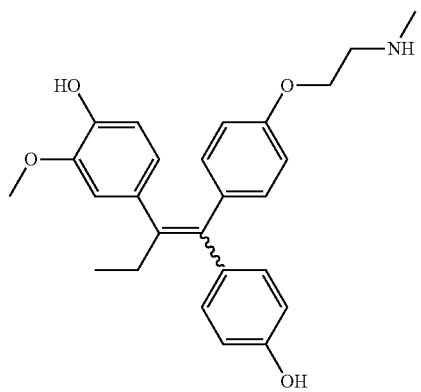

To a stirred solution of 4-(1-(4-(2-Chloroethoxy)phenyl)-1-(4-hydroxyphenyl)-but-1-en-2-yl)-2-methoxyphenol (88 mg, impure) in 10 mL MeOH was added 2 mL CH$_3$NH$_2$ (aq). After the mixture was heated at 85° C. for 24 h., the solvent was removed in vacuo, EtOAc was added, the mixture was washed with water and brine, dried over Na$_2$SO$_4$, filtered and the filtrate was evaporated in vacuo. The residue was purified by column chromatography (CH$_2$Cl$_2$/MeOH(NH$_3$ gas)=10/1) to give the desired product (42 mg, 48% yield, Z/E=1/1) as a white solid. m/z=420[M+1]$^+$.

Example 20

4-(1-(4-((1-Methylpyrrolidin-2-yl)methoxy)phenyl)-2-phenylbut-1-enyl)phenol

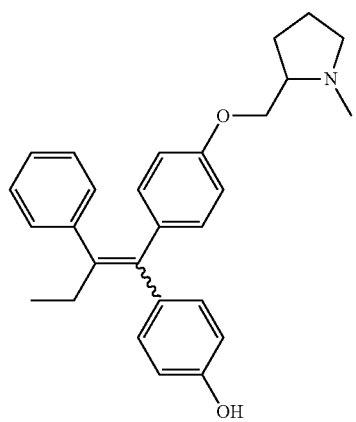 [SMILES: CCC(=C(c1ccc(O)cc1)c1ccc(OCC2CCCN2C)cc1)c1ccccc1]

Following same procedure of Mitsunobu reaction as described in example 16, step D, 4,4'-(2-phenylbut-1-ene-1,1-diyl)diphenol (220 mg, 0.473 mmol) was reacted with (1-methylpyrrolidin-2-yl)methanol (82 mg, 0.712 mmol, made from DL-proline Following *Arch. Pharm. Phamz. Med. Chem.* 1996, 329, 95-104.) to give 65 mg desired product (33% yield). m/z=414[M+1]⁺.

Example 21

4-(1-(3-Fluoro-4-(2-(methylamino)ethoxy)phenyl)-2-phenylbut-1-enyl)phenol

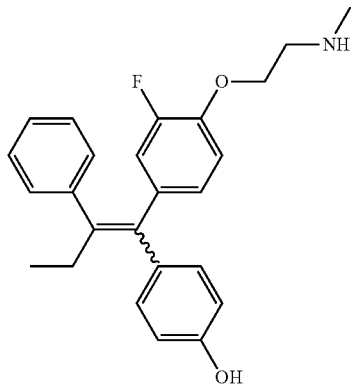 [SMILES: CCC(=C(c1ccc(O)cc1)c1ccc(OCCNC)c(F)c1)c1ccccc1]

Step A: 3-fluoro-4-methoxybenzonitrile

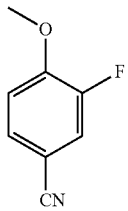

A mixture of 4-bromo-2-fluoro-1-methoxybenzene (30.0 g, 146 mmol) and CuCN (15.6 g, 174 mmol) in dry DMF (45 mL) was stirred at 120° C. overnight. The reaction mixture was cooled to room temperature, diluted with water and extracted with ethyl acetate. The extract was washed with water and brine, dried, and concentrated to give 20.0 g (91% yield) of the product as a yellow solid. ¹H NMR (400 MHz, CDCl₃) δ 7.44 (dd, J=8.8 Hz, 2.0 Hz, 1H), 7.36 (dd, J=10.8 Hz, 2.0 Hz, 1H), 7.02 (dd, J=8.8 Hz, 8.4 Hz, 1H), 3.96 (s, 3H).

Step B: 3-fluoro-4-hydroxybenzonitrile

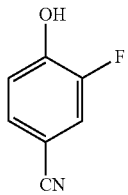

BBr₃ (20 mL, 0.211 mol) was added to 3-fluoro-4-methoxybenzonitrile (15.6 g, 0.103 mol) in dichloromethane (100 mL) at 0° C. The mixture was refluxed for 3 days under a nitrogen atmosphere. The reaction mixture was quenched with ice water and extracted with dichloromethane. The organic layer was washed with water and brine and then dried over sodium sulfate. Solvent evaporation under reduced pressure gave 13.3 g (94%) of the product as a gray solid. ¹H NMR (400 MHz, CDCl₃) δ 7.38-7.42 (m, 2H), 7.09 (dd, J=8.8 Hz, 8.4 Hz, 1H), 5.68 (s, 1H).

Step C: 4-(2-bromoethoxy)-3-fluorobenzonitrile

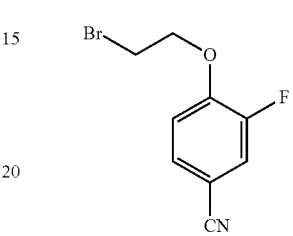

A suspension of 3-fluoro-4-hydroxybenzonitrile (1.2 g, 8.76 mmol), anhydrous K₂CO₃ (2.43 g, 17.6 mmol) and 1,2-dibromoethane (4.5 mL, 52.0 mmol) in DMF (6 mL) was stirred at 60° C. overnight under a nitrogen atmosphere. The reaction mixture was filtered and the filtrate was extracted with ethyl acetate. The extract was washed with water and brine, dried over sodium sulfate. Solvent evaporation under reduced pressure, followed by column chromatography over silica gel (eluent: petroleum ether/ethyl acetate=5/1), gave 1.52 g (71%) of the subtitle compound as a colorless oil. ¹H NMR (400 MHz, CDCl₃) δ 7.43 (d, J=9.2 Hz, 1H), 7.40 (d, J=12.0 Hz, 1H), 7.03 (dd, J=8.0 Hz, 8.4 Hz, 1H), 4.42 (t, J=6.2 Hz, 2H), 3.68 (t, J=6.2 Hz, 2H).

Step D: 4-(2-bromoethoxy)-3-fluorobenzoic acid

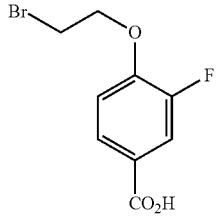

4-(2-Bromoethoxy)-3-fluorobenzonitrile (3.78 g, 15.5 mmol) in water (18 mL) and concentrated sulfuric acid (18 mL) was heated at 110° C. for 12 hours. The solution was then cooled to room temperature and neutralized with solid sodium bicarbonate. Acidification with glacial acetic acid leads to a white solid precipitate, which was collected by filtration and dissolved in dichloromethane. The resulting solution was dried over anhydrous sodium sulfate, filtered, and concentrated to give the product as a beige-colored solid (2.65 g, 65% yield). ¹H NMR (400 MHz, DMSO-d⁶) δ 13.00

(brs, 1H), 7.44 (d, J=8.4 Hz, 1H), 7.69 (d, J=12.0 Hz, 1H), 7.29 (dd, J=8.8 Hz, 8.4 Hz, 1H), 4.48 (t, J=5.2 Hz, 2H), 3.85 (t, J=5.2 Hz, 2H).

Step E: 4-(2-bromoethoxy)-3-fluorobenzoyl chloride

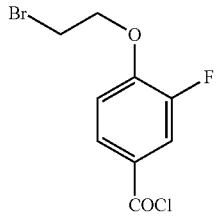 [SMILES: O=C(Cl)c1ccc(OCCBr)c(F)c1]

4-(2-Bromoethoxy)-3-fluorobenzoic acid (1.08 g, 4.1 mmol) and thionyl chloride (10 mL) were refluxed for 7 h. The excess of thionyl chloride was removed by repeated evaporation with dry toluene in vacuo, giving 1.07 g (93% yield) subtitle compound as a brown oil. $^1$H NMR (400 MHz, CDCl$_3$) δ 7.93 (d, J=8.8 Hz, 1H), 7.86 (d, J=11.2 Hz, 1H), 7.04 (dd, J=8.4 Hz, 8.4 Hz, 1H), 4.46 (t, J=6.4 Hz, 2H), 3.70 (t, J=6.4 Hz, 2H).

Step F: (4-(2-bromoethoxy)-3-fluorophenyl)(4-methoxyphenyl)-methanone

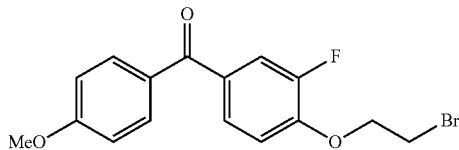 [SMILES: COc1ccc(C(=O)c2ccc(OCCBr)c(F)c2)cc1]

To a solution of 4-(2-bromoethoxy)-3-fluorobenzoyl chloride (1.07 g, 3.80 mmol) and anhydrous AlCl$_3$ (1.01 g, 7.60 mmol) in dry dichloromethane (18 mL) was added anisole (822 mg, 7.60 mmol) in 2 mL dichloromethane at 0° C. After stirring at rt for 6 h, the mixture was poured into 3 N HCl and extracted with dichloromethane twice. The extracts were combined, washed with sat. NaHCO$_3$ and brine, dried over Na$_2$SO$_4$, filtered, concentrated, and purified by column chromatography over silica gel (eluent: petroleum ether/ethyl acetate=10/1 to 5/1) to give 1.05 g (77% yield) of the subtitle compound as a white solid. $^1$H NMR (400 MHz, CDCl$_3$) δ 7.79 (d, J=8.8 Hz, 2H), 7.58 (d, J=11.6 Hz, 1H), 7.55 (d, J=8.4 Hz, 1H), 7.03 (dd, J=8.0 Hz, 8.4 Hz, 1H), 6.98 (d, J=9.2 Hz, 2H), 4.44 (t, J=6.4 Hz, 2H), 3.90 (s, 3H), 3.70 (t, J=6.4 Hz, 2H).

Step G: (4-(2-bromoethoxy)-3-fluorophenyl)(4-hydroxyphenyl)-methanone

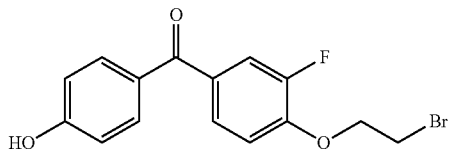 [SMILES: O=C(c1ccc(O)cc1)c1ccc(OCCBr)c(F)c1]

BBr$_3$ (0.5 mL, 5.29 mmol) was added to (4-(2-bromoethoxy)-3-fluorophenyl)(4-methoxyphenyl)methanone (930 mg, 2.63 mmol) in dichloromethane (6 mL) at 0° C. Stirring was continued at room temperature for 2 h under a nitrogen atmosphere. The reaction mixture was quenched with ice water and extracted with dichloromethane and the white suspension was filtered off. The organic layer was washed with water and brine and then dried over sodium sulfate. Solvent evaporation under reduced pressure, followed by purification by column chromatography over silica gel (eluent: petroleum ether/ethyl acetate=5/1 to 2/1) gave 536 mg (60% yield) of the subtitle compound as a beige solid. $^1$H NMR (400 MHz, CDCl$_3$) δ 7.74 (d, J=8.4 Hz, 2H), 7.59 (d, J=12.4 Hz, 1H), 7.56 (d, J=8.0 Hz, 1H), 7.03 (dd, J=8.0 Hz, 8.0 Hz, 1H), 6.92 (d, J=8.4 Hz, 2H), 5.88 (s, 1H), 4.44 (t, J=6.4 Hz, 2H), 3.70 (t, J=6.4 Hz, 2H).

Step H: 4-(1-(4-(2-bromoethoxy)-3-fluorophenyl)-2-phenylbut-1-enyl)phenol

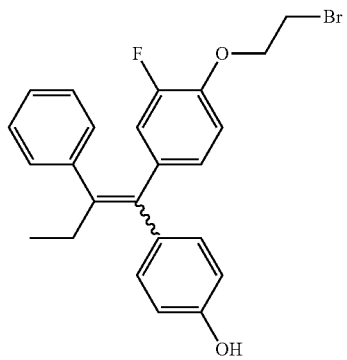 [SMILES: CCC(=C(c1ccc(O)cc1)c1ccc(OCCBr)c(F)c1)c1ccccc1]

Following general procedure of McMurry reaction as described in example 1, step B, (4-(2-bromoethoxy)-3-fluorophenyl)(4-hydroxyphenyl)methanone (311 mg, 0.917 mmol) was reacted with propiophenone (246 mg, 1.83 mmol) to give 403 mg desired product (99.6% yield, Z/E=1/1) as a beige solid.

Step I: 4-(1-(3-fluoro-4-(2-(methylamino)ethoxy)phenyl)-2-phenylbut-1-enyl)phenol

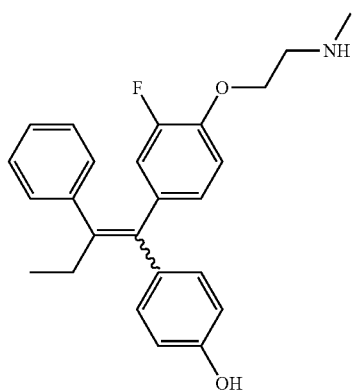 [SMILES: CCC(=C(c1ccc(O)cc1)c1ccc(OCCNC)c(F)c1)c1ccccc1]

To a stirred solution of 4-(1-(4-(2-bromoethoxy)-3-fluorophenyl)-2-phenyl but-1-enyl)phenol (111 mg, 0.25 mmol)

in 5 mL MeOH was added 1 mL CH$_3$NH$_2$ (30% aq) and the mixture was heated at 85° C. for 18 h. The mixture was extracted with EtOAc. The extract was washed with water and brine, dried over Na$_2$SO$_4$, filtered, concentrated, and purified by column chromatography (CH$_2$Cl$_2$/MeOH (NH$_3$ gas)=10/1) to give the desired product (56 mg, 57% yield, Z/E=1/1) as a beige solid. $^1$H NMR (400 MHz, CDCl$_3$) δ 7.08-7.11 (m, 5H), 7.03 & 6.77 (d, J=8.6 Hz, 2H), 6.91-6.96 (m, 1H), 6.76 & 6.44 (d, J=8.4 Hz, 2H), 6.51-6.58 (m, 2H), 4.17 & 4.01 (t, J=5.0 Hz, 2H), 3.03 & 2.93 (t, J=5.0 Hz, 2H), 2.55 & 2.48 (s, 3H), 2.47 (q, J=7.6 Hz, 2H), 0.91 (t, J=7.6 Hz, 3H); m/z=392 [M+1]$^+$.

Example 22

(Z)-2-fluoro-4-(1-(4-hydroxyphenyl)-1-(4-(2-(methylamino)ethoxy)phenyl)but-1-en-2-yl)phenol

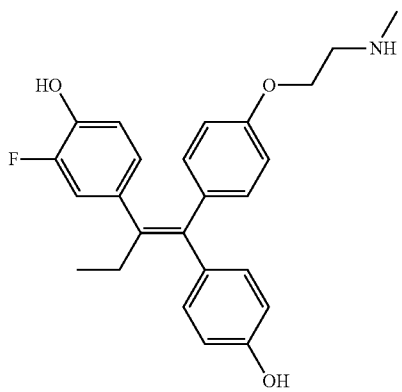 [SMILES: CC/C(=C(\c1ccc(O)cc1)c1ccc(OCCNC)cc1)c1ccc(O)c(F)c1]

Step A: 1-(3-fluoro-4-methoxyphenyl)propan-1-one

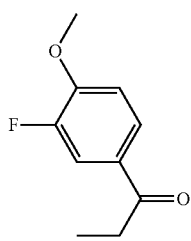

To a solution of 3-fluoro-4-methoxybenzonitrile (350 mg, 2.32 mmol) in 15 mL anhydrous THF was added ethylmagnesium bromide (1 M in Et$_2$O, 4.63 mL) at 0° C. The reaction mixture was stirred at rt overnight, then quenched with sat. NaHCO$_3$, extracted with EtOAc, washed with brine, dried and evaporated. The residue was purified by column chromatography (eluent: petroleum ether/EtOAc=5/1) over silica gel to give the product (239 mg, 57% yield) as a yellow solid.

Step B: 1-(3-fluoro-4-hydroxyphenyl)propan-1-one

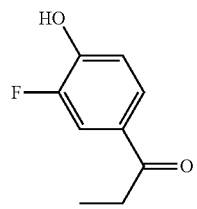

1-(3-Fluoro-4-methoxyphenyl)propan-1-one (421 mg, 2.31 mmol) in 20 mL 40% HBr was refluxed for 1 h., neutralized with solid Na$_2$CO$_3$ at 0° C., and extracted with EtOAc. The extract was washed with brine, dried, concentrated, and purified by column chromatography (eluent: petroleum ether/EtOAc=5/1) over silica gel to give the product (257 mg, 66% yield) as a yellow solid.

Step C: 4-(1-(4-(2-chloroethoxy)phenyl)-1-(4-hydroxyphenyl)but-1-en-2-yl)-2-fluorophenol

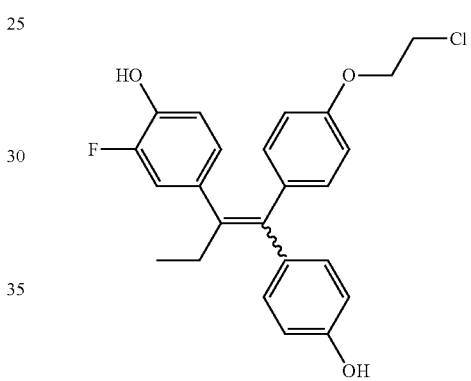

Following general procedure of McMurry reaction as described in example 1, step B, 1-(3-fluoro-4-hydroxyphenyl)propan-1-one (255 mg, 1.52 mmol) was reacted with (4-(2-chloroethoxy)phenyl)(4-hydroxyphenyl)methanone (629 mg, 2.27 mmol) to give 549 mg desired product (88% yield).

Step D: (Z)-2-fluoro-4-(1-(4-hydroxyphenyl)-1-(4-(2-(methylamino)-ethoxy)phenyl)but-1-en-2-yl)phenol

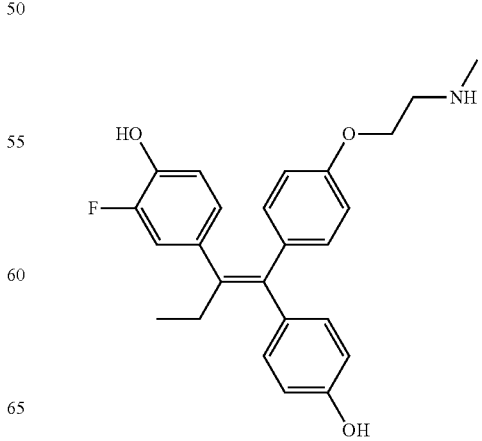

To a stirred solution of 4-(1-(4-(2-chloroethoxy)phenyl)-1-(4-hydroxyphenyl) but-1-en-2-yl)-2-fluorophenol (310 mg, 0.75 mmol) in 10 mL MeOH was added 2 mL CH₃NH₂ (30% aq). The reaction mixture was heated at 85° C. for 13 h. and extracted with EtOAc. The extract was washed with water and brine, dried over Na₂SO₄, filtered, concentrated, and purified by column chromatography (CH₂Cl₂/MeOH(NH₃ gas)=10/1) to give the (Z)-product (39 mg, white solid) and (E)-product (14 mg, black brown crystal). m/z=408[M+1]⁺.

Example 23

(E)-2-fluoro-4-(1-(4-hydroxyphenyl)-1-(4-(2-(methylamino)ethoxy) phenyl)but-1-en-2-yl)phenol

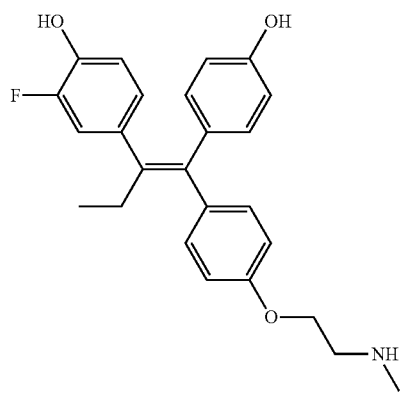 [SMILES: CC/C(=C(/c1ccc(O)cc1)c1ccc(OCCNC)cc1)c1ccc(O)c(F)c1]

The title compound was separated as described in example 22 (14 mg, black brown crystal). m/z=408[M+1]⁺.

Example 24

2-Fluoro-4-(1-(4-(2-(methylamino)ethoxy)phenyl)-2-phenylbut-1-enyl)phenol

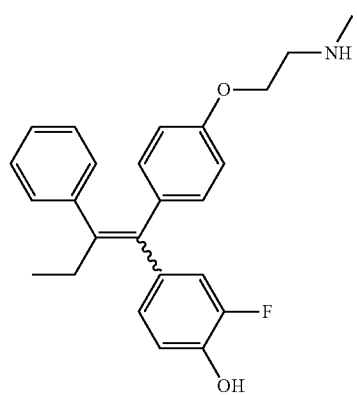 [SMILES: CCC(=C(c1ccc(OCCNC)cc1)c1ccc(O)c(F)c1)c1ccccc1]

Step A: 3-fluoro-4-methoxybenzoic acid

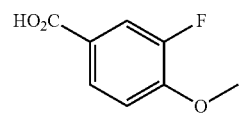

3-Fluoro-4-methoxybenzonitrile (2.0 g, 13.2 mmol) in water (5 mL) and concentrated sulphuric acid (5 mL) was heated at 110° C. for 4 hours. The solution was then cooled to room temperature and neutralized with solid sodium carbonate. Acidification with glacial acetic acid leads to a white precipitate, which was collected by filtration and dissolved in dichloromethane. The resulting solution was dried over sodium sulfate, filtered, and concentrated to give the product as a beige-colored solid (2.03 g, 90% yield).

Step B: 3-fluoro-4-methoxybenzoyl chloride

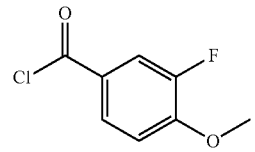

3-Fluoro-4-methoxybenzoic acid (830 mg, 4.88 mmol) and thionyl chloride (10 mL) were refluxed for 2 h. The excess thionyl chloride was removed by repeated evaporation with dry toluene in vacuo, giving the subtitle compound as a brown solid, which would be used for the next step directly.

Step C: (4-(2-chloroethoxy)phenyl)(3-fluoro-4-methoxyphenyl)-methanone

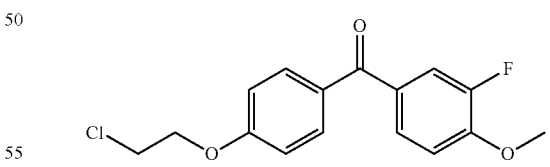

To a solution of 3-fluoro-4-methoxybenzoyl chloride from the last step and anhydrous AlCl₃ (1.30 g, 9.76 mmol) in dry dichloromethane (18 mL) was added (2-chloroethoxy)benzene (1.53 g, 9.76 mmol) in 2 mL dichloromethane at 0° C. After stirring at rt for 25 min, the mixture was poured into 3 N HCl. The mixture was extracted with dichloromethane. The extract was washed with sat. NaHCO₃ and brine, dried over Na₂SO₄, filtered, and concentrated to give the subtitle compound, which would be used for the next step directly.

Step D: (4-(2-chloroethoxy)phenyl)(3-fluoro-4-hydroxyphenyl)-methanone

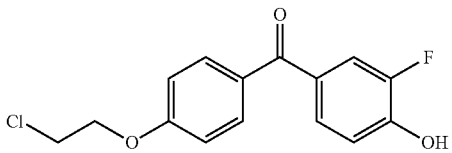 [SMILES: O=C(c1ccc(OCCCl)cc1)c1ccc(O)c(F)c1]

(4-(2-Chloroethoxy)phenyl)(3-fluoro-4-methoxyphenyl) methanone from the previous step in 20 mL 40% HBr was refluxed for 1 h., neutralized with solid Na$_2$CO$_3$ at 0° C., and extracted with EtOAc. The extract was washed with brine, dried, concentrated, and purified by column chromatography (eluent: petroleum ether/EtOAc=5/1 to 2/1) over silica gel to give the subtitle compound (731 mg, 51% yield for 3 steps) as a yellow solid.

Step E: 4-(1-(4-(2-chloroethoxy)phenyl)-2-phenyl-but-1-enyl)-2-fluoro phenol

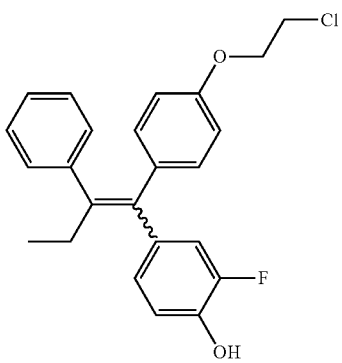 [SMILES: CCC(=C(c1ccc(OCCCl)cc1)c1ccc(O)c(F)c1)c1ccccc1]

Following general procedure of McMurry reaction as described in example 1, step B, (4-(2-chloroethoxy)phenyl) (3-fluoro-4-hydroxyphenyl)methanone (350 mg, 1.19 mmol) was reacted with propiophenone (319 mg, 2.38 mmol) to give the desired product (quant.) as a yellow solid.

Step F: 2-fluoro-4-(1-(4-(2-(methylamino)ethoxy) phenyl)-2-phenylbut-1-enyl)phenol

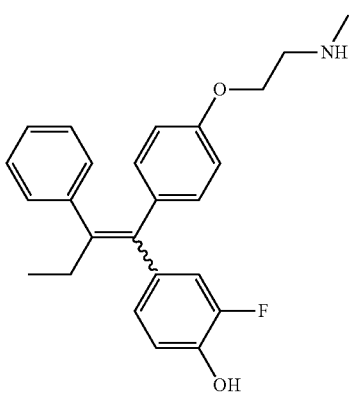 [SMILES: CCC(=C(c1ccc(OCCNC)cc1)c1ccc(O)c(F)c1)c1ccccc1]

To a stirred solution of 4-(1-(4-(2-chloroethoxy)phenyl)-2-phenylbut-1-enyl)-2-fluorophenol in 5 mL MeOH was added 2 mL CH$_3$NH$_2$ (30% aq) and heated at 85° C. overnight. The mixture was extracted with EtOAc, washed with water and brine, dried over Na$_2$SO$_4$, filtered, concentrated, and purified by column chromatography (CH$_2$Cl$_2$/MeOH (NH$_3$ gas)=10/1) to give the desired product (59% yield, Z/E=1/1 as a white solid. m/z=392[M+1]$^+$.

Example 25

(Z)-4-(1-(5-(2-(dimethylamino)ethoxy)pyrimidin-2-yl)-2-phenylbut-1-enyl)phenol hydrochloride

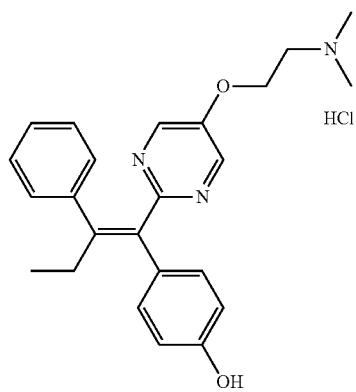 [SMILES: CC/C(=C(\c1ccc(O)cc1)c1ncc(OCCN(C)C)cn1)c1ccccc1 ; Cl]

Step A: (5-bromopyrimidin-2-yl)(4-(tetrahydro-2H-pyran-2-yloxy)-phenyl)methanone

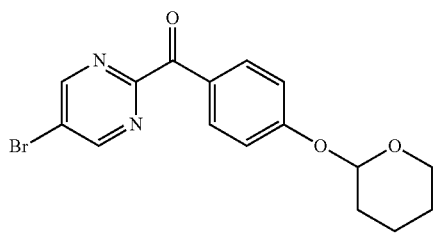 [SMILES: O=C(c1ccc(OC2CCCCO2)cc1)c1ncc(Br)cn1]

Following same procedure of Grignard reaction as described in example 1, step A, 2-(4-bromophenoxy)tetrahydro-2H-pyran (2.57 g, 10 mmol) was reacted with 5-bromopyrimidine-2-carbonitrile (0.92 g, 5 mmol) to give 910 mg desired product (50%).

Step B: (4-(tetrahydro-2H-pyran-2-yloxy)phenyl)(5-(4,4,5,5-tetramethyl-1,3,2-dioxaborolan-2-yl)pyrimidin-2-yl)methanone

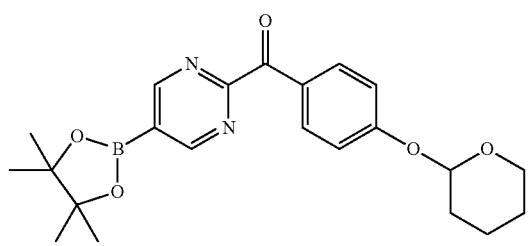 [SMILES: CC1(C)OB(c2cnc(C(=O)c3ccc(OC4CCCCO4)cc3)nc2)OC1(C)C]

A mixture of (5-bromopyrimidin-2-yl)(4-(tetrahydro-2H-pyran-2-yloxy)-phenyl)methanone (363 mg, 1 mmol), 4,4,4',4',5,5,5',5'-octamethyl-2,2'-bi(1,3,2-dioxaborolane) (508 mg, 2 mmol), PdCl$_2$(DPPF) (73.1 mg, 0.1 mmol) and KOAc (200 mg, 2 mmol) in 30 mL of dioxane was heated at 95° C. for 5 h and cooled. The reaction was concentrated and purified by column chromatography to give the desired product as a yellow oil (329 mg, 80% yield).

Step C: (5-hydroxypyrimidin-2-yl)(4-(tetrahydro-2H-pyran-2-yloxy)-phenyl)methanone

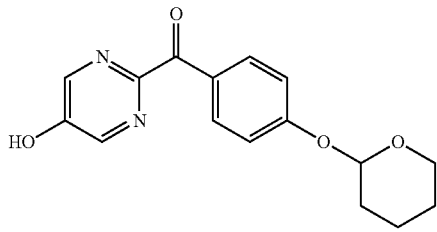 [SMILES: O=C(c1ccc(OC2CCCCO2)cc1)c1ncc(O)cn1]

To a solution of (4-(tetrahydro-2H-pyran-2-yloxy)phenyl) (5-(4,4,5,5-tetramethyl-1,3,2-dioxaborolan-2-yl)pyrimidin-2-yl)methanone (410 mg, 1 mmol) in 20 mL of THF was added 0.5 mL 33% H$_2$O$_2$ and the reaction was stirred for 1 h at rt. The reaction was then quenched with aq. Na$_2$SO$_3$, extracted with EtOAc, washed with water and brine, dried, filtered, concentrated, and purified by column chromatography to give the desired product (240 mg, 80% yield).

Step D: (5-(2-(dimethylamino)ethoxy)pyrimidin-2-yl)(4-(tetrahydro-2H-pyran-2-yloxy)phenyl)methanone

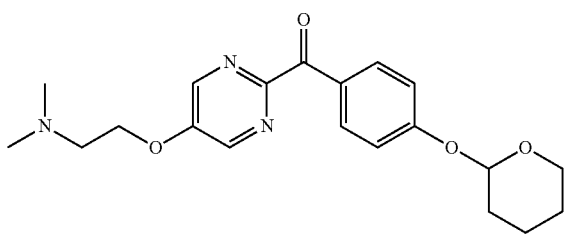 [SMILES: CN(C)CCOc1cnc(C(=O)c2ccc(OC3CCCCO3)cc2)nc1]

To a mixture of (5-hydroxypyrimidin-2-yl)(4-(tetrahydro-2H-pyran-2-yloxy) phenyl)methanone (300 mg, 1 mmol), 2-(dimethylamino)ethanol (180 mg, 2 mmol) and PPh$_3$ (524 mg, 2 mmol) in 50 mL of THF was added DIAD (404 mg, 2 mmol) dropwise and the mixture was stirred overnight at rt. The mixture was concentrated and purified by flash chromatography to give the product (297 mg, 80% yield)

Step E: (Z)-4-(1-(5-(2-(dimethylamino)ethoxy)pyrimidin-2-yl)-2-phenyl but-1-enyl)phenol hydrochloride

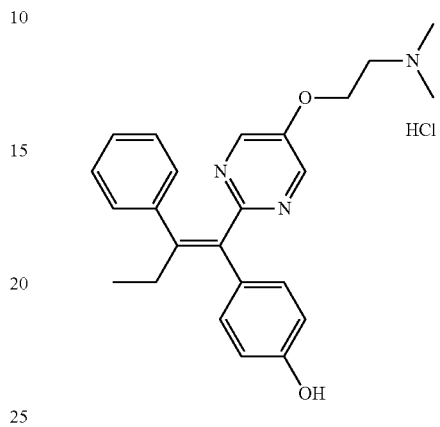

Following general procedure of McMurry reaction as described in example 1, step B, (5-(2-(dimethylamino)ethoxy)pyrimidin-2-yl)(4-(tetrahydro-2H-pyran-2-yloxy) phenyl)methanone (753 mg, 2 mmol) was reacted with propiophenone (800 mg, 6 mmol) to give Z/E mixed product. The pure (Z) and (E) isomer were separated by preparative HPLC. Evaporation of the (Z)-isomer from 3 N HCl in MeOH to afford the title compound (16 mg). $^1$H NMR (400 MHz, CD$_3$OD) δ 8.30 (s, 2H), 7.06-7.13 (m, 7H), 6.77 (d, J=8.4 Hz, 2H), 4.40 (t, J=4.8 Hz, 2H), 3.57 (t, J=4.8 Hz, 2H), 2.95 (s, 6H), 2.58 (q, J=7.2 Hz, 2H), 0.95 (t, J=7.2 Hz, 3H); m/z=390 [M-HCl+1]$^+$.

Example 26

(E)-4-(1-(5-(2-(dimethylamino)ethoxy)pyrimidin-2-yl)-2-phenylbut-1-enyl)phenol hydrochloride

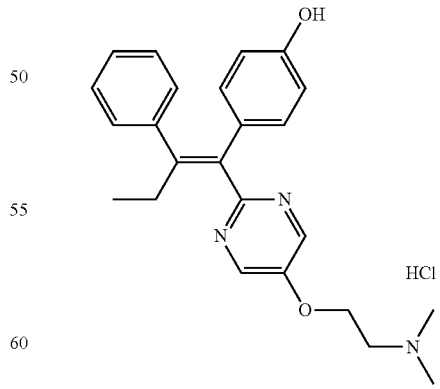

The title compound (16 mg) was obtained in the same way as described in example 25, step E. $^1$H NMR (400 MHz, CD$_3$OD) δ 8.62 (s, 2H), 7.14-7.20 (m, 5H), 6.70 (d, J=8.4 Hz, 2H), 6.43 (d, J=8.8 Hz, 2H), 4.57 (t, J=5.2 Hz, 2H), 3.67 (t, J=5.2 Hz, 2H), 3.02 (s, 6H), 2.32 (q, J=7.2 Hz, 2H), 0.90 (t, J=7.2 Hz, 3H); m/z=390[M−HCl+1]⁺.

Example 27

4-(1-(5-(2-(Dimethylamino)ethoxy)pyridin-2-yl)-2-phenylbut-1-enyl)phenol

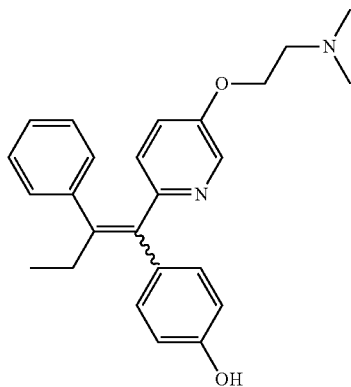 [SMILES: CCC(=C(c1ccc(O)cc1)c1ccc(OCCN(C)C)cn1)c1ccccc1]

Step A:
5-hydroxy-N-methoxy-N-methylpicolinamide

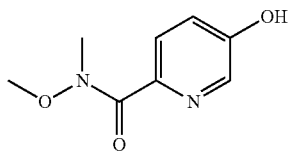

To a suspension of 5-hydroxypicolinic acid (1.0 eq), HATU (1.2 eq) and N-methoxymethanamine hydrochloride (1.2 eq) in dry DMF was added DIEtOAc (2.5 eq) dropwise at rt. The mixture was then stirred overnight at rt. After addition with water, the mixture was extracted with CH₂Cl₂. The extract was dried, concentrated, and purified by column chromatography to give the desired product (87% yield).

Step B: 5-(2-(dimethylamino)ethoxy)-N-methoxy-N-methylpicolinamide

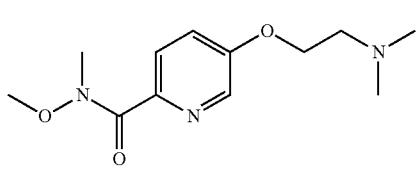

To a stirred solution of 5-hydroxy-N-methoxy-N-methylpicolinamide (1.0 eq), 2-(dimethylamino)ethanol (1.2 eq) and PPh₃ (1.2 eq) in 5 mL anhydrous THF under nitrogen was added DIAD (1.2 eq) dropwise at 0° C. The reaction was stirred overnight at rt., quenched with water, and extracted with EtOAc. The extract was dried, concentrated, and purified by column chromatography to give the desired product (40% yield).

Step C: (5-(2-(dimethylamino)ethoxy)pyridin-2-yl)(4-(tetrahydro-2H-pyran-2-yloxy)phenyl)methanone

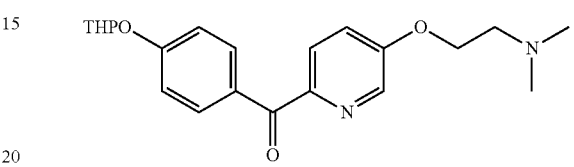

To a solution of 2-(4-iodophenoxy)tetrahydro-2H-pyran (1.1 eq) in THF was added a solution of nbutyllitium in hexane (1.1 eq) at −78° C. The mixture was stirred at −78° C. for 20 min. To the mixture was added a solution of 5-(2-(dimethylamino)-ethoxy)-N-methoxy-N-methylpicolinamide (1.0 eq) in THF at −78° C. After 2 h, isopropanol and water was added to the mixture, and the cold bath was removed. The mixture was stirred at room temperature for 20 min. The mixture was extracted with ethyl acetate. The extract was washed with 0.5 N HCl, sodium bicarbonate (sat.), and brine, dried over sodium sulfate, filtered, concentrated, and purified by column chromatography (silica gel) to give the subtitle compound (47% yield).

Step D: 4-(1-(5-(2-(dimethylamino)ethoxy)pyridin-2-yl)-2-phenylbut-1-enyl)phenol

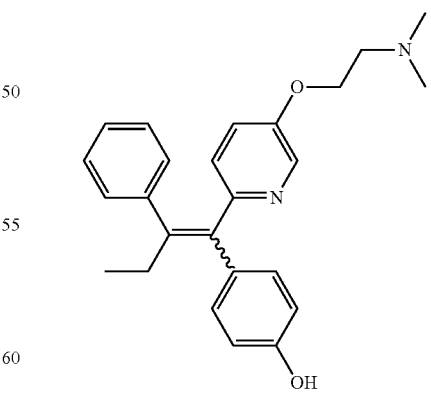

Following general procedure of McMurry reaction as described in example 1, step B, (5-(2-(dimethylamino)ethoxy)pyridin-2-yl)(4-(tetrahydro-2H-pyran-2-yloxy) phenyl)methanone (1 eq) was reacted with propiophenone (2 eq) to give the desired product (Z/E=1/1). m/z=389[M+1]⁺.

Example 28

4-(1-(6-(3-(Dimethylamino)propyl)pyridin-3-yl)-2-phenylbut-1-enyl)phenol hydrochloride

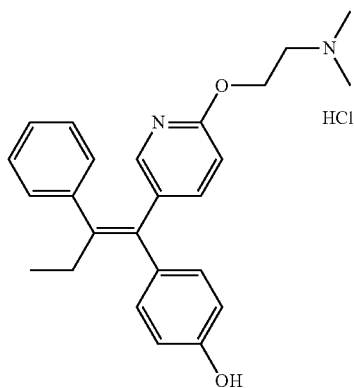 [SMILES: CC/C(=C(\c1ccc(O)cc1)c1ccc(OCCN(C)C)nc1)c1ccccc1 ; Cl]

Step A: (6-chloropyridin-3-yl)(4-methoxyphenyl)methanone

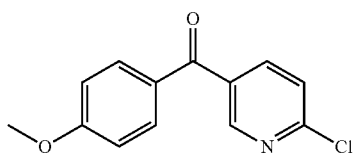 [SMILES: COc1ccc(C(=O)c2ccc(Cl)nc2)cc1]

To a solution of 6-chloronicotinonitrile (1.39 g, 10 mmol) in 100 mL of THF was added (4-methoxyphenyl)magnesium bromide (15 mmol) dropwise at 0° C. The mixture was then stirred at 0° C. for 1 h. and then 50 mL sat. NH₄Cl solution was added. The mixture was extracted with ethyl acetate and the organic layer was washed with brine, dried over Na$_2$SO$_4$, filtered, concentrated, and purified by flash chromatography to give the product (1.24 g, 50% yield).

Step B: (6-(3-(dimethylamino)prop-1-ynyl)pyridin-3-yl)(4-methoxy phenyl)methanone

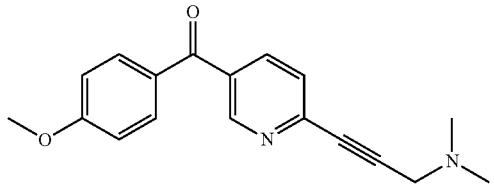

A 25 ml Schlenk flask was charged with (6-chloropyridin-3-yl)(4-methoxy-phenyl)methanone (124 mg, 0.5 mmol), Pd(PPh$_3$)$_2$Cl$_2$ (18 mg, 0.025 mmol), CuI (10 mg, 0.05 mmol), Et$_3$N (10 mL), and N,N-dimethylpropargylamine (83 mg, 1.0 mmol). The flask was flushed with argon three times and the mixture was stirred at 80° C. for 24 h. The solvent was evaporated under vacuum and the residue was purified by column chromatography to give the product (118 mg, 80% yield).

Step C: (6-(3-(dimethylamino)propyl)pyridin-3-yl)(4-methoxy-phenyl)methanone

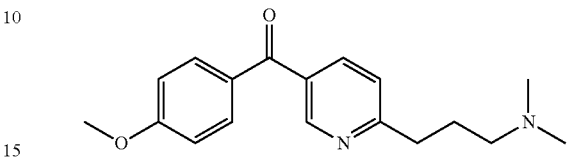

A flask was charged with (6-(3-(dimethylamino)prop-1-ynyl)pyridin-3-yl)-(4-methoxyphenyl)methanone (294 mg, 1 mmol) and Riney Ni (0.2 eq), and 20 mL methanol. The mixture was stirred under hydrogen at room temperature and atmospheric pressure for 2 h. The catalyst was filtered off through a pad of celite, washed with EtOAc. The filtrate was concentrated under reduced pressure to give the product (284 mg, 95% yield).

Step D: (6-(3-(dimethylamino)propyl)pyridin-3-yl)(4-hydroxy-phenyl)methanone

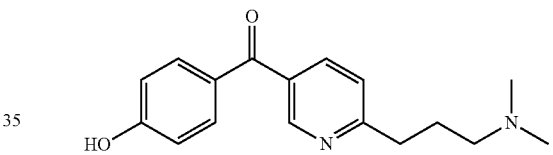

To a solution of (6-(3-(dimethylamino)propyl)pyridin-3-yl)(4-methoxy-phenyl)methanone (298 mg, 1 mmol) in 10 mL of methanol was added 10 mL of 48% HBr at rt and the mixture was heated to reflux for 3 h and cooled. The solvent was evaporated to give the crude product, which was used without further purification (284 mg, 100% yield).

Step E: 4-(1-(6-(3-(dimethylamino)propyl)pyridin-3-yl)-2-phenylbut-1-enyl)phenol hydrochloride

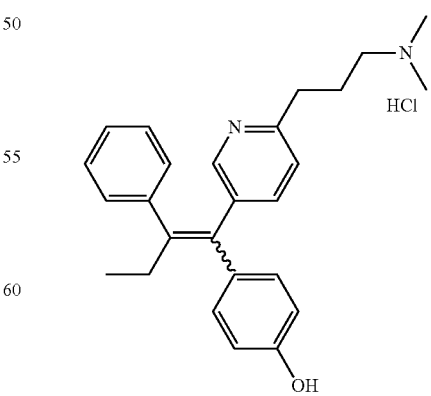

Following general procedure of McMurry reaction as described in example 1, step B, (6-(3-(dimethylamino)propyl)pyridin-3-yl)(4-hydroxyphenyl)methanone (568 mg, 2 mmol) was reacted with propiophenone (800 mg, 6 mmol) to give 55 mg desired product (7% yield, Z/E=1/1). m/z=387 [M-HCl+1]$^+$.

Example 29

6-(1-(4-(2-(Methylamino)ethoxy)phenyl)-2-phenyl-but-1-enyl)pyridin-3-ol

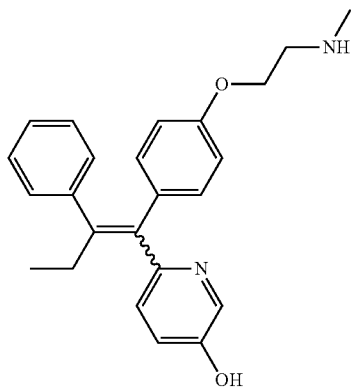 [SMILES: CCC(=C(c1ccc(OCCNC)cc1)c1ccc(O)cn1)c1ccccc1]

Step A: tert-butyl 2-(4-bromophenoxy)ethyl(methyl)carbamate

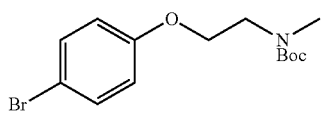 [SMILES: CN(CCOc1ccc(Br)cc1)C(=O)OC(C)(C)C]

To a stirred solution of tert-butyl 2-hydroxyethyl(methyl)carbamate (1.5 eq), 4-bromophenol (1.0 eq) and PPh$_3$ (1.5 eq) in anhydrous THF under nitrogen was added DIAD (1.5 eq) dropwise at 0° C. The reaction was stirred at rt. for 48 h., quenched with water, and extracted with EtOAc. The extract was dried, concentrated, and purified by column chromatography to give the desired product.

Step B: tert-butyl 2-(4-(5-hydroxypicolinoyl)phenoxy)ethyl-(methyl)carbamate

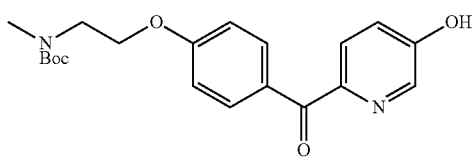 [SMILES: CN(CCOc1ccc(C(=O)c2ccc(O)cn2)cc1)C(=O)OC(C)(C)C]

Mg (3.5 eq) was added to a 3-neck round bottom flask containing 50 mL anhydrous THF. The mixture was heated to 55° C. Iodine chips (2 grains) were added in one lot followed by addition of 0.1 mL ethyl bromide. Tert-butyl 2-(4-bromophenoxy)ethyl(methyl)carbamate (3.0 eq) was dissolved in 30 mL anhydrous THF, 3 mL of this solution was added at once to Mg-THF suspension. The reaction was initiated after 30 min and reflux started. The remaining solution of tert-butyl 2-(4-bromophenoxy)ethyl(methyl)carbamate was added dropwise in such speed that the reaction mixture remained reflux. After addition, the reaction mixture was further reflux for 2 h and cooled to rt. 5-Hydroxy-N-methoxy-N-methylpicolinamide (1.0 eq) in 20 mL THF was added dropwise at rt, stirred for 30 min. at rt., quenched with sat NH$_4$Cl (aq), and extracted with EtOAc. The extract was dried, concentrated, and purified by column chromatography to give the desired product.

Step C: 6-(1-(4-(2-(methylamino)ethoxy)phenyl)-2-phenylbut-1-enyl)pyridin-3-ol

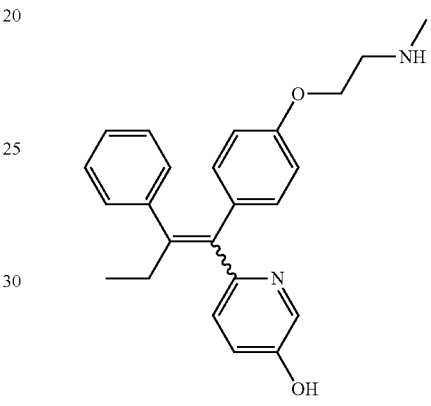

Following general procedure of McMurry reaction as described in example 1, step B, tert-butyl 2-(4-(5-hydroxypicolinoyl)phenoxy)ethyl(methyl)carbamate (1.0 eq) was reacted with propiophenone (3.0 eq) to give the desired product (Z/E=1/1). m/z=375[M+1]$^+$.

Example 30

4-(2-Phenyl-1-(6-(3-(pyrrolidin-1-yl)propyl)pyridin-3-yl)but-1-enyl)phenol

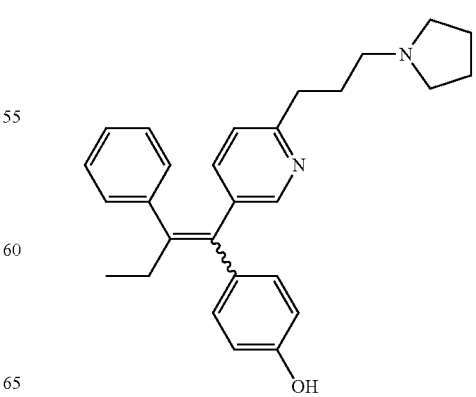

Step A: 2-(4-iodophenoxy)tetrahydro-2H-pyran

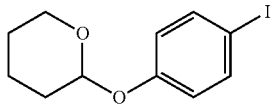 [SMILES: Ic1ccc(OC2CCCCO2)cc1]

4-Iodophenol 10.0 g (45.5 mmol) was dissolved in 20 mL 3,4-dihydro-2H-pyran, then one drop of concentrated sulfuric acid was added, the reaction mixture was stirred for 30 min, then the mixture was poured into 1000 mL of n-hexane, filtered and washed with 300 mL (100 mL×3) hexane, dried in vacuum to afford the desired product as white solid (9.1 g, 65.9% yield).

Step B: 6-chloro-N-methoxy-N-methylnicotinamide

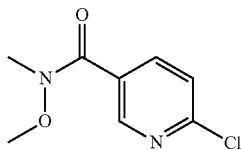

Oxalyl chloride 12.1 g (95.2 mmol) was added dropwise to a solution of 6-chloronicotinic acid 10.0 g (63.5 mmol) in 100 mL tetrahydrofuran. The reaction mixture was stirred at room temperature for 1 h, and then concentrated to give a residue, which was dissolved in 50 mL dichloromethane. The solution thus formed was added to a solution of N,O-dimethylhydroxylamine hydrochloride 12.4 g (126.9 mmol) and triethylamine 25.7 g (253.9 mmol) in 100 mL dichloromethane, stirred at room temperature for 1 h., concentrated, and purified by column chromatography to afford the desired product as colorless oil (9.4 g, 73.8% yield).

Step C: 1-(prop-2-ynyl)pyrrolidine

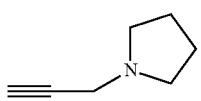

3-Bromoprop-1-yne (60.5 g, 0.50 mol) was slowly added to methylamine (70.1 g, 1.0 mol) at −10° C. After addition, the mixture was stirred at room temperature overnight, and then distilled on a rectification column to afford the desired product as a colorless oil (45.5 g, 83.5% yield).

Step D: (6-chloropyridin-3-yl)(4-(tetrahydro-2H-pyran-2-yloxy)-phenyl)methanone

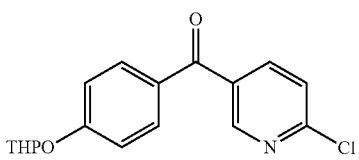

2-(4-Iodophenoxy)tetrahydro-2H-pyran (18.2 g, 59.9 mmol) was dissolved in 100 mL dry tetrahydrofuran and cooled to −78° C. under nitrogen atmosphere, and then n-butyllithium was added dropwise to the solution. After addition, the solution was stirred at −78° C. for 0.5 h, 6-chloro-N-methoxy-N-methylnicotinamide (8.0 g, 39.9 mmol) in 50 mL tetrahydrofuran was added dropwise and keep the temperature under −78° C. for 2 h. 100 mL of saturated aqueous ammonium chloride was added. The mixture was extracted with ethyl acetate. The extract was dried, concentrated, and purified by column chromatography to give the desired product as yellow solid (8.4 g, 66.3% yield).

Step E: (6-(3-(pyrrolidin-1-yl)prop-1-ynyl)pyridin-3-yl)(4-(tetrahydro-2H-pyran-2-yloxy)phenyl)methanone

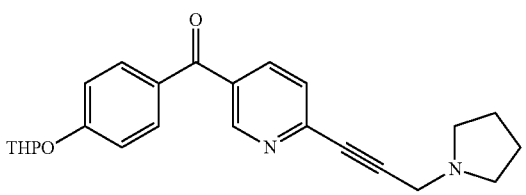

A 100 mL Schlenk flask was charged with (6-chloropyridin-3-yl)(4-(tetrahydro-2H-pyran-2-yloxy)phenyl)methanone (4.0 g, 12.6 mmol), tetrakis(triphenylphosphine) palladium(0) (1.5 g, 1.3 mmol, 10 mol %), cuprous iodide (0.48 g, 2.5 mmol, 20 mol %), triethylamine 50 mL and 1-(prop-2-ynyl)pyrrolidine (2.8 g, 25.2 mmol), and then the flask was flushed with nitrogen three times. The mixture was stirred at 80° C. for 2 h. The solvent was evaporated under vacuum and the residue was purified by column chromatography to afford the desired product as a yellow solid (2.2 g, 44.9% yield).

Step F: (6-(3-(pyrrolidin-1-yl)propyl)pyridin-3-yl)(4-(tetrahydro-2H-pyran-2-yloxy)phenyl)methanone

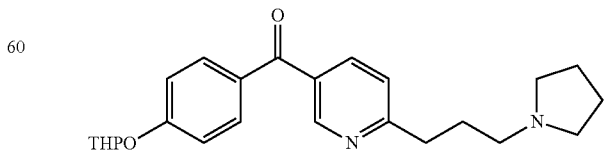

Raney nickel (0.3 g, 0.6 mmol, 10 mol %) was added to a solution of (6-(3-(pyrrolidin-1-yl)prop-1-ynyl)pyridin-3-yl)

(4-(tetrahydro-2H-pyran-2-yloxy)phenyl)methanone (2.2 g, 5.6 mmol) in 20 mL methanol at room temperature, and the reaction mixture was stirred for 1 h under hydrogen atmosphere. The nickel was filtered off and the filtrate was concentrated in vacuo to afford the desired product as a yellow solid (1.7 g, 77.3% yield).

Step G: 4-(2-phenyl-1-(6-(3-(pyrrolidin-1-yl)propyl)pyridin-3-yl)but-1-enyl)phenol

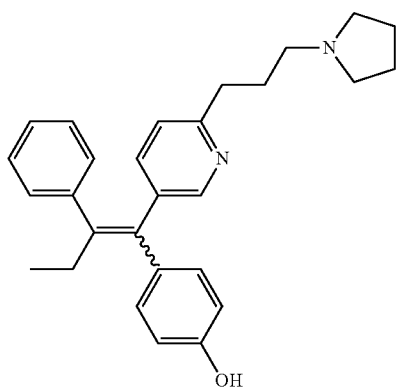

Following the general procedure of McMurry reaction as described in example 1, step B, (6-(3-(pyrrolidin-1-yl)propyl)pyridin-3-yl)(4-(tetrahydro-2H-pyran-2-yl-oxy)phenyl)methanone (1.0 g, 2.5 mmol) was reacted with propiophenone (1.0 g, 7.6 mmol) to give 186 mg desired product (17.8% yield, Z/E=3/1). m/z=413[M+1]$^{+}$.

Example 31

4-(2-Phenyl-1-(4-(3-(pyrrolidin-1-yl)propyl)phenyl)but-1-enyl)phenol

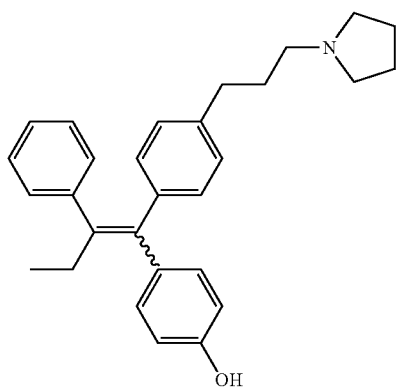 [SMILES: CCC(=C(c1ccc(O)cc1)c1ccc(CCCN2CCCC2)cc1)c1ccccc1]

Step A: (4-(3-(pyrrolidin-1-yl)prop-1-ynyl)phenyl)(4-(tetrahydro-2H-pyran-2-yloxy)phenyl)methanone

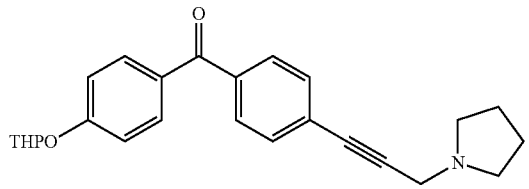

A 25 mL Schlenk flask was charged with (4-iodophenyl)(4-(tetrahydro-2H-pyran-2-yloxy)phenyl)methanone (408 mg, 1 mmol), Pd(PPh$_3$)$_2$Cl$_2$ (18 mg, 0.025 mmol), CuI (10 mg, 0.05 mmol), Et$_3$N (10 ml) and 1-(prop-2-ynyl)pyrrolidine (165 mg, 1.5 mmol). The flask was flushed with argon three times and the mixture was stirred at 90° C. for 3 h. The solvent was evaporated under vacuum and the residue was purified by columnchromatography to give the desired product (312 mg, 80% yield)

Step B: (4-(3-(pyrrolidin-1-yl)propyl)phenyl)(4-(tetrahydro-2H-pyran-2-yloxy)phenyl)methanone

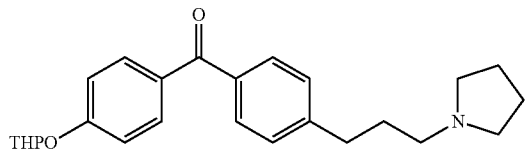

A flask was charged with (4-(3-(pyrrolidin-1-yl)prop-1-ynyl)phenyl)(4-(tetrahydro-2H-pyran-2-yloxy)phenyl)methanone (391 mg, 1 mmol), Riney Ni (0.2 eq), and 20 mL of methanol. The mixture was stirred under hydrogen at room temperature and atmospheric pressure for 2 h. After complete conversion (TLC monitoring), the catalyst was filtered off through a pad of celite, and washed with EtOAc. The filtrate was concentrated under reduced pressure to give the product (375 mg, 95% yield).

Step C: 4-(2-phenyl-1-(4-(3-(pyrrolidin-1-yl)propyl)phenyl)but-1-enyl)-phenol

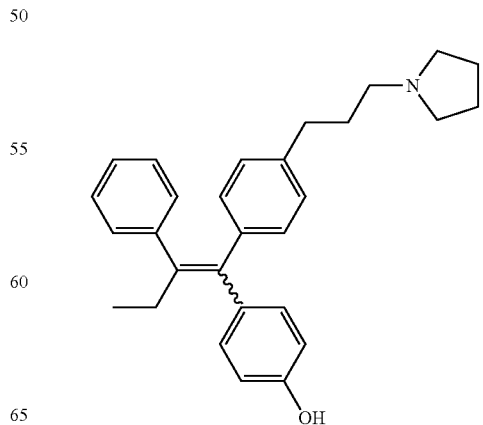

Following general procedure of McMurry reaction as described in example 1, step B, (4-(3-(pyrrolidin-1-yl)propyl)phenyl)(4-(tetrahydro-2H-pyran-2-yloxy)phenyl)methanone (798 mg, 2 mmol) was reacted with propiophenone (800 mg, 6 mmol) to give 208 mg desired product (25%, Z/E=1/1). m/z=412[M+1]⁺.

Example 32

4-(1-(6-(3-(Methylamino)propyl)pyridin-3-yl)-2-phenylbut-1-enyl)phenol

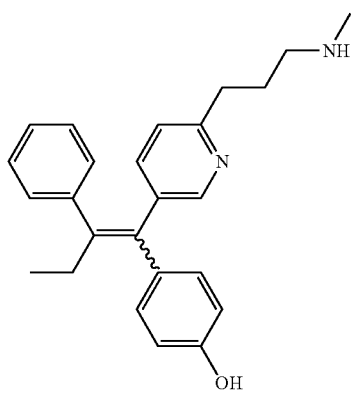 [SMILES: CCC(=C(c1ccc(O)cc1)c1ccc(CCCNC)nc1)c1ccccc1]

Step A: N-methylprop-2-yn-1-amine

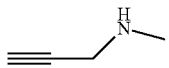

Allyl bromide 64.0 g (0.54 mol) was added to 120 mL of anhydrous methylamine cooled with solid carbon dioxide. The mixture was sealed in a sealtube and kept at room temperature overnight. The tube was opened and the contents heated to 45° C. to expel excess methylamine. Dry ether (100 mL) was then added and the methylamine hydrochloride was removed by filtration. Distillation of the filtrate gave the desired product as a colorless oil (5.0 g, 13.4% yield), b.p. 82-84° C.

Step B: tert-butyl methyl(prop-2-ynyl)carbamate

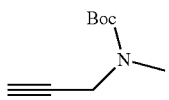

Di-tertbutyl dicarbonate (2.7 mL, 11.7 mmol) was slowly added to a stirring solution of N-methylpropargylamine 0.8 g (1.0 mL, 11.8 mmol) in 20 mL of methanol at 25° C. The mixture was allowed to stir for 1 h. All volatiles were removed in vacuo to afford crude Boc-N-methylpropargylamine as a light yellow oil (1.9 g, 97% yield).

Step C: tert-butyl methyl(3-(5-(4-(tetrahydro-2H-pyran-2-yloxy)benzoyl)-pyridin-2-yl)prop-2-ynyl)carbamate

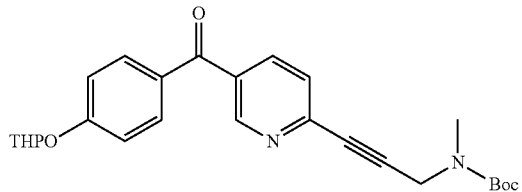

A 25 mL Schlenk flask was charged with (6-chloropyridin-3-yl)(4-(tetrahydro-2H-pyran-2-yloxy)phenyl)methanone (318 mg, 1.0 mmol), tetrakis(triphenylphos-phine)Palladium (0) (116 mg, 0.1 mmol, 10 mol %), cuprous iodide (38 g, 0.2 mmol, 20 mol %), triethylamine (5 mL), and tert-butyl methyl (prop-2-ynyl)carbamate (169 mg, 1 mmol). The flask was flushed with nitrogen three times and the mixture was stirred at 80° C. for 2 h. The solvent was evaporated under vacuum and the residue was purified by column chromatography to afford the desired product as yellow solid (180 mg, 40% yield).

Step D: tert-butyl methyl(3-(5-(4-(tetrahydro-2H-pyran-2-yloxy)benzoyl)-pyridin-2-yl)propyl)carbamate

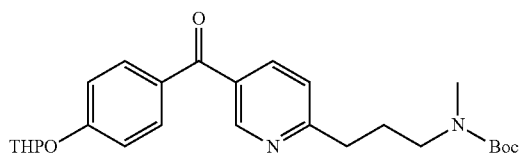

Raney nickel (2.4 mg, 0.04 mmol, 10 mol %) was added to a solution of tert-butylmethyl(3-(5-(4-(tetrahydro-2H-pyran-2-yloxy)benzoyl)pyridin-2-yl)prop-2-ynyl)carbamate (180 mg, 0.4 mmol) in 3 mL methanol at room temperature, and the reaction mixture was stirred for 1 h under hydrogen atmosphere. The nickel was filtered off and the filtrate was concentrated in vacuo to afford the desired product as a yellow solid (100 mg, 55.6% yield).

Step E: 4-(1-(6-(3-(methylamino)propyl)pyridin-3-yl)-2-phenylbut-1-enyl)phenol

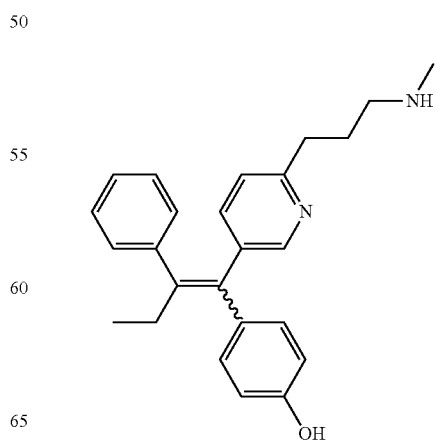

Following general procedure of McMurry reaction as described in example 1, step B, tert-butyl methyl(3-(5-(4-(tetrahydro-2H-pyran-2-yloxy)benzoyl)pyridin-2-yl)propyl)carbamate (100 mg, 0.22 mmol) was reacted with propiophenone (88 mg, 0.66 mmol) to give 16 mg desired product (20% yield, Z/E=1/1). m/z=373[M+1]+.

Example 33

4-(1-(4-(3-(Methylamino)propyl)phenyl)-2-phenyl-but-1-enyl)phenol

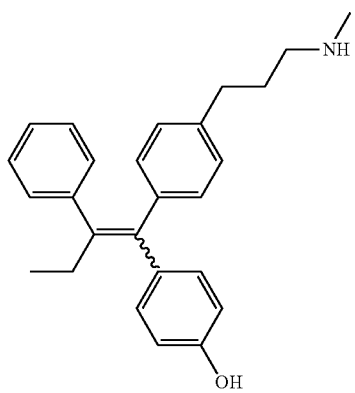 [SMILES: CCC(=C(c1ccc(O)cc1)c1ccc(CCCNC)cc1)c1ccccc1]

Step A: tert-butyl methyl(3-(4-(4-(tetrahydro-2H-pyran-2-yloxy)benzoyl)-phenyl)prop-2-ynyl)carbamate

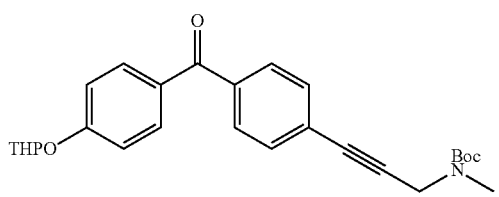

A 25 mL Schlenk flask was charged with (4-iodophenyl)(4-(tetrahydro-2H-pyran-2-yloxy)phenyl)methanone (408 mg, 1 mmol), Pd(PPh₃)₂Cl₂ (18 mg, 0.025 mmol), CuI (10 mg, 0.05 mmol), Et₃N (10 mL), and tert-butyl methyl(prop-2-ynyl)carbamate (255 mg, 1.5 mmol). The flask was flushed with argon three times and the mixture was stirred at 90° C. for 3 h. The solvent was evaporated under vacuum and the residue was purified by columnchromatography to give the desired product (270 mg, 60% yield).

Step B: tert-butyl methyl(3-(4-(4-(tetrahydro-2H-pyran-2-yloxy)benzoyl)-phenyl)propyl)carbamate

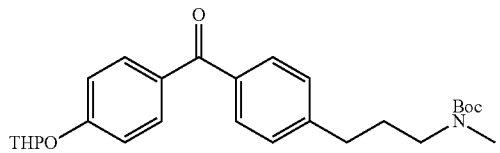

A flask was charged with tert-butyl methyl(3-(4-(4-(tetrahydro-2H-pyran-2-yloxy)benzoyl)phenyl)prop-2-ynyl)carbamate (450 mg, 1 mmol), Riney Ni (0.2 eq), and 20 mL of methanol. The mixture was stirred under hydrogen at room temperature and atmospheric pressure for 2 h. After complete conversion (TLC monitoring), the catalyst was filtered off through a pad of celite, and washed with EtOAc. The filtrate was concentrated under reduced pressure to give the product (364 mg, 80% yield).

Step C: 4-(1-(4-(3-(methylamino)propyl)phenyl)-2-phenylbut-1-enyl)-phenol

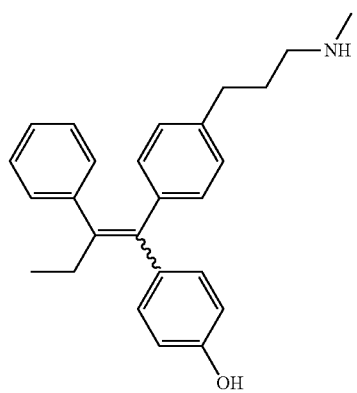 [SMILES: CCC(=C(c1ccc(O)cc1)c1ccc(CCCNC)cc1)c1ccccc1]

Following general procedure of McMurry reaction as described in example 1, step B, tert-butyl methyl(3-(4-(4-(tetrahydro-2H-pyran-2-yloxy)benzoyl)phenyl)-propyl)carbamate (909 mg, 2 mmol) was reacted with propiophenone (800 mg, 6 mmol) to give 224 mg desired product (30%, Z/E=1/1). m/z=372[M+1]$^+$.

Example 34

4-(1-(3-Fluoro-4-(3-(pyrrolidin-1-yl)prop-1-ynyl)phenyl)-2-phenylbut-1-enyl)phenol

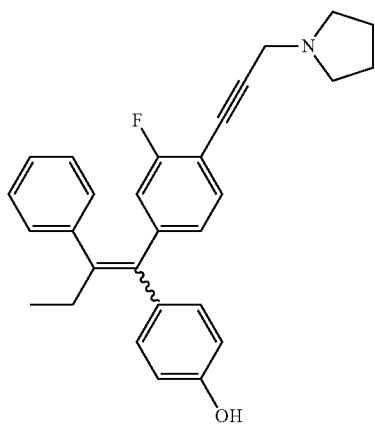 [SMILES: CCC(=C(c1ccc(O)cc1)c1ccc(C#CCN2CCCC2)c(F)c1)c1ccccc1]

Step A: (4-bromo-3-fluorophenyl)(4-(tetrahydro-2H-pyran-2-yloxy)-phenyl)methanone

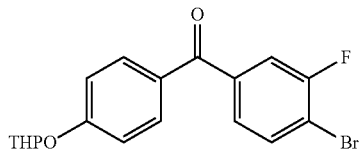

To a solution of 4-bromo-3-fluoro-N-methoxy-N-methylbenzamide (1.00 g, 3.8 mmol) in dry tetrahydrofuran at 0° C. under nitrogen was added dropwise (4-(tetrahydro-2H-pyran-2-yloxy)phenyl)magnesium bromide (7.6 mmol). After addition, the reaction mixture was let warm to room temperature, stirred for 2 h., quenched with saturated ammonium chloride, and extracted with ethyl acetate. The extract was dried over sodium sulfate, concentrated, and purified by column chromatography to give the desired product as a colorless oil (1.10 g, 76% yield).

Step B: (3-fluoro-4-(3-(pyrrolidin-1-yl)prop-1-ynyl)phenyl)(4-(tetrahydro-2H-pyran-2-yloxy)phenyl)methanone

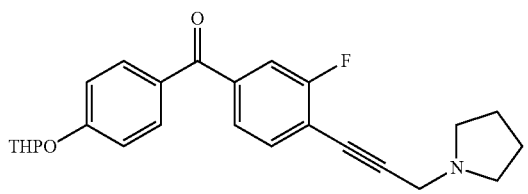

A 100 mL Schlenk flask was charged with (4-bromo-3-fluorophenyl)(4-(tetrahydro-2H-pyran-2-yloxy)phenyl)methanone (1.10 g, 2.90 mmol), tetrakis(tri-phenylphosphine)Palladium(0) (0.34 g, 0.29 mmol, 10 mol %), cuprous iodide (0.11 g, 0.58 mmol, 20 mol %), triethylamine (20 mL), and 1-(prop-2-ynyl)pyrrolidine (0.63 g, 5.80 mmol), and the flask was flushed with nitrogen three times. The mixture was stirred at 80° C. for 2 h. The solvent was evaporated under vacuum and the residue was purified by column chromatography to afford the desired product as a yellow solid (0.43 g, 36.4% yield).

Step C: 4-(1-(3-fluoro-4-(3-(pyrrolidin-1-yl)prop-1-ynyl)phenyl)-2-phenylbut-1-enyl)phenol

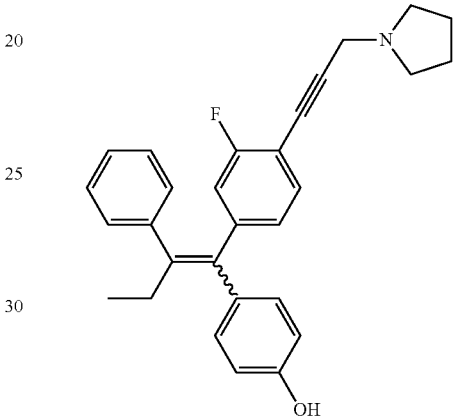

Following general procedure of McMurry reaction as described in example 1, step B, (3-fluoro-4-(3-(pyrrolidin-1-yl)prop-1-ynyl)phenyl)(4-(tetrahydro-2H-pyran-2-yloxy)phenyl)methanone (155 mg, 0.38 mmol) was reacted with propiophenone (152 mg, 1.13 mmol) to give 58 g desired product (36% yield, Z/E=1/1). m/z=426[M+1]$^+$.

Example 35

(Z)-4-(1-(4-hydroxyphenyl)-1-(4-(2-(methylamino)ethoxy)phenyl)but-1-en-2-yl)cyclohexanone

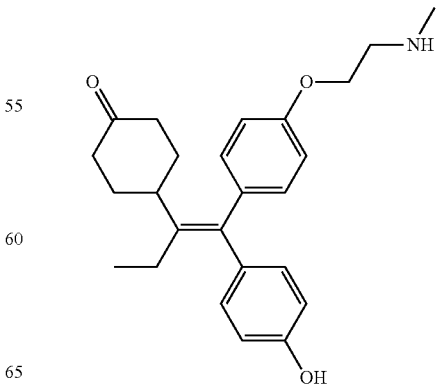

Step A: triethyl 4-oxocyclohexane-1,1,3-tricarboxylate

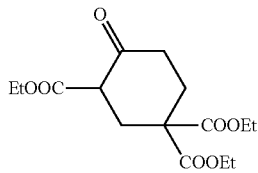 [SMILES: CCOC(=O)C1CC(C(=O)OCC)(C(=O)OCC)CCC1=O]

To a solution of 23.0 g of sodium hydride in 280 mL of anhydrous THF was added a solution of 40.0 g of diethyl malonate in 80 mL of THF at 40° C. over a period of 30 minutes. After addition the mixture was stirred for one hour, the temperature decreased to 15° C., and a solution of 52.5 g ethyl acetate in 80 mL THF, was added. After the mixture was stirred at 45° C. for 30 minutes, 100 mL water was added, and the mixture was extracted with ethyl acetate. The extract was concentrated and purified by silica gel chromatography (EtOAc:petroleum ether=50:11) to give the product of triethyl 4-oxocyclohexane-1,1,3-tricarboxylate (40 g, 38.1% yield).

Step B: 4-oxocyclohexanecarboxylic acid

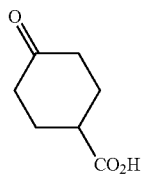

A mixture of triethyl 4-oxocyclohexane-1,1,3-tricarboxylate (31.4 g, 0.1 mol), concentrate hydrochloride acid (30 mL), and water (145 mL) was refluxed overnight, and then extracted with ethyl acetate. The extract was concentrated and purified by silic gel chromatography (CH$_2$Cl$_2$:MeOH=80:1) to give the product of 4-oxocyclohexanecarboxylic acid (4.2 g, 29% yield).

Step C: N-methoxy-N-methyl-4-oxocyclohexanecarboxamide

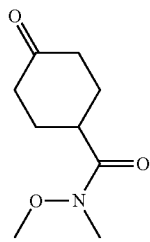

To a solution of 4-oxocyclohexanecarboxylic acid (4.2 g, 0.0293 mol) in CH$_2$Cl$_2$ (20 mL) was added oxalyl chloride (5.2 g, 0.44 mol) slowly, stirred at room temperature for 1 hour and concentrated, then 20 mL CH$_2$Cl$_2$ was added, followed by addition of Et$_3$N (9 g, 0.116 mol) and N,O-dimethylhydroxylamine hydrochloride (3.5 g, 0.0359 mol). The reaction mixture was stirred for 2 hours, and then 100 mL water was added. The mixture was extracted with ethyl acetate. The extract was concentrated and purified by column chromatography to give the desired product (2.1 g, 39% yield).

Step D: N-methoxy-N-methyl-1,4-dioxaspiro[4.5]decane-8-carboxamide

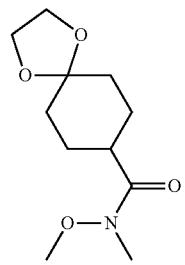 [SMILES: CON(C)C(=O)C1CCC2(CC1)OCCO2]

A mixture of N-methoxy-N-methyl-4-oxocyclohexanecarboxamide (2.1 g, 0.114 mol), glycol (0.9 g, 0.136 mol) and toluenesulfonate (0.1 g, cat) in toluene (30 mL) was refluxed overnight and then concentrated. Water was added, and the mixture was extracted with ethyl acetate. The extract was concentrated and purified by silica gel column chromatography (CH$_2$Cl$_2$:MeOH=100:1) to give the desired product (1 g, 38.4% yield).

Step E: 1-(1,4-dioxaspiro[4.5]decan-8-yl)propan-1-one

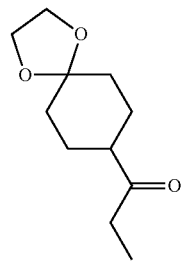

To a solution of N-methoxy-N-methyl-1,4-dioxaspiro[4.5]decane-8-carboxamide (1 g, 0.0043 mol) in anhydrous Et$_2$O (20 mL) was added EtMgBr (9 g, 0.043 mol). The reaction mixture was refluxed overnight, and then 200 mL water was added. The mixture was extracted with ethyl acetate. The extract was concentrated and purified by silica gel column chromatography (CH$_2$Cl$_2$:MeOH=150:1) to give the desired product (0.259 g, 26% yield).

Step F: (Z)-4-(1-(4-(2-chloroethoxy)phenyl)-2-(1,4-dioxaspiro[4.5]decan-8-yl)but-1-enyl)phenol

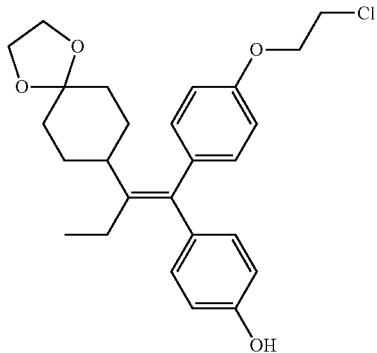 [SMILES: CC/C(=C(\c1ccc(O)cc1)c1ccc(OCCCl)cc1)C1CCC2(CC1)OCCO2]

Following general procedure of McMurry reaction as described in example 1, step B, 1-(1,4-dioxaspiro[4.5]decan-8-yl)propan-1-one (259 mg, 1.3 mmol) was reacted with (4-(2-chloroethoxy)phenyl)(4-hydroxyphenyl)methanone (360 mg, 1.3 mmol) to give 90 mg title compound (Z-isomer, 16% yield) and 110 mg E-isomer (19% yield) as well.

Step G: (Z)-4-(1-(4-(2-(methylamino)ethoxy)phenyl)-2-(1,4-dioxaspiro-[4.5]decan-8-yl)but-1-enyl)phenol

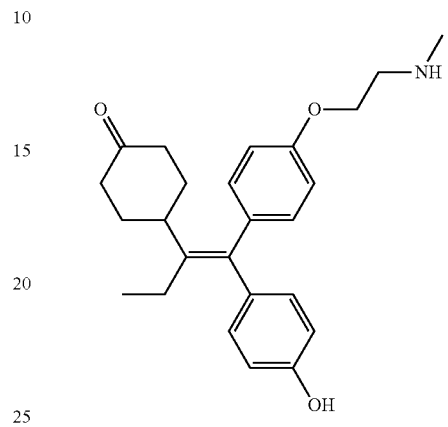

A mixture of (Z)-4-(1-(4-(2-chloroethoxy)phenyl)-2-(1,4-dioxaspiro[4.5]decan-8-yl)but-1-enyl)phenol (90 mg, 0.20 mol), 30% aqueous of CH$_3$NH$_2$ (5 mL), and MeOH (5 mL) was heated at 85° C. in a sealed tube overnight, concentrated, and purified by column chromatography to give the desired product (90 mg).

Step H: (Z)-4-(1-(4-hydroxyphenyl)-1-(4-(2-(methylamino)ethoxy)-phenyl)but-1-en-2-yl)cyclohexanone

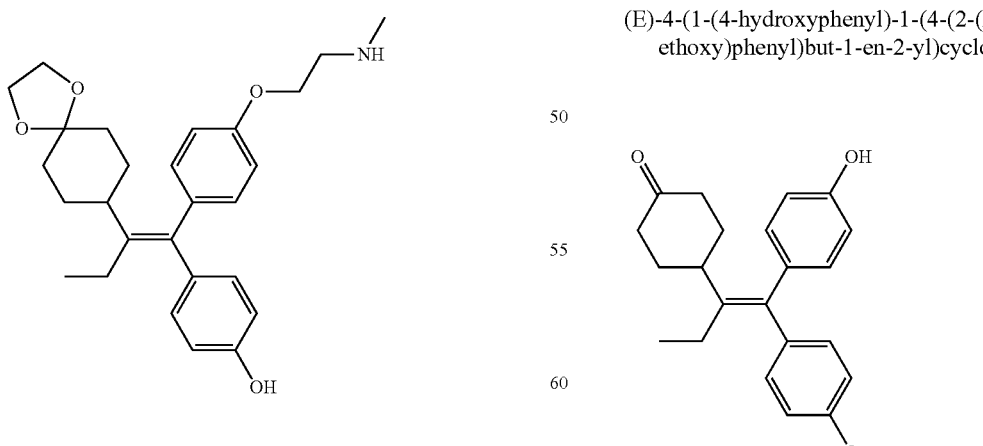

To a solution of (Z)-4-(1-(4-(2-(methylamino)ethoxy)phenyl)-2-(1,4-dioxaspiro[4.5]decan-8-yl)but-1-enyl)phenol (90 mg) in MeOH (10 mL) was added aqueous of HCl (3 M, 1.5 mL), the mixture was stirred at room temperature for 2 hours, 20 mL water was added, pH was adjusted to 7-8 by addition of aqueous NaHCO$_3$, and the mixture was extracted with ethyl acetate. The extract was dried, concentrated, and purified by column chromatography (CH$_2$Cl$_2$:MeOH=150:1) to give the desired product (22 mg, 27.5% yield). m/z=394 [M+1]$^+$.

Example 36

(E)-4-(1-(4-hydroxyphenyl)-1-(4-(2-(methylamino)ethoxy)phenyl)but-1-en-2-yl)cyclohexanone The title compound (32 mg, 39.5%) was obtained in the same way as described in example 35, step F, G & H, from the E-isomer (made from example 35, step F). m/z=394[M+1]⁺.

Example 37

(Z)-4-(1-(4-hydroxyphenyl)-1-(4-(2-(methylamino)ethoxy)phenyl)but-1-en-2-yl)-1-methylpyridin-2(1H)-one

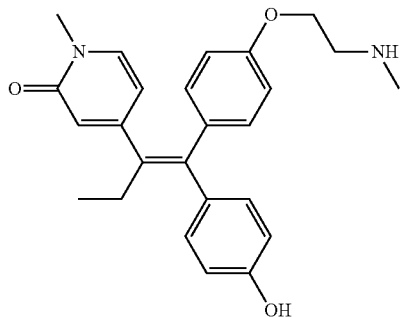 [SMILES: CC/C(=C(\c1ccc(O)cc1)c1ccc(OCCNC)cc1)c1ccn(C)c(=O)c1]

Step A: 2-oxo-1,2-dihydropyridine-4-carboxylic acid

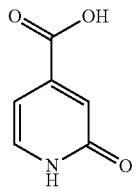

To a stirred solution of 2-chloroisonicotinic acid (15 g, 1.0 eq) in 200 mL water at 0° C. was added KOH (40 g, 7.5 eq). Then the reaction mixture was heated to reflux for 36 h., cooled, and 3 N HCl (aq) was added to pH=1~3. The precipitate was collected by filtration and washed with water to give the product as a white solid (13.1 g, 99% yield). ¹H NMR (400 MHz, DMSO-d⁶) δ 12.80 (brs, 2H), 7.47 (d, J=6.4 Hz, 1H), 6.79 (s, 1H), 6.50 (dd, J=6.8 Hz, 1.6 Hz, 1H).

Step B: methyl 1-methyl-2-oxo-1,2-dihydropyridine-4-carboxylate

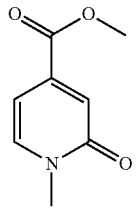

To a solution of 2-oxo-1,2-dihydropyridine-4-carboxylic acid (5 g, 1.0 eq) in 100 mL DMF was added 60% NaH (4.3 g, 3.0 eq) slowly at 0° C., and the mixture was stirred for 30 min at rt. Then CH₃I (15.3 g, 3.0 eq) was added dropwise at 0° C. After the reaction was stirred at rt overnight, the reaction mixture was quenched with water and extracted with EtOAc. The extract was dried, concentrated, and purified by column chromatography to give the desired product (1.5 g, 25% yield). ¹H NMR (400 MHz, CDCl₃) δ 7.34 (d, J=7.2 Hz, 1H), 7.21 (d, J=2.0 Hz, 1H), 6.65 (dd, J=6.8 Hz, 2.0 Hz, 1H), 3.91 (s, 3H), 3.57 (s, 3H).

Step C: 1-methyl-2-oxo-1,2-dihydropyridine-4-carboxylic acid

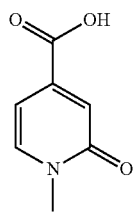

To a stirred solution of methyl 1-methyl-2-oxo-1,2-dihydropyridine-4-carboxylate (1 g, 1.0 eq) in 25 mL MeOH was added a solution of LiOH·H₂O (755 mg, 3.0 eq) in 5 mL water at rt. The reaction was then stirred at rt for 2 h. Then the solvent was removed in vacuo, and water was added to the residue, followed by addition of 3N HCl (aq) to adjust pH=1~3. The product was collected by filtration and washed with water to give the product as white solid (540 mg, 60% yield). ¹H NMR (400 MHz, DMSO-d⁶) δ 13.56 (brs, 1H), 7.80 (d, J=7.2 Hz, 1H), 6.83 (d, J=1.6 Hz, 1H), 6.53 (d, J=6.8 Hz, 1.6 Hz, 1H), 3.46 (s, 3H).

Step D: N-methoxy-N,1-dimethyl-2-oxo-1,2-dihydropyridine-4-carboxamide

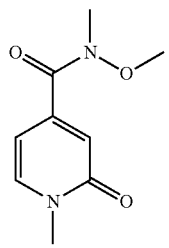

A suspension of 1-methyl-2-oxo-1,2-dihydropyridine-4-carboxylic acid (540 mg, 1.0 eq), EDCI (811 mg, 1.2 eq) and HOBt (572 mg, 1.2 eq) in 20 mL CH₂Cl₂ was stirred at r.t. for 5 min Then N-methoxymethanamine hydrochloride (413 mg, 1.2 eq) and Et₃N (1.1 g, 3.0 eq) were added, and the reaction was stirred at rt overnight. Water was added, and the mixture was extracted with CH₂Cl₂. The extract was dried, concentrated, and purified by column chromatography to give the desired product (555 mg, 80% yield). ¹H NMR (400 MHz, CDCl₃) δ 7.32 (d, J=6.8 Hz, 1H), 6.78 (s, 1H), 6.32 (dd, J=6.8 Hz, 1.6 Hz, 1H), 3.61 (s, 3H), 3.57 (s, 3H), 3.32 (s, 3H).

Step E: 1-methyl-4-propionylpyridin-2(1H)-one

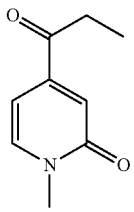

To a solution of N-methoxy-N,1-dimethyl-2-oxo-1,2-dihydropyridine-4-carboxamide (200 mg, 1.0 eq) in 10 mL anhydrous THF was added 3 M EtBrMg (0.7 mL, 2 eq) slowly at 0° C. The reaction was stirred at rt for 1 h., quenched with sat NH$_4$Cl (aq), and extracted with CH$_2$Cl$_2$. The extract was dried, concentrated, and purified by column chromatography to give the desired product (105 mg, 62% yield). $^1$H NMR (400 MHz, CDCl$_3$) δ 7.35 (d, J=6.8 Hz, 1H), 7.06 (d, J=2.0 Hz, 1H), 6.61 (dd, J=6.8 Hz, 1.6 Hz, 1H), 3.57 (s, 3H), 2.89 (q, J=7.2 Hz, 2H), 1.20 (t, J=7.2 Hz, 3H).

Step F: 4-(1-(4-(2-chloroethoxy)phenyl)-1-(4-hydroxyphenyl)but-1-en-2-yl)-1-methylpyridin-2(1H)-one

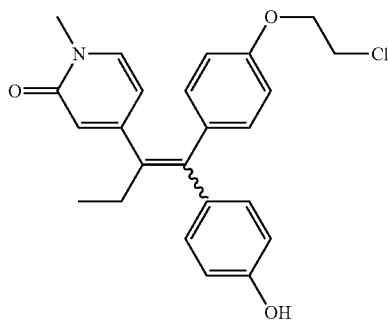 [SMILES: CCC(=C(c1ccc(O)cc1)c1ccc(OCCCl)cc1)c1ccn(C)c(=O)c1]

Following general procedure of McMurry reaction as described in example 1, step B, 1-methyl-4-propionylpyridin-2(1H)-one (105 mg, 1.0 eq) was reacted with (4-(2-chloroethoxy)phenyl)(4-hydroxyphenyl)methanone (352 mg, 2.0 eq) to give the desired product (Z/E=1:1).

Step G: (Z)-4-(1-(4-hydroxyphenyl)-1-(4-(2-(methylamino)ethoxy) phenyl)but-1-en-2-yl)-1-methylpyridin-2(1H)-one

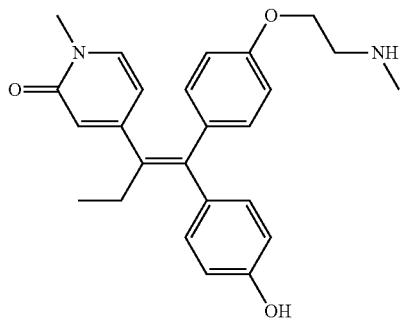 [SMILES: CC/C(=C(\c1ccc(O)cc1)c1ccc(OCCNC)cc1)c1ccn(C)c(=O)c1]

To a stirred solution of 4-(1-(4-(2-chloroethoxy)phenyl)-1-(4-hydroxyphenyl)-but-1-en-2-yl)-1-methylpyridin-2 (1H)-one (30 mg, 1.0 eq) in 10 mL MeOH was added 5 mL 30% CH$_3$NH$_2$ (aq), and the mixture was then heated at 85° C. for 36 h. Then the solvent was removed in vacuo, water was added to the residue and extracted with EtOAc. The extract was dried, concentrated, and purified by column chromatography to give the desired product (3 mg, Z-isomer), E-isomer (2 mg), and Z/E mixture (230 mg, 49% yield) as well. $^1$H NMR (400 MHz, CDCl$_3$) δ 6.96-6.98 (m, 3H), 6.84 (d, J=8.8 Hz, 2H), 6.77 (d, J=8.4 Hz, 2H), 6.57 (d, J=8.8 Hz, 2H), 6.47 (d, J=2.0 Hz, 1H), 5.78 (dd, J=6.8 Hz, 2.0 Hz, 1H), 3.98 (t, J=5.2 Hz, 2H), 3.47 (s, 3H), 2.96 (t, J=5.2 Hz, 2H), 2.52 (s, 3H), 2.36-2.38 (m, 2H), 0.92 (t, J=7.2 Hz, 3H); m/z=405[M+1]$^+$.

Example 38

(E)-4-(1-(4-hydroxyphenyl)-1-(4-(2-(methylamino)ethoxy)phenyl)but-1-en-2-yl)-1-methylpyridin-2(1H)-one

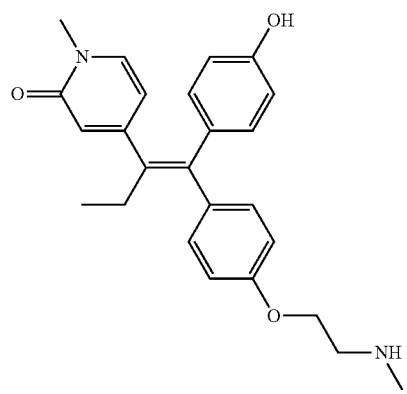 [SMILES: CC/C(=C(/c1ccc(O)cc1)c1ccc(OCCNC)cc1)c1ccn(C)c(=O)c1]

The title compound was obtained by example 37. $^1$H NMR (400 MHz, CDCl$_3$) δ 7.08 (d, J=8.4 Hz, 2H), 6.99 (d, J=6.8 Hz, 1H), 6.84 (d, J=8.8 Hz, 2H), 6.79 (d, J=8.4 Hz, 2H), 6.53 (d, J=8.4 Hz, 2H), 6.51 (d, J=1.6 Hz, 1H), 5.83 (dd, J=7.2 Hz, 2.0 Hz, 1H), 4.08 (t, J=5.2 Hz, 2H), 2.99 (t, J=5.2 Hz, 2H), 2.52 (s, 3H), 2.41 (q, J=7.2 Hz, 2H), 0.97 (t, J=7.6 Hz, 3H); m/z=405[M+1]$^+$.

Example 39

(Z)-4-(1-(6-(2-(methylamino)ethylthio)pyridin-3-yl)-2-phenylbut-1-enyl)phenol

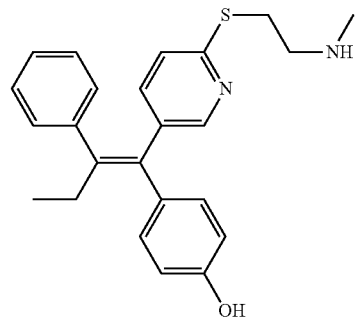 [SMILES: CC/C(=C(\c1ccc(O)cc1)c1ccc(SCCNC)nc1)c1ccccc1]

Step A: 2-(methylamino)ethanol hydrochloride

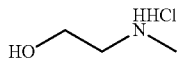

A solution of 2-(methylamino)ethanol (20 g, 1.0 eq) in 50 mL concentrated HCl was stirred at rt for 2 h, and then concentrated to give the product (quant). ¹H NMR (400 MHz, DMSO-d⁶) δ 8.95 (brs, 2H), 3.65 (t, J=5.2 Hz, 2H), 2.94 (t, J=5.6 Hz, 2H), 2.50-2.54 (m, 3H).

Step B: 2-chloro-N-methylethanamine hydrochloride

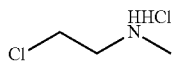

To a stirred solution of 2-(methylamino)ethanol hydrochloride (29.7 g, 1.0 eq) in 150 mL CHCl₃ was added sulfuryl dichloride (41 g, 1.3 eq) dropwise at 0° C. After refluxing for 3 h, the reaction was cooled to rt. Then solvent was removed in vacuo, and the residue was stirred in 100 mL 1:10 CH₂Cl₂/petroleum ether to give a suspension. The product was collected by filtration (28 g, 80% yield). ¹H NMR (400 MHz, DMSO-d⁶) δ 9.24 (brs, 2H), 3.93 (t, J=6.0 Hz, 2H), 3.28 (t, J=6.0 Hz, 2H), 2.56 (s, 3H).

Step C: 2-(methylamino)ethanethiol hydrochloride

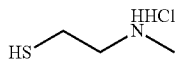

To a stirred solution of 2-chloro-N-methylethanamine hydrochloride (15 g, 1.0 eq) in 150 mL water was added Na₂S₂O₃ (18.5 g, 1.0 eq), and the mixture was then heated to reflux for 48 h. After cooling to rt, the solvent was removed in vacuo. The crude salt was dissolved in 60 mL 6M HCl (aq) and heated at 90° C. for 4 h. The solvent was removed in vacuo and the residue was purified by column chromatography to give the desired product. ¹H NMR (400 MHz, DMSO-d⁶) δ 4.95 (brs, 2H), 2.90 (s, 4H), 2.37 (s, 3H).

Step D: (Z)-4-(1-(6-(2-(methylamino)ethylthio)pyridin-3-yl)-2-phenylbut-1-enyl)phenol

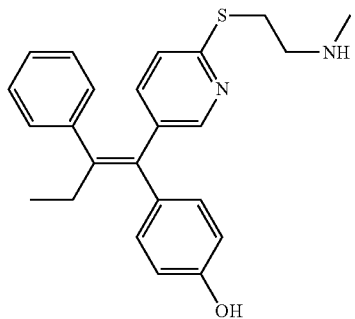 [SMILES: CC/C(=C(\c1ccc(O)cc1)c1ccc(SCCNC)nc1)c1ccccc1]

To a stirred solution of 2-(methylamino)ethanethiol hydrochloride (217 mg, 10 eq) in 20 mL anhydrous THF was added NaH (120 mg, 12 eq) at 0° C. After the mixture was stirred at rt for 1 h, (Z)-4-(1-(6-chloropyridin-3-yl)-2-phenylbut-1-enyl)-phenol (80 mg, 1.0 eq, made from example 1) was added. The reaction mixture was heated under reflux for 48 h, cooled, quenched with sat. NH₄Cl, and extracted with CH₂Cl₂. The extract was dried, concentrated, and purified by column chromatography to give the desired product (75 mg, 81% yield). ¹H NMR (400 MHz, CDCl₃) δ 7.89 (dd, J=2.4 Hz, 0.8 Hz, 1H), 7.13-7.21 (m, 3H), 7.05-7.10 (m, 4H), 6.95 (dd, J=8.4 Hz, 2.4 Hz, 1H), 6.83 (d, J=8.4 Hz, 1H), 6.79 (d, J=8.4 Hz, 2H), 3.23 (t, J=6.4 Hz, 2H), 2.84 (t, J=6.4 Hz, 2H), 2.50 (q, J=7.2 Hz, 2H), 2.41 (s, 3H), 0.93 (t, J=7.2 Hz, 3H); m/z=391[M+1]⁺.

Example 40

(E)-4-(1-(6-(methyl(2-(methylamino)ethyl)amino)pyridin-3-yl)-2-phenylbut-1-enyl)phenol

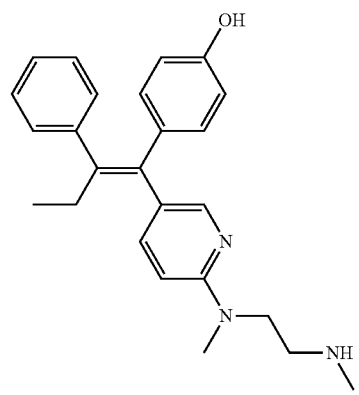 [SMILES: CC/C(=C(/c1ccc(O)cc1)c1ccc(N(C)CCNC)nc1)c1ccccc1]

Following the same procedure as described in example 39, step D, (E)-4-(1-(6-chloropyridin-3-yl)-2-phenylbut-1-enyl)phenol (100 mg, 1.0 eq, made from example 2) was reacted with N,N'-dimethylethane-1,2-diamine (262 mg, 10.0 eq) to give the desired product. ¹H NMR (400 MHz, CDCl₃) δ 8.07 (d, J=2.4 z, 1H), 7.06-7.14 (m, 6H), 6.69 (d, J=8.8 Hz, 2H), 6.49 (d, J=8.8 Hz, 1H), 6.43 (d, J=8.8 Hz, 2H), 3.71 (t, J=6.4 Hz, 2H), 3.08 (s, 3H), 2.88 (t, J=6.4 Hz, 2H), 2.53 (q, J=7.6 Hz, 2H), 2.48 (s, 3H), 0.95 (t, J=7.6 Hz, 3H); m/z=388[M+1]⁺.

Example 41

(Z)-5-(1-(4-hydroxyphenyl)-1-(4-(2-(methylamino)ethoxy)phenyl)but-1-en-2-yl)pyridin-2-ol

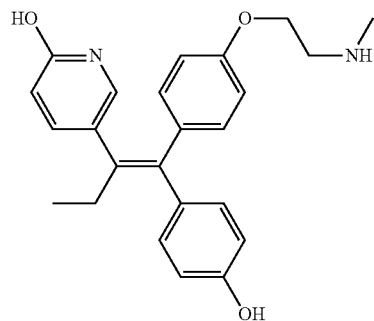 [SMILES: CC/C(=C(\c1ccc(O)cc1)c1ccc(OCCNC)cc1)c1ccc(O)nc1]

Step A:
6-hydroxy-N-methoxy-N-methylnicotinamide

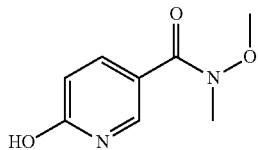

To a stirred solution of 6-hydroxynicotinic acid (5.0 g, 1.0 eq), EDCI (8.3 g, 1.2 eq) and HOBt (5.8 g, 1.2 eq) in 150 mL CH$_2$Cl$_2$ were added N-methoxymethanamine hydrochloride (4.2 g, 1.2 eq) and Et$_3$N (14.5 g, 4.0 eq) at rt, the mixture was stirred at rt overnight, water was added, and the mixture was extracted with CH$_2$Cl$_2$. The extract was dried, concentrated, and purified by column chromatography to give the desired product (3.5 g, 53% yield). $^1$H NMR (400 MHz, DMSO-d$^6$) δ 11.82 (brs, 1H), 7.87 (d, J=2.8 Hz, 1H), 7.72 (dd, J=9.6 Hz, 2.8 Hz, 1H), 6.32 (d, J=9.6 Hz, 1H), 3.59 (s, 3H), 3.20 (s, 3H).

Step B: 1-(6-hydroxypyridin-3-yl)propan-1-one

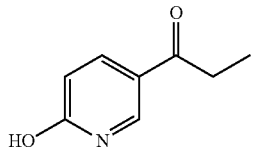

To a solution of 6-hydroxy-N-methoxy-N-methylnicotinamide (800 mg, 1.0 eq) in 20 mL anhydrous THF was added 3 M EtMgBr (6 mL, 4.0 eq) dropwise at 0° C. The reaction mixture was stirred at rt for 2 h., quenched with sat NH$_4$Cl, and extracted with CH$_2$Cl$_2$. The extract was dried, concentrated, and purified by column chromatography to give the desired product (320 mg, 48%). $^1$H NMR (400 MHz, CDCl$_3$) δ 12.13 (brs, 1H), 8.11 (d, J=2.4 Hz, 1H), 8.05 (dd, J=10.0 Hz, 2.8 Hz, 1H), 6.60 (d, J=9.6 Hz, 1H), 2.79 (q, J=7.2 Hz, 2H), 1.22 (t, J=7.2 Hz, 3H).

Step C: (Z)-5-(1-(4-(2-chloroethoxy)phenyl)-1-(4-hydroxyphenyl)-but-1-en-2-yl)pyridin-2-ol

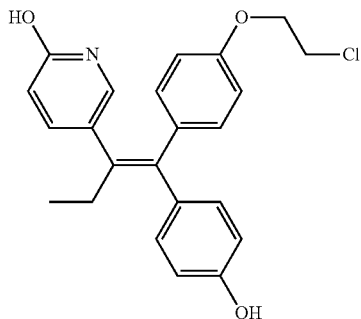 [SMILES: CC/C(=C(\c1ccc(O)cc1)c1ccc(OCCCl)cc1)c1ccc(O)nc1]

Following general procedure of McMurry reaction as described in example 1, step B, 1-(6-hydroxypyridin-3-yl)propan-1-one (0.3 g, 1.0 eq) was reacted with (4-(2-chloroethoxy)phenyl)(4-hydroxyphenyl)methanone (1.37 g, 2.5 eq) to give the desired Z-product (Z and E isomer can be separated via column chromatography).

Step D: (Z)-5-(1-(4-hydroxyphenyl)-1-(4-(2-(methylamino)ethoxy)-phenyl)but-1-en-2-yl)pyridin-2-ol

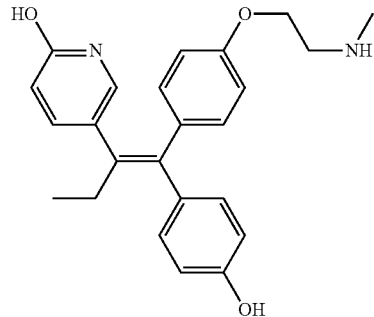 [SMILES: CC/C(=C(\c1ccc(O)cc1)c1ccc(OCCNC)cc1)c1ccc(O)nc1]

Following the same procedure as described in example 11, step D, (Z)-5-(1-(4-(2-chloroethoxy)phenyl)-1-(4-hydroxyphenyl)but-1-en-2-yl)pyridin-2-ol (0.02 g, 1.0 eq) was reacted with MeNH$_2$ (30% wt in water, 10 mL) in MeOH (20 mL) under reflux to give the desired product. $^1$H NMR (400 MHz, DMSO-d$^6$) δ 9.37 (brs, 1H), 7.13 (dd, J=9.2 Hz, 2.8 Hz, 1H), 6.96 (s, 1H), 6.91 (d, J=8.8 Hz, 2H), 6.81 (d, J=8.4 Hz, 2H), 6.71 (d, J=8.4 Hz, 4H), 6.12 (d, J=9.2 Hz, 1H), 3.97 (t, J=5.6 Hz, 2H), 2.93 (t, J=5.6 Hz, 2H), 2.40 (s, 3H), 2.29 (q, J=7.2 Hz, 2H), 0.90 (t, J=7.2 Hz, 3H); m/z=391[M+1]$^+$.

Example 42

6-(1-(4-Hydroxyphenyl)-1-(4-(2-(methylamino)ethoxy)phenyl)but-1-en-2-yl)pyridin-3-ol

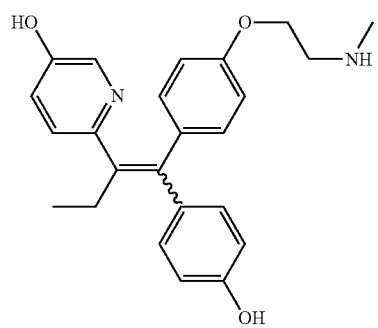 [SMILES: CCC(=C(c1ccc(O)cc1)c1ccc(OCCNC)cc1)c1ccc(O)cn1]

Step A:
5-hydroxy-N-methoxy-N-methylpicolinamide

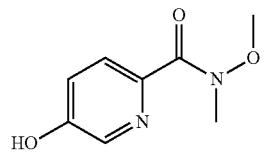

Following the same procedure as described in example 41, step A, 5-hydroxypicolinic acid (6.2 g, 1.0 eq) was reacted with N,O-dimethylhydroxylamine hydrochloride (5.2 g, 1.2 eq) to get the desired product with column chromatography (4.25 g, 52% yield).

Step B: 1-(5-hydroxypyridin-2-yl)propan-1-one

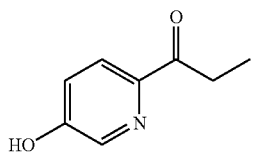

Following the same procedure as described in example 11, step B, 5-hydroxy-N-methoxy-N-methylpicolinamide (0.5 g, 1.0 eq) was reacted with EtMgBr (6.0 mL, 4.0 eq) to get the desired product (0.2 g, 48% yield).

Step C: 6-(1-(4-(2-chloroethoxy)phenyl)-1-(4-hydroxyphenyl)but-en-2-yl)pyridin-3-ol

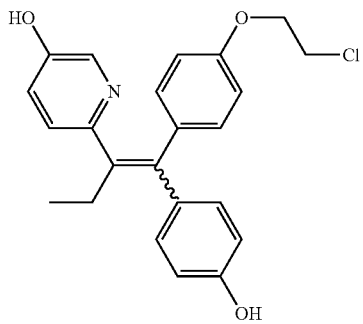 [SMILES: CCC(=C(c1ccc(O)cc1)c1ccc(OCCCl)cc1)c1ccc(O)cn1]

Following general procedure of McMurry reaction as described in example 1, step B, 1-(5-hydroxypyridin-2-yl)propan-1-one (0.15 g, 1.0 eq) was reacted with (4-(2-chloroethoxy)phenyl)(4-hydroxyphenyl)methanone (0.549 g, 2.0 eq) to give the desired product (Z/E=1/1).

Step D: 6-(1-(4-hydroxyphenyl)-1-(4-(2-(methylamino)ethoxy)phenyl)-but-1-en-2-yl)pyridin-3-ol

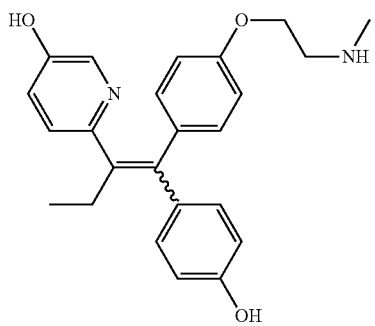 [SMILES: CCC(=C(c1ccc(O)cc1)c1ccc(OCCNC)cc1)c1ccc(O)cn1]

Following the same procedure as described in example 11, step D, 6-(1-(4-(2-chloroethoxy)phenyl)-1-(4-hydroxyphenyl)but-1-en-2-yl)pyridin-3-ol (0.22 g, 1.0 eq) was reacted with MeNH$_2$ (30% wt in water, 10 mL) in MeOH (20 mL) under reflux to give the desired product (Z/E=1/1). $^1$H NMR (400 MHz, DMSO-d$^6$) δ 9.31 (brs, 1H), 8.09 (d, J=2.4 Hz, 1H), 7.08 (d, J=8.0 Hz, 1H), 6.92-6.97 (m, 2H), 6.81 (d, J=8.8 Hz, 1H), 6.75 (d, J=8.4 Hz, 1H), 6.55-6.69 (m, 4H), 6.45 (d, J=8.4 Hz, 1H), 4.06 (t, J=5.2 Hz, 1H), 3.93 (t, J=5.2 Hz, 1H), 2.93 (t, J=5.6 Hz, 1H), 2.85 (t, J=5.6 Hz, 1H), 2.46-2.50 (m, 2H), 2.40 (s, 1.5H), 2.35 (s, 1.5H), 0.83 (t, J=7.2 Hz, 3H); m/z=391[M+1]$^+$.

Example 43

1-(3-(Dimethylamino)propyl)-4-(1-(4-hydroxyphenyl)-2-phenylbut-1-enyl)pyridin-2(1H)-one

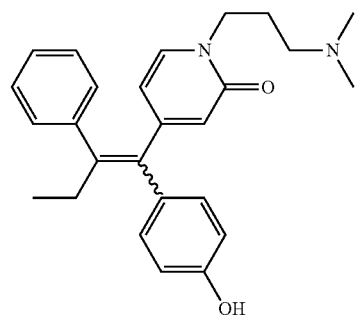 [SMILES: CCC(=C(c1ccc(O)cc1)c1ccn(CCCN(C)C)c(=O)c1)c1ccccc1]

Step A: 3-chloro-N,N-dimethylpropan-1-amine hydrochloride

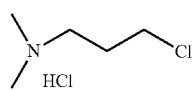

To a stirred solution of 3-(dimethylamino)propan-1-ol (15 g, 1.0 eq) in 150 mL CHCl$_3$ was added sulfuryl dichloride (21 g, 1.2 eq) dropwise at 0° C. The reaction mixture was then heated under reflux for 5 h. After cooling to rt, the solvent was removed in vacuo to give the crude product, which was washed with solution of (CH$_2$Cl$_2$:petroleum ether=1:10, 50 mL) to give the desired product (22 g, 98% yield).

Step B: N-methoxy-N-methyl-2-oxo-1,2-dihydropyridine-4-carboxamide

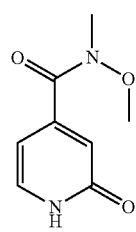

To a suspension of 2-oxo-1,2-dihydropyridine-4-carboxylic acid (8.0 g, 1.0 eq), EDCI (13.2 g, 1.2 eq) and HOBt (9.3 g, 1.2 eq) in 150 mL CH$_2$Cl$_2$ were added N-methoxymethanamine hydrochloride (6.8 g, 1.2 eq) and Et₃N (26.2 g, 4.5 eq). The reaction mixture was stirred at rt overnight, concentrated, and purified by column chromatography to give the desired product (6.3, 60% yield). ¹H NMR (400 MHz, CDCl₃) δ 12.79 (s, 1H), 7.40 (d, J=6.8 Hz, 1H), 6.77 (s, 1H), 6.43 (dd, J=6.8 Hz, 1.6 Hz, 1H), 3.62 (s, 3H), 3.34 (s, 3H).

Step C: 1-(3-(dimethylamino)propyl)-N-methoxy-N-methyl-2-oxo-1,2-dihydropyridine-4-carboxamide

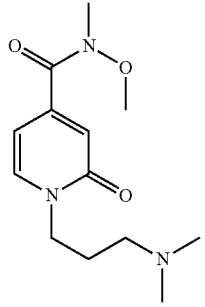 [SMILES: CON(C)C(=O)c1ccn(CCCN(C)C)c(=O)c1]

A stirred mixture of N-methoxy-N-methyl-2-oxo-1,2-dihydropyridine-4-carbox-amide (200 mg, 1.0 eq), 3-chloro-N, N-dimethylpropan-1-amine hydrochloride (350 mg, 2.0 eq) and K₂CO₃ (455 mg, 3.0 eq) in 20 mL acetone was heated under reflux overnight. After cooling to rt, water was added, and the mixture was extracted with CH₂Cl₂. The extract was dried, concentrated, and purified by column chromatography to give the desired product (255 mg, 87% yield). ¹H NMR (400 MHz, CDCl₃) δ 7.40 (d, J=7.2 Hz, 1H), 6.75 (d, J=1.2 Hz, 1H), 6.30 (dd, J=6.8 Hz, 2.0 Hz, 1H), 4.02 (t, J=7.2 Hz, 2H), 3.62 (s, 3H), 3.33 (s, 3H), 2.30 (t, J=6.8 Hz, 2H), 2.23 (s, 6H), 1.93 (t, J=7.2 Hz, 2H).

Step D: 1-(3-(dimethylamino)propyl)-4-(4-(tetrahydro-2H-pyran-2-yloxy)benzoyl)pyridin-2(1H)-one

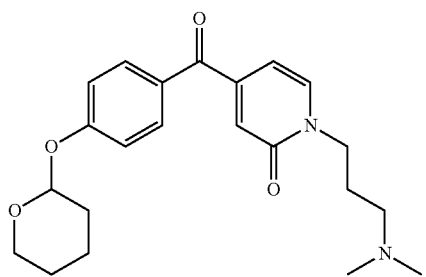 [SMILES: CN(C)CCCn1ccc(C(=O)c2ccc(OC3CCCCO3)cc2)cc1=O]

Mg (440 mg, 3.5 eq) was added to a 3-neck round bottom flask containing 50 mL anhydrous THF, and the mixture was heated to 55° C. Iodine chips (2 grains) were added in one lot followed by 0.1 mL ethyl bromide. 2-(4-Bromophenoxy)-tetrahydro-2H-pyran (4.0 g, 3.0 eq) was dissolved in 30 mL anhydrous THF, and 3 mL of this solution was added at once to the Mg-THF suspension. The reaction was initiated after 30 min and reflux started. the remaining solution of 2-(4-bromophenoxy)-tetrahydro-2H-pyran was added dropwise maintaining the reflux temperature over 5 min. After addition, the reaction mixture was further reflux for 2 h., cooled to rt, 1-(3-(dimethylamino)propyl)-N-methoxy-N-methyl-2-oxo-1,2-dihydro-pyridine-4-carboxamide (1.4 g, 1.0 eq) in 20 mL THF was added dropwise at rt, stirred at rt for 30 min., quenched with sat NH₄Cl (aq), and extracted with EtOAc. The extract was dried, concentrated, and purified by column chromatography to give the desired product (1.6 g, 80% yield). ¹H NMR (400 MHz, CDCl₃) δ 7.85 (d, J=9.2 Hz, 2H), 7.48 (d, J=6.8 Hz, 1H), 7.11 (d, J=9.2 Hz, 2H), 6.75 (d, J=1.6 Hz, 1H), 6.44 (dd, J=6.8 Hz, 2.0 Hz, 1H), 5.55 (t, J=2.8 Hz, 1H), 4.05 (t, J=7.2 Hz, 2H), 3.82-3.88 (m, 1H), 3.62-3.66 (m, 1H), 2.32 (t, J=6.4 Hz, 2H), 2.24 (s, 6H), 1.88-2.08 (m, 5H), 1.62-1.74 (m, 4H).

Step E: 1-(3-(dimethylamino)propyl)-4-(1-(4-hydroxyphenyl)-2-phenyl but-1-enyl)pyridin-2(1H)-one

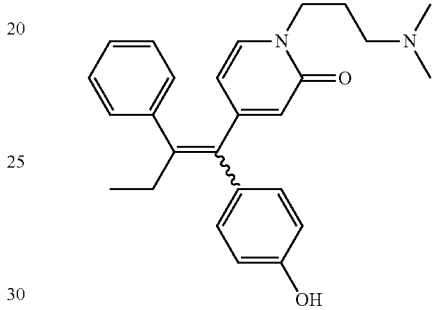

Following general procedure of McMurry reaction as described in example 1, step B, propiophenone (0.838 g, 3.0 eq) was reacted with 1-(3-(dimethylamino) propyl)-4-(4-hydroxybenzoyl)pyridin-2(1H)-one (0.8 g, 1.0 eq) to give the desired product (Z was prepared by preparative HPLC). ¹H NMR (400 MHz, DMSO-d⁶) δ 9.54 (brs, 1H), 7.34 (d, J=6.8 Hz, 1H), 7.17-7.29 (m, 5H), 7.04 (d, J=8.4 Hz, 2H), 6.79 (d, J=8.4 Hz, 2H), 5.83 (d, J=1.6 Hz, 1H), 5.75 (dd, J=6.8 Hz, 1.6 Hz, 1H), 3.75 (t, J=6.8 Hz, 2H), 2.93 (t, J=6.8 Hz, 2H), 2.73 (s, 6H), 2.37 (q, J=7.2 Hz, 2H), 1.86-1.90 (m, 2H), 0.83 (t, J=7.2 Hz, 3H); m/z=403[M+1]⁺.

Example 44

4-(2-(2,3-Dihydrobenzofuran-5-yl)-1-(4-(2-(methylamino)ethoxy)phenyl)but-1-enyl)phenol

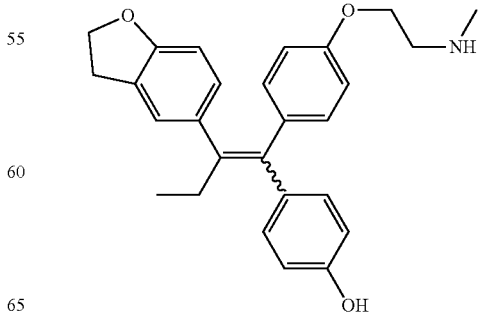

Step A: 1-(2,3-dihydrobenzofuran-5-yl)propan-1-one

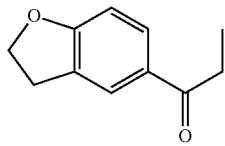

To a stirred solution of 2,3-dihydrobenzohran (10 g, 1.0 eq) in 200 mL CH$_2$Cl$_2$ at 0° C. was added dropwise a solution of propionyl chloride (14 g, 1.8 eq) and AlCl$_3$ (11.1 g, 1.0 eq) in 200 mL CH$_2$Cl$_2$ while maintaining the temperature at 0° C. After addition was complete, the reaction was stirred at rt for 1 h. Then ice water was added to quench the reaction and the mixture was extracted with CH$_2$Cl$_2$. The extract was washed with brine, dried and evaporated in vacuo. Hexane (100 mL) was added to the residue, and cooled to 0° C. and stirred for 30 min, then filtered and washed with cold hexane and dried to give the product as a white solid (11.8 g, 80%). $^1$H NMR (400 MHz, CDCl$_3$) δ 7.86 (s, 1H), 7.81 (d, J=8.4 Hz, 1H), 6.80 (d, J=8.4 Hz, 1H), 4.66 (t, J=8.8 Hz, 2H), 3.25 (t, J=8.8 Hz, 2H), 2.94 (q, J=7.2 Hz, 2H), 1.21 (t, J=7.2 Hz, 3H).

Step B: (4-(2-chloroethoxy)phenyl)(4-methoxyphenyl)methanone

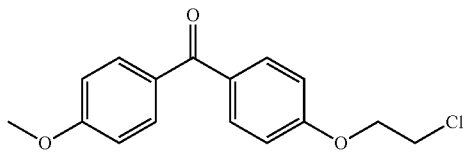 [SMILES: COc1ccc(C(=O)c2ccc(OCCCl)cc2)cc1]

To a stirred solution of 1-(2-chloroethoxy)benzene (48 g, 1.0 eq) in 400 mL CH$_2$Cl$_2$ at 0° C. was added dropwise a solution of 4-methoxybenzoyl chloride (62 g, 1.2 eq) and AlCl$_3$ (49 g, 1.2 eq) in 400 mL CH$_2$Cl$_2$ while maintaining the temperature at 0° C. After the addition, the reaction was stirred at rt for 1 h. Then added ice water to quench the reaction and extracted with CH$_2$Cl$_2$. The extract was washed with brine, dried and evaporated in vacuo. Hexane (500 mL) was added to the residue, cooled to 0° C. and stirred for 30 min, then filtered and washed with cold hexane and dried to give the product as a white solid (85 g, 96%). $^1$H NMR (400 MHz, CDCl$_3$) δ7.79 (dd, J=6.8 Hz, 2.0 Hz, 4H), 6.97 (dd, J=8.8 Hz, 2.0 Hz, 4H), 4.32 (t, J=6.0 Hz, 2H), 3.89 (s, 3H), 3.86 (t, J=6.0 Hz, 2H).

Step C: (4-(2-chloroethoxy)phenyl)(4-hydroxyphenyl)methanone

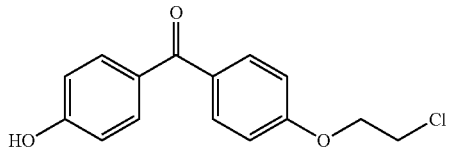

To a stirred solution of (4-(2-chloroethoxy)phenyl)(4-methoxyphenyl)methanone (20 g, 1.0 eq) in 150 mL CH$_2$Cl$_2$ was added BBr$_3$ (52 g, 3.0 eq) dropwise at 0° C. The reaction was stirred for 4 h at rt, then quenched with 500 mL ice water. The suspension was filtered and washed with water to give the product (16 g, 85%). $^1$H NMR (400 MHz, DMSO-d$^6$) δ 10.36 (s, 1H), 7.69 (dd, J=6.8 Hz, 2.0 Hz, 2H), 7.64 (dd, J=6.8 Hz, 2.0 Hz, 2H), 7.11 (dd, J=7.2 Hz, 2.0 Hz, 2H), 6.90 (dd, J=6.8 Hz, 2.0 Hz, 2H), 4.38 (t, J=5.2 Hz, 2H), 4.01 (t, J=5.2 Hz, 2H).

Step D: 4-(1-(4-(2-chloroethoxy)phenyl)-2-(2,3-dihydrobenzofuran-5-yl) but-1-enyl)phenol

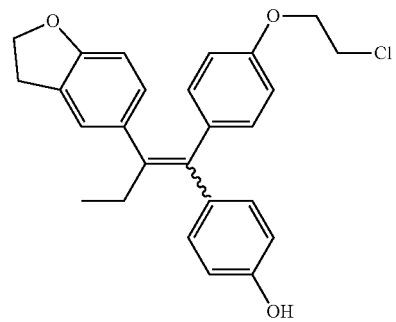 [SMILES: CCC(=C(c1ccc(O)cc1)c1ccc(OCCCl)cc1)c1ccc2c(c1)CCO2]

To a suspension of Zn (595 mg, 6 eq) in 20 mL anhydrous THF was added TiCl$_4$ (0.5 mL, 3 eq) dropwise at 0° C. under nitrogen. The mixture was then heated to reflux for 1 h and cooled to rt. Then a solution of 1-(2,3-dihydrobenzofuran-5-yl)propan-1-one (670 mg, 2.5 eq) and (4-(2-chloroethoxy)phenyl)(4-hydroxyphenyl)methanone (420 mg, 1.0 eq) in 10 mL anhydrous THF was added dropwise at 0° C. After the addition, the reaction mixture was heated to reflux for 1 h, cooled and quenched with sat. NaHCO$_3$, filtered and the filtrate was extracted with EtOAc. The extract was dried and evaporated under reduced pressure. The residue was purified by column chromatography to give the desired product (500 mg, 78%, Z/E=1/1).

Step E: 4-(2-(2,3-dihydrobenzofuran-5-yl)-1-(4-(2-(methylamino)ethoxy)-phenyl)but-1-enyl)phenol

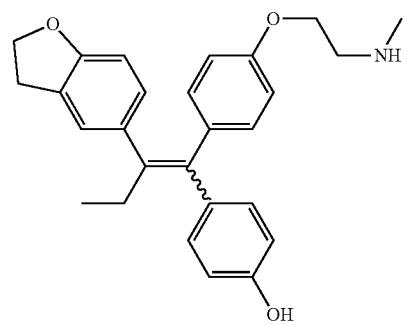 [SMILES: CCC(=C(c1ccc(O)cc1)c1ccc(OCCNC)cc1)c1ccc2c(c1)CCO2]

To a stirred solution of 4-(1-(4-(2-chloroethoxy)phenyl)-2-(2,3-dihydrobenzofuran-5-yl)but-1-enyl)phenol (500 mg, 1.0 eq) in 20 mL MeOH, 10 mL CH$_3$NH$_2$ (aq) was added and heated at 85° C. for 24 h. The solvent was removed in vacuo, water was added to the residue and extracted with EtOAc. The extract was dried, concentrated, and purified by column chromatography to give the desired product (Z/E=1/1). $^1$H NMR (400 MHz, CDCl$_3$) δ 7.10 & 7.01 (d, J=8.8 Hz, 2H), 6.92 (s, 1H), 6.83 (d, J=8.4 Hz, 1H), 6.82 & 6.74 (d, J=8.8 Hz, 2H), 6.79 & 6.75 (d, J=8.8 Hz, 2H), 6.57 (d, J=8.4 Hz, 1H), 6.51 & 6.45 (d, J=8.8 Hz, 2H), 4.51 (t, J=8.4 Hz, 2H), 4.10 & 3.96 (t, J=4.8 Hz, 2H), 3.09 (t, J=8.8 Hz, 2H), 3.01 & 2.93 (t, J=4.8 Hz, 2H), 2.54 & 2.50 (s, 3H), 2.39-2.46 (m, 2H), 0.90-0.94 (m, 3H); m/z=416 [M+1]$^+$.

Example 45

(Z)-4-(2-(1H-indazol-5-yl)-1-(4-(2-(methylamino)ethoxy)phenyl)but-1-enyl)phenol

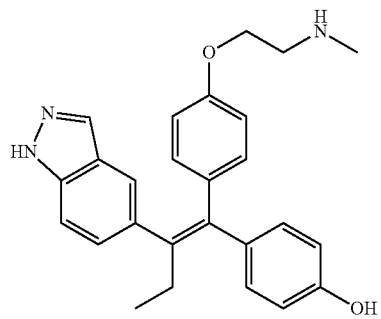 [SMILES: CC/C(=C(\c1ccc(O)cc1)c1ccc(OCCNC)cc1)c1ccc2[nH]ncc2c1]

Step A: methy 4-amino-3-methylbenzoate

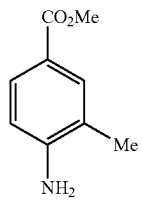

To a stirred solution of methyl 3-methyl-4-nitrobenzoate (50 g, 1.0 eq) in 1 L MeOH were added at rt a solution of NH$_4$Cl (137 g, 10 eq) in 60 mL H$_2$O and Fe power (96 g, 7 eq), and the resulting mixture is heated at reflux for 4 h. The reaction mixture was allowed to cool to rt, filtered, and water was added. The mixture was extracted with EtOAc. The extract was dried, washed with water, and concentrated to give the desired product directly as a white solid (26 g, 62%).

Step B: 4-(methoxycarbonyl)-2-methylbenzenediazonium tetrafluoro-borate

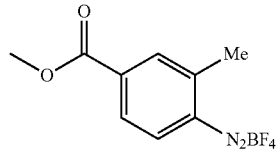

To an aqueous solution of NaNO$_2$ (12.54 g, 2.0 eq) in 75 mL H$_2$O at 0° C. was added dropwise cooled solution of methyl 4-amino-3-methylbenzoate (15 g, 1.0 eq) in HBF$_4$(aq) (40% in water). After addition, the mixture was stirred for 15 min at ambient temperature. The precipitate was filtered, washed with ice-cold water, and dried, to give the desired product as a white solid (16 g, 90%).

Step C: methyl 1H-indazole-5-carboxylate

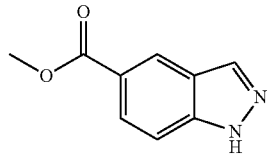

A suspension of BF$_4$ salt (12 g, 1.0 eq), potassium acetated (KOAc, 16.6 g, 2.5 eq) and 18-crown-6 (1.8 g, 0.1 eq) in CHCl$_3$ (200 mL) was stirred at rt for 24 h, and the residue was partitioned between water and EtOAc. The organic layer was washed with brine, dried with Na$_2$SO$_4$ and concentrated to give the desired product (6.5 g, 55%).

Step D: 1H-indazole-5-carboxylic acid

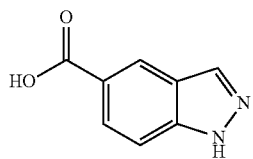 [SMILES: O=C(O)c1ccc2[nH]ncc2c1]

To a stirred solution of methyl 1H-indazole-5-carboxylate (6.5 g, 1.0 eq) in 200 mL MeOH was added a solution of NaOH (4.4 g, 3.0 eq) in 150 mL H$_2$O. The mixture was refluxed for 1 h. The organic solvent was removed in vacuo, the remaining aqueous solution was washed with EtOAc, acidified with 3 N HCl to pH=5-6, and the precipitate was collected by filtration, and washed with water, to give the desired product as a yellow solid (6.2 g, 98%).

Step E: N-methoxy-N-methyl-1H-indazole-5-carboxamide

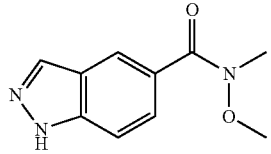

To a mixture of 1H-indazole-5-carboxylic acid (6.0 g, 1.0 eq), N,O-dimethylhydroxylamine hydrochloride (5.4 g, 1.5 eq), HOBt (6.0 g, 1.2 eq) and EDCI (8.5 g, 1.2 eq) in 100 mL CH$_2$Cl$_2$ was added Et$_3$N (15 g, 4.0 eq) dropwise at 0° C. After addition, the mixture was stirred at rt overnight, concentrated, and purified by column chromatography to give the desired product (4.4 g, 58%). ¹H NMR (400 MHz, CDCl₃) δ 10.40 (s, 1H), 8.23 (s, 1H), 8.16 (s, 1H), 7.78 (d, J=8.8 Hz, 1H), 7.52 (d, J=8.8 Hz, 1H), 3.56 (s, 3H), 3.42 (s, 3H).

Step F: 1-(1H-indazol-5-yl)propan-1-one

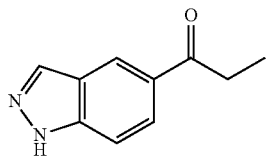

EtMgBr (3 M, 2.0 eq, 6.5 mL) was added to a solution of N-methoxy-N-methyl-1H-indazole-5-carboxamide (2 g, 1.0 eq) in dry THF at 0° C. Once addition was complete, the mixture was stirred for 2 h, and extracted by EtOAc. The extract was dried, concentrated, and purified by column chromatography with petroleum ether:EtOAc=1:1 to give the desired product (1.8 g, 95%). ¹H NMR (400 MHz, CDCl₃) δ 11.20 (s, 1H), 8.45 (s, 1H), 8.22 (s, 1H), 8.06 (d, J=8.0 Hz, 1H), 7.27 (d, J=8.0 Hz, 1H), 3.08 (q, J=7.6 Hz, 2H), 1.28 (t, J=7.6 Hz, 3H).

Step G: 4-(1-(4-(2-chloroethoxy)phenyl)-2-(1H-indazol-5-yl)but-1-enyl)-phenol

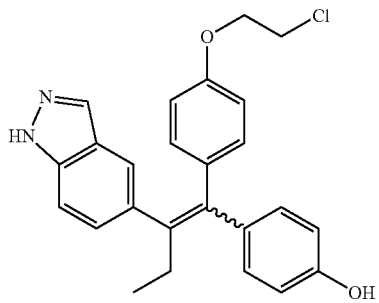 [SMILES: CCC(=C(c1ccc(O)cc1)c1ccc(OCCCl)cc1)c1ccc2[nH]ncc2c1]

To a stirred mixture of Zn power (1.65 g, 10.0 eq) in dry THF at rt under N₂ was slowly added TiCl₄ (4.0 eq, 1.1 mL). The resulting mixture was heated at reflux for 1 h and cooled to rt. A mixture of 1-(1H-indazol-5-yl)propan-1-one (1.3 g, 3.0 eq) and (4-(2-chloroethoxy)phenyl)(4-hydroxyphenyl)methanone (0.7 g, 1.0 eq) in dry THF was added, warmed to 80° C., refluxed for additional 1 h, quenched with Na₂CO₃ (aq), and extracted with EtOAc. The extract was dried, concentrated, and purified by column chromatography to give the title product (0.3 g, 70%, Z/E=1/1). ¹H NMR (400 MHz, CDCl₃) δ 7.96 (s, 1H), 7.53 (s, 1H), 7.18 (d, J=8.8 Hz, 2H), 7.12 (d, J=8.4 Hz, 2H), 6.90 (d, J=8.8 Hz, 2H), 6.71-6.88 (m, 1H), 6.72 (d, J=8.8 Hz, 2H), 6.43 (d, J=8.8 Hz, 1H), 4.35 (t, J=7.2 Hz, 1H), 4.24 (t, J=7.2 Hz, 1H), 3.83 (t, J=6.0 Hz, 1H), 3.70 (t, J=6.0 Hz, 1H), 2.47-2.54 (m, 2H), 0.93 (t, J=7.2 Hz, 3H).

Step H: (Z)-4-(2-(1H-indazol-5-yl)-1-(4-(2-(methylamino)ethoxy)-phenyl)but-1-enyl)phenol

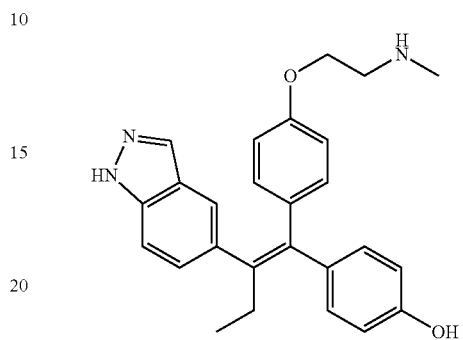

To a stirred solution of 4-(2-(1H-indazol-5-yl)-1-(4-(2-(methylamino)ethoxy)-phenyl)but-1-enyl)phenol (0.3 g, 1.0 eq) in 20 mL MeOH was added 10 mL MeNH₂ (30% wt in water). The mixture was refluxed overnight. The organic solvent was removed in vacuo, and the remaining mixture was extracted with EtOAc. The extract was dried, concentrated, and purified by column chromatography with CH₂Cl₂:MeOH (NH₃)=10:1 to give the desired Z-isomer product (5 mg) and E-isomer product (11 mg) as well. ¹H NMR (400 MHz, DMSO-d⁶) δ 12.92 (s, 1H), 9.11 (s, 1H), 7.93 (s, 1H), 7.50 (s, 1H), 7.30 (d, J=8.8 Hz, 1H), 7.01-7.19 (m, 2H), 6.88 (d, J=9.2 Hz, 2H), 6.60 (d, J=9.2 Hz, 2H), 6.36 (d, J=8.8 Hz, 2H), 4.03 (t, J=6.0 Hz, 2H), 2.85 (t, J=6.0 Hz, 2H), 2.20-2.40 (m, 5H), 0.81 (t, J=6.0 Hz, 3H); m/z=414[M+1]⁺.

Example 46

(E)-4-(2-(1H-indazol-5-yl)-1-(4-(2-(methylamino)ethoxy)phenyl)but-1-enyl)phenol

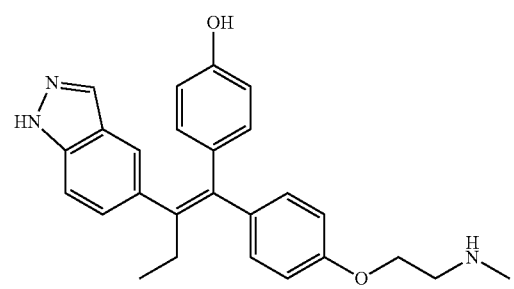 [SMILES: CC/C(=C(/c1ccc(O)cc1)c1ccc(OCCNC)cc1)c1ccc2[nH]ncc2c1]

The title compound (E-isomer, 11 mg) was separated via Example 2. ¹H NMR (400 MHz, DMSO-d⁶) δ 12.92 (s, 1H), 9.41 (s, 1H), 7.92 (s, 1H), 7.51 (s, 1H), 7.30 (d, J=8.4 Hz, 1H), 6.98-7.16 (m, 2H), 6.60-6.80 (m, 4H), 6.36 (d, J=8.8 Hz, 2H), 3.82 (t, J=6.0 Hz, 2H), 2.67 (t, J=6.0 Hz, 2H), 2.40-2.50 (m, 5H), 0.79 (t, J=6.8 Hz, 3H); m/z=414[M+1]⁺.

Example 47

4-(2-(Benzo[d]oxazol-5-yl)-1-(4-(2-(methylamino)ethoxy)phenyl)but-1-enyl)phenol

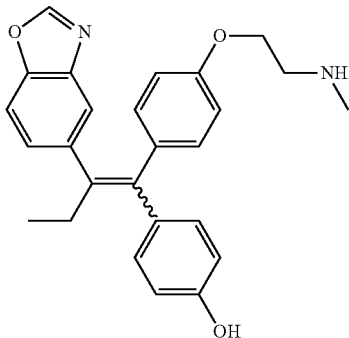 [SMILES: CCC(=C(c1ccc(O)cc1)c1ccc(OCCNC)cc1)c1ccc2ocnc2c1]

Step A: 4-hydroxy-3-nitrobenzoic acid

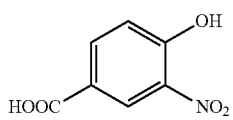

A mixture of 4-chloro-3-nitrobenzoic acid (20 g, 1.0 eq) and NaOH (20.5 g, 2.0 eq) in 100 mL H$_2$O was reflux at 100° C. overnight. After cooling to rt, con. HCl was added to pH=7. The precipitate thus formed was isolated by filtration, washed with cold water, and dried, to give the desired product as a white solid (18.4 g, 98%).

Step B: 3-amino-4-hydroxybenzoic acid

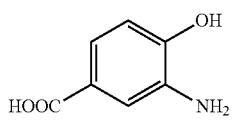

A mixture of 4-hydroxy-3-nitrobenzoic acid (10 g, 1.0 eq) and 2 g Pd/C in 100 mL MeOH was stirred at rt under H$_2$ (1 atm) overnight, and then filtered. The filtrate was concentrated under reduced pressure to afford the desired product (8.0 g, 95%). $^1$H NMR (400 MHz, DMSO-d$^6$) δ 10.00 (brs, 1H), 7.19 (s, 1H), 7.07 (d, J=8.4 Hz, 1H), 6.67 (d, J=8.4 Hz, 1H).

Step C: benzo[d]oxazole-5-carboxylic acid

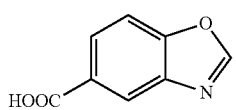 [SMILES: O=C(O)c1ccc2ocnc2c1]

A mixture of 3-amino-4-hydroxybenzoic acid (8.0 g, 1.0 eq) and 60 mL CH(OEt)$_3$ was heated to reflux for 3 h, and then cooled to rt. The remaining CH(OEt)$_3$ was removed under reduced pressure to give the desired product (7.8 g, 92%). $^1$H NMR (400 MHz, DMSO-d$^6$) δ 13.00 (brs, 1H), 8.85 (s, 1H), 8.30 (s, 1H), 8.03 (d, J=8.8 Hz, 1H), 7.85 (d, J=8.8 Hz, 1H).

Step D: N-methoxy-N-methylbenzo[d]oxazole-5-carboxamide

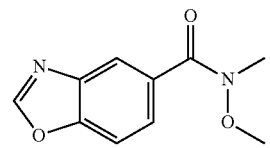

To a solution of benzo[d]oxazole-5-carboxylic acid (7.8 g, 1.0 eq), N,O-dimethylhydroxylamine hydrochloride (7.0 g, 1.5 eq), HOBt (7.76 g, 1.2 eq) and EDCI (11 g, 1.2 eq) in 100 mL CH$_2$Cl$_2$ was added Et$_3$N (19 g, 4.0 eq) dropwise at 0° C. The mixture was then stirred at rt overnight, concentrated, and purified by column chromatography with petroleum ether:EtOAc=1:1 to give the desired product (6.0 g, 51%). $^1$H NMR (400 MHz, CDCl$_3$) δ 8.18 (s, 1H), 8.16 (1H), 7.80 (d, J=8.4 Hz, 1H), 7.62 (d, J=8.0 Hz, 1H), 3.56 (s, 3H), 3.41 (s, 3H).

Step E: 1-(benzo[d]oxazol-5-yl)propan-1-one

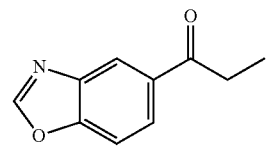

EtMgBr (1 M, 2.0 eq, 58 mL) was added to a solution of N-methoxy-N-methylbenzo[d]oxazole-5-carboxamide (6 g, 1.0 eq) in dry THF at 0° C., Once addition was complete, the mixture was stirred for 2 h. The reaction mixture was quenched with saturated NH$_4$Cl and extracted with EtOAc. The extract was dried, concentrated, and purified by column chromatography with petroleum ether:EtOAc=1:1 to give the desired product (0.6 g, 12%)

Step F: 4-(2-(benzo[d]oxazol-5-yl)-1-(4-(2-chloroethoxy)phenyl)but-1-enyl)phenol

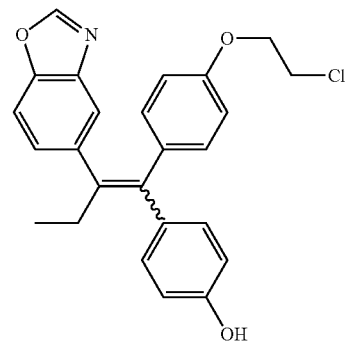 [SMILES: CCC(=C(c1ccc(O)cc1)c1ccc(OCCCl)cc1)c1ccc2ocnc2c1]

According to general procedure of McMurry reaction as example 1, step D described, 1-(benzo[d]oxazol-5-yl)propan-1-one (0.6 g, 1.0 eq) was reacted with (4-(2-chloroethoxy)phenyl)(4-hydroxyphenyl)methanone (1.42 g, 1.5 eq) to give 0.23 g desired product (15%, Z/E=1/1) as a white solid.

Step G: 4-(2-(benzo[d]oxazol-5-yl)-1-(4-(2-(methylamino)ethoxy)phenyl)but-1-enyl)phenol

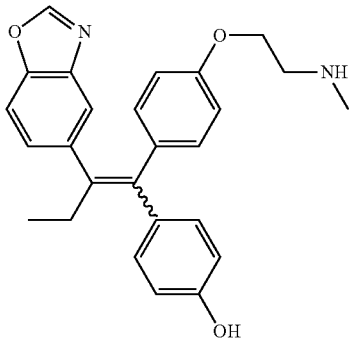 [SMILES: CCC(=C(c1ccc(O)cc1)c1ccc(OCCNC)cc1)c1ccc2ocnc2c1]

According to the same procedure as example 1, step E described, 4-(2-(benzo[d]oxazol-5-yl)-1-(4-(2-chloroethoxy)phenyl)but-1-enyl)phenol (0.1 g, 1.0 eq) was reacted with MeNH₂ (30% wt in water, 10 mL) in MeOH (20 mL) under reflux to give 20 mg desired product (25%, Z/E=1/1). ¹H NMR (400 MHz, CDCl₃) δ 7.08 (d, J=8.4 Hz, 2H), 7.01 (d, J=8.8 Hz, 2H), 6.82 (d, J=8.4 Hz, 2H), 6.68-6.80 (m, 6H), 6.58-6.64 (m, 4H), 6.49-6.55 (m, 4H). 6.46 (d, J=8.8 Hz, 2H), 5.89 (s, 2H), 4.09 (t, J=5.6 Hz, 2H), 3.97 (t, J=5.2 Hz, 2H), 3.00 (t, J=5.2 Hz, 2H), 2.92 (t, J=5.6 Hz, 2H), 2.54 (s, 3H), 2.50 (s, 3H), 2.39-2.49 (m, 4H), 0.80-1.00 (m, 6H).

Example 48

4-(4-Chloro-2-(2,3-dihydrobenzofuran-5-yl)-1-(4-(2-(methylamino)ethoxy)phenyl)but-1-enyl)phenol

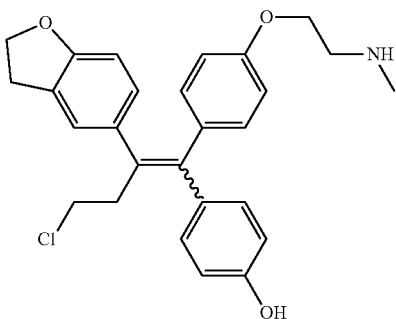 [SMILES: CNCCOc1ccc(C(=C(CCCl)c2ccc3c(c2)CCO3)c2ccc(O)cc2)cc1]

Step A: 3-chloro-1-(2,3-dihydrobenzofuran-5-yl)propan-1-one

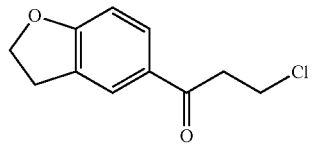 [SMILES: O=C(CCCl)c1ccc2c(c1)CCO2]

To a solution of AlCl₃ (2.22 g, 1.0 eq) in 50 mL CH₂Cl₂ was added 3-chloropropanoyl chloride (2.54 g, 1.2 eq) dropwise. The mixture was stirred at rt for 10 min, then 2,3-dihydrobenzofuran (2.0 g, 1.0 eq) was added. After stirring at rt overnight, the mixture was quenched with cold water and then extracted with CH₂Cl₂. The extract was dried over Na₂SO₄, filtered, the filtrate was concentrated and purified by column chromatography on silica gel to give the desired product (1.5 g, 62%). ¹H NMR (400 MHz, CDCl₃) δ 7.86 (s, 1H), 7.80 (d, J=8.4 Hz, 1H), 6.83 (d, J=8.4 Hz, 1H), 4.68 (t, J=8.8 Hz, 2H), 3.92 (t, J=6.8 Hz, 2H), 3.40 (t, J=8.8 Hz, 2H), 3.26 (t, J=6.8 Hz, 2H).

Step B: (4-hydroxyphenyl)(4-(2-(methylamino)ethoxy)phenyl)methanone

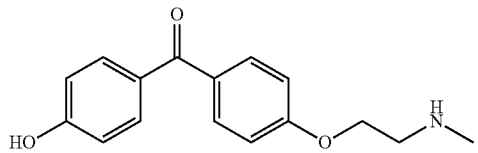 [SMILES: CNCCOc1ccc(C(=O)c2ccc(O)cc2)cc1]

According to the same procedure as example 1, step E described, (4-(2-chloroethoxy)phenyl)(4-hydroxyphenyl)methanone (2.0 g, 1.0 eq) was reacted with MeNH₂ (30% wt in water, 30 mL) in MeOH (30 mL) under reflux to give the desired product (1.4 g, 65%). ¹H NMR (400 MHz, DMSO-d⁶) δ 7.67 (d, J=8.8 Hz, 2H), 7.60 (d, J=8.8 Hz, 2H), 7.06 (d, J=8.8 Hz, 2H), 6.85 (d, J=8.8 Hz, 2H), 4.18 (t, J=5.6 Hz, 2H), 2.89 (t, J=6.0 Hz, 2H), 2.37 (s, 3H).

Step C: 4-(4-chloro-2-(2,3-dihydrobenzofuran-5-yl)-1-(4-(2-(methyl-amino)ethoxy)phenyl)but-1-enyl)phenol

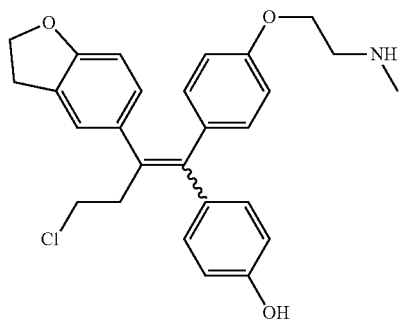 [SMILES: CNCCOc1ccc(C(=C(CCCl)c2ccc3c(c2)CCO3)c2ccc(O)cc2)cc1]

According to general procedure of McMurry reaction as example 1, step D described, 3-chloro-1-(2,3-dihydrobenzofuran-5-yl)propan-1-one (0.85 g, 1.0 eq) was reacted with (4-hydroxyphenyl)(4-(2-(methylamino)ethoxy)phenyl)methanone (1.0 g, 1.0 eq) to give 1.2 g desired product (85%, Z/E=1/1). $^1$H NMR (400 MHz, DMSO-d$^6$) δ 9.87 (s, 1H), 7.02-7.54 (m, 6H), 6.70-6.84 (m, 5H), 4.22 (t, J=8.4 Hz, 2H), 4.03 (t, J=6.0 Hz, 2H), 3.48 (t, J=5.6 Hz, 2H), 2.89-3.05 (m, 4H), 2.42 (s, 3H), 2.13 (t, J=8.4 Hz, 2H); m/z=450[M+1]$^+$.

Example 49

4-(2-(2,3-Dihydrobenzofuran-5-yl)-1-(3-fluoro-4-(2-(methylamino)ethoxy)phenyl)but-1-enyl)phenol

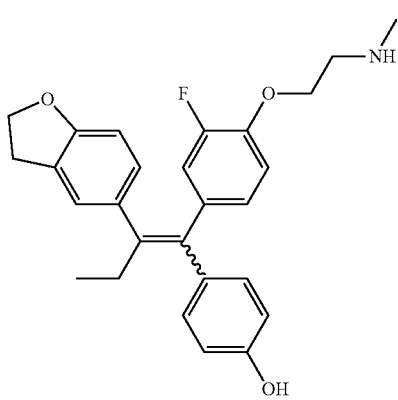 [SMILES: CCC(=C(c1ccc(O)cc1)c1ccc(OCCNC)c(F)c1)c1ccc2c(c1)CCO2]

Step A: 3-fluoro-4-methoxybenzonitrile

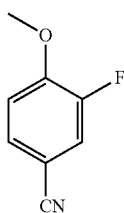

A mixture of 4-bromo-2-fluoro-1-methoxybenzene (30.0 g, 146 mmol) and CuCN (15.6 g, 174 mmol) in dry DMF (45 mL) was stirred at 120° C. overnight. The reaction mixture was cooled to room temperature, diluted with water and extracted with ethyl acetate. The organic layer was washed with water and brine and then dried over sodium sulfate. Solvent evaporation under reduced pressure gave 20.0 g (91%) of the subtitle compound as a yellow solid. $^1$H NMR (400 MHz, CDCl$_3$) δ 7.44 (dd, J=8.8 Hz, 2.0 Hz, 1H), 7.36 (dd, J=10.8 Hz, 2.0 Hz, 1H), 7.02 (dd, J=8.8 Hz, 8.4 Hz, 1H), 3.96 (s, 3H).

Step B: 3-fluoro-4-hydroxybenzonitrile

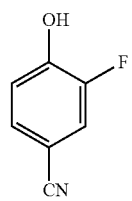

BBr$_3$ (20 mL, 0.211 mol) was added to 3-fluoro-4-methoxybenzonitrile (15.6 g, 0.103 mol) in dichloromethane (100 mL) at 0° C. Stirring was continued under reflux for 3 days under a nitrogen atmosphere. The reaction mixture was quenched with ice water and extracted with dichloromethane. The organic layer was washed with water and brine and then dried over sodium sulfate. Solvent evaporation under reduced pressure gave 13.3 g (94%) of the subtitle compound as a gray solid. $^1$H NMR (400 MHz, CDCl$_3$) δ 7.38-7.42 (m, 2H), 7.09 (dd, J=8.8 Hz, 8.4 Hz, 1H), 5.68 (s, 1H).

Step C: 4-(2-bromoethoxy)-3-fluorobenzonitrile

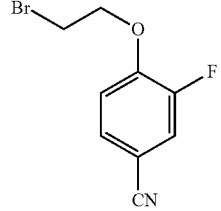 [SMILES: N#Cc1ccc(OCCBr)c(F)c1]

A suspension of 3-fluoro-4-hydroxybenzonitrile (1.2 g, 8.76 mmol), anhydrous K$_2$CO$_3$ (2.43 g, 17.6 mmol) and 1,2-dibromoethane (4.5 mL, 52.0 mmol) in DMF (6 mL) was stirred at 60° C. overnight under a nitrogen atmosphere. The reaction mixture was filtered and extracted with ethyl acetate. The extract was washed with water and brine, dried over sodium sulfate, filtered, concentrated, and purified by column chromatography over silica gel (eluent: petroleum ether/ethyl acetate=5/1) to give 1.52 g (71%) of the subtitle compound as a colorless oil. $^1$H NMR (400 MHz, CDCl$_3$) δ 7.43 (d, J=9.2 Hz, 1H), 7.40 (d, J=12.0 Hz, 1H), 7.03 (dd, J=8.0 Hz, 8.4 Hz, 1H), 4.42 (t, J=6.2 Hz, 2H), 3.68 (t, J=6.2 Hz, 2H).

Step D: 4-(2-bromoethoxy)-3-fluorobenzoic acid

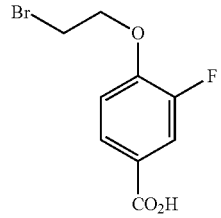 [SMILES: O=C(O)c1ccc(OCCBr)c(F)c1]

4-(2-Bromoethoxy)-3-fluorobenzonitrile (3.78 g, 15.5 mmol) in water (18 mL) and concentrated sulfuric acid (18 mL) was heated at 110° C. for 12 hours. The solution was then cooled to room temperature and neutralized with solid sodium bicarbonate. Acidification with glacial acetic acid gave a white solid precipitate, which was collected by filtration and dissolved in dichloromethane. The resultant solution was dried over sodium sulfate. The dichloromethane solution was then filtered and evaporated to give the product as a beige-colored solid (2.65 g, 65%). $^1$H NMR (400 MHz, DMSO-d$^6$) δ 13.00 (brs, 1H), 7.44 (d, J=8.4 Hz, 1H), 7.69 (d, J=12.0 Hz, 1H), 7.29 (dd, J=8.8 Hz, 8.4 Hz, 1H), 4.48 (t, J=5.2 Hz, 2H), 3.85 (t, J=5.2 Hz, 2H).

Step E: 4-(2-bromoethoxy)-3-fluorobenzoyl chloride

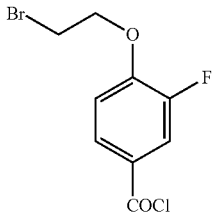 [SMILES: O=C(Cl)c1ccc(OCCBr)c(F)c1]

4-(2-Bromoethoxy)-3-fluorobenzoic acid (1.08 g, 4.1 mmol) and thionyl chloride (10 mL) were refluxed for 7 h. The excess thionyl chloride was removed by repeated evaporation with dry toluene in vacuo, giving 1.07 g (93%) the subtitle compound as a brown oil. $^1$H NMR (400 MHz, CDCl$_3$) δ 7.93 (d, J=8.8 Hz, 1H), 7.86 (d, J=11.2 Hz, 1H), 7.04 (dd, J=8.4 Hz, 8.4 Hz, 1H), 4.46 (t, J=6.4 Hz, 2H), 3.70 (t, J=6.4 Hz, 2H).

Step F: (4-(2-bromoethoxy)-3-fluorophenyl)(4-methoxyphenyl)methanone

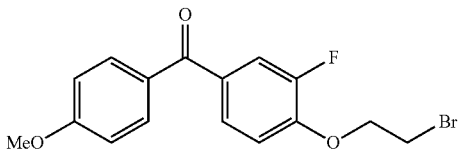 [SMILES: COc1ccc(C(=O)c2ccc(OCCBr)c(F)c2)cc1]

To a solution of 4-(2-bromoethoxy)-3-fluorobenzoyl chloride (1.07 g, 3.80 mmol) and anhydrous AlCl$_3$ (1.01 g, 7.60 mmol) in dry dichloromethane (18 mL) was added anisole (822 mg, 7.60 mmol) in 2 mL dichloromethane at 0° C. After stirring at rt for 6 h, the mixture was poured into 3 N HCl, and extracted with dichloromethane. The extract was washed with sat. NaHCO$_3$ and brine, dried over Na$_2$SO$_4$, filtered, concentrated, and purified by column chromatography over silica gel (eluent: petroleum ether/ethyl acetate=10/1 to 5/1) to give 1.05 g (77%) of the subtitle compound as a white solid. $^1$H NMR (400 MHz, CDCl$_3$) δ 7.79 (d, J=8.8 Hz, 2H), 7.58 (d, J=11.6 Hz, 1H), 7.55 (d, J=8.4 Hz, 1H), 7.03 (dd, J=8.0 Hz, 8.4 Hz, 1H), 6.98 (d, J=9.2 Hz, 2H), 4.44 (t, J=6.4 Hz, 2H), 3.90 (s, 3H), 3.70 (t, J=6.4 Hz, 2H).

Step G: (4-(2-bromoethoxy)-3-fluorophenyl)(4-hydroxyphenyl)methanone

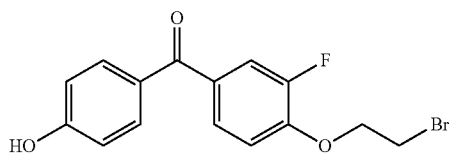

BBr$_3$ (0.5 mL, 5.29 mmol) was added to (4-(2-bromoethoxy)-3-fluorophenyl)(4-methoxyphenyl)methanone (930 mg, 2.63 mmol) in dichloromethane (6 mL) at 0° C. Stirring was continued at room temperature for 2 h under a nitrogen atmosphere. The reaction mixture was quenched with ice water and extracted with dichloromethane. The extract was washed with water and brine, dried over sodium sulfate, filtered, concentrated, and purified by column chromatography over silica gel (eluent: petroleum ether/ethyl acetate=5/1 to 2/1) to give 536 mg (60%) of the subtitle compound as a beige solid. $^1$H NMR (400 MHz, CDCl$_3$) δ 7.74 (d, J=8.4 Hz, 2H), 7.59 (d, J=12.4 Hz, 1H), 7.56 (d, J=8.0 Hz, 1H), 7.03 (dd, J=8.0 Hz, 8.0 Hz, 1H), 6.92 (d, J=8.4 Hz, 2H), 5.88 (s, 1H), 4.44 (t, J=6.4 Hz, 2H), 3.70 (t, J=6.4 Hz, 2H).

Step H: 4-(1-(4-(2-bromoethoxy)-3-fluorophenyl)-2-phenylbut-1-enyl)-phenol

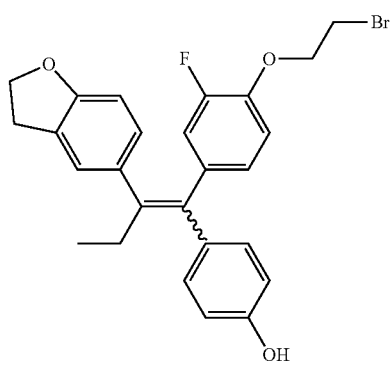 [SMILES: CCC(=C(c1ccc(O)cc1)c1ccc(OCCBr)c(F)c1)c1ccc2c(c1)CCO2]

According to general procedure of McMurry reaction as example 1, step D described, (4-(2-bromoethoxy)-3-fluorophenyl)(4-hydroxyphenyl)methanone (150 mg, 0.442 mmol) was reacted with 1-(2,3-dihydrobenzofuran-5-yl)propan-1-one (94 mg, 0.533 mmol, made by example 1, step A) to give 145 mg desired product (68%, Z/E=1/1) as a gray solid.

Step I: 4-(2-(2,3-dihydrobenzofuran-5-yl)-1-(3-fluoro-4-(2-(methyl-amino)ethoxy)phenyl)but-1-enyl)phenol

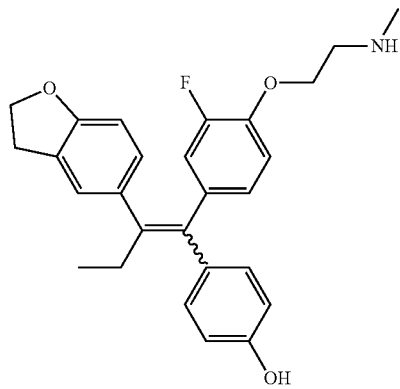 [SMILES: CCC(=C(c1ccc(O)cc1)c1ccc(OCCNC)c(F)c1)c1ccc2c(c1)CCO2]

To a stirred solution of 4-(1-(4-(2-bromoethoxy)-3-fluorophenyl)-2-phenylbut-1-enyl)phenol (111 mg, 0.25 mmol) in 5 mL MeOH was added 1 mL CH$_3$NH$_2$ (30% aq) and heated at 85° C. for 18 h. The organic solvent was removed in vacuo, and the remaining mixture was extracted with EtOAc. The extract was washed with water and brine, dried over Na$_2$SO$_4$, filtered, concentrated, and purified by column chromatography (CH$_2$Cl$_2$/MeOH(NH$_3$ gas)=10/1) to give the desired product (56 mg, 57%, Z/E=5/4) as a beige solid. $^1$H NMR (400 MHz, CDCl$_3$) δ 7.04 & 6.71 (d, J=8.6 Hz, 2H), 6.91-7.00 (m, 2H), 6.82 (m, 1H), 6.79 & 6.49 (d, J=8.8 Hz, 2H), 6.53-6.63 (m, 3H), 4.52 (t, J=8.8 Hz, 2H), 4.27 & 4.14 (t, J=4.8 Hz, 2H), 3.16 & 3.12 (t, J=4.8 Hz, 2H), 3.09 (t, J=8.4 Hz, 2H), 2.65 & 2.60 (s, 3H), 2.41 (q, J=7.4 Hz, 2H), 0.92 (t, J=7.4 Hz, 3H); m/z=434[M+1]$^+$.

Example 50

4-(2-(Benzo[c][1,2,5]thiadiazol-5-yl)-1-(4-(2-(methylamino)ethoxy)phenyl)but-1-enyl)phenol

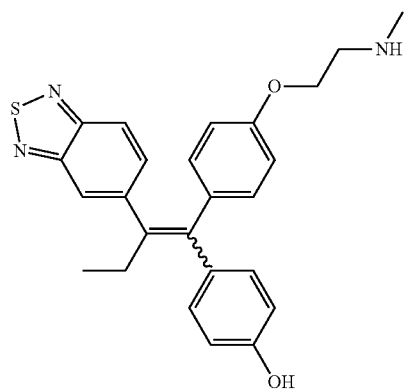 [SMILES: CCC(=C(c1ccc(O)cc1)c1ccc(OCCNC)cc1)c1ccc2nsnc2c1]

Step A: N-(2-nitro-4-propionylphenyl)acetamide

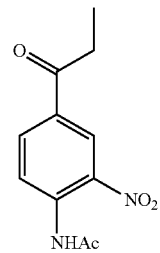 [SMILES: CCC(=O)c1ccc(NC(C)=O)c([N+](=O)[O-])c1]

To a solution of N-(4-propionylphenyl)acetamide (1.91 g, 10 mmol) in 20 mL of concentrated H$_2$SO$_4$ was added 2 mL 98% HNO$_3$ over 10 minutes while maintain the temperature at −10° C. After stirring for 0.5 h, the mixture was poured into 100 mL of cold water. The precipitate was collected by filtration and washed with water to give the crude product (1.18 g, 50%), which was used directly in the next step.

Step B: 1-(4-amino-3-nitrophenyl)propan-1-one

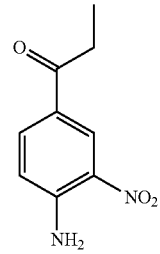

A solution of N-(2-nitro-4-propionylphenyl)acetamide (3.36 g, 10 mmol) in 30 mL 35% HCl was heated to reflux for 1 h and cooled. The pH was adjusted to 7 by adding aqueous ammonia under stirring. The precipitate was collected by filtration to give the desired product as a yellow solid (1.75 g, 90%).

Step C: 1-(3,4-diaminophenyl)propan-1-one

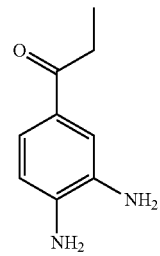

To a solution of 1-(4-amino-3-nitrophenyl)propan-1-one (1.94 g, 10 mmol) in 50 mL of methanol was added 0.5 g 10% Pd/C and the mixture was hydrogenated under H$_2$ (1 atm) at rt for 1 h. The mixture was filtered and the filtrated was concentrated to give the desired product (1.48 g, 90%).

Step D:
1-(benzo[c][1,2,5]thiadiazol-5-yl)propan-1-one

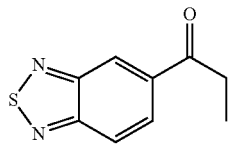

To a solution of aniline (1.86 g, 20 mmol) in 50 mL of toluene was added SOCl$_2$ (2.6 g, 22 mmol) dropwise at 0° C. and the mixture was then refluxed for 2 h. After cooling to rt, 1-(3,4-diaminophenyl)propan-1-one (1.65 g, 10 mmol) was added. The mixture was refluxed for 2 h, cooled, concentrated, and purified by flash chromatography to give the desired product (960 mg, 50%) as a yellow solid. $^1$H NMR (400 MHz, CDCl$_3$) δ 8.62 (s, 1H), 8.21 (d, J=9.2 Hz, 1H), 8.06 (d, J=9.2 Hz, 1H), 3.15 (q, J=7.2 Hz, 2H), 1.30 (t, J=7.2 Hz, 3H).

Step E: 4-(2-(benzo[c][1,2,5]thiadiazol-5-yl)-1-(4-(2-chloroethoxy)-phenyl)but-1-enyl)phenol

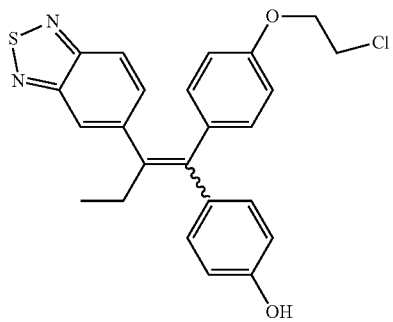 [SMILES: CCC(=C(c1ccc(O)cc1)c1ccc(OCCCl)cc1)c1ccc2nsnc2c1]

According to general procedure of McMurry reaction as example 1, step D described, 1-(benzo[c][1,2,5]thiadiazol-5-yl)propan-1-one (552 mg, 2 mmol) was reacted with (4-(2-chloroethoxy)phenyl)(4-hydroxyphenyl)methanone (384 mg, 2 mmol) to give the desired product (83 mg, 10%, Z/E=1/1).

Step F: 4-(2-(benzo[c][1,2,5]thiadiazol-5-yl)-1-(4-(2-(methylamino)-ethoxy)phenyl)but-1-enyl)phenol

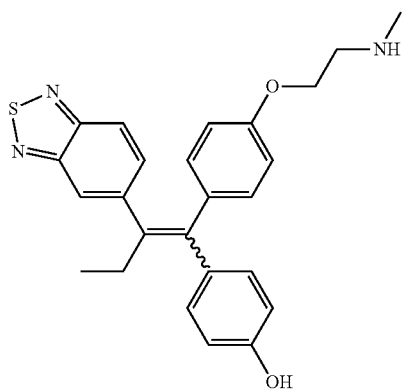 [SMILES: CCC(=C(c1ccc(O)cc1)c1ccc(OCCNC)cc1)c1ccc2nsnc2c1]

To a stirred solution of 4-(2-(benzo[c][1,2,5]thiadiazol-5-yl)-1-(4-(2-chloro-ethoxy)phenyl)but-1-enyl)phenol (83 mg) in 10 mL MeOH was added 3 mL CH$_3$NH$_2$ (30% aq.) and heated at 85° C. for 15 h. The organic solvent was removed in vacuo, and the remaining mixture was extracted with EtOAc. The extract was washed with water and brine, dried over Na$_2$SO$_4$, filtered, concentrated, and purified by column chromatography (CH$_2$Cl$_2$/MeOH(NH$_3$ gas)=50/1) to give the desired product (11 mg, Z/E=1/1) as a yellow solid. $^1$H NMR (400 MHz, CDCl$_3$) δ 7.81 (s, 1H), 7.68 (d, J=9.2 Hz, 1H), 7.15 & 7.06 (d, J=8.4 Hz, 2H), 6.86 (d, J=8.8 Hz, 1H), 6.79 (d, J=8.4 Hz, 2H), 6.78 & 6.72 (d, J=8.6 Hz, 2H), 6.48 & 6.42 (d, J=8.6 Hz, 2H), 4.12 & 3.92 (t, J=4.8 Hz, 2H), 3.03 & 2.91 (t, J=4.8 Hz, 2H), 2.60 (q, J=7.2 Hz, 2H), 2.55 & 2.47 (s, 3H), 0.97 (t, J=7.2 Hz, 3H); m/z=432[M+1]$^+$.

Example 51

(Z)-4-(2-(1-methyl-1H-benzo[d]imidazol-5-yl)-1-(4-(2-(methylamino)ethoxy)phenyl)but-1-enyl)phenol

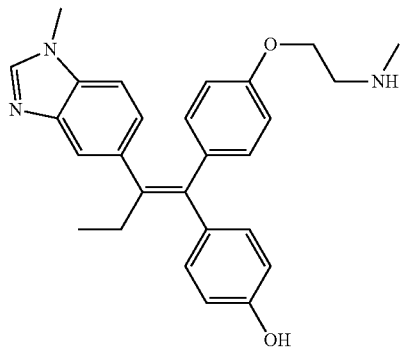 [SMILES: CC/C(=C(\c1ccc(O)cc1)c1ccc(OCCNC)cc1)c1ccc2c(c1)ncn2C]

Step A: 4-(methylamino)-3-nitrobenzoic acid

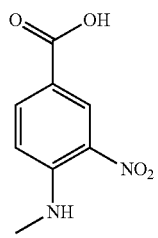

A solution of 4-chloro-3-nitrobenzoic acid (30 g, 1.0 eq) in 200 mL CH$_3$NH$_2$ (aq) was stirred at 100° C. for 14 h, cooled, and concentrated in vacuo. The residue was poured into 200 mL 2N HCl (aq) at ° C. The suspension was filtered and washed with water to give the product as yellow solid (quant). $^1$H NMR (400 MHz, DMSO-d$^6$) δ 8.58 (d, J=2.0 Hz, 1H), 8.51 (d, J=5.2 Hz, 1H), 7.95 (dd, J=9.2 Hz, 2.0 Hz, 1H), 7.02 (d, J=9.2 Hz, 1H), 2.98 (s, 3H).

Step B: 3-amino-4-(methylamino)benzoic acid

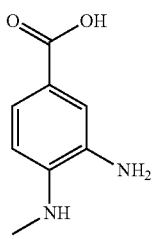

A mixture of 4-(methylamino)-3-nitrobenzoic acid (29 g, 1.0 eq) and Pd/C (5 g, 10%) in 300 mL MeOH was stirred at rt under hydrogen for 48 h and filtered. The filtrate was concentrated in vacuo to give the product (9 g, 36.5%). $^1$H NMR (400 MHz, DMSO-d$^6$) δ 7.21 (dd, J=8.4 Hz, 2.0 Hz, 1H), 7.14 (d, J=2.0 Hz, 1H), 6.37 (d, J=8.4 Hz, 1H), 5.28 (brs, 1H), 4.60 (brs, 2H), 2.76 (s, 3H).

Step C:
1-methyl-1H-benzo[d]imidazole-5-carboxylic acid

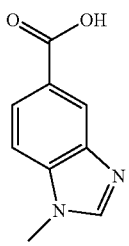

To a stirred solution of 3-amino-4-(methylamino)benzoic acid (9 g, 1.0 eq) in 50 mL water, was added 50 mL formic acid and heated at 85° C. overnight. The mixture was cooled, concentrated in vacuo, and dissolved in water. Then 2N HCl was added to adjust pH to 1-3. The suspension was filtered and washed with water to give the product (9.7 g, 84%). $^1$H NMR (400 MHz, DMSO-d$^6$) δ 9.48 (s, 1H), 8.37 (s, 1H), 8.12 (d, J=8.8 Hz, 1H), 8.00 (d, J=8.8 Hz, 1H), 4.06 (s, 3H).

Step D: N-methoxy-N,1-dimethyl-1H-benzo[d]imidazole-5-carboxamide

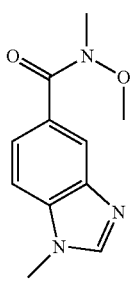

A suspension of 1-methyl-1H-benzo[d]imidazole-5-carboxylic acid (9.7 g, 1.0 eq), EDCI (10.5 g, 1.2 eq), and HOBt (7.4 g, 1.2 eq) in 150 mL CH$_2$Cl$_2$ was stirred at rt for 5 min, and then N-methoxymethanamine hydrochloride (6.7 g, 1.5 eq) and Et$_3$N (18.5 g, 4.0 eq) were added. The reaction mixture was stirred at rt overnight. Water was added and extracted with CH$_2$Cl$_2$. The extract was dried, concentrated, and purified by column chromatography to give the desired product (9.5 g, 80%). $^1$H NMR (400 MHz, CDCl$_3$) δ 8.20 (d, J=1.2 Hz, 1H), 7.93 (s, 1H), 7.72 (dd, J=8.8 Hz, 1.6 Hz, 1H), 7.40 (dd, J=8.4 Hz, 0.8 Hz, 1H), 3.87 (s, 3H), 3.57 (s, 3H), 3.40 (s, 3H).

Step E:
1-(1-methyl-1H-benzo[d]imidazol-5-yl)propan-1-one

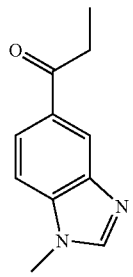

To a solution of N-methoxy-N,1-dimethyl-1H-benzo[d]imidazole-5-carboxamide (900 mg, 1.0 eq) in 30 mL anhydrous THF was added 3 M EtBrMg (9 mL, 6.0 eq) slowly at 0° C. The reaction was stirred at rt overnight, quenched with sat NH$_4$Cl (aq), and extracted with CH$_2$Cl$_2$. The extract was dried, concentrated, and purified by column chromatography to give the desired product (730 mg, 94%). $^1$H NMR (400 MHz, CDCl$_3$) δ 8.44 (s, 1H), 8.04 (J=8.4 Hz, 1.6 Hz, 1H), 7.95 (s, 1H), 7.43 (d, J=8.4 Hz, 1H), 3.89 (s, 3H), 3.10 (q, J=7.2 Hz, 2H), 1.27 (t, J=7.2 Hz, 3H).

Step F: (Z)-4-(1-(4-(2-chloroethoxy)phenyl)-2-(1-methyl-1H-benzo[d]-imidazol-5-yl)but-1-enyl)phenol

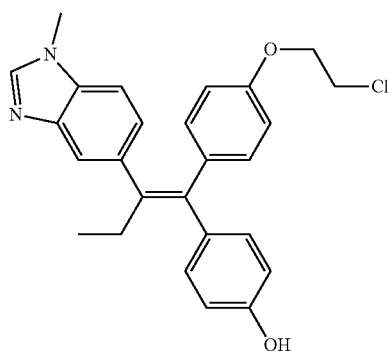 [SMILES: CC/C(=C(\c1ccc(O)cc1)c1ccc(OCCCl)cc1)c1ccc2c(c1)ncn2C]

According to general procedure of McMurry reaction as example 1, step D described, 1-(1-methyl-1H-benzo[d]imidazol-5-yl)propan-1-one (730 mg, 2.2 eq) was reacted with (4-(2-chloroethoxy)phenyl)(4-hydroxyphenyl)methanone (500 mg, 1.0 eq) to give the separated (Z)-isomer and (E)-isomer of the product. (Z)-isomer: $^1$H NMR (400 MHz, CDCl$_3$) δ 7.81 (s, 1H), 7.62 (s, 1H), 7.11-7.15 (m, 3H), 7.01 (dd, J=8.4 Hz, 1.2 Hz, 1H), 6.83 (dd, J=6.8 Hz, 2.0 Hz, 2H), 6.79 (dd, J=6.8 Hz, 2.0 Hz, 2H), 6.49 (dd, J=6.8 Hz, 2.0 Hz, 2H), 4.05 (t, J=5.6 Hz, 2H), 3.79 (s, 3H), 3.69 (t, J=6.0 Hz, 2H), 2.53 (q, J=7.2 Hz, 2H), 0.91 (t, J=7.2 Hz, 3H).

Step G: (Z)-4-(2-(1-methyl-1H-benzo[d]imidazol-5-yl)-1-(4-(2-(methyl-amino)ethoxy)phenyl)but-1-enyl)phenol

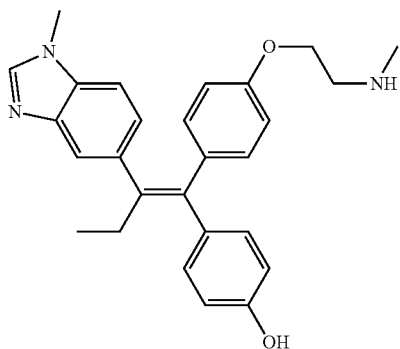 [SMILES: CC/C(=C(\c1ccc(O)cc1)c1ccc(OCCNC)cc1)c1ccc2c(c1)ncn2C]

To a stirred solution of (Z)-4-(1-(4-(2-chloroethoxy)phenyl)-2-(1-methyl-1H-benzo[d]imidazol-5-yl)but-1-enyl)phenol (20 mg, 1.0 eq) in 10 mL MeOH was added 5 mL CH$_3$NH$_2$ (aq) and heated at 85° C. for 72 h. The organic solvent was removed in vacuo, water was added to the residue, and extracted with EtOAc. The extract was dried, concentrated, and purified by column chromatography to give the desired (Z)-product. $^1$H NMR (400 MHz, CDCl$_3$) δ 7.80 (s, 1H), 7.60 (s, 1H), 7.13 (d, J=8.4 Hz, 1H), 7.08 (d, J=8.4 Hz, 2H), 7.01 (d, J=9.2 Hz, 1H), 6.80 (d, J=8.4 Hz, 2H), 6.75 (d, J=8.8 Hz, 2H), 6.45 (d, J=8.4 Hz, 2H), 3.89 (t, J=5.2 Hz, 2H), 3.80 (s, 3H), 2.88 (t, J=5.2 Hz, 2H), 2.52 (q, J=7.2 Hz, 2H), 2.46 (s, 3H), 0.88 (t, J=7.2 Hz, 3H); m/z=428[M+1]$^+$.

Example 52

(E)-4-(2-(1-methyl-1H-benzo[d]imidazol-5-yl)-1-(4-(2-(methylamino)ethoxy)phenyl)but-1-enyl)phenol

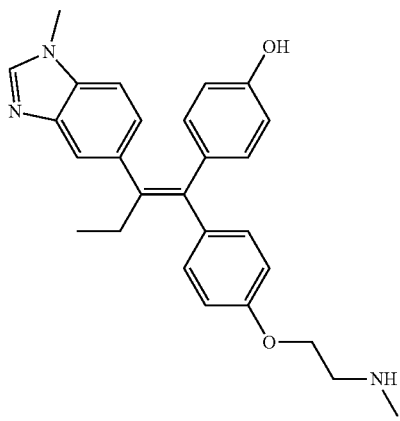 [SMILES: CC/C(=C(/c1ccc(O)cc1)c1ccc(OCCNC)cc1)c1ccc2c(c1)ncn2C]

According to the same procedure as example 1, step E described, (E)-4-(1-(4-(2-chloroethoxy)phenyl)-2-(1-methyl-1H-benzo[d]imidazol-5-yl)but-1-enyl)phenol (made by example 8, step F) was reacted with MeNH$_2$ (30% wt in water) in MeOH under reflux to give the desired (E)-product. $^1$H NMR (400 MHz, CDCl$_3$) δ 7.78 (s, 1H), 7.63 (s, 1H), 7.18 (d, J=8.8 Hz, 2H), 7.13 (d, J=8.4 Hz, 1H), 7.01 (dd, J=8.4 Hz, 1.2 Hz, 1H), 6.88 (d, J=8.8 Hz, 2H), 6.72 (d, J=8.4 Hz, 2H), 6.40 (d, J=8.4 Hz, 2H), 4.10 (t, J=5.2 Hz, 2H), 3.77 (s, 3H), 2.99 (t, J=5.2 Hz, 2H), 2.50-2.55 (m, 5H), 0.91 (t, J=7.2 Hz, 3H); m/z=428[M+1]$^+$.

Example 53

4-(2-(Benzofuran-5-yl)-1-(4-(2-(methylamino)ethoxy)phenyl)but-1-enyl)phenol

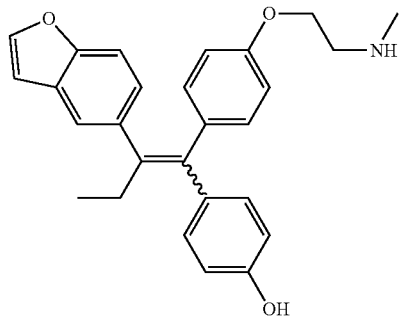 [SMILES: CCC(=C(c1ccc(O)cc1)c1ccc(OCCNC)cc1)c1ccc2occc2c1]

Step A: 1-(benzofuran-5-yl)propan-1-one

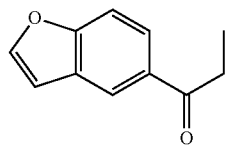

A solution of 1-(2,3-dihydrobenzofuran-5-yl)propan-1-one (40 g, 1.0 eq) and 4,5-dichloro-3,6-dioxocyclohexa-1,4-diene-1,2-dicarbonitrile (62 g, 1.2 eq) in 400 mL anhydrous 1,4-dioxane was refluxed overnight, cooled, quenched with sat NaHCO$_3$ (aq), and extracted with EtOAc. The extract was washed with brine, dried, concentrated, and purified by column chromatography to give the desired product (10.3 g, 26%). $^1$H NMR (400 MHz, CDCl$_3$) δ 8.27 (d, J=2.0 Hz, 1H), 7.98 (dd, J=8.8 Hz, 2.0 Hz, 1H), 7.69 (d, J=2.0 Hz, 1H), 7.54 (d, J=8.4 Hz, 1H), 6.86 (d, J=2.0 Hz, 1H), 3.07 (q, J=7.2 Hz, 2H), 1.26 (t, J=7.2 Hz, 3H).

123

Step B: 4-(2-(benzofuran-5-yl)-1-(4-(2-chloroethoxy)phenyl)but-1-enyl)phenol

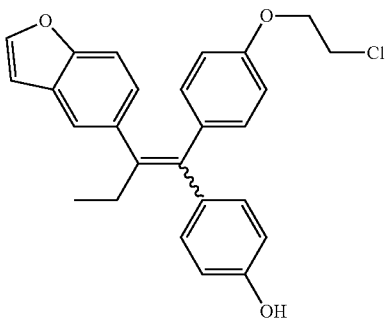 [SMILES: CCC(=C(c1ccc(O)cc1)c1ccc(OCCCl)cc1)c1ccc2occc2c1]

According to general procedure of McMurry reaction as example 1, step D described, 1-(benzofuran-5-yl)propan-1-one (250 mg, 1.0 eq) was reacted with (4-(2-chloroethoxy)phenyl)(4-hydroxyphenyl)methanone (794 mg, 2.0 eq) to give 480 mg desired product (80%, Z/E=1/1).

Step C: 4-(2-(benzofuran-5-yl)-1-(4-(2-(methylamino)ethoxy)phenyl)-but-1-enyl)phenol

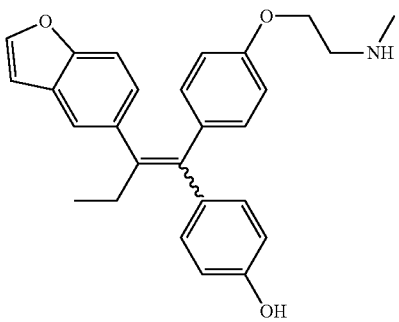 [SMILES: CCC(=C(c1ccc(O)cc1)c1ccc(OCCNC)cc1)c1ccc2occc2c1]

To a stirred solution of 4-(2-(benzofuran-5-yl)-1-(4-(2-chloroethoxy)phenyl) but-1-enyl)phenol (480 mg, 1.0 eq) in 15 mL MeOH was added 5 mL CH$_3$NH$_2$ (aq) and the mixture was heated at 85° C. for 48 h. The organic solvent was removed in vacuo, water was added to the residue and extracted with EtOAc. The extract was dried, concentrated, and purified by column chromatography to give the desired product (230 mg, 49%, Z/E=1/1). $^1$H NMR (400 MHz, CDCl$_3$) δ 7.55 (d, J=2.0 Hz, 1H), 7.36 (s, 1H), 7.27 (d, J=8.8 Hz, 1H), 7.15 (d, J=8.8 Hz, 1H), 7.08 (d, J=8.8 Hz, 1H), 7.01 (d, J=8.8 Hz, 1H), 6.87 (d, J=8.8 Hz, 1H), 6.78 (d, J=8.4 Hz, 1H), 6.74 (d, J=8.8 Hz, 1H), 6.69 (d, J=8.8 Hz, 1H), 6.65 (d, J=2.0 Hz, 1H), 6.47 (d, J=8.8 Hz, 1H), 6.41 (d, J=8.4 Hz, 1H), 4.11 (t, J=4.8 Hz, 1H), 3.92 (t, J=4.8 Hz, 1H), 3.01 (t, J=5.2 Hz, 1H), 2.89 (t, J=5.2 Hz, 1H), 2.45-2.54 (m, 5H), 0.89-0.94 (m, 3H); m/z=414[M+1]$^+$.

Example 54

4-(2-(2-Chlorobenzofuran-5-yl)-1-(4-(2-(methylamino)ethoxy)phenyl)but-1-enyl)phenol

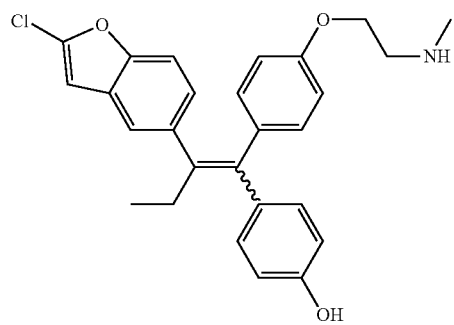 [SMILES: CCC(=C(c1ccc(O)cc1)c1ccc(OCCNC)cc1)c1ccc2oc(Cl)cc2c1]

Step A: 5-(2-ethyl-1,3-dioxolan-2-yl)benzofuran

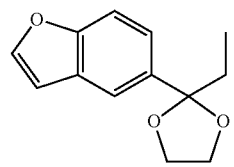 [SMILES: CCC1(c2ccc3occc3c2)OCCO1]

A solution of 1-(benzofuran-5-yl)propan-1-one (650 mg, 1.0 eq), ethane-1,2-diol (3.5 g, 15.0 eq) and 4-methylbenzenesulfonic acid (65 mg, 0.1 eq) in 20 mL toluene was refluxed for 72 h, cooled, quenched with sat. NaHCO$_3$ (aq) and extracted with EtOAc. The extract was washed with brine, dried, concentrated, and purified by column chromatography to give the desired product (710 mg, 87%). $^1$H NMR (400 MHz, CDCl$_3$) δ 7.69 (d, J=2.0 Hz, 1H), 7.62 (d, J=2.4 Hz, 1H), 7.45 (d, J=8.4 Hz, 1H), 7.39 (dd, J=8.4 Hz, 1.6 Hz, 1H), 6.76 (dd, J=2.4 Hz, 0.4 Hz, 1H), 4.02-4.05 (m, 2H), 3.78-3.81 (m, 2H), 1.96 (q, J=7.2 Hz, 2H), 0.89 (t, J=7.2 Hz, 3H).

Step B: 2-chloro-5-(2-ethyl-1,3-dioxolan-2-yl)benzofuran

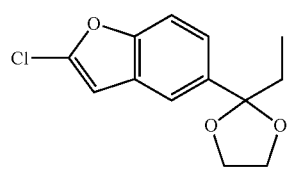 [SMILES: CCC1(c2ccc3oc(Cl)cc3c2)OCCO1]

To a stirred solution of 5-(2-ethyl-1,3-dioxolan-2-yl)benzofuran (350 mg, 1.0 eq) in 20 mL anhydrous THF was added 2.5 M n-BuLi solution in hexane (1.6 mL, 2.4 eq) dropwise at 0° C., and the mixture was stirred at 0° C. for 50 min under nitrogen. A solution of hexachloroethane (915 mg, 2.4 eq) in 10 mL anhydrous THF was added dropwise. The reaction was stirred at rt for 1 h, quenched with sat NH₄Cl (aq), and extracted with EtOAc. The extract was dried, concentrated, and purified by column chromatography to give the desired product (260 mg, 65%). ¹H NMR (400 MHz, CDCl₃) δ 7.58 (d, J=0.4 Hz, 1H), 7.37-7.38 (m, 2H), 6.57 (s, 1H), 4.01-4.05 (m, 2H), 3.77-3.80 (m, 2H), 1.94 (q, J=7.6 Hz, 2H), 0.88 (t, J=7.2 Hz, 3H).

Step C: 1-(2-chlorobenzofuran-5-yl)propan-1-one

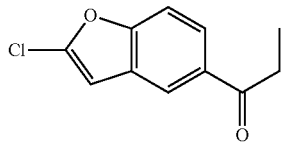

To a stirred solution of 2-chloro-5-(2-ethyl-1,3-dioxolan-2-yl)benzofuran (250 mg, 1.0 eq) in 15 mL MeOH was added 3 mL 3N HCl (aq) at rt. The reaction was stirred for 30 min at rt, quenched with sat NaHCO₃ (aq), and extracted with EtOAc. The extract was washed with brine, dried, concentrated, and purified by column chromatography to give the desired product (140 mg, 68%). ¹H NMR (400 MHz, CDCl₃) δ 8.15 (d, J=1.6 Hz, 1H), 7.95 (dd, J=8.4 Hz, 1.6 Hz, 1H), 7.48 (d, J=8.8 Hz, 1H), 6.68 (s, 1H), 3.06 (q, J=6.8 Hz, 2H), 1.25 (t, J=6.8 Hz, 3H).

Step D: 4-(2-(2-chlorobenzofuran-5-yl)-1-(4-(2-chloroethoxy)phenyl)but-1-enyl)phenol

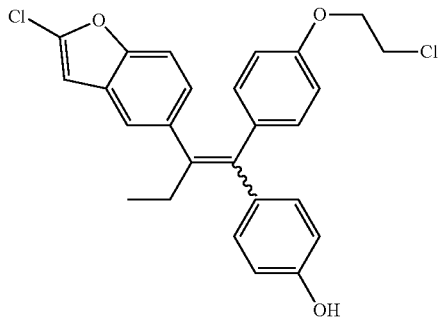 [SMILES: CCC(=C(c1ccc(O)cc1)c1ccc(OCCCl)cc1)c1ccc2oc(Cl)cc2c1]

According to general procedure of McMurry reaction as example 1, step D described, 1-(2-chlorobenzofuran-5-yl)propan-1-one (140 mg, 1.0 eq) was reacted with (4-(2-chloroethoxy)phenyl)(4-hydroxyphenyl)methanone (371 mg, 2.0 eq) to give 220 mg desired product (72%, Z/E=1/1). ¹H NMR (400 MHz, CDCl₃) δ 7.23 (s, 1H), 7.21 (d, J=8.4 Hz, 1H), 7.16 & 7.10 (d, J=8.6 Hz, 2H), 7.00 & 6.99 (d, J=8.4 Hz, 1H), 6.90 & 6.81 (d, J=8.6 Hz, 2H), 6.76 & 6.70 (d, J=8.8 Hz, 2H), 6.52 & 6.44 (d, J=9.0 Hz, 2H), 6.45 (s, 1H), 4.73 & 4.48 (s, 1H), 4.26 & 4.08 (t, J=6.0 Hz, 2H), 3.83 & 3.72 (t, J=6.0 Hz, 2H), 2.50 (q, J=7.2 Hz, 2H), 0.91 (t, J=7.2 Hz, 3H).

Step E: 4-(2-(2-chlorobenzofuran-5-yl)-1-(4-(2-(methylamino)ethoxy) phenyl)but-1-enyl)phenol

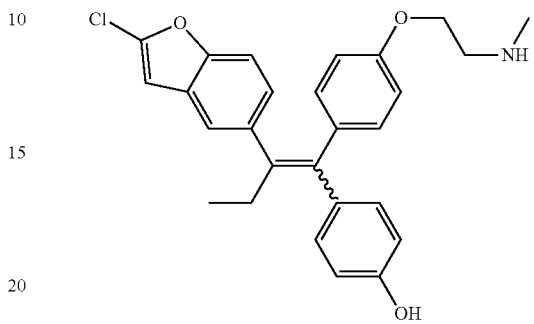

To a stirred solution of 4-(2-(2-chlorobenzofuran-5-yl)-1-(4-(2-chloroethoxy)-phenyl)but-1-enyl)phenol (220 mg, 1.0 eq) in 15 mL MeOH was added 5 mL CH₃NH₂ (aq) and heated at 85° C. for 48 h. The organic solvent was removed in vacuo, water was added to the residue and extracted with EtOAc. The extract was dried, concentrated, and purified by column chromatography to give the desired product (105 mg, 48%, Z/E=1/1). ¹H NMR (400 MHz, CDCl₃) δ 7.23 (s, 1H), 7.20 (d, J=8.4 Hz, 1H), 7.14 & 7.08 (d, J=8.4 Hz, 2H), 7.00 (d, J=8.4 Hz, 1H), 6.87 & 6.78 (d, J=8.8 Hz, 2H), 6.73 & 6.69 (d, J=8.8 Hz, 2H), 6.49 & 6.42 (d, J=8.6 Hz, 2H), 6.45 (s, 1H), 4.10 & 3.92 (t, J=5.0 Hz, 2H), 3.00 & 2.89 (t, J=5.0 Hz, 2H), 2.53 & 2.46 (s, 3H), 2.50 (q, J=7.6 Hz, 2H), 0.91 (t, J=7.6 Hz, 3H); m/z=448[M+1]⁺.

Example 55

(Z)-4-(2-(2-Chlorobenzofuran-5-yl)-1-(4-(2-(methylamino)ethoxy)phenyl)but-1-enyl)phenol

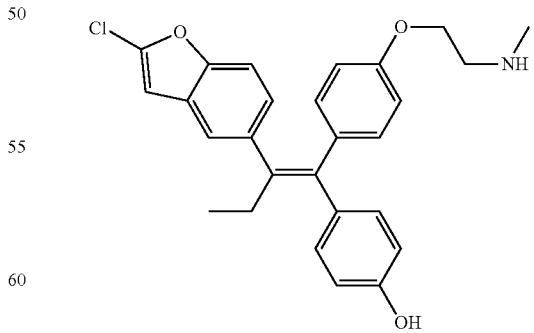

The title compound (Z-isomer) was separated by preparative HPLC from the Z/E mixture made by example 11. ¹H NMR (400 MHz, DMSO-d⁶) δ 9.43 (brs, 1H), 7.37 (d, J=8.4 Hz, 1H), 7.32 (s, 1H), 7.04 (d, J=8.4 Hz, 1H), 6.99 (d, J=8.4

Hz, 2H), 6.90 (s, 1H), 6.75 (d, J=8.0 Hz, 2H), 6.70 (d, J=8.8 Hz, 2H), 6.56 (d, J=8.4 Hz, 2H), 3.84 (t, J=5.4 Hz, 2H), 2.73 (t, J=5.4 Hz, 2H), 2.43 (q, J=7.4 Hz, 2H), 2.26 (s, 3H), 0.84 (t, J=7.4 Hz, 3H); m/z=448[M+1]⁺.

Example 56

(E)-4-(2-(2-Chlorobenzofuran-5-yl)-1-(4-(2-(methylamino)ethoxy)phenyl)but-1-enyl)phenol

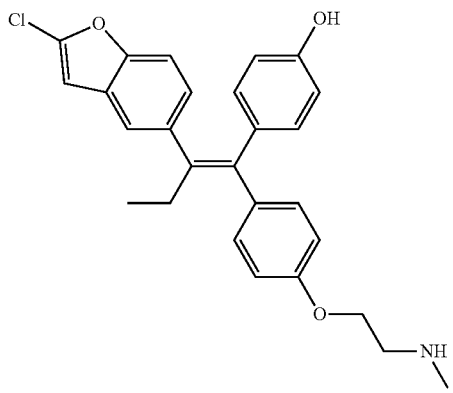 [SMILES: CC/C(=C(/c1ccc(O)cc1)c1ccc(OCCNC)cc1)c1ccc2oc(Cl)cc2c1]

The title compound (E-isomer) was separated by preparative HPLC from the Z/E mixture made by example 11. ¹H NMR (400 MHz, CDCl₃) δ 7.24 (s, 1H), 7.20 (d, J=8.4 Hz, 1H), 7.13 (d, J=6.8 Hz, 2H), 7.00 (d, J=8.6 Hz, 1H), 6.83 (d, J=8.8 Hz, 2H), 6.66 (d, J=6.8 Hz, 2H), 6.45 (s, 1H), 6.41 (d, J=6.4 Hz, 2H), 4.08 (t, J=5.0 Hz, 2H), 2.99 (t, J=5.2 Hz, 2H), 2.51 (s, 3H), 2.49 (q, J=7.4 Hz, 2H), 0.91 (t, J=7.4 Hz, 3H); m/z=448[M+1]⁺.

Example 57

(Z)-2-(4-(2-(2-chlorobenzofuran-5-yl)-1-(4-methoxyphenyl)but-1-enyl)phenoxy)-N-methylethanamine

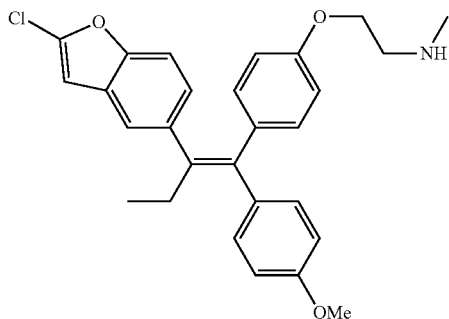 [SMILES: CC/C(=C(\c1ccc(OC)cc1)c1ccc(OCCNC)cc1)c1ccc2oc(Cl)cc2c1]

Step A: 2-chloro-5-(1-(4-(2-chloroethoxy)phenyl)-1-(4-methoxyphenyl)-but-1-en-2-yl)benzofuran

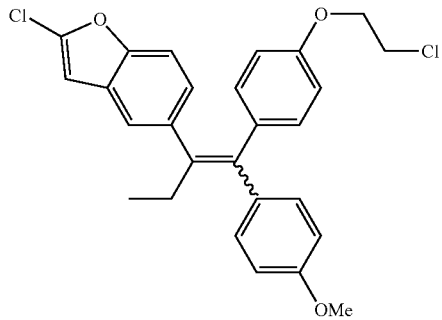 [SMILES: CCC(=C(c1ccc(OC)cc1)c1ccc(OCCCl)cc1)c1ccc2oc(Cl)cc2c1]

According to general procedure of McMurry reaction as example 1, step D described, 1-(2-chlorobenzofuran-5-yl)propan-1-one (200 mg, 1.0 eq) was reacted with (4-methoxyphenyl)(4-(2-(methylamino)ethoxy)phenyl)methanone (418 mg, 1.5 eq, by example 1, step B) to give 440 mg desired product (98%, Z/E=1/1).

Step B: (Z)-2-(4-(2-(2-chlorobenzofuran-5-yl)-1-(4-methoxyphenyl)but-1-enyl)phenoxy)-N-methylethanamine

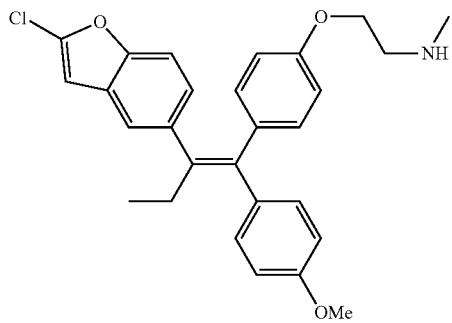 [SMILES: CC/C(=C(\c1ccc(OC)cc1)c1ccc(OCCNC)cc1)c1ccc2oc(Cl)cc2c1]

According to the same procedure as example 1, step E described, 2-chloro-5-(1-(4-(2-chloroethoxy)phenyl)-1-(4-methoxyphenyl)but-1-en-2-yl)benzofuran (440 mg, 1.0 eq) was reacted with MeNH₂ (30% wt in water, 10 mL) in MeOH (20 mL) under reflux to give the desired (Z)-product (Z and E isomer can be separated via column chromatography). ¹H NMR (400 MHz, CDCl₃) δ 7.24 (d, J=2.0 Hz, 1H), 7.20 (d, J=8.4 Hz, 1H), 7.15 (d, J=8.8 Hz, 2H), 7.01 (dd, J=8.4 Hz, 2.0 Hz, 1H), 6.88 (d, J=8.8 Hz, 2H), 6.74 (d, J=8.8 Hz, 2H), 6.51 (d, J=8.8 Hz, 2H), 6.45 (s, 1H), 3.92 (t, J=5.2 Hz, 2H), 3.83 (s, 3H), 2.88 (t, J=5.2 Hz, 2H), 2.50 (q, J=7.6 Hz, 2H), 2.45 (s, 3H), 0.92 (t, J=7.6 Hz, 3H); m/z=462[M+1]⁺.

Example 58

4-(1-(4-(2-(Azepan-1-yl)ethoxy)phenyl)-2-(2-chlorobenzofuran-5-yl)but-1-enyl)phenol

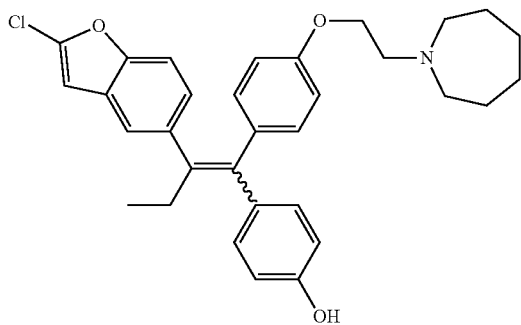 [SMILES: CCC(=C(c1ccc(O)cc1)c1ccc(OCCN2CCCCCC2)cc1)c1ccc2oc(Cl)cc2c1]

According to the same procedure as example 1, step E described, 4-(2-(2-chlorobenzofuran-5-yl)-1-(4-(2-chloroethoxy)phenyl)but-1-enyl)phenol (220 mg, 1.0 eq, made by example 11, step D) was reacted with azepane (500 mg) in MeOH under reflux to give the desired product (105 mg, 48%, Z/E=1/1). ¹H NMR (400 MHz, CDCl₃) δ 7.22 (d, J=1.6 Hz, 1H), 7.19 (d, J=8.4 Hz, 1H), 7.14 (d, J=8.4 Hz, 1H), 7.07 (d, J=8.8 Hz, 1H), 6.97-7.01 (m, 1H), 6.87 (d, J=8.4 Hz, 1H), 6.84 (d, J=8.4 Hz, 1H), 6.75 (d, J=8.8 Hz, 1H), 6.76 (d, J=8.8 Hz, 1H), 6.50 (d, J=8.4 Hz, 1H), 6.45 (d, J=8.8 Hz, 1H), 6.43-6.44 (m, 1H), 4.46-4.48 (m, 1H), 4.25-4.27 (m, 1H), 3.00-3.71 (m, 6H), 2.44-2.51 (m, 2H), 1.73-2.00 (m, 8H), 0.91 (t, J=7.6 Hz, 3H); m/z=516[M+1]⁺.

Example 59

4-(2-(2,3-Dihydrobenzofuran-5-yl)-1-(6-(2-(methylamino)ethoxy)pyridin-3-yl)but-1-enyl)phenol

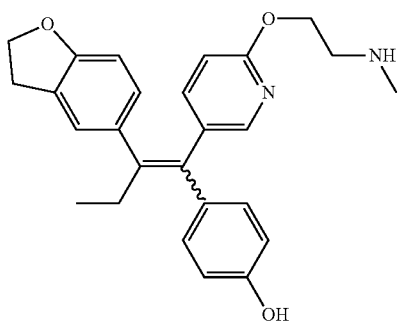 [SMILES: CCC(=C(c1ccc(O)cc1)c1ccc(OCCNC)nc1)c1ccc2c(c1)CCO2]

Step A: (6-chloropyridin-3-yl)(4-(tetrahydro-2H-pyran-2-yloxy)phenyl)-methanone

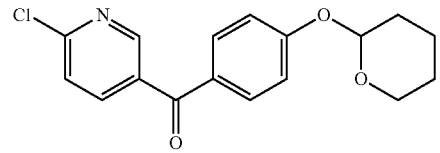 [SMILES: O=C(c1ccc(OC2CCCCO2)cc1)c1ccc(Cl)nc1]

Mg (1.67 g, 1.2 eq) was added to dry THF (50 mL), the mixture was heated to 55° C., I₂ was added in one lot followed by EtBr. 2-(4-Bromophenoxy)tetrahydro-2H-pyran (16 g, 1.1 eq) was dissolved in THF, and part of this solution was added at once to the Mg-THF mixture. After the reaction was Initiated, the remaining above solution was added and the mixture was refluxed for 2 h to give the MgBr-THF solution, ready for the next step. 6-Chloronicotinoyl chloride (10.0 g, 1.0 eq) was added to dry THF, cooled to 0° C. under N₂, and then the above MgBr-THF solution was added dropwise over 20 min. The mixture was warmed to rt and stirred overnight. Water was added and extracted by EtOAc. The extract was concentrated and purified by column chromatography with petroleum ether:EtOAc=5:1 to give the desired product of the (6-chloropyridin-3-yl)(4-(tetrahydro-2H-pyran-2-yloxy) phenyl)methanone (13.6 g) in 76% yield. ¹H NMR (400 MHz, CDCl₃) δ 8.78 (s, 1H), 8.05 (d, J=8.4 Hz, 1H), 7.78 (d, J=8.0 Hz, 2H), 7.46 (d, J=8.4 Hz, 1H), 7.15 (d, J=8.0 Hz, 2H), 5.56 (t, J=3.2 Hz, 1H), 3.83-3.90 (m, 1H), 3.63-3.67 (m, 1H), 2.02-2.05 (m, 1H), 1.89-1.92 (m, 2H), 1.69-1.75 (m, 2H), 1.59-1.65 (m, 1H).

Step B: 4-(1-(6-chloropyridin-3-yl)-2-(2,3-dihydrobenzofuran-5-yl)but-1-enyl)phenol

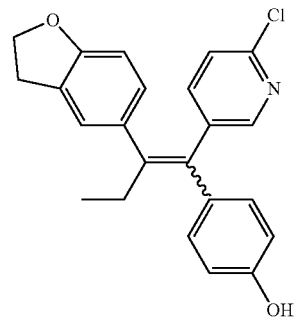 [SMILES: CCC(=C(c1ccc(O)cc1)c1ccc(Cl)nc1)c1ccc2c(c1)CCO2]

According to general procedure of McMurry reaction as example 1, step D described, 1-(2,3-dihydrobenzofuran-5-yl) propan-1-one (610 mg, 1.1 eq) was reacted with (6-chloropyridin-3-yl)(4-(tetrahydro-2H-pyran-2-yloxy)phenyl) methanone (1.0 g, 1.0 eq) to give 440 mg desired product (37%, Z/E=1/1).

Step C: 4-(2-(2,3-dihydrobenzofuran-5-yl)-1-(6-(2-(methylamino)-ethoxy)pyridin-3-yl)but-1-enyl)phenol

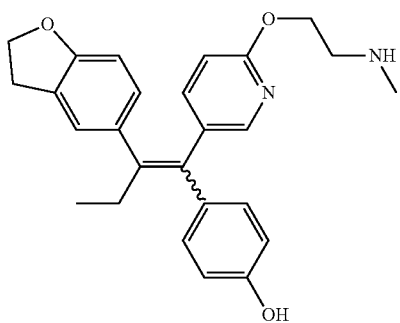 [SMILES: CCC(=C(c1ccc(O)cc1)c1ccc(OCCNC)nc1)c1ccc2c(c1)CCO2]

To a stirred solution of 2-(methylamino)ethanol (875 mg, 10 eq) in 20 mL anhydrous THF was added NaH (373 mg, 8.0 eq) at 0° C., and the mixture was stirred at rt for 1 h, 4-(1-(6-Chloropyridin-3-yl)-2-(2,3-dihydrobenzofuran-5-yl)but-1-enyl)phenol (440 mg, 1.0 eq) was added. The mixture was refluxed for 16 h, cooled, quenched with sat. NH$_4$Cl, and extracted with CH$_2$Cl$_2$. The extract was dried, concentrated, and purified by column chromatography to give the desired product (197 mg, 41%). $^1$H NMR (400 MHz, CDCl$_3$) δ 8.06 (d, J=2.4 Hz, 0.5H), 7.60 (d, J=2.0 Hz, 0.5H), 7.32 (dd, J=8.4 Hz, 2.4 Hz, 0.5H), 7.07 (dd, J=8.4 Hz, 2.4 Hz, 0.5H), 7.03 (d, J=8.8 Hz, 1H), 6.93 (d, J=8.4 Hz, 1H), 6.83 (d, J=8.4 Hz, 0.5H), 6.78 (d, J=8.4 Hz, 1.5H), 6.69 (d, J=8.4 Hz, 1H), 6.65 (d, J=8.4 Hz, 0.5H), 6.59 (d, J=8.0 Hz, 1H), 6.49 (d, J=8.8 Hz, 1H), 6.36 (d, J=8.4 Hz, 0.5H), 4.53 (t, J=8.4 Hz, 2H), 4.46 (t, J=5.2 Hz, 1H), 4.31 (t, J=5.2 Hz, 1H), 3.10 (t, J=8.4 Hz, 2H), 3.05 (t, J=5.2 Hz, 1H), 2.96 (t, J=5.2 Hz, 1H), 2.55 (s, 1.5H), 2.50 (s, 1.5H), 2.45 (q, J=7.6 Hz, 2H), 0.94 (t, J=7.2 Hz, 3H); m/z=417[M+1]$^+$.

Example 60

4-(2-(2-Chlorobenzofuran-5-yl)-1-(4-(2-(pyrrolidin-1-yl)ethoxy)phenyl)but-1-enyl)phenol

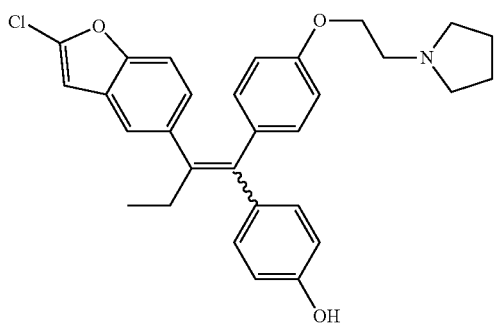 [SMILES: CCC(=C(c1ccc(O)cc1)c1ccc(OCCN2CCCC2)cc1)c1ccc2oc(Cl)cc2c1]

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with pyrrolidine (1 mL) in MeOH (3 mL) under reflux to give the desired product (51 mg, 68%, Z/E=1/2.6) as a yellow solid. $^1$H NMR (400 MHz, CDCl$_3$) δ 7.24 (s, 1H), 7.20 (d, J=9.2 Hz, 1H), 7.09 & 7.06 (d, J=8.4 Hz, 2H), 7.00 (d, J=8.8 Hz, 1H), 6.78 & 6.72 (d, J=8.2 Hz, 2H), 6.68 (d, J=8.6 Hz, 2H), 6.46 & 6.45 (s, 1H), 6.41 & 6.27 (d, J=8.4 Hz, 2H), 4.10 & 3.89 (t, J=5.8 Hz, 2H), 2.94 & 2.83 (t, J=6.2 Hz, 2H), 2.68 & 2.61 (m, 4H), 2.49 (q, J=7.4 Hz, 2H), 1.84 & 1.81 (m, 4H), 0.91 (t, J=7.4 Hz, 3H); m/z=488 [M+1]$^+$.

Example 61

4-(2-(2-Chlorobenzofuran-5-yl)-1-(4-(2-(piperidin-1-yl)ethoxy)phenyl)but-1-enyl)phenol

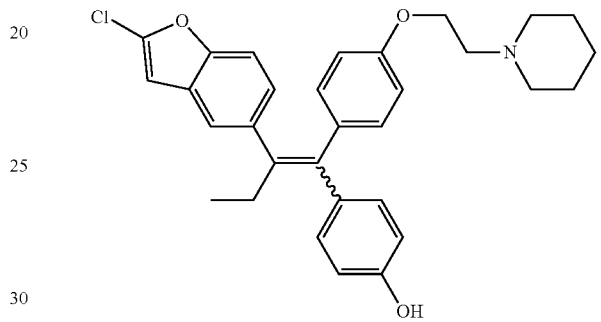

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with piperidine (1 mL) in MeOH (3 mL) under reflux to give the desired product (63 mg, 82%, Z/E=1/1) as a light yellow solid. $^1$H NMR (400 MHz, CDCl$_3$) δ 7.24 & 7.22 (s, 1H), 7.21 (d, J=9.2 Hz, 1H), 7.09 & 7.06 (d, J=8.6 Hz, 2H), 7.01 & 6.99 (d, J=8.8 Hz, 1H), 6.78 & 6.69 (d, J=8.2 Hz, 2H), 6.68 & 6.66 (d, J=8.6 Hz, 2H), 6.47 & 6.45 (s, 1H), 6.42 & 6.25 (d, J=8.6 Hz, 2H), 4.10 & 3.90 (t, J=6.0 Hz, 2H), 2.81 & 2.70 (t, J=6.0 Hz, 2H), 2.48-2.57 (m, 6H), 1.47-1.68 (m, 6H), 0.89-0.93 (m, 3H); m/z=502 [M+1]$^+$.

Example 62

4-(2-(2-Chlorobenzofuran-5-yl)-1-(4-(2-morpholinoethoxy)phenyl)but-1-enyl)phenol

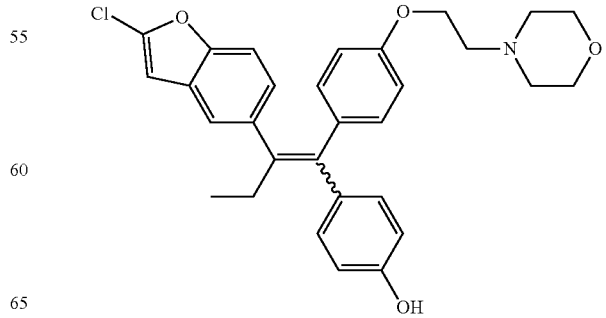

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with morpholine (1 mL) in MeOH (3 mL) under reflux to give the desired product (61 mg, 79%, Z/E=1/2) as a light yellow solid. $^1$H NMR (400 MHz, CDCl$_3$) δ 7.23 (s, 1H), 7.21 (d, J=8.4 Hz, 1H), 7.13 & 7.09 (d, J=8.6 Hz, 2H), 7.00 (d, J=8.4 Hz, 1H), 6.83 & 6.80 (d, J=8.6 Hz, 2H), 6.72 & 6.69 (d, J=8.6 Hz, 2H), 6.45 (s, 1H), 6.43 (d, J=8.8 Hz, 2H), 4.12 & 3.94 (t, J=5.6 Hz, 2H), 3.76 & 3.71 (t, J=4.8 Hz, 4H), 2.83 & 2.71 (t, J=5.6 Hz, 2H), 2.61 & 2.52 (t, J=4.4 Hz, 4H), 2.49 (q, J=7.2 Hz, 2H), 0.91 (t, J=7.2 Hz, 3H); m/z=504[M+1]$^+$.

Example 63

4-(2-(2-Chlorobenzofuran-5-yl)-1-(4-(2-(4-methylpiperazin-1-yl)ethoxy)phenyl)but-1-enyl)phenol

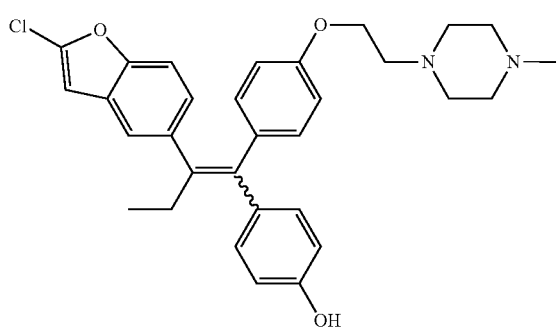 [SMILES: CCC(=C(c1ccc(O)cc1)c1ccc(OCCN2CCN(C)CC2)cc1)c1ccc2oc(Cl)cc2c1]

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with 1-methylpiperazine (1 mL) in MeOH (8 mL) under reflux to give the desired product (60 mg, 76%, Z/E=1/1.7) as a yellow solid. $^1$H NMR (400 MHz, CDCl$_3$) δ 7.23 (s, 1H), 7.20 (d, J=8.8 Hz, 1H), 7.12 & 7.08 (d, J=8.8 Hz, 2H), 7.00 (d, J=8.8 Hz, 1H), 6.83 & 6.78 (d, J=8.8 Hz, 2H), 6.72 & 6.69 (d, J=8.8 Hz, 2H), 6.45 & 6.44 (s, 1H), 6.42 (d, J=8.8 Hz, 2H), 4.12 & 3.93 (t, J=5.6 Hz, 2H), 2.84 & 2.73 (t, J=5.6 Hz, 2H), 2.40-2.62 (m, 10H), 2.31 & 2.82 (s, 3H), 0.91 (t, J=7.2 Hz, 3H); m/z=517[M+1]$^+$.

Example 64

4-(2-(2-Chlorobenzofuran-5-yl)-1-(4-(2-(diethylamino)ethoxy)phenyl)but-1-enyl)phenol

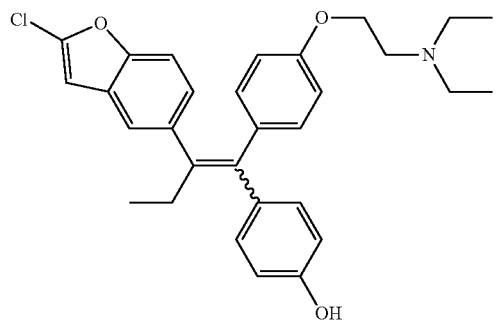 [SMILES: CCC(=C(c1ccc(O)cc1)c1ccc(OCCN(CC)CC)cc1)c1ccc2oc(Cl)cc2c1]

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with diethylamine (3 mL) in MeOH (8 mL) under reflux to give the desired product (61 mg, 81%, Z/E=1/1.25) as a brown solid. $^1$HNMR (400 MHz, CDCl$_3$) δ 7.23 (s, 1H), 7.20 (d, J=8.4 Hz, 1H), 7.12 & 7.09 (d, J=8.8 Hz, 2H), 7.00 & 6.99 (d, J=8.4 Hz, 1H), 6.83 & 6.80 (d, J=8.8 Hz, 2H), 6.71 & 6.69 (d, J=8.4 Hz, 2H), 6.45 (s, 1H), 6.43 (d, J=8.8 Hz, 2H), 4.08 & 3.90 (t, J=5.8 Hz, 2H), 2.92 & 2.80 (t, J=5.8 Hz, 2H), 2.69 & 2.62 (q, J=7.0 Hz, 4H), 2.50 (q, J=7.6 Hz, 2H), 1.10 & 1.04 (q, J=7.2 Hz, 6H), 0.91 (t, J=7.6 Hz, 3H); m/z=490[M+1]$^+$.

Example 65

4-(2-(2-Chlorobenzofuran-5-yl)-1-(4-(2-(ethylamino)ethoxy)phenyl)but-1-enyl)phenol

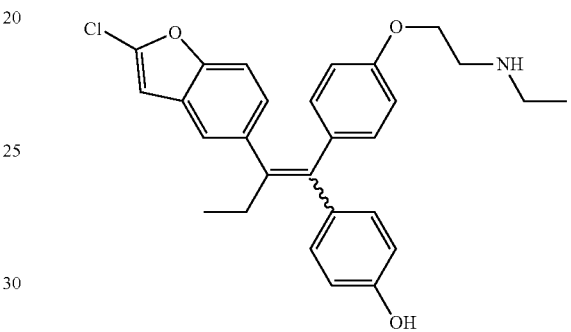

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with ethanamine (3 mL) in MeOH (8 mL) under reflux to give the desired product (38 mg, 54%, Z/E=1/1.2) as a white solid. $^1$H NMR (400 MHz, CDCl$_3$) δ 7.23 (s, 1H), 7.20 (d, J=8.4 Hz, 1H), 7.12 & 7.03 (d, J=8.6 Hz, 2H), 6.99 (d, J=8.8 Hz, 1H), 6.83 & 6.75 (d, J=8.8 Hz, 2H), 6.71 & 6.65 (d, J=8.6 Hz, 2H), 6.44 (s, 1H), 6.45 & 6.40 (d, J=8.4 Hz, 2H), 4.10 & 3.92 (t, J=4.8 Hz, 2H), 3.04 & 2.93 (t, J=4.8 Hz, 2H), 2.78 & 2.71 (q, J=7.2 Hz, 2H), 2.50 (q, J=7.2 Hz, 2H), 1.18 & 1.13 (q, J=7.2 Hz, 3H), 0.91 (t, J=7.2 Hz, 3H); m/z=462[M+1]$^+$.

Example 66

4-(2-(2-Chlorobenzofuran-5-yl)-1-(4-(2-(dimethylamino)ethoxy)phenyl)but-1-enyl)phenol

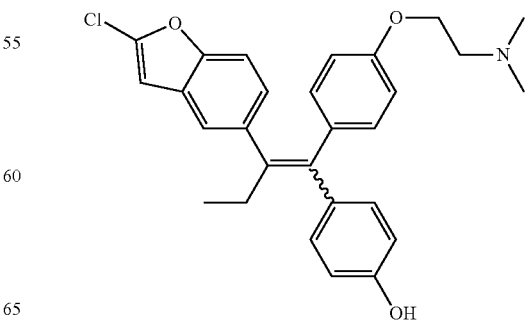

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with dimethylamine (1 mL) in MeOH (8 mL) under reflux to give the desired product (27 mg, 38%, Z/E=1/1.2) as a white solid. $^1$H NMR (400 MHz, CDCl$_3$) δ 7.23 & 7.21 (s, 1H), 7.20 (d, J=8.8 Hz, 1H), 7.08 & 7.06 (d, J=9.2 Hz, 2H), 7.00 & 6.97 (d, J=8.4 Hz, 1H), 6.79 & 6.67 (d, J=8.6 Hz, 2H), 6.66 (d, J=8.4 Hz, 2H), 6.45 & 6.24 (d, J=8.8 Hz, 2H), 6.43 & 6.41 (s, 1H), 4.10 & 3.89 (t, J=5.2 Hz, 2H), 2.86 & 2.75 (t, J=5.2 Hz, 2H), 2.49 (q, J=7.2 Hz, 2H), 2.44 & 2.37 (s, 6H), 0.91 (t, J=7.2 Hz, 3H); m/z=462[M+1]$^+$.

Example 67

4-(2-(2-Chlorobenzofuran-5-yl)-1-(4-(2-(piperazin-1-yl)ethoxy)phenyl)but-1-enyl)phenol

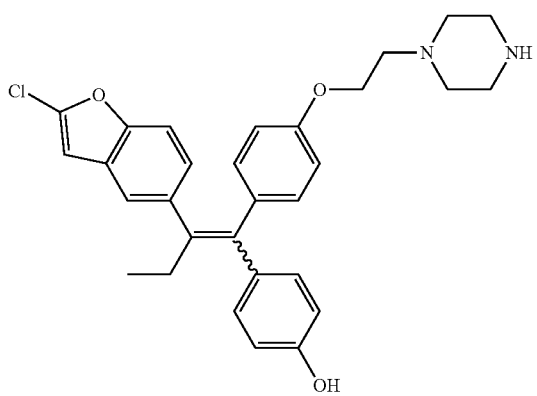 [SMILES: CCC(=C(c1ccc(O)cc1)c1ccc(OCCN2CCNCC2)cc1)c1ccc2oc(Cl)cc2c1]

According to the same procedure as example 1, step E described, 4-(2-(2-chlorobenzofuran-5-yl)-1-(4-(2-chloroethoxy)phenyl)but-1-enyl)phenol (70 mg, 1.0 eq, made by example 11, step D) was reacted with tert-butyl piperazine-1-carboxylate (500 mg) in MeOH (3 mL) under reflux and separated via column chromatography, followed by treatment with 1 mL trifluoroacetic acid in 3 mL CH$_2$Cl$_2$ and then purified by column chromatography to give the desired product (Z/E=1/1) as a white solid. m/z=503[M+1]$^+$.

Example 68

4-(2-(2-Chlorobenzofuran-5-yl)-1-(6-(2-(methylamino)ethoxy)pyridin-3-yl)but-1-enyl)phenol

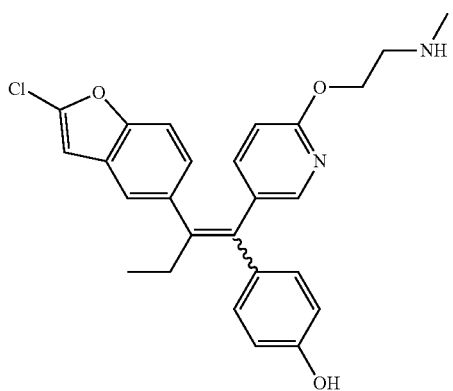 [SMILES: CCC(=C(c1ccc(O)cc1)c1ccc(OCCNC)nc1)c1ccc2oc(Cl)cc2c1]

According to the same procedure as example 16, step C described, 4-(2-(2-chlorobenzofuran-5-yl)-1-(6-chloropyridin-3-yl)but-1-enyl)phenol (70 mg, 1.0 eq) was reacted with 2-(methylamino)ethanol (128 mg, 10 eq) to give the desired product (Z/E=1/1). m/z=449[M+1]$^+$.

Example 69

4-(2-(2-Chlorobenzofuran-5-yl)-1-(6-(2-(methylamino)ethylthio)pyridin-3-yl)but-1-enyl)phenol

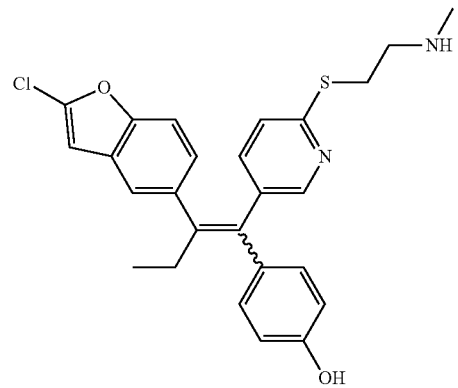 [SMILES: CCC(=C(c1ccc(O)cc1)c1ccc(SCCNC)nc1)c1ccc2oc(Cl)cc2c1]

Step A: 2-(methylamino)ethanol hydrochloride

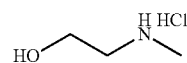

A solution of 2-(methylamino)ethanol (20 g, 1.0 eq) in 50 mL concentrated HCl was stirred at rt for 2 h and concentrated to give the product (quant). $^1$H NMR (400 MHz, DMSO-d$^6$) δ 8.95 (brs, 2H), 3.65 (t, J=5.2 Hz, 2H), 2.94 (t, J=5.6 Hz, 2H), 2.50-2.54 (m, 3H).

Step B: 2-chloro-N-methylethanamine hydrochloride

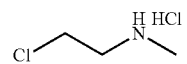

To a stirred solution of 2-(methylamino)ethanol hydrochloride (29.7 g, 1.0 eq) in 150 mL CHCl$_3$ was added sulfuryl dichloride (41 g, 1.3 eq) dropwise at 0° C. After refluxing for 3 h, the reaction was cooled to rt. Then solvent was removed in vacuo, the residue was suspended in 100 mL solution (CH$_2$Cl$_2$:petroleum ether=1:10), and filtered to give the desired product (28 g, 80%). $^1$H NMR (400 MHz, DMSO-d$^6$) δ 9.24 (brs, 2H), 3.93 (t, J=6.0 Hz, 2H), 3.28 (t, J=6.0 Hz, 2H), 2.56 (s, 3H).

Step C: 2-(methylamino)ethanethiol hydrochloride

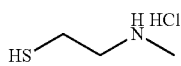

To a stirred solution of 2-chloro-N-methylethanamine hydrochloride (15 g, 1.0 eq) in 150 mL water was added $Na_2S_2O_3$ (18.5 g, 1.0 eq), and the mixture was refluxed for 48 h. After cooling to rt, the solvent was removed in vacuo. The crude salt was dissolved in 60 mL 6 M HCl (aq) and heated at 90° C. for 4 h. The solvent was removed in vacuo and the residue was purified by column chromatography to give the desired product. $^1$H NMR (400 MHz, DMSO-d$^6$) δ 4.95 (brs, 2H), 2.90 (s, 4H), 2.37 (s, 3H).

Step D: 4-(2-(2-chlorobenzofuran-5-yl)-1-(6-(2-(methylamino)ethylthio)-pyridin-3-yl)but-1-enyl)phenol

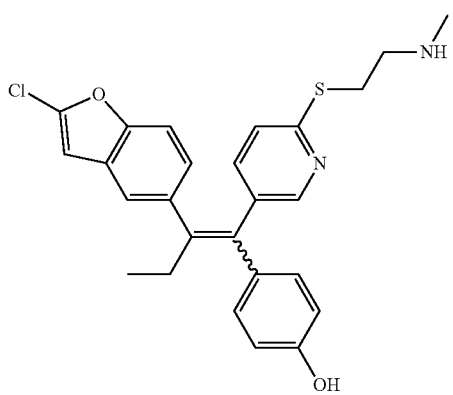

According to the same procedure as example 16, step C described, 4-(2-(2-chlorobenzofuran-5-yl)-1-(6-chloropyridin-3-yl)but-1-enyl)phenol (70 mg, 1.0 eq) was reacted with 2-(methylamino)ethanethiol hydrochloride (217 mg, 10 eq) to give the desired product (Z/E=1/1). m/z=465[M+1]$^+$.

Example 70

4-(2-(2-Chlorobenzofuran-5-yl)-1-(6-(methyl(2-(methylamino)ethyl)amino)pyridin-3-yl)but-1-enyl) phenol

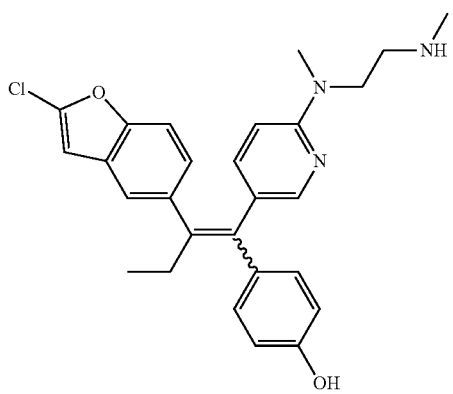 [SMILES: CCC(=C(c1ccc(O)cc1)c1ccc(N(C)CCNC)nc1)c1ccc2oc(Cl)cc2c1]

According to the same procedure as example 16, step C described, 4-(2-(2-chlorobenzofuran-5-yl)-1-(6-chloropyridin-3-yl)but-1-enyl)phenol (70 mg, 1.0 eq) was reacted with N,N'-dimethylethane-1,2-diamine (150 mg, 10 eq) to give the desired product (Z/E=1/1). m/z=462[M+1]$^+$.

Example 71

4-(2-(2-Chlorobenzofuran-5-yl)-1-(6-(3-(pyrrolidin-1-yl)propyl)pyridin-3-yl)but-1-enyl)phenol

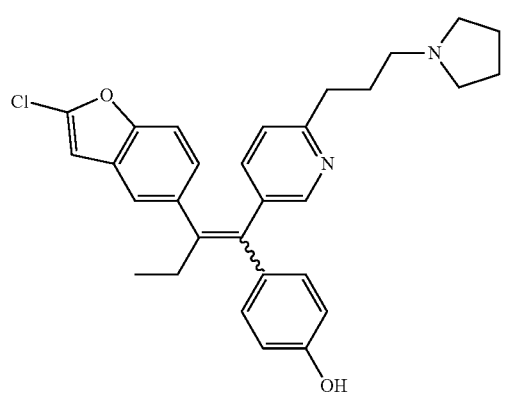 [SMILES: CCC(=C(c1ccc(O)cc1)c1ccc(CCCN2CCCC2)nc1)c1ccc2oc(Cl)cc2c1]

Step A: 2-(4-iodophenoxy)tetrahydro-2H-pyran

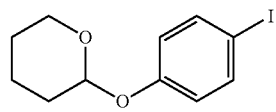 [SMILES: Ic1ccc(OC2CCCCO2)cc1]

4-Iodophenol 10.0 g (45.5 mmol) was dissolved in 20 mL 3,4-dihydro-2H-pyran, then one drop of concentrated sulfuric acid was added, the reaction mixture was stirred for 30 min, then the mixture was poured into 1000 mL of n-hexane, filtered, washed with 300 mL (100 mL×3) hexane, and dried in vacuum to afford the desired product as a white solid (9.1 g, 65.9%).

Step B: 6-chloro-N-methoxy-N-methylnicotinamide

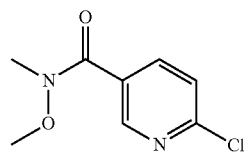

Oxalyl chloride 12.1 g (95.2 mmol) was added dropwise to a solution of 6-chloronicotinic acid 10.0 g (63.5 mmol) in 100 mL tetrahydrofuran. The reaction mixture was stirred at room temperature for 1 h, and then concentrated in vacuo to give a residue. The residue was dissolved in 50 mL dichloromethane to give a solution, which was added to a solution of N,O-dimethylhydroxylamine hydrochloride (12.4 g, 126.9 mmol) and triethylamine (25.7 g, 253.9 mmol) in 100 mL dichloromethane, stirred at room temperature for another 1 h, concentrated, and purified by column chromatography to afford the desired product as a colorless oil (9.4 g, 73.8%).

Step C: 1-(prop-2-ynyl)pyrrolidine

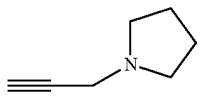

3-Bromoprop-1-yne (60.5 g, 0.50 mol) was slowly added to methylamine (70.1 g, 1.0 mol) at −10° C. After addition, the mixture was stirred at room temperature overnight. The mixture was distilled on a rectification column to afford the desired product as a colorless oil (45.5 g, 83.5%).

Step D: (6-chloropyridin-3-yl)(4-(tetrahydro-2H-pyran-2-yloxy)phenyl)-methanone

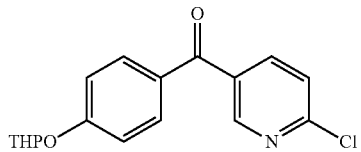

2-(4-Iodophenoxy)tetrahydro-2H-pyran (18.2 g, 59.9 mmol) was dissolved in 100 mL dry tetrahydrofuran and cooled to −78° C. under nitrogen atmosphere, and then n-butyllithium was added dropwise to the solution. After addition, the solution was stirred at −78° C. for 0.5 h, 6-chloro-N-methoxy-N-methylnicotinamide (8.0 g, 39.9 mmol) in 50 mL tetrahydrofuran was added dropwise and keep the temperature under −78° C. for 2 h. Then 100 mL of aqueous saturated ammonium chloride was added. The mixture was extracted with ethyl acetate. The extract was dried over sodium sulfate, concentrated in vacuo, and purified by column chromatography to give the desired product as a yellow solid (8.4 g, 66.3%).

Step E: (6-(3-(pyrrolidin-1-yl)prop-1-ynyl)pyridin-3-yl)(4-(tetrahydro-2H-pyran-2-yloxy)phenyl)methanone

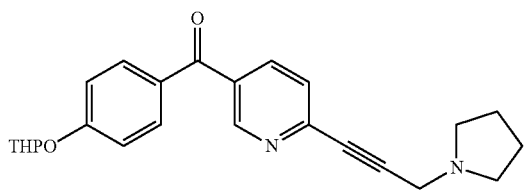

A 100 mL Schlenk flask was charge with (6-chloropyridin-3-yl)(4-(tetrahydro-2H-pyran-2-yloxy)phenyl)methanone (4.0 g, 12.6 mmol), tetrakis(triphenylphosphine) palladium (0) (1.5 g, 1.3 mmol, 10 mol %), cuprous iodide (0.48 g, 2.5 mmol, 20 mol %), triethylamine 50 mL and 1-(prop-2-ynyl)pyrrolidine (2.8 g, 25.2 mmol). The flask was flushed with nitrogen three times and the mixture was stirred at 80° C. for 2 h. The solvent was evaporated under vacuum and the residue was purified by column chromatography to afford the desired product as a yellow solid (2.2 g, 44.9%).

Step F: (6-(3-(pyrrolidin-1-yl)propyl)pyridin-3-yl)(4-(tetrahydro-2H-pyran-2-yloxy)phenyl)methanone

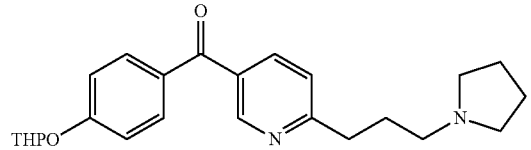

Raney nickel (0.3 g, 0.6 mmol, 10 mol %) was added to the solution of (6-(3-(pyrrolidin-1-yl)prop-1-ynyl)pyridin-3-yl)(4-(tetrahydro-2H-pyran-2-yloxy)phenyl)methanone (2.2 g, 5.6 mmol) in 20 mL methanol at room temperature, and the reaction mixture was stirred for 1 h under hydrogen atmosphere. Filtered off the nickel and the filtrate was concentrated in vacuo to afford the desired product as a yellow solid (1.7 g, 77.3%).

Step G: 4-(2-(2-chlorobenzofuran-5-yl)-1-(6-(3-(pyrrolidin-1-yl)propyl)-pyridin-3-yl)but-1-enyl)phenol

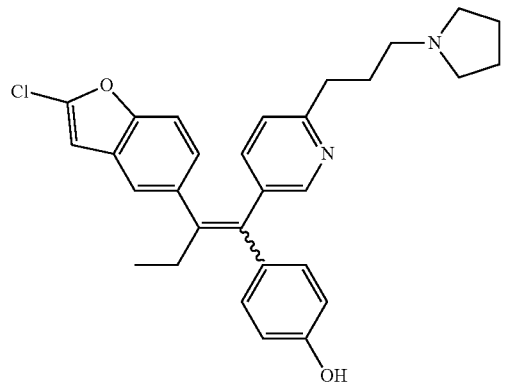 [SMILES: CCC(=C(c1ccc(O)cc1)c1ccc(CCCN2CCCC2)nc1)c1ccc2oc(Cl)cc2c1]

According to general procedure of McMurry reaction as example 1, step D described, 6-(3-(pyrrolidin-1-yl)propyl)pyridin-3-yl)(4-(tetrahydro-2H-pyran-2-yloxy)phenyl)methanone was reacted with 1-(2-chlorobenzofuran-5-yl)propan-1-one to give the desired product (Z/E=1/1). m/z=487 [M+1]$^+$.

Biological Activity

Generation of IC$_{50}$ Data

In Vitro Growth Inhibitory Potency of Anti-Estrogen Activity in MCF-7 Cells:

The estrogen receptor α (ERα) high expression human breast cancer MCF-7 cells (#HTB-22, A.T.C.C.) were cultured in DMEM medium supplemented by 10% fetal bovine serum (Gibco®) and 10 μg/ml bovine insulin (Sigma®). The cells were maintained in 75 cm$^2$ cell culture flask (Corning®) filled with 15 ml medium, 95% air and 5% CO$_2$. Cells were split twice a week in a single layer cell culture.

For experiments related to 17β-Estradiol (E$_2$), cells at logarithm growing stage were pretreated for two days without E$_2$, the phenol red DMEM medium was replaced by the phenol red free DMEM/F12 medium, and FBS was replaced by 10% charcoal stripped FBS to remove the steroid and greatly decrease the hormone levels. Cells were seeded in 96 well cell culture plates (Corning®) with 4×10$^3$/well density, cultured in E$_2$ free DMEM/F12 medium at 37° C. for 24 hours, 95% air and 5% CO$_2$. All the compounds were stocked in DMSO as 0.01 M, serial diluted by the culture medium and added to the cells in the presence of proper E$_2$ concentration. The final concentrations of compounds and DMSO were 3×10$^{-10}$~1×10$^{-5}$ M and 0.1%. Cells were incubated at 37° C. for 7 days, medium containing E$_2$ and compounds were changed every two days to maintain the chemical activity.

7 Days later, the viable cell numbers were calculated by the ATP amount from the luciferase quantity measurement (Cell Titre Glo® luciferase kit, Promega®). This method can be used to evaluate the stimulating estrogenicity of estrogen dependent cell growth under the condition of E$_2$ free. The estrogenicity was tested by percentage compared to the maximum growth stimulation (100%) by E$_2$. In this study, the percentage antagonist effects were evaluated by compared to the complete inhibition (100%) at the dose of 1×10$^{-5}$ M. The inhibition curves were generated by the reading numbers with the program Prism® 5, IC$_{50}$ values were calculated.

Biological Data for Selected Compounds

Selected compounds prepared as described above were assayed following the biological procedures described herein. The results are given in the table below:

| Structure | Growth inhibitory potency in MCF-7 cells IC$_{50}$ (nM) |
|---|---|
| [structure] | <100 |
| [structure] | <100 |
| [structure] | <100 |

| Structure | Growth inhibitory potency in MCF-7 cells IC$_{50}$ (nM) |
| --- | --- |
| (structure) | <100 |
| (structure) | <100 |
| (structure) | <100 |
| (structure) | <100 |

-continued

| Structure | Growth inhibitory potency in MCF-7 cells IC$_{50}$ (nM) |
|---|---|
| | <100 |
| | <100 |
| | <100 |
| | <100 |

-continued

| Structure | Growth inhibitory potency in MCF-7 cells IC$_{50}$ (nM) |
|---|---|
| (structure) | <100 |
| (structure) | <100 |
| (structure) | <500 |
| (structure) | <100 |

-continued

| Structure | Growth inhibitory potency in MCF-7 cells IC$_{50}$ (nM) |
|---|---|
| (structure) | <500 |
| (structure) | <100 |
| (structure) | <100 |
| (structure) | <100 |

| Structure | Growth inhibitory potency in MCF-7 cells IC$_{50}$ (nM) |
|---|---|
| 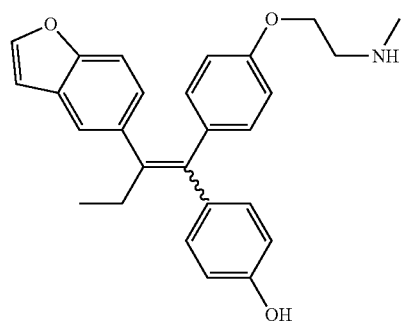 [SMILES: CCC(=C(c1ccc(O)cc1)c1ccc(OCCNC)cc1)c1ccc2occc2c1] | <100 |
| 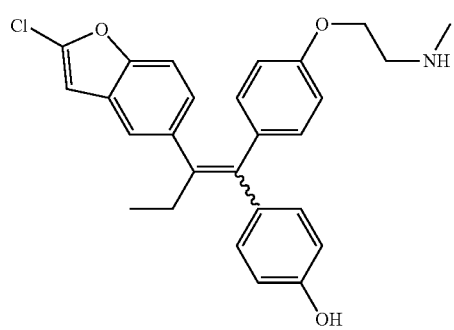  Z | <100 |
| 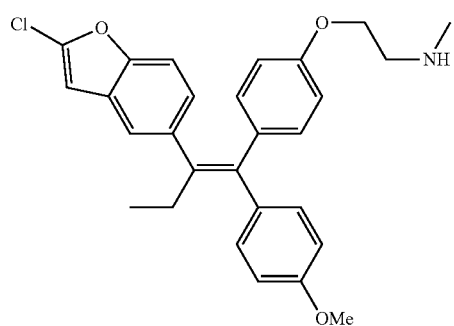 [SMILES: CC/C(=C(\c1ccc(OC)cc1)c1ccc(OCCNC)cc1)c1ccc2oc(Cl)cc2c1] | <500 |
| 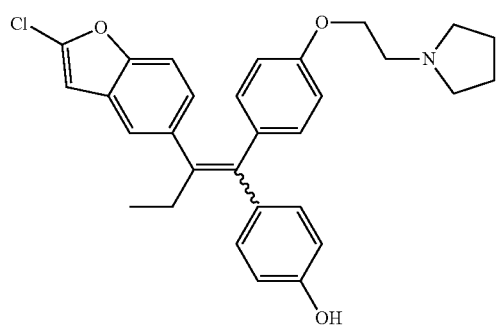 [SMILES: CCC(=C(c1ccc(O)cc1)c1ccc(OCCN2CCCC2)cc1)c1ccc2oc(Cl)cc2c1] | <100 |

-continued
| Structure | Growth inhibitory potency in MCF-7 cells IC$_{50}$ (nM) |
|---|---|
| 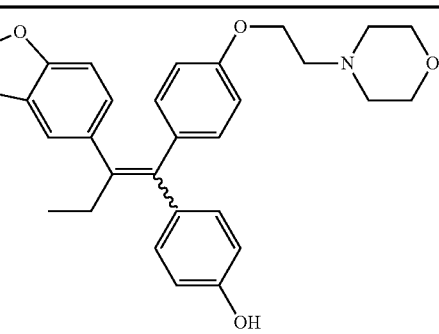 | <100 |
| 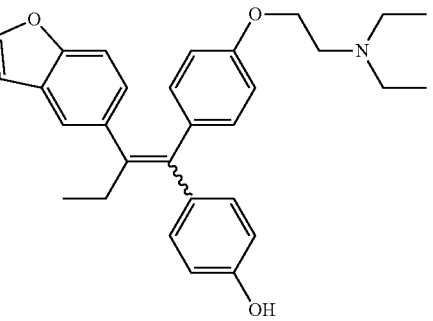 | <100 |
| 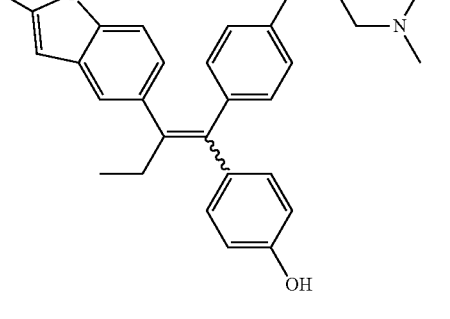 | <100 |
| 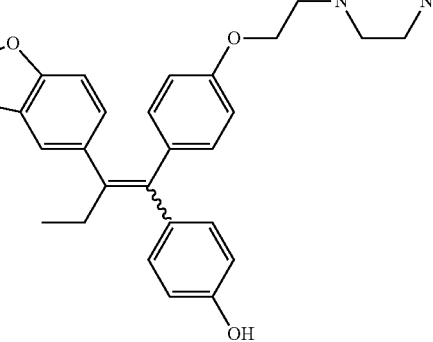 | <100 |

-continued
| Structure | Growth inhibitory potency in MCF-7 cells IC$_{50}$ (nM) |
|---|---|
| 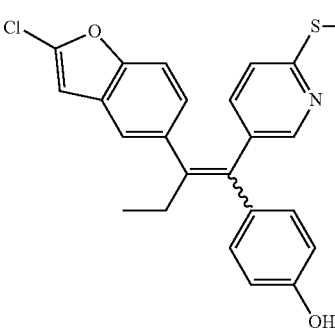 | <100 |
| 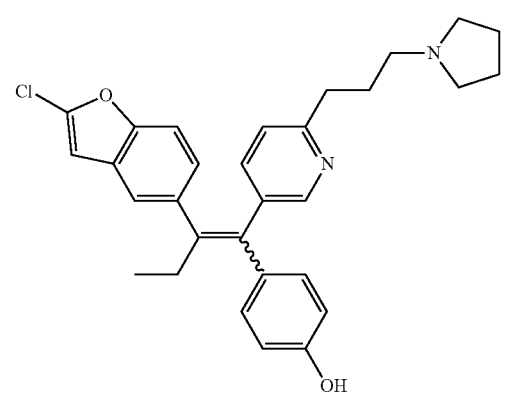 [SMILES: CCC(=C(c1ccc(O)cc1)c1ccc(CCCN2CCCC2)nc1)c1ccc2oc(Cl)cc2c1] | <100 |
| 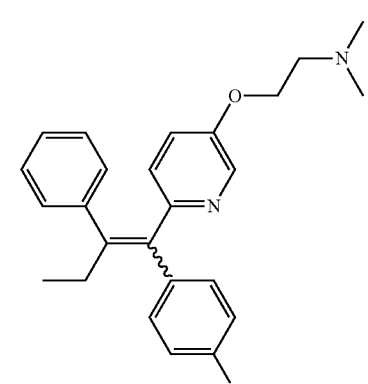 | <500 |
| 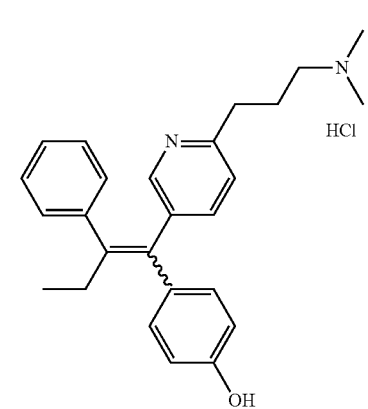 [SMILES: CCC(=C(c1ccc(O)cc1)c1ccc(CCCN(C)C)nc1)c1ccccc1 ; Cl] | <100 |

-continued

| Structure | Growth inhibitory potency in MCF-7 cells IC$_{50}$ (nM) |
|---|---|
| | <100 |
| | <100 |
| | <100 |
| | <100 |

| Structure | Growth inhibitory potency in MCF-7 cells IC$_{50}$ (nM) |
|---|---|
| 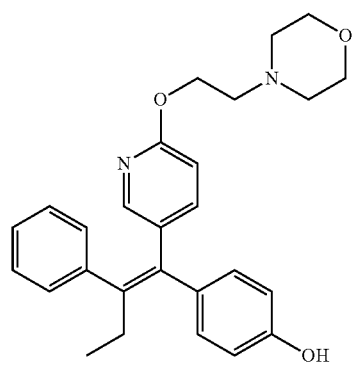 [SMILES: CC/C(=C(\c1ccc(O)cc1)c1ccc(OCCN2CCOCC2)nc1)c1ccccc1] | <100 |
| 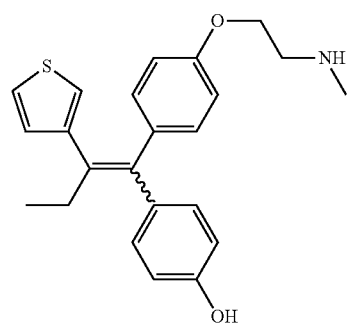 [SMILES: CCC(=C(c1ccc(O)cc1)c1ccc(OCCNC)cc1)c1ccsc1] | <100 |
| 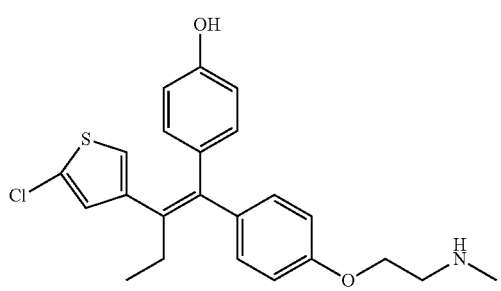 [SMILES: CC/C(=C(/c1ccc(O)cc1)c1ccc(OCCNC)cc1)c1csc(Cl)c1] | <500 |
| 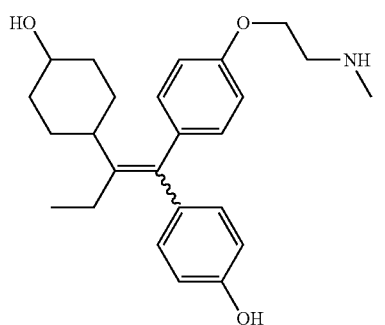 [SMILES: CCC(=C(c1ccc(O)cc1)c1ccc(OCCNC)cc1)C1CCC(O)CC1] | <500 |

-continued

| Structure | Growth inhibitory potency in MCF-7 cells IC$_{50}$ (nM) |
|---|---|
| | <100 |
| | <100 |
| | <100 |
| 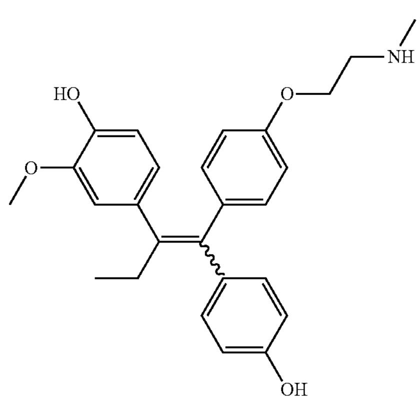 | <500 |

-continued

| Structure | Growth inhibitory potency in MCF-7 cells IC$_{50}$ (nM) |
|---|---|
| (structure) | <500 |
| (structure) | <100 |
| (structure) | <100 |
| (structure) | <100 |

-continued
| Structure | Growth inhibitory potency in MCF-7 cells IC$_{50}$ (nM) |
|---|---|
| 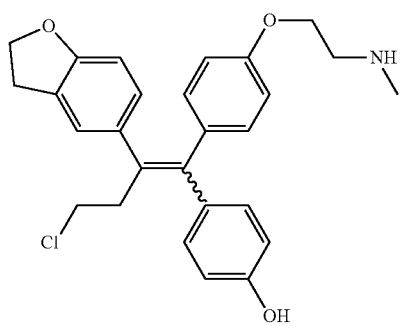 [SMILES: CNCCOc1ccc(C(=C(CCCl)c2ccc3c(c2)CCO3)c2ccc(O)cc2)cc1] | <100 |
| 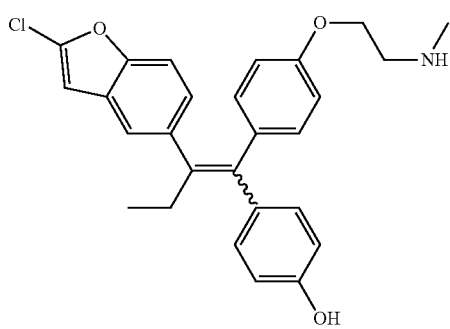 Z/E = 1/1 | <100 |
| 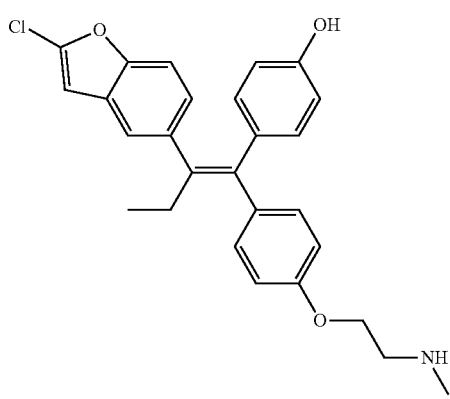 E | <100 |
| 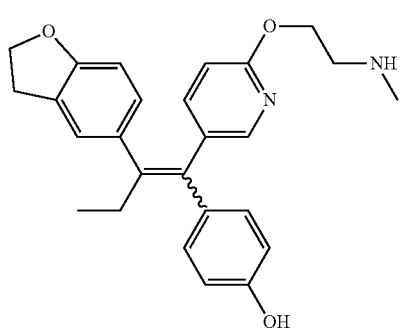 [SMILES: CCC(=C(c1ccc(O)cc1)c1ccc(OCCNC)nc1)c1ccc2c(c1)CCO2] | <100 |

-continued
| Structure | Growth inhibitory potency in MCF-7 cells IC$_{50}$ (nM) |
|---|---|
| 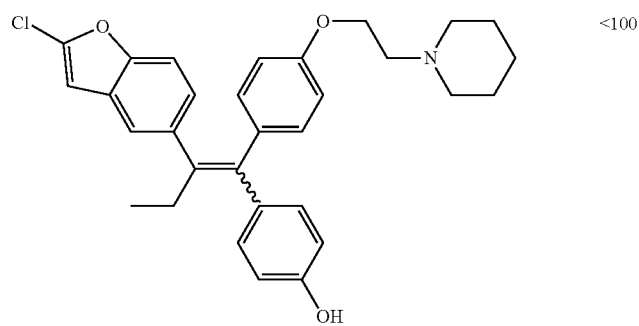 | <100 |
| 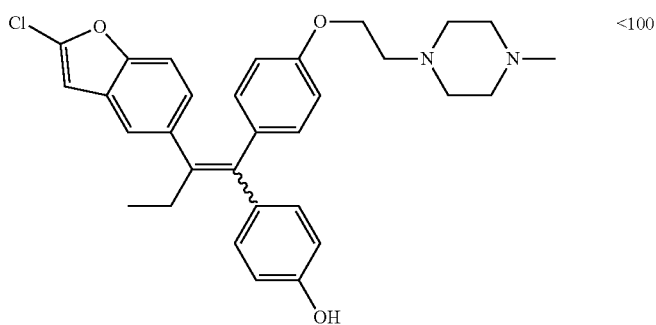 | <100 |
| 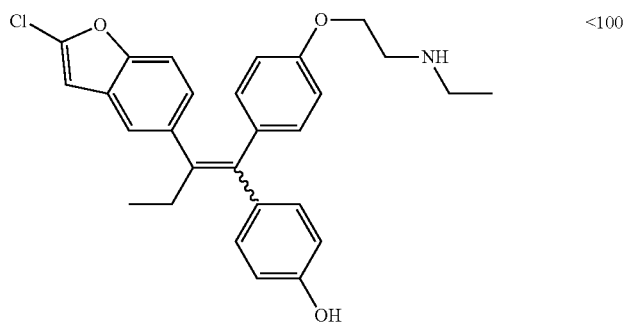 | <100 |
| 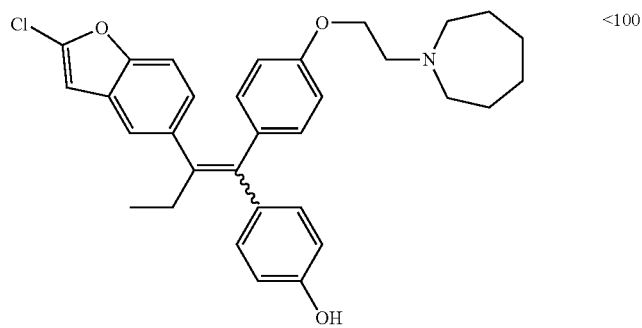 | <100 |

| Structure | Growth inhibitory potency in MCF-7 cells IC$_{50}$ (nM) |
|---|---|
| 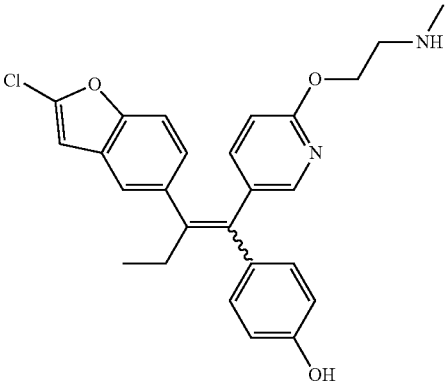 | <100 |
| 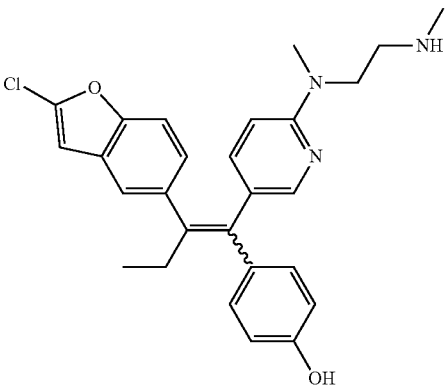 [SMILES: CCC(=C(c1ccc(O)cc1)c1ccc(N(C)CCNC)nc1)c1ccc2oc(Cl)cc2c1] | <100 |

The representative compounds of the present invention show potent anti-estrogen activities in MCF-7 cells.

Toxicity

Studies further show that the compounds of the present invention have relatively low toxicities.

As shown in FIGURE and the table below, 21 days after the nude mouse was administered with Tamoxifen (20 mg/kg), the weight dropped by 20%, and a higher dose of 30 mg/kg of an exemplary compound of the present application, shown below as CT-946-01, led to a weight gain of 7%.

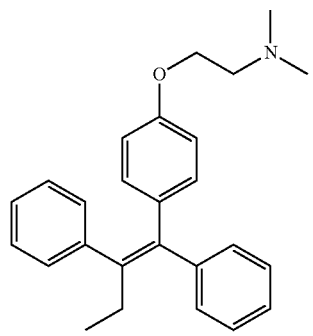

Tamoxifen

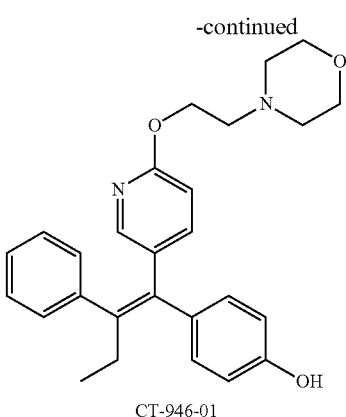

CT-946-01

Anti-Tumor (MCF-7) Effect and Weight Change:

| Compound | Dose (PO, QD) | TGI (%) 21 days | BW (% of vehicle) |
|---|---|---|---|
| Tamoxifen | 20 mg/kg | 22.4 | 80.0 |
| CT-946-01 | 10 mg/kg | 108 | 104 |
| CT-946-01 | 30 mg/kg | 104 | 107 |

PO: per os; QD: quapua die; TGI: Target Group Index; BW: Body Weight

While preferred embodiments of the present invention have been shown and described herein, such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It is intended that the following claims define the scope of aspects of the invention and that methods and structures within the scope of these claims and their equivalents be covered thereby.

What is claimed is:

1. A compound of formula I:

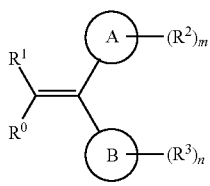

Formula I wherein
R¹ is

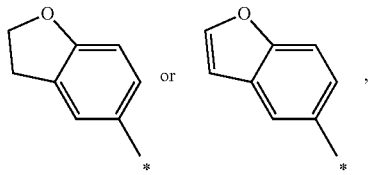

wherein the 5-membered ring is optionally and independently substituted with one or more groups selected from the group consisting of halogen, —OH, —SH, alkyl, halogenated alkyl and alkoxy; and R⁰ is alkyl; wherein R⁰ is optionally and independently substitued with one or more groups consisting of halogen, —OH, —NH₂, and alkoxy;

ring A and ring B are each independently selected from aryl and pyridinyl;

R² is selected from halogen, —OH, alkyl, alkoxy, alkysulfanyl, monoalkylamino and dialkylamino, wherein the alkyl, alkoxy, alkylsulfanyl, monoalkylamino and dialkyamino groups are each optionally and independently substituted with —NR₄R₅, wherein R₄ and R₅ are each independently hydrogen, alkyl or cycloalkyl, or R₄ and R₅, together with the nitrogen atom to which they attach, form a hetrocyclyl which is optionally substituted with alkyl; and R³ is selected from the group consisting of halogen, —OH, —NH₂, —CN, —SH, —COOH, alkyl, cycloalkyl, alkoxy, alkylsulfanyl, monoalkylamino, and dialkylamino, wherein the alkyl, cycloalkyl, alkoxy, alkylsulfanyl, monoalkylamino, and dialkylamino, are each optionally substituted with —OH or —NR₄R₅, wherein R₄ and R₅ are each independently hydrogen, alkyl or cycloalkyl, or R₄ and R₅, together with the nitrogen atom to which they attach, form a heterocyclyl which is optionally substituted with alkyl;

m and n are the number of groups R² on ring A and the number of groups R³ on ring B, respectively, and m is selected from 1, 2 or 3 and n is selected from 0, 1, 2 or 3, or a pharmaceutically acceptable salt, stereoisomer, solvate, polymorph, tautomer or prodrug thereof.

2. The compound according to claim 1, or a pharmaceutically acceptable salt, stereoisomer, solvate, polymorph, tautomer or prodrug thereof, wherein:

ring A is selected from phenyl and pyridinyl, and R² is at least at the para-position of the phenyl or pyridinyl; or ring B is selected from phenyl and pyridinyl, and R³ is at least at the para-position of the phenyl or pyridinyl.

3. The compound according to claim 1, or a pharmaceutically acceptable salt, stereoisomer, solvate, polymorph, tautomer or prodrug thereof, wherein:

m and n are each independently 1 or 2.

4. The compound according to claim 1, wherein the compound is selected from the group consisting of:

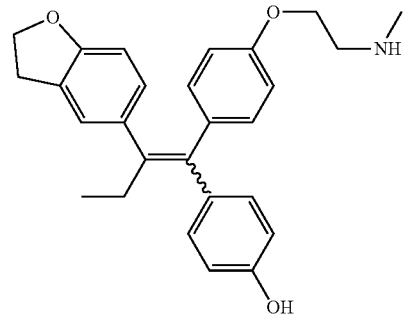

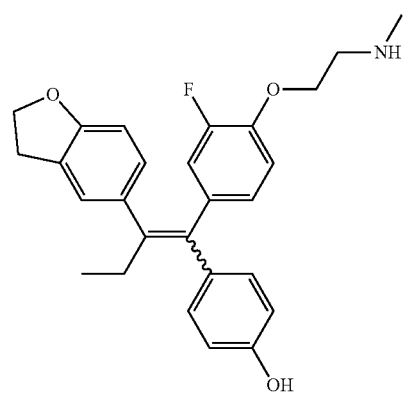

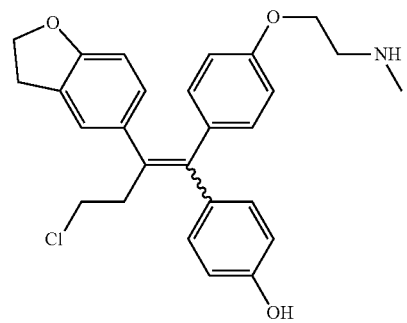

173
-continued
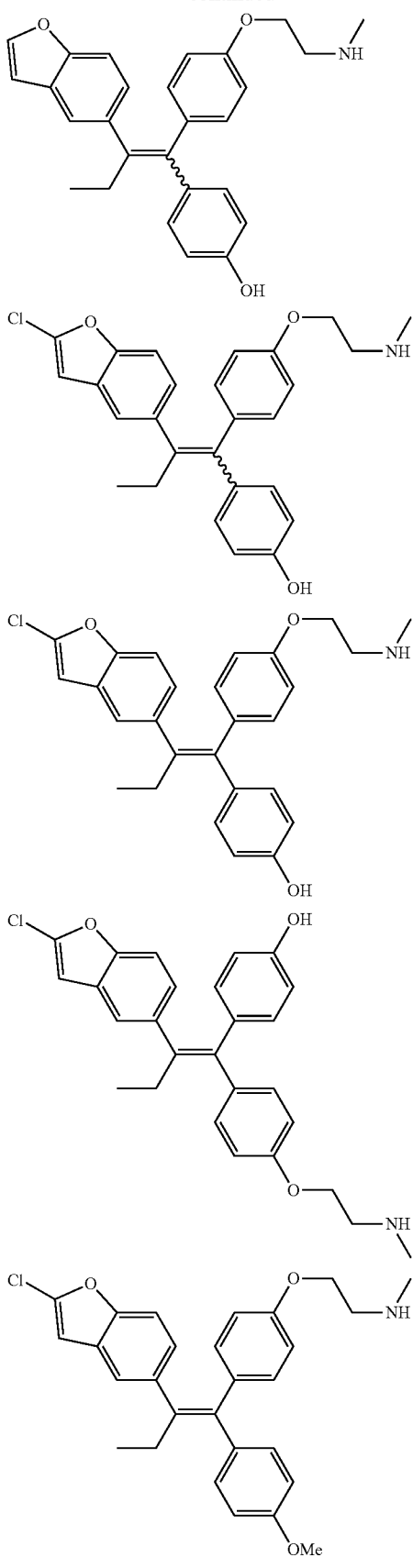
174
-continued
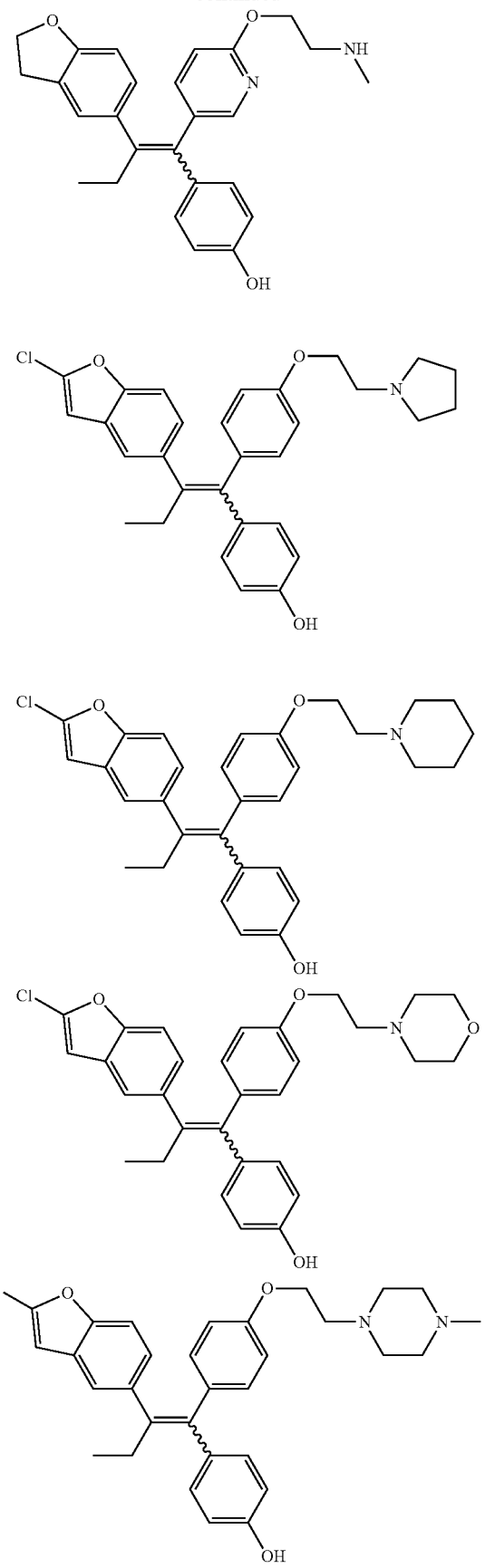

175
-continued
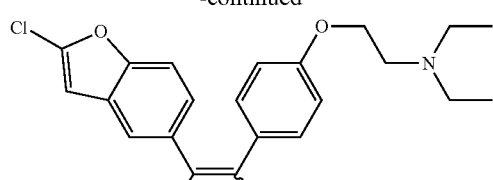
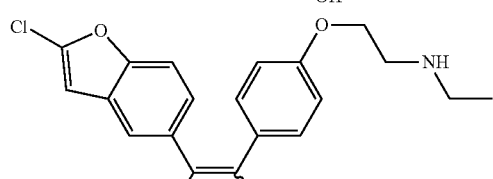
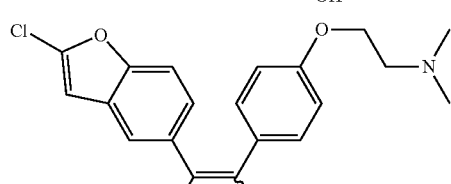
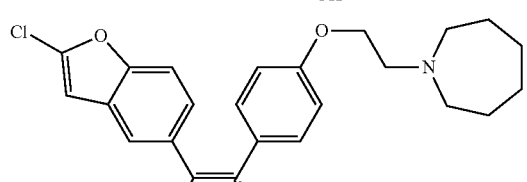
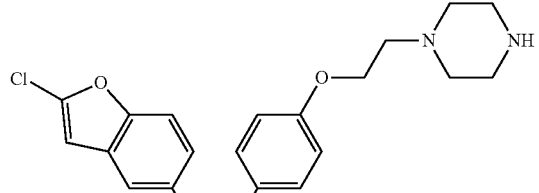
176
-continued
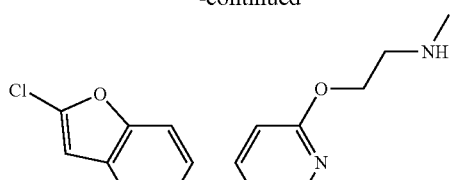
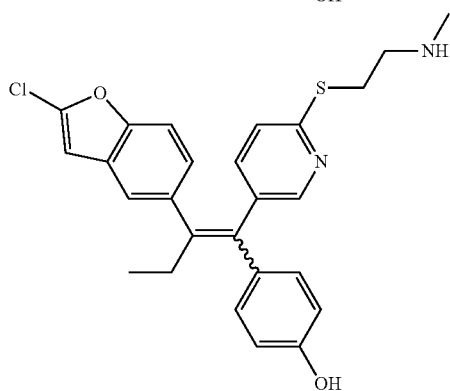
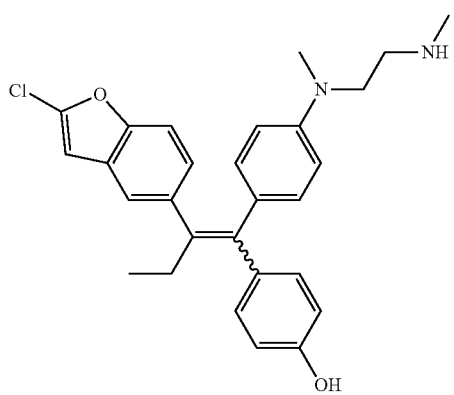
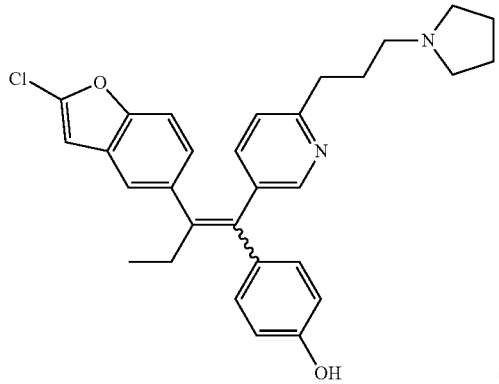
and
or a pharmaceutically acceptable salt, stereoisomer, solvate, polymorph, tautomer or prodrug thereof.
5. A pharmaceutical composition, comprising a compound of formula I:

Formula I

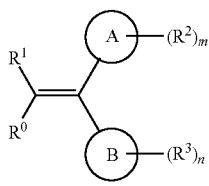

wherein
R¹ is

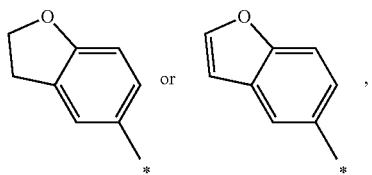

wherein the 5-membered ring is optionally and independently substituted with one or more groups selected from the group consisting of halogen, —OH, —SH, alkyl, halogenated alkyl and alkoxy; and R⁰ is alkyl; wherein R⁰ is optionally and independently substituted with one or more groups selected from the group consisting of halogen, —OH, —NH₂, and alkoxy; ring A and ring B are each independently selected from aryl and pyridinyl;

R² is selected from halogen, —OH, alkyl, alkoxy, alkylsulfanyl, monoalkylamino and dialkylamino, wherein the alkyl, alkoxy, alkylsulfanyl, monoalkylamino and dialkylamino groups are each optionally and independently substituted substituted with —NR₄R₅, wherein R₄ and R₅ are each independently hydrogen, alkyl or cycloalkyl, or R₄ and R₅, together with the nitrogen atom to which they attach, form a heterocyclyl which is optionally substituted with alkyl; and R³ is selected from the group consisting of halogen, —OH, —NH₂, —CN, —SH, —COOH, alkyl, cycloalkyl, alkoxy, alkylsulfanyl, monoalkylamino, and dialkylamino, wherein the alkyl, cycloalkyl, alkoxy, alkylsulfanyl, monoalkylamino, and dialkylamino are each optionally substituted with —OH heterocyclyl or NR₄R₅, wherein R₄ and R₅ are each independently hydrogen, alkyl or cycloalkyl, or R₄ and R₅, together with the nitrogen atom to which they attach, form a heterocyclyl which is optionally substituted with alkyl;

m and n are the number of groups R² on ring A and the number of groups R³ on ring B, respectively, and m is selected from 1, 2 or 3 and n is selected from 0, 1, 2 or 3, or a pharmaceutically acceptable salt, stereoisomer, solvate, polymorph, tautomer or prodrug thereof.

6. A method for treating estrogen-dependent diseases and conditions in humans, which method comprises administering to a human in need thereof, a therapeutically effective amount of a compound of formula I:

Formula I

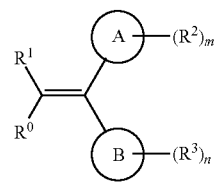

wherein
R¹ is

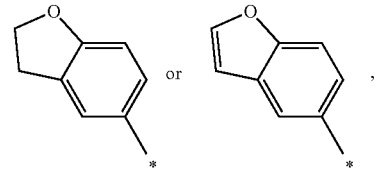

wherein the 5-membered ring is optionally and independently substituted with one or more groups selected from the group consisting of halogen, —OH, —SH, alkyl, halogenated alkyl and alkoxy; and R⁰ is alkyl; wherein R⁰ is optionally and independently substituted with one or more groups selected from the group consisting of halogen, —OH, —NH₂, and alkoxy; ring A and ring B are each independently selected from aryl and pyridinyl;

R² is selected from halogen, —OH, alkyl, alkoxy, alkylsulfanyl, monoalkylamino and dialkylamino, wherein the alkyl, alkoxy, alkylsulfanyl, monoalkylamino and dialkylamino groups are each optionally and independently substituted substituted with —NR₄R₅, wherein R₄ and R₅ are each independently hydrogen, alkyl or cycloalkyl, or R₄ and R₅, together with the nitrogen atom to which they attach, form a heterocyclyl which is optionally substituted with alkyl; and R³ is selected from the group consisting of halogen, —OH, —NH₂, —CN, —SH, —COOH, alkyl, cycloalkyl, alkoxy, alkylsulfanyl, monoalkylamino, and dialkylamino, wherein the alkyl, cycloalkyl, alkoxy, alkylsulfanyl, monoalkylamino, and dialkylamino are each optionally substituted with —OH or —NR₄R₅, wherein R₄ and R₅ are each independently hydrogen, alkyl or cycloalkyl, or R₄ and R₅, together with the nitrogen atom to which they attach, form a heterocyclyl which is optionally substituted with alkyl;

m and n are the number of groups R² on ring A and the number of groups R³ on ring B, respectively, and m is selected from 1, 2 or 3 and n is selected from 0, 1, 2 or 3, or a pharmaceutically acceptable salt, stereoisomer, solvate, polymorph, tautomer or prodrug thereof;

wherein said estrogen-dependent diseases and conditions are selected from the group consisting of menopausal disorders, or postmenopausal disorders, vasomotor symptoms, urogenital atrophy, vulvar vaginal atrophy, atrophic vaginitis, endometriosis, female sexual dysfunction, depression, diabetes, bone demineralization, and osteoporosis.

* * * * *